United States Patent
Andrews et al.

(10) Patent No.: US 9,790,210 B2
(45) Date of Patent: Oct. 17, 2017

(54) N-(MONOCYCLIC ARYL),N'-PYRAZOLYL-UREA, THIOUREA, GUANIDINE AND CYANOGUANIDINE COMPOUNDS AS TRKA KINASE INHIBITORS

(71) Applicant: Array BioPharma Inc., Boulder, CO (US)

(72) Inventors: Steven Wade Andrews, Boulder, CO (US); James F. Blake, Boulder, CO (US); Barbara J. Brandhuber, Boulder, CO (US); Timothy Kercher, San Diego, CA (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 70 days.

(21) Appl. No.: 14/442,604

(22) PCT Filed: Nov. 12, 2013

(86) PCT No.: PCT/US2013/069732
§ 371 (c)(1),
(2) Date: May 13, 2015

(87) PCT Pub. No.: WO2014/078325
PCT Pub. Date: May 22, 2014

(65) Prior Publication Data
US 2016/0280692 A1    Sep. 29, 2016

Related U.S. Application Data

(60) Provisional application No. 61/725,928, filed on Nov. 13, 2012.

(51) Int. Cl.

| | | |
|---|---|---|
| C07D 231/00 | (2006.01) |
| C07D 403/00 | (2006.01) |
| C07D 401/00 | (2006.01) |
| C07D 211/72 | (2006.01) |
| C07D 413/00 | (2006.01) |
| C07D 405/12 | (2006.01) |
| C07D 403/12 | (2006.01) |
| C07D 401/14 | (2006.01) |
| C07D 231/40 | (2006.01) |
| C07D 231/44 | (2006.01) |
| C07D 401/04 | (2006.01) |
| C07D 413/12 | (2006.01) |
| C07D 231/52 | (2006.01) |
| C07D 401/12 | (2006.01) |
| C07D 405/04 | (2006.01) |
| A61K 31/4155 | (2006.01) |

(52) U.S. Cl.
CPC ......... C07D 405/12 (2013.01); C07D 231/40 (2013.01); C07D 231/44 (2013.01); C07D 231/52 (2013.01); C07D 401/04 (2013.01); C07D 401/12 (2013.01); C07D 401/14 (2013.01); C07D 403/12 (2013.01); C07D 405/04 (2013.01); C07D 413/12 (2013.01); A61K 31/4155 (2013.01)

(58) Field of Classification Search
CPC .. C07D 231/04; C07D 403/04; C07D 401/12; C07D 401/04; C07D 403/12; A61K 31/5377; A61K 31/4439; A61K 31/454; A61K 31/497; A61K 31/4155
USPC ................... 548/371.4, 365.4; 546/290, 187; 544/140, 371; 514/407, 341, 235.8, 514/254.05
See application file for complete search history.

(56) References Cited

U.S. PATENT DOCUMENTS 5,849,779 A    12/1998  Hirota et al.
5,998,424 A    12/1999  Galemmo, Jr. et al.
(Continued)

FOREIGN PATENT DOCUMENTS

EP    0761658 A1   12/1997
EP    1043995 B1   11/2006
(Continued)

OTHER PUBLICATIONS

Tsuzuki, Y., et al., Tetrahedron Asymmetry 12 (2001), 2989-2997.
(Continued)

*Primary Examiner* — Shengjun Wang
(74) *Attorney, Agent, or Firm* — Viknins Harris Padys Malen LLP

(57) ABSTRACT

Compounds of Formula (I) or stereoisomers, tautomers, or pharmaceutically acceptable salts, solvates or prodrugs thereof, wherein Ring A, Ring C and X are as defined herein, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

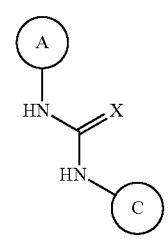

10 Claims, No Drawings

(56) References Cited

U.S. PATENT DOCUMENTS

| | | |
|---|---|---|
| 6,197,798 B1 | 3/2001 | Fink et al. |
| 6,410,533 B1 | 6/2002 | Hirth et al. |
| 7,223,782 B2 | 5/2007 | Atkinson et al. |
| 7,625,915 B2 | 12/2009 | Dumas et al. |
| 8,592,454 B2 | 11/2013 | Shirai et al. |
| 9,163,017 B2 | 10/2015 | Degoey et al. |

FOREIGN PATENT DOCUMENTS

| | | |
|---|---|---|
| EP | 2033955 A1 | 3/2009 |
| EP | 1451160 B1 | 1/2010 |
| EP | 2336105 B9 | 9/2014 |
| JP | 2005206527 A | 8/2005 |
| WO | 9804521 A1 | 2/1998 |
| WO | 9923091 A1 | 5/1999 |
| WO | 9932110 A1 | 7/1999 |
| WO | 0039116 A1 | 7/2000 |
| WO | 0043384 A1 | 7/2000 |
| WO | 0112188 A1 | 2/2001 |
| WO | 0202525 A2 | 1/2002 |
| WO | 02088101 A2 | 11/2002 |
| WO | 02090326 A1 | 11/2002 |
| WO | 03037274 A2 | 5/2003 |
| WO | 03045920 A1 | 6/2003 |
| WO | 03051275 A2 | 6/2003 |
| WO | 2004005262 A2 | 1/2004 |
| WO | 2004032870 A2 | 4/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008131276 A1 | 10/2008 |
| WO | 2008150899 A1 | 12/2008 |
| WO | 2009140128 A2 | 11/2009 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010075376 A2 | 7/2010 |
| WO | 2010077680 A2 | 7/2010 |
| WO | 2010104488 A1 | 9/2010 |
| WO | 2010125799 A1 | 11/2010 |
| WO | 2011006074 A1 | 1/2011 |
| WO | 2011032291 A1 | 3/2011 |
| WO | 2011146336 A1 | 11/2011 |
| WO | 2012158413 A2 | 11/2012 |
| WO | 2013063214 A1 | 5/2013 |
| WO | 2013096226 A1 | 6/2013 |
| WO | 2013176970 A1 | 11/2013 |
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078378 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |

OTHER PUBLICATIONS

Wadhwa, S., et al., Journal of Biosciences, 2003, 28(2), 181-188.
Wang, T., et al., Expert Opinion in Therapeutic Patents (2009) 19(3):305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.
Kane, J.L., et al., (203) Bioorg. Med. Chem. Lett., 13, 4463-4466.
Patent Cooperation Treaty, International Searching Authority, Search Report and Written Opinion for PCT/US2013/069732, Dec. 20, 2013, 13 Pages.
Adriaenssens, E., et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7592.
Bouhana, Karyn S., et al., "Comparison of Analgesic Effects of an Allosteric Inhibitor of TrkA to that of an ATP site inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L. J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti- and 3,4-syn-substituted aminopyrrolidines via lithium amide conjugate addition, Org. Biomol. Chem., 2007, 5, 1961-1969.
Delafoy, L. et al. (2003) Pain 105, 489-497.
Demelo-Jorge, M. et al., Cell Host & Microbe (2007) 1(4), 251-261.
Dimola, F. F, et. al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et al., Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.
Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.
Kaymakcioglu, B.K., et al., European Journal of Pharmaceutical Sciences (2005) 26(1), 97-103.
Lamb, K. et al. (2003) Neurogastroenterol. Motil. 15, 355-361.
Li, L. et al. (2003) Mol. Cell. Neurosci. 23, 232-250.
Li, Y.-G., et al., Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.

(56) References Cited

OTHER PUBLICATIONS

McCarthy, C. and Walker, E., Expert Opin. Ther. Patents (2014) 24(7):731-744.
McMahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.
Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A., et al., American Journal of Respiratory Cell and Molecular Biology, 2001, 25(4), pp. 439-446.
Ro, L. S. et al., Pain, Feb. 1999, 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.

N-(MONOCYCLIC ARYL),N'-PYRAZOLYL-UREA, THIOUREA, GUANIDINE AND CYANOGUANIDINE COMPOUNDS AS TRKA KINASE INHIBITORS

RELATED APPLICATIONS

This application is a 371 filing of PCT Application No. PCT/US2013/069732, filed Nov. 12, 2013, which claims priority to U.S. Provisional Application Ser. No. 61/725,928 filed Nov. 13, 2012, each of which is incorporated herein by reference in its entirety.

BACKGROUND OF THE INVENTION

The present invention relates to novel compounds, to pharmaceutical compositions comprising the compounds, to processes for making the compounds and to the use of the compounds in therapy. More particularly, it relates to monocyclic aryl and heteroaryl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) BJU International, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819).

The TrkA receptor is also thought to be critical to the disease process in the infection of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., Bone (2000) 26(6) 625-633). In addition, localization of NGF was observed in almost all bone-forming cells (K. Asaumi, et al.). Recently, it was demonstrated that a Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

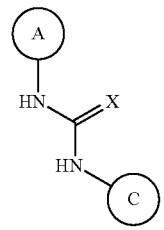

or stereoisomers, tautomers, or pharmaceutically acceptable salts, solvates or prodrugs thereof, wherein Ring A, Ring C and X are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, useful in the treatment of diseases, conditions and/or disorders modulated by TrkA.

A representative compound of the invention (See Table B below), was found to be highly selective for TrkA over a panel of about 230 other kinases at 10 µM concentration. In addition, compounds of the invention such as those shown in Table A below, were found to be at least 1000 fold more selective for TrkA versus p38α.

One embodiment provides a compound of Formula I:

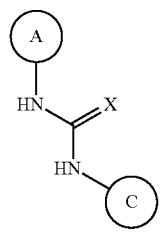

I-1 or stereoisomers, tautomers, or pharmaceutically acceptable salts, solvates or prodrugs thereof, wherein:

Ring A is formula A-1, A-2, A-3, A-4, A-5 or A-6

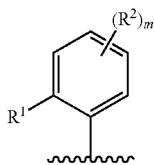

A-1

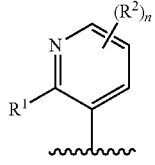

A-2

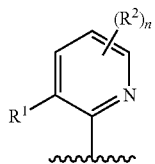

A-3

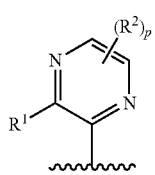

A-4

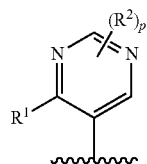

A-5

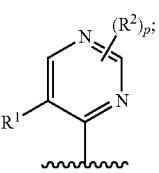

A-6 m is 0, 1, 2, 3 or 4;
n is 0, 1, 2 or 3;
p is 0, 1 or 2;
$R^1$ is formula $R^1$-1, $R^1$-2 or $R^1$-3

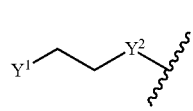

$R^1$-1

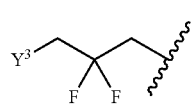

$R^1$-2

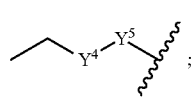

$R^1$-3

$Y^1$ is $CH_3CH_2$, $CF_3CH_2$—, $CH_3O$—, $F_3CO$—, $F_2CHO$—, $FCH_2O$—, CHS—, $F_3CS$—, $F_2CHS$—, or $FCH_2S$—;
$Y^2$ is O, S, NH, MeN— or $CH_2$;
$Y^3$ is $CH_3O$—, $CH_3S$—, MeNH— or $Me_2N$—;
$Y^4$ is $CH_2$ and $Y^5$ is S or O, or $Y^4$ is S or O and $Y^5$ is $CH_2$;
$R^2$ is halogen, (1-3C)alkyl (optionally substituted with 1-3 fluoros), (1-3C)alkoxy (optionally substituted with 1-3 fluoros), $CH_3OCH_2$— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros;
X is O, S, NH or N—CN;
Ring C is formula C-1 or C-2

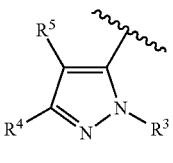

C-1

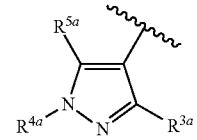

C-2

R³ is (1-6C)alkyl, hydroxy(1-6C)alkyl, Ar², hetCyc¹, (3-7C)cycloalkyl, or hetAr²;

Ar² is phenyl optionally substituted with one or more groups independently selected from halogen and (1-6C) alkyl;

hetCyc¹ is a 5-6-membered saturated or partially unsaturated heterocyclic ring having 1-2 ring heteroatoms independently selected from N and O;

hetAr² is a 5-6 membered heteroaryl ring having 1-3 ring heteroatoms independently selected from N, O and S and optionally substituted with one or more groups independently selected from (1-6C)alkyl and halogen;

R⁴ is H, OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, aminocarbonyl(1-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, hetCyc²C(═O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)aminocarboxy, hetCyc²C(═O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C) alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl) CH₂— (3-6C cycloalkyl)C(═O)—, (1-3C alkoxy)(1-6C) alkyl, (1-6C)alkoxy, (1-6C)alkylsulfonyl, NH₂, (1-6C alkyl) amino, di(1-3C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

hetAr⁵ is a group selected from the structures:

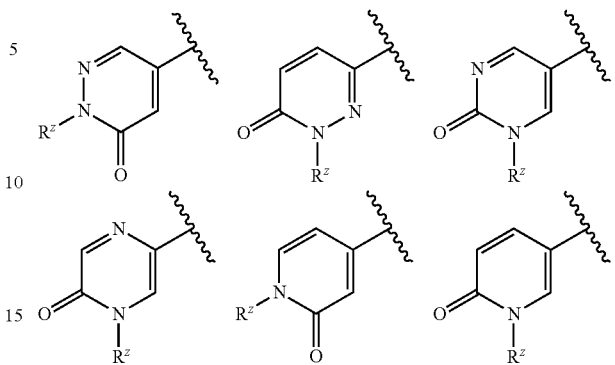

where R^z is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6C alkyl)OC(═O)—, aminocarbonyl, (1-6C)alkylthio, hydroxy(1-6C)alkyl, (1-6C alkyl)SO₂—, HOC(═O)— and (1-3C alkoxy)(1-3C alkyl) OC(═O)—;

R⁵ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (═O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6C)acyl, (1-6C)alkyl and oxo, and said sulfur ring atom is optionally oxidized to S(═O) or SO₂;

R^{3a} is hydrogen, halogen, (1-6C)alkyl, trifluoro(1-6C) alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R^{4a} is hydrogen, (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(═O)—, aminocarbonyl, (1-6C)alkylthio, hydroxy(1-6C)alkyl, (1-6C alkyl) SO₂—, HOC(═O)— and (1-3C alkoxy)(1-3C alkyl)OC (═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-

6C)alkyl, (3-6C)cycloalkyl, (3-6C cycloalkyl)CH$_2$— (3-6C cycloalkyl)C(=O)—, (1-3C alkoxy)(1-6C)alkyl, (1-6C) alkoxy, (1-6C)alkylsulfonyl, NH$_2$, (1-6C alkyl)amino, di(1-6C alkyl)amino and (1-3C trifluoroalkoxy)(1-3C)trifluoroalkyl; and R$^{5a}$ is hydrogen, halogen, (1-6C)alkyl, trifluoro(1-6C) alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In one embodiment, Formula I includes compounds of Formula I-1:

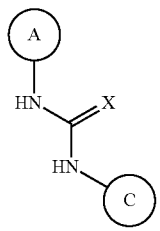

I-1 or stereoisomers, tautomers, or pharmaceutically acceptable salts, solvates or prodrugs thereof, wherein:

Ring A is formula A-1, A-2, A-3, A-4, A-5 or A-6

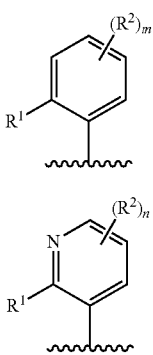

A-1

A-2

A-3

A-4

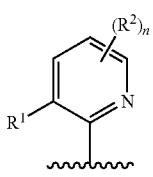

A-5

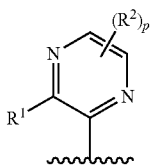

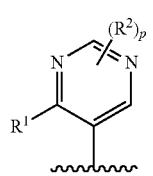

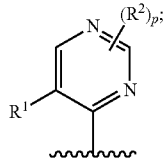

A-6 m is 0, 1, 2, 3 or 4;
n is 0, 1, 2 or 3;
p is 0, 1 or 2;
R$^1$ is formula R$^1$-1, R$^1$-2 or R$^1$-3

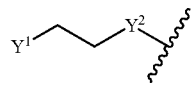

R$^1$-1

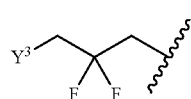

R$^1$-2

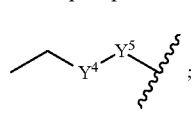

R$^1$-3

Y$^1$ is CH$_3$CH$_2$, CF$_3$CH$_2$—, CH$_3$O—, F$_3$CO—, F$_2$CHO—, FCH$_2$O—, CH$_3$S—, F$_3$CS—, F$_2$CHS—, or FCH$_2$S—;
Y$^2$ is O, S, NH, MeN— or CH$_2$;
Y$^3$ is CH$_3$O—, CH$_3$S—, MeNH— or Me$_2$N—;
Y$^4$ is CH$_2$ and Y$^5$ is S or O, or Y$^4$ is S or O and Y$^5$ is CH$_2$;
R$^2$ is halogen, (1-3C)alkyl (optionally substituted with 1-3 fluoros), (1-3C)alkoxy (optionally substituted with 1-3 fluoros), CH$_3$OCH$_2$— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros;
X is O, S, NH or N—CN;
Ring C is formula C-1 or C-2

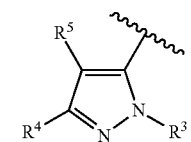

C-1

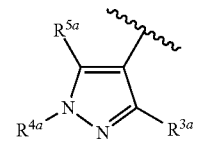

C-2

R$^3$ is (1-6C)alkyl, hydroxy(1-6C)alkyl, Ar$^2$, hetCyc$^1$, (3-7C)cycloalkyl, or hetAr$^2$;
Ar$^2$ is phenyl optionally substituted with one or more groups independently selected from halogen and (1-6C) alkyl;
hetCyc$^1$ is a 5-6-membered saturated or partially unsaturated heterocyclic ring having 1-2 ring heteroatoms independently selected from N and O;

hetAr² is a 5-6 membered heteroaryl ring having 1-3 ring heteroatoms independently selected from N, O and S and optionally substituted with one or more groups independently selected from (1-6C)alkyl and halogen;

R⁴ is H, OH, (1-6C)alkyl, monofluoro(1-6C)alkyl, difluoro(1-6C)alkyl, trifluoro(1-6C)alkyl, tetrafluoro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, aminocarbonyl(1-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C)alkoxy, di(1-3C alkyl)aminocarboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Arᵃ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

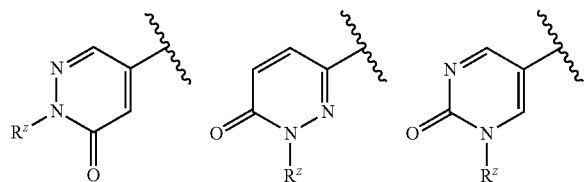

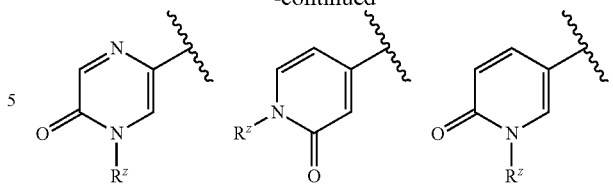

where Rᶻ is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6C alkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R³ᵃ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R⁴ᵃ is (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and R⁵ᵃ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

In embodiment, Formula I includes compounds of Formula I-2

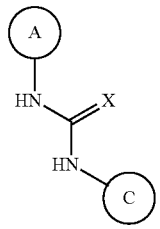

I-2 or stereoisomers, tautomers, or pharmaceutically acceptable salts, solvates or prodrugs thereof, wherein:

Ring A is formula A-1, A-2, A-3, A-4, A-5 or A-6

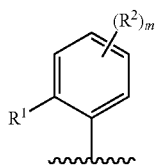

A-1

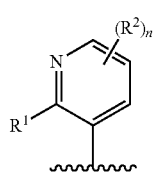

A-2

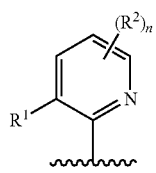

A-3

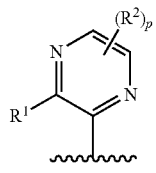

A-4

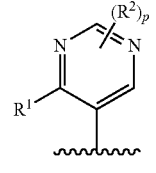

A-5

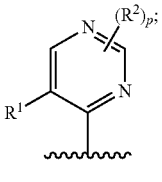

A-6 m is 0, 1, 2, 3 or 4;
n is 0, 1, 2 or 3;
p is 0, 1 or 2;
$R^1$ is formula $R^1$-1, $R^1$-2 or $R^1$-3

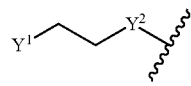

$R^1$-1

$R^1$-2

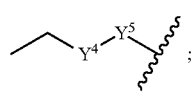

$R^1$-3

$Y^1$ is $CH_3CH_2$, $CF_3CH_2$—, $CH_3O$—, $F_3CO$—, $F_2CHO$—, $FCH_2O$—, $CH_3S$—, $F_3CS$—, $F_2CHS$—, or $FCH_2S$—;

$Y^2$ is O, S, NH, MeN— or $CH_2$;

$Y^3$ is $CH_3O$—, $CH_3S$—, MeNH— or $Me_2N$—;

$Y^4$ is $CH_2$ and $Y^5$ is S or O, or $Y^4$ is S or O and $Y^5$ is $CH_2$;

$R^2$ is halogen, (1-3C)alkyl (optionally substituted with 1-3 fluoros), (1-3C)alkoxy (optionally substituted with 1-3 fluoros), $CH_3OCH_2$— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros;

X is O, S, NH or N—CN;

Ring C is formula C-1 or C-2

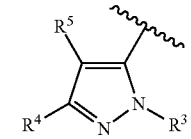

C-1

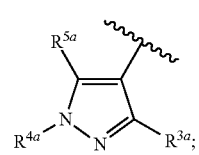

C-2

$R^3$ is (1-6C)alkyl, hydroxy(1-6C)alkyl, $Ar^2$, $hetCyc^1$, (3-7C)cycloalkyl, or $hetAr^2$;

$Ar^2$ is phenyl optionally substituted with one or more groups independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more groups independently selected from (1-6C)alkyl and halogen;

$R^4$ is H, OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr³(1-6C)alkyl, Ar³(1-6C)alkyl, (1-6C)alkoxy, monofluoro(1-6C)alkoxy, difluoro(1-6C) alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, aminocarbonyl(1-6C)alkoxy, hydroxyl-carbonyl(1-6C)alkoxy, hetCyc²(1-6C)alkoxy, hetAr³(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr⁴, hetAr⁴—O—, Ar⁴, hetCyc²(O)CH₂—, (1-4C alkoxycarbonyl)(1-6C)alkoxy, hydroxycarbonyl(1-6C)alkoxy, hetCyc²C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)aminocarboxy, hetCyc²C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc³, halogen, CN, trifluoromethylsulfonyl, N-(1-3C alkyl)oxadiazolonyl, or hetAr⁵;

hetCyc² is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, (1-6C)acyl and halogen;

hetCyc³ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr³ is a 5-membered heteroaryl ring having 1-3 ring atoms independently selected from N, O and S and optionally substituted with (1-6C)alkyl;

Ar³ is phenyl optionally substituted with (1-4C)alkoxy;

hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

hetAr⁵ is a group selected from the structures:

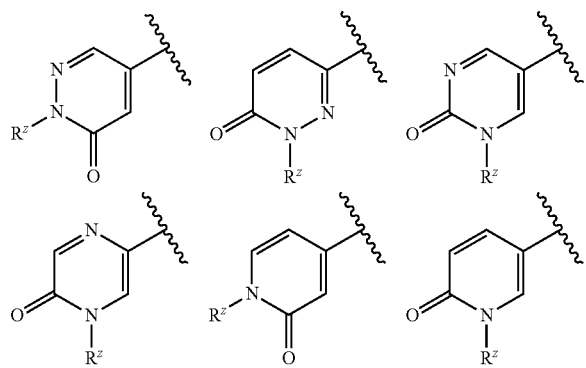

where R² is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros;

Ar⁴ is phenyl optionally substituted with one or more groups independently selected from (1-6C)alkyl, halogen, CN, CF₃, CF₃O—, (1-6C)alkoxy, (1-6C alkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—;

R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or R⁴ and R⁵ together with the atoms to which they are attached form a 5-6 membered saturated, partially unsaturated or unsaturated carbocyclic ring optionally substituted with one or more substituents independently selected from (1-6C)alkyl, or R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂;

R³ᵃ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

R⁴ᵃ is (1-6C)alkyl, trifluoro(1-6C)alkyl, phenyl [optionally substituted with one or more groups independently selected from (1-6C)alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino and (1-3C trifluoroalkoxy)(1-3C)trifluoroalkyl; and R⁵ᵃ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C) alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", "(1-3C)alkoxy", "(1-6C)alkoxy" and "(2-6C)alkoxy" refer to an —OR radical where R is (1-4C) alkyl, (1-3C)alkyl, (1-6C)alkyl, or (2-6C)alkyl, respectively, as defined above. Examples include methoxy, ethoxy, and the like.

"(1-6C)acyl" means a RC(=O)— radical where R is a linear saturated monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C) alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"(1-3C Alkoxy)(1-6C)alkoxy" means a (1-6C)alkoxy group as defined herein, wherein one of the carbon atoms is substituted with a (1-3C)alkoxy group as defined herein. Examples include methoxymethoxy, methoxyethoxy, and the like.

"(1-3C Alkoxy)aminocarbonyl" means a (1-3C alkyl)-O—NH—C(=O)— group.

"(1-6C)Alkoxycarbonyl" and "(1-4C)alkoxycarbonyl" mean a (1-6C)—O—C(=O)— and (1-4C)—O—(=O)— group, respectively.

"(1-4C Alkoxycarbonyl)(1-6C alkoxy)" means a (1-6C) alkoxy group as defined herein wherein one of the carbon atoms is substituted with one (1-4C alkoxy)carbonyl group, i.e., an alkyl-O—C(=O)— group.

"(1-3C Alkoxy)hydroxycarbonylalkyl" means a hydroxycarbonylalkyl group as defined herein wherein one of the carbon atoms is substituted with one (1-3C alkoxy) group.

"Amino" means a —NRR' group where R and R' are independently selected from hydrogen or (1-3C)alkyl as defined herein. Examples include H$_2$N—, CH$_3$NH—, (CH$_3$)$_2$N, and the like. "Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Amino(2-6C)alkoxy" means a (2-6C)alkoxy group as defined herein, wherein one of the carbon atoms is substituted with one —NRR' group where R and R' are independently selected from hydrogen or (1-3C)alkyl as defined herein.

"Aminocarbonyl" means a RR'NCO— radical where R and R' are independently hydrogen or (1-6C)alkyl as defined herein. Examples include H$_2$NCO—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Aminocarbonyl(1-6C)alkoxy" means a (1-6C)alkoxy as defined herein, wherein one of the carbon atoms is substituted with one aminocarbonyl group as defined herein.

"(1-3C)Alkylamido(1-6C)alkoxy" means a (1-6C)alkoxy as defined herein, wherein one of the carbon atoms is substituted with one alkylamido group, i.e., substituted with a (1-3C)C(=O)NH— group.

"(1-4C alkyl)carboxy" means a R'—C(=O)O— group where R' is (1-4C)alkyl.

"(1-3C)Alkylsulfonamido" means a (1-3C) alkylSO$_2$NH— radical where (1-3C)alkyl is as defined herein "(1-3C Alkylsulfonamido)(1-6C)alkyl" means a linear saturated hydrocarbon radical of one to six carbon atoms or a branched saturated monovalent hydrocarbon radical of three to six carbons substituted with one (1-3C)alkylsulfonamido group as defined herein.

"(1-3C)Alkylsulfonamido(1-6C)alkoxy" means a (1-6C) alkoxy group as defined herein wherein one of the carbon atoms is substituted with one (1-3C)alkylsulfonamido group as defined herein.

"(1-3C)Alkylsulfonyl" means a —SO$_2$R radical where R is (1-3C)alkyl as defined above, e.g., methylsulfonyl, and the like.

"(1-3C Alkylsulfonyl)(1-6C)alkoxy" means a (1-6C) alkoxy group as defined herein, wherein one of the carbon atoms is substituted with a (1-3C)alkylsulfonyl group.

"Hydroxycarbonyl" means HOC(=O)—.

"(1-4C alkyl)carboxy(1-6C)alkyl" means a (1-6C)alkyl group as defined herein wherein one of the carbon atoms is substituted with a (1-4C alkyl)carboxy group as defined herein.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Dihydroxy(2-6C)alkoxy" means a (2-6C)alkoxy group as defined herein, wherein two of the carbon atoms are substituted with a hydroxy group.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring system having one or more ring heteroatoms as recited for the specific heteroaryl group, wherein the heteroaryl is optionally substituted with substituents as defined for that particular heteroaryl group.

"hetCyc²C(=O)(1-6C)alkoxy" means a (1-6C)alkoxy as defined herein, wherein one of the carbon atoms is substituted with a hetCyc²C(=O) group, wherein hetCyc² is as defined herein.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined herein, wherein one of the carbon atoms is substituted with a hydroxy group.

"Hydroxy(1-3C alkoxy)(1-6C)alkoxy" means a (1-3C alkoxy)(1-6C)alkoxy as defined herein, wherein one of the carbon atoms is substituted with a hydroxy group.

"Hydroxydifluoro(1-6C)alkyl" means a difluoro(1-6C)alkyl group as defined herein, wherein one of the carbon atoms is substituted with a hydroxy group.

"Hydroxytrifluoro(1-6C)alkoxy" means a trifluoro(1-6C)alkoxy group as defined herein, wherein one of the carbon atoms is substituted with a hydroxy group.

"Hydroxycarbonylalkyl" means a linear saturated hydrocarbon radical of one to six carbon atoms or a branched saturated monovalent hydrocarbon radical of three to six carbons substituted with one —COOH group. Examples include 2-hydroxycarbonylethyl, 1-, 2-, or 3-hydroxycarbonylpropyl, and the like.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"Trifluoro(1-3C alkyl)amido" means a (1-3C alkyl)C(=O)NH— group wherein one of the carbons is substituted with three fluoros.

"Trifluoro(1-6C)alkoxy" means a (1-6C)alkoxy group as defined herein, wherein one of the carbon atoms is substituted with three fluoros.

"Sulfamido(1-6C)alkyl" means a linear saturated hydrocarbon radical of one to six carbon atoms or a branched saturated monovalent hydrocarbon radical of three to six carbons substituted with one sulfamido ($H_2NSO_2NH$—) group.

It should be noted that compounds of the invention may contain groups that may exist in tautomeric forms, such as heteroatom substituted heteroaryl or heterocyclic groups and the like, which are illustrated in the following general and specific examples:

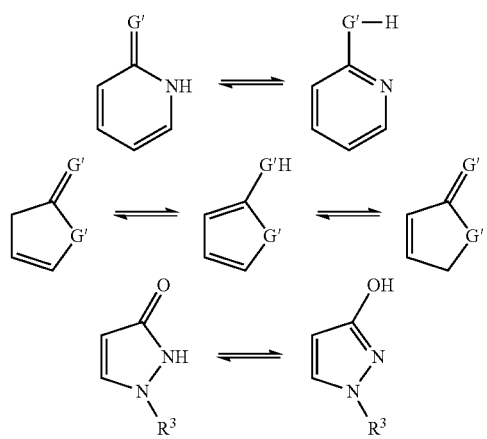

where G'=O, S, or NR, and though one form is named, described, displayed and/or claimed herein, all the tautomeric forms are intended to be inherently included in such name, description, display and/or claim.

In one embodiment of Formula I, X is O.
In one embodiment, X is S.
In one embodiment, X is NH.
In one embodiment, X is N—CN.
In one embodiment of Formula I, $R^1$ is formula $R^1$-1:

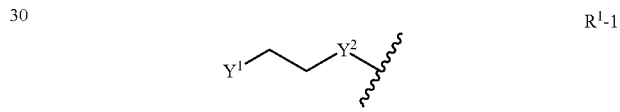

where $Y^1$ is $CH_3CH_2$—, $CF_3CH_2$—, $CH_3O$—, $F_3CO$—, $F_2CHO$—, $FCH_2O$—, $CH_3S$—, $F_3CS$—, $F_2CHS$—, or $FCH_2S$—, and $Y^2$ is O, S, NH, MeN— or $CH_2$. In one embodiment, formula $R^1$-1 includes the structures:

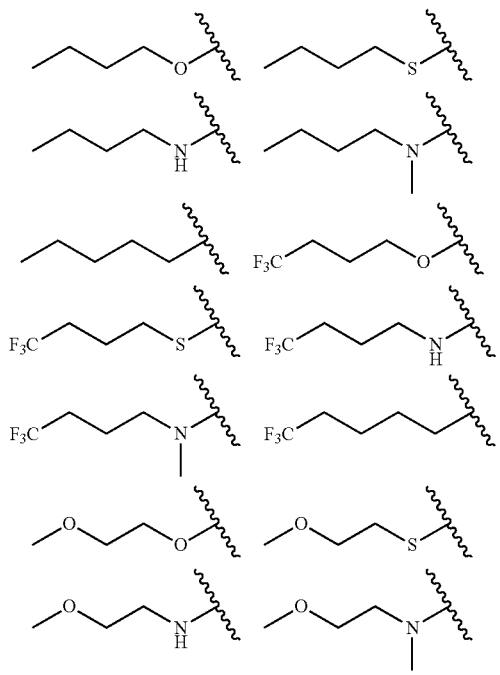

-continued

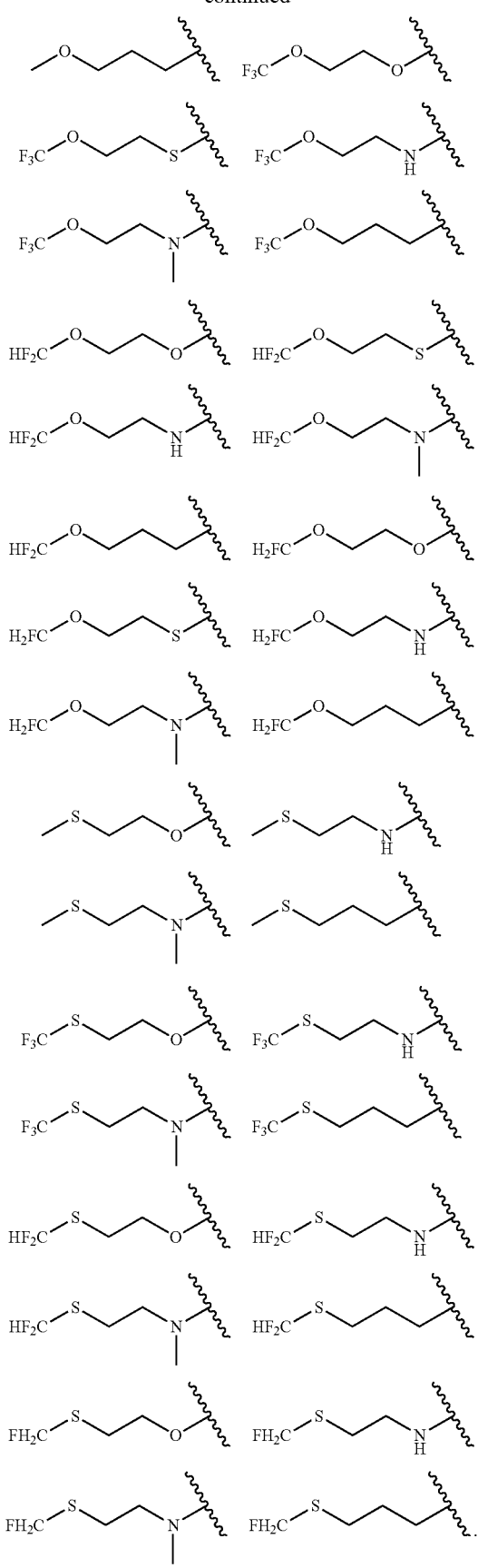

In one embodiment, R¹-1 is selected from the structures:

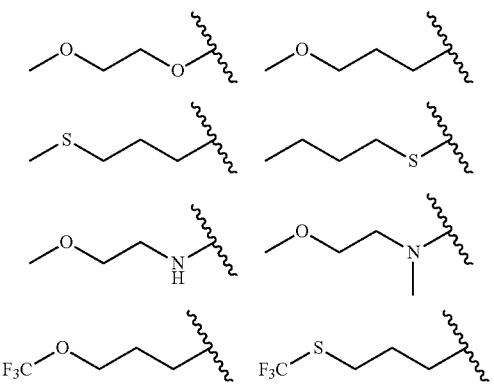

In one embodiment, R¹-1 is selected from the structures:

In one embodiment of Formula I, R¹ is formula R¹-2

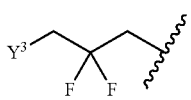

R¹-2 where $Y^3$ is $CH_3O-$, $CH_3S-$, MeNH— or $Me_2N-$. In one embodiment, formula R¹-2 includes the structures:

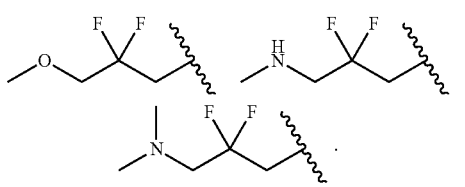

In one embodiment of Formula I, R¹ is formula R¹-3

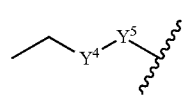

R¹-3 where $Y^4$ is $CH_2$ and $Y^5$ is S or O, or $Y^4$ is S or O and $Y^5$ is $CH_2$. In one embodiment, formula R¹-3 includes the structures:

In one embodiment, R² is halogen. In one embodiment, R² is F or Cl.

In one embodiment, R² is (1-3C)alkyl optionally substituted with 1-3 fluoros. In one embodiment, R² is CH₃, CF₃, F₂CH, FCH₂ or CF₃CH₂. In one embodiment, R² is CH₃ or CF₃.

In one embodiment, R² is (1-3C)alkoxy optionally substituted with 1-3 fluoros. In one embodiment, R² is CF₃O—.

In one embodiment, R² is CH₃OCH₂— optionally substituted with 1-3 fluoros. In one embodiment, R² is CH₃OCH₂— or CF₃OCH₂—.

In one embodiment, R² is (1-3C alkyl)sulfanyl. In one embodiment, R² is CH₃S—.

In one embodiment, R² is di(1-3C)alkylamino. In one embodiment, R² is Me₂N—.

In one embodiment, R² is cyclopropyl or cyclobutyl optionally substituted with 1-2 fluoros.

In one embodiment, R² is azetidinyl optionally substituted with 1-2 fluoros.

In one embodiment, R² is F, Cl, CH₃ or CF₃.

In one embodiment of Formula I, Ring A is Formula A-1:

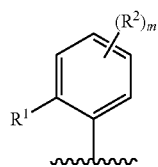

A-1 where R¹ is as defined for Formula I; m is 0, 1, 2, 3 or 4; and R² halogen, (1-3C)alkyl (optionally substituted with 1-3 fluoros), (1-3C)alkoxy (optionally substituted with 1-3 fluoros), CH₃OCH₂— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros.

In one embodiment Ring A is A-1, R¹ is as defined for Formula I; m is 0, 1, 2, 3 or 4; and R² is selected from F, Cl, CF₃, CH₃, CH₂S—, cyclopropyl, cyclobutyl, azetidinyl, Me₂N—, F₂CH—, FCH₂—CF₃CH₂—, CF₃O—, CH₃OCH₂, and CF₃OCH₂, wherein each of said cyclopropyl, cyclobutyl and azetidinyl is optionally substituted with 1 to 2 fluoros.

In one embodiment when Ring A is A-1, R¹ is as defined for Formula I; m is 0, 1, 2, 3 or 4; and R² is selected from F, Cl, CF₃ and CH₃.

In one embodiment Ring A is A-1, R¹ is as defined for Formula I; m is 0, 1 or 2, and R² is selected from F, Cl, CF₃ and CH₃.

In one embodiment Ring A is A-1, m is 0, 1, 2, 3 or 4; and R² is selected from F, Cl, CF₃, CH₃, CH₂S—, cyclopropyl, cyclobutyl, azetidinyl, FCH₂—CF₃CH₂—, CF₃O—, CH₃OCH₂, and CF₃OCH₂ (wherein each of said cyclopropyl, cyclobutyl and azetidinyl is optionally substituted with 1-2 fluoros); and R¹ is selected from the structures:

In one embodiment Ring A is A-1, m is 0, 1, or 2; and R² is selected from F, Cl, CF₃ and CH₃; and R¹ is selected from the structures:

In one embodiment of Formula I, Ring A is formula A-2 or A-3

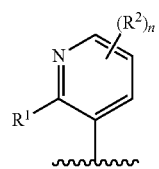

A-2

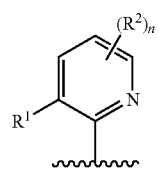

A-3 where R¹ is as defined for Formula I; n is 0, 1, 2, or 3; and R² halogen, (1-3C)alkyl (optionally substituted with 1-3 fluoros), (1-3C)alkoxy (optionally substituted with 1-3 fluoros), CH₃OCH₂— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros.

In one embodiment Ring A is A-2 or A-3, R¹ is as defined for Formula I; n is 0, 1, 2, or 3; and R² is selected from F, Cl, CF₃, CH₃, CH₂S—, cyclopropyl, cyclobutyl, azetidinyl, Me₂N—, F₂CH—, FCH₂—CF₃CH₂—, CF₃O—, CH₃OCH₂, and CF₃OCH₂, wherein each of said cyclopropyl, cyclobutyl and azetidinyl is optionally substituted with 1 to 2 fluoros.

In one embodiment when Ring A is A-2 or A-3, R¹ is as defined for Formula I; n is 0, 1, 2 or 3; and R² is selected from F, Cl, CF₃ and CH₃.

In one embodiment Ring A is A-2, le is as defined for Formula I; n is 0, 1, 2 or 3; and R² is selected from F, Cl, CF₃ and CH₃.

In one embodiment Ring A is A-3, R¹ is as defined for Formula I; n is 0, 1, 2 or 3; and R² is selected from F, Cl, CF₃ and CH₃.

In one embodiment Ring A is A-2 or A-3, n is 0, 1, 2 or 3; and R² is selected from F, Cl, CF₃, CH₃, CH₂S—, cyclopropyl, cyclobutyl, azetidinyl, Me₂N—, F₂CH—, FCH₂—CF₃CH₂—, CF₃O—, CH₃OCH₂, and CF₃OCH₂, (wherein each of said cyclopropyl, cyclobutyl and azetidinyl is optionally substituted with 1 to 2 fluoros); and R¹ is selected from the structures:

In one embodiment Ring A is A-2, 1e is as defined for Formula I; n is 0, 1, 2 or 3; $R^2$ is selected from F, Cl, $CF_3$ and $CH_3$; and $R^1$ is selected from the structures:

In one embodiment Ring A is A-3, $R^1$ is as defined for Formula I; n is 0, 1, 2 or 3; $R^2$ is selected from F, Cl, $CF_3$ and $CH_3$; and $R^1$ is selected from the structures:

In one embodiment of Formula I, Ring A is A-4, A-5 or A-6:

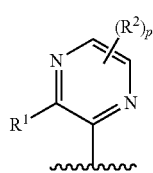
A-4

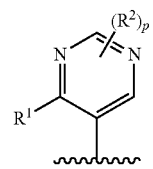
A-5

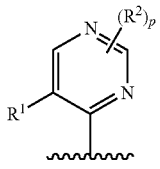
A-6 where $R^1$ is as defined for Formula I; p is 0, 1, or 2; and $R^2$ halogen, (1-3C)alkyl (optionally substituted with 1-3 fluoros), (1-3C)alkoxy (optionally substituted with 1-3 fluoros), $CH_3OCH_2$— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros.

In one embodiment Ring A is A-4, A-5 or A-6, $R^1$ is as defined for Formula I; p is 0, 1, or 2; and $R^2$ is selected from F, Cl, $CF_3$, $CH_3$, $CH_2S$—, cyclopropyl, cyclobutyl, azetidinyl, $Me_2N$—, $F_2CH$—, $FCH_2$—$CF_3CH_2$—, $CF_3O$—, $CH_3OCH_2$, and $CF_3OCH_2$, wherein each of said cyclopropyl, cyclobutyl and azetidinyl is optionally substituted with 1 to 2 fluoros.

In one embodiment Ring A is A-4, A-5 or A-6, $R^1$ is as defined for Formula I; p is 0, 1, or 2; and $R^2$ is selected from F, Cl, $CF_3$ and $CH_3$.

In one embodiment Ring A is A-4, A-5 or A-6, p is 0, 1, or 2; and $R^2$ is selected from F, Cl, $CF_3$, $CH_3$, $CH_2S$—, cyclopropyl, cyclobutyl, azetidinyl, $Me_2N$—, $F_2CH$—, $FCH_2$—$CF_3CH_2$—, $CF_3O$—, $CH_3OCH_2$, and $CF_3OCH_2$ (wherein each of said cyclopropyl, cyclobutyl and azetidinyl is optionally substituted with 1 to 2 fluoros); and $R^1$ is selected from the structures:

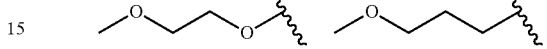

In one embodiment Ring A is A-4, A-5 or A-6, p is 0, 1, or 2; and $R^2$ is selected from F, Cl, $CF_3$, and $CH_3$; and $R^1$ is selected from the structures:

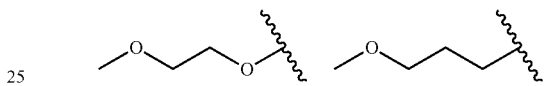

Reference will now be made to Ring C.
In one embodiment, Ring C is formula C-1:

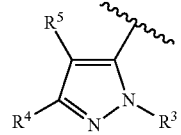
C-1 where $R^3$, $R^4$ and $R^5$ are as defined for Formula I.

In one embodiment, $R^3$ is (1-6C)alkyl. In one embodiment, $R^3$ is methyl or ethyl.

In one embodiment, $R^3$ is hydroxy(1-6C)alkyl. An example of $R^3$ is 2-hydroxyethyl.

In one embodiment, $R^3$ is $Ar^2$, where $Ar^2$ is phenyl optionally substituted with one or more groups independently selected from halogen and (1-6C)alkyl.

In one embodiment, $R^3$ when represented by $Ar^2$ is phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, $R^3$ when represented by $Ar^2$ is phenyl, 2-fluorophenyl, 3-fluorophenyl, 4-fluorophenyl, 2-methylphenyl, 3-methylphenyl or 4-methylphenyl. In one embodiment, $R^3$ is phenyl.

In one embodiment, $R^3$ is $hetCyc^1$, where $hetCyc^1$ is a 5-6-membered saturated or partially unsaturated heterocyclic ring having 1-2 ring heteroatoms independently selected from N and O. In one embodiment, $R^3$ is a pyrrolidinyl, tetrahydrofuranyl, imidazolidinyl, piperidinyl, piperazinyl, tetrahydropyranyl, or morpholinyl ring. In one embodiment, $R^3$ is tetrahydro-2H-pyran-4-yl.

In one embodiment, $R^3$ is (3-7C)cycloalkyl. In one embodiment $R^3$ is cyclohexyl.

In one embodiment, $R^3$ is $hetAr^2$, where $hetAr^2$ is 5-6 membered heteroaryl ring having 1-3 ring heteroatoms independently selected from N, O and S and optionally substituted with one or more substituents independently selected from (1-6C)alkyl and halogen. In one embodiment, $R^3$ is thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, $R^3$ is pyrazolyl, pyridyl or pyridazinyl optionally substituted with one or more groups independently selected from (1-6C) alkyl and halogen. In one embodiment, $R^3$ is pyrazolyl, pyridyl or pyridazinyl optionally substituted with (1-6C) alkyl or halogen. In one embodiment, $R^3$ when represented by $hetAr^2$ is 1-methyl-1H-pyrazol-4-yl, pyrid-2-yl, pyrid-3-yl, pyrid-4-yl, pyridazinyl or 3-chloropyrid-5-yl.

In one embodiment, $R^3$ is selected from $Ar^2$ and $hetAr^2$.

In one embodiment, $R^3$ is $Ar^2$. In one embodiment, $R^3$ is phenyl.

In one embodiment, $R^4$ is OH.

In one embodiment, $R^4$ is (1-6C)alkyl. In one embodiment, $R^4$ is methyl, ethyl, isopropyl or tert-butyl.

In one embodiment, $R^4$ is monofluoro(1-6C)alkyl, difluoro(1-6C)alkyl, trifluoro(1-6C)alkyl, tetrafluoro(2-6C)alkyl or pentafluoro(2-6C)alkyl. In one embodiment, $R^4$ is fluoromethyl, 2-fluoroethyl, difluoromethyl and 2,2-difluoroethyl, trifluoromethyl, 2,2,2-trifluoroethyl, 3,3,3-trifluoropropyl, 2,2,3,3-tetrafluoropropyl or 2,2,3,3,3-pentafluoropropyl In one embodiment, $R^4$ is trifluoro(1-6C)alkyl. In one embodiment, $R^4$ is $CF_3$.

In one embodiment, $R^4$ is cyano(1-6C)alkyl. In one embodiment, $R^4$ is cyanomethyl or 2-cyanopropan-2-yl.

In one embodiment, $R^4$ is hydroxy(1-6C)alkyl. In one embodiment, $R^4$ is hydroxymethyl, 2-hydroxyethyl, 2-hydroxypropyl, 2-hydroxy-2-methylpropyl or 1-hydroxy-2-methylpropan-2-yl.

In one embodiment, $R^4$ is dihydroxy(2-6C)alkyl. In one embodiment, $R^4$ is 2,3-dihydroxypropyl.

In one embodiment, $R^4$ is (1-3C alkoxy)(1-6C)alkyl. In one embodiment, $R^4$ is methoxymethyl, 2-methoxyethyl or 3-methoxypropyl.

In one embodiment, $R^4$ is amino(1-6C)alkyl. In one embodiment, $R^4$ is aminomethyl, 2-aminoethyl or 3-aminopropyl.

In one embodiment, $R^4$ is aminocarbonyl(1-6C)alkyl. In one embodiment, $R^4$ is aminocarbonylmethyl and 2-(aminocarbonyl)ethyl.

In one embodiment, $R^4$ is (1-3C)alkylsulfonamido(1-6C) alkyl. In one embodiment, $R^4$ is $CH_3SO_2NHCH_2$— or $CH_3SO_2NHCH_2CH_2$—.

In one embodiment, $R^4$ is hydroxycarbonyl(1-6C)alkyl. In one embodiment, $R^4$ is HOC(=O)$CH_2$— and HOC(=O) $CH_2CH_2$—.

In one embodiment, $R^4$ is $hetAr^3$(1-6C)alkyl, where $hetAr^3$ is a 5-membered heteroaryl ring having 1-3 ring atoms independently selected from N, S and O and optionally substituted with (1-6C)alkyl. In one embodiment, $hetAr^3$ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, $R^4$ when represented by $hetAr^3$ (1-6C) alkyl is (1-methyl-1H-1,2,4-triazol-3-yl)methyl or (5-methyl-1,3,4-oxadiazol-2-yl)methyl.

In one embodiment, $R^4$ is $Ar^3$(1-6C)alkyl, where phenyl optionally substituted with (1-4C)alkoxy or hydroxy(1-4C) alkyl. In one embodiment, $Ar^3$(1-6C)alkyl is benzyl.

In one embodiment, $R^4$ is (1-6C)alkoxy. Examples include methoxy and ethoxy.

In one embodiment, $R^4$ is monofluoro(1-6C)alkoxy, difluoro(1-6C)alkoxy trifluoro(1-6C)alkoxy, tetrafluoro(2-6C) alkoxy or pentafluoro(2-6C)alkoxy. In one embodiment, $R^4$ is fluoromethoxy, 2-fluoroethoxy, 2,2-difluoromethoxy, trifluoromethoxy, 2,2,2-trifluoroethoxy or 2,2-difluoroethoxy. In one embodiment, $R^4$ is 2-fluoroethoxy.

In one embodiment, $R^4$ is cyano(1-6C)alkoxy. In one embodiment, $R^4$ is cyanomethoxy or 2-cyanoethoxy.

In one embodiment, $R^4$ is hydroxy(1-6C)alkoxy. In one embodiment, $R^4$ is 2-hydroxy-2-methylpropoxy, 2-hydroxyethoxy, 2-hydroxypropoxy, 2-hydroxy-2-methylpropoxy or 2-hydroxybutoxy.

In one embodiment, $R^4$ is dihydroxy(2-6C)alkoxy. In one embodiment, $R^4$ is 2,3-dihydroxypropoxy or 3-hydroxy-2-(hydroxymethyl)propoxy.

In one embodiment, $R^4$ is amino(2-6C)alkoxy. In one embodiment, $R^4$ is $H_2NCH_2CH_2O$—.

In one embodiment, $R^4$ is $hetCyc^2$(1-6C)alkoxy, where $hetCyc^2$ is a 4-6 membered heterocyclic ring having 1-2 ring heteroatoms independently selected from N and O, wherein $hetCyc^2$ is optionally substituted with 1-2 groups independently selected from (1-6C)alkyl, (1-4C alkoxy)carbonyl, (1-6C)acyl and halogen. In one embodiment, $hetCyc^2$ is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, $R^4$ when represented by $hetCyc^2$(1-6C)alkoxy is oxetan-2-ylmethoxy, 2-(oxetan-2-yl)propoxy, 2-morpholinoethoxy, piperazinylethyoxy or piperidinylethoxy optionally substituted with 1-2 groups independently selected from (1-6C)alkyl, (1-4C alkoxy) carbonyl, (1-6C)acyl and halogen.

In one embodiment, $R^4$ is $hetCyc^2$(1-6C)alkoxy, where $hetCyc^2$ is a 4-6 membered heterocyclic ring having 1-2 ring heteroatoms independently selected from N and O, wherein $hetCyc^2$ is optionally substituted with 1-2 groups independently selected from (1-6C)alkyl, (1-4C alkoxy)carbonyl, and (1-6C)acyl. In one embodiment, $hetCyc^2$ is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, $R^4$ when represented by $hetCyc^2$(1-6C)alkoxy is oxetan-2-ylmethoxy, 2-(oxetan-2-yl)propoxy, 2-morpholinoethoxy, piperazinylethyoxy or piperidinylethoxy optionally substituted with 1-2 groups independently selected from (1-6C)alkyl, (1-4C alkoxy)carbonyl and (1-6C)acyl.

In one embodiment, $R^4$ is represented by the structures:

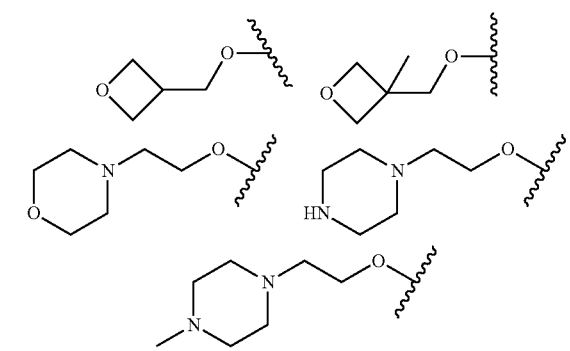

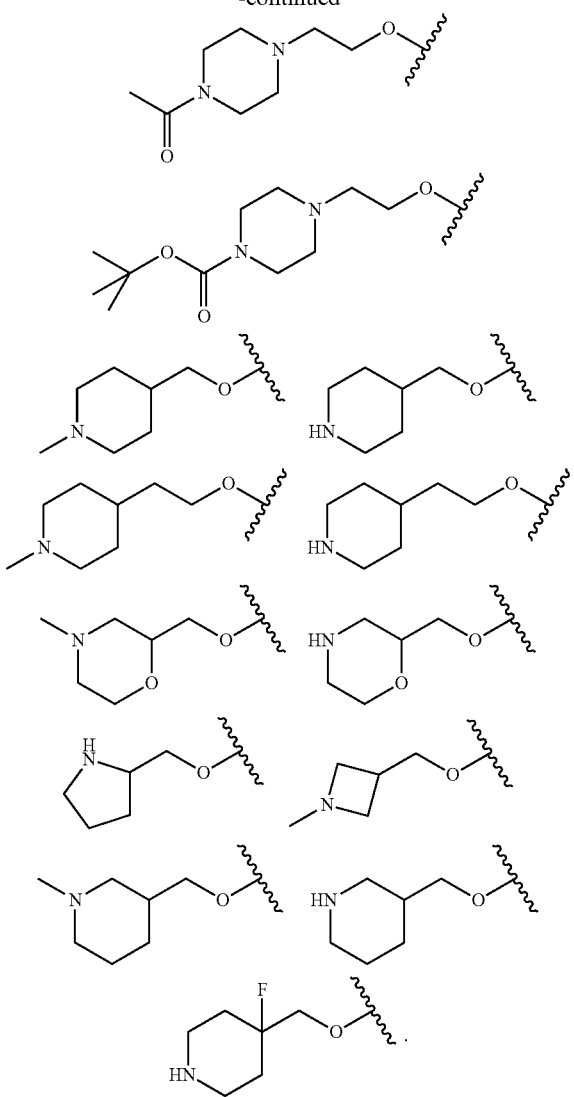

In one embodiment, R⁴ is represented by the structures:

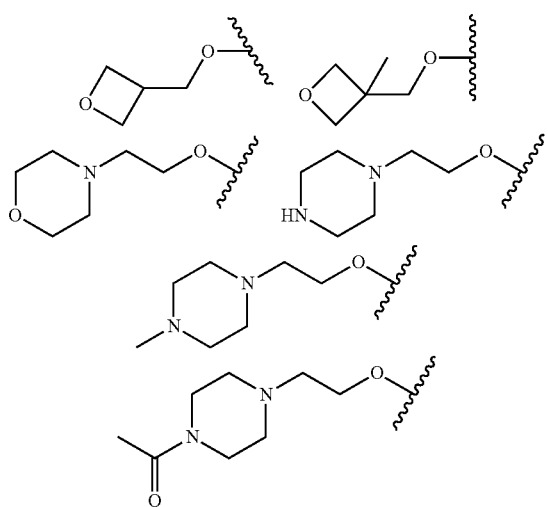

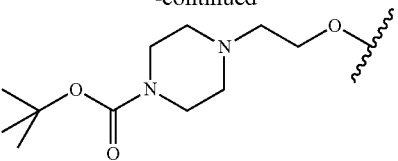

In one embodiment, $R^4$ is hetAr³(1-6C)alkoxy, where hetAr³ is a 5-membered heteroaryl ring having 1-3 ring atoms independently selected from N, S and O and optionally substituted with (1-6C)alkyl. In one embodiment, hetAr³ is a thienyl, furyl, imidazolyl, pyrazolyl, thiazolyl, isothiazolyl, oxazolyl, isoxazolyl, triazolyl, thiadiazolyl or oxadiazolyl ring optionally substituted with (1-6C)alkyl. In one embodiment, hetAr³ is triazolyl or oxadiazolyl ring optionally substituted with a (1-6C)alkyl group such as a methyl group. In one embodiment, $R^4$ when represented by hetAr³(1-6C)alkoxy is (1-methyl-1H-1,2,4-triazol-3-yl)methoxy or (5-methyl-1,3,4-oxadiazol-2-yl)methoxy, which can be represented by the structures:

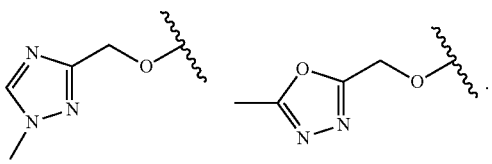

In one embodiment, $R^4$ is Ar³(1-6C)alkoxy, where Ar^a is phenyl optionally substituted with (1-4C)alkoxy. In one embodiment, $R^4$ is phenylmethoxy or (4-methoxyphenyl)methoxy having the structures:

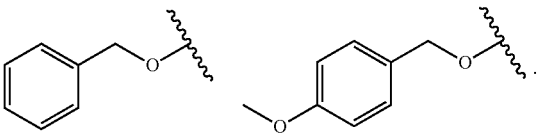 [SMILES: *OCc1ccccc1 ; *OCc1ccc(OC)cc1]

In one embodiment, $R^4$ is (1-4C alkoxy)(1-6C)alkoxy. In one embodiment, $R^4$ is (2-methoxy)ethoxy having the structure:

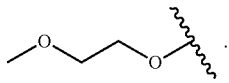 [SMILES: *OCCOC]

In one embodiment, $R^4$ is (1-3Calkylsulfonyl)(1-6C)alkoxy. In one embodiment, $R^4$ is (2-methylsulfonyl)ethoxy having the structure:

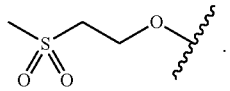 [SMILES: *OCCS(C)(=O)=O]

In one embodiment, $R^4$ is (3-6C)cycloalkyl optionally substituted with F, OH, (1-6C alkyl), (1-6C)alkoxy or (1-3C alkoxy)(1-6C)alkyl. Examples include cyclopropyl, cyclobutyl, cyclopentyl, cyclohexyl, 2-hydroxycyclobutyl.

In one embodiment, R⁴ is cyclopropyl or 2-hydroxycyclobutyl. In one embodiment, R⁴ is cyclopropyl.

In one embodiment, R⁴ is hetAr⁴, where hetAr⁴ is a 5-6 membered heteroaryl ring having 1-3 ring heteroatoms independently selected from N, S and O and optionally substituted with one or more substituents independently selected from (1-6C)alkyl, halogen, CN, hydroxy(1-6C) alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C) alkoxy, (1-6C)alkylsulfonyl, NH₂, (1-6C alkyl)amino, di(1-6C alkyl)amino, (1-3C trifluoroalkoxy), fluoro(1-6C alkyl) amino, difluoro(1-6C alkyl)amino, trifluoro(1-6C alkyl) amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C) alkyl, halogen, CN, hydroxy(1-6C)alkyl, trifluoro(1-6C) alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C) alkylsulfonyl, NH₂, (1-6C alkyl)amino, di(1-6C alkyl) amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl optionally substituted with one or more substituents independently selected from (1-6C) alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C) alkylsulfonyl, NH₂, (1-6C alkyl)amino, di(1-6C alkyl) amino, (1-3C trifluoroalkoxy)(1-3C)trifluoroalkyl and cyclopropylNH—.

In one embodiment, R⁴ is hetAr⁴, where hetAr⁴ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, or 1,2,4-oxadiazolyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment, R⁴ is hetAr⁴, where hetAr⁴ is pyridyl, pyrimidinyl or pyridazinyl optionally substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N—, and cyclopropylNH—.

In one embodiment, R⁴ when represented by hetAr⁴ is selected from the structures:

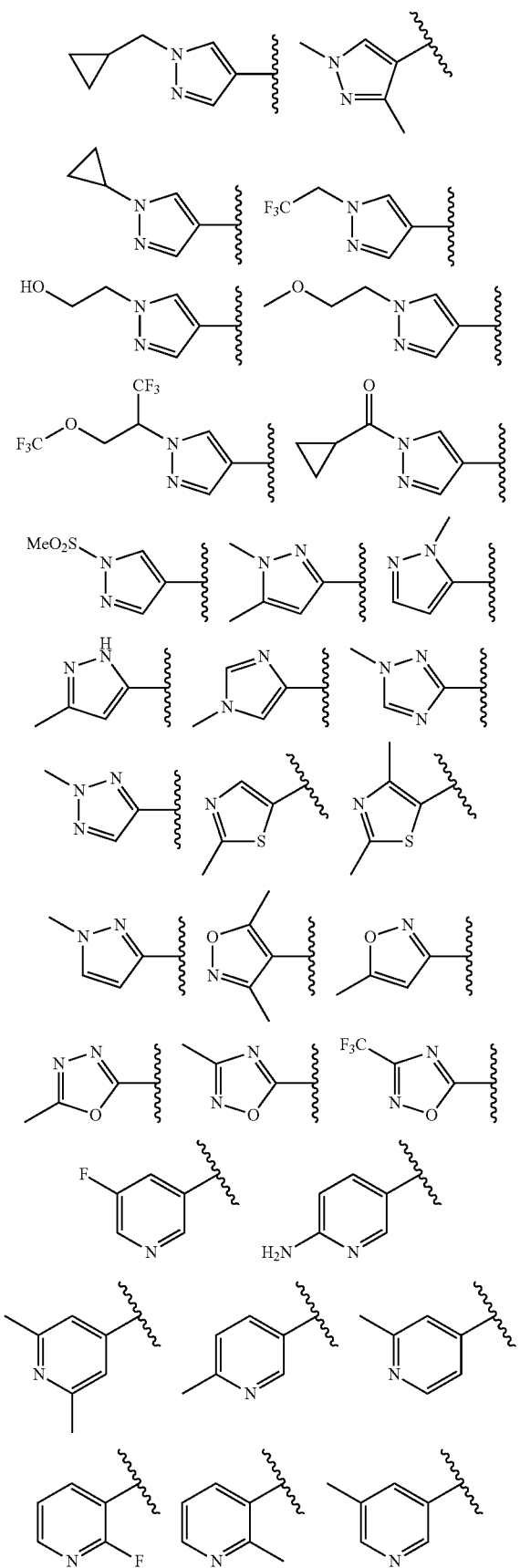

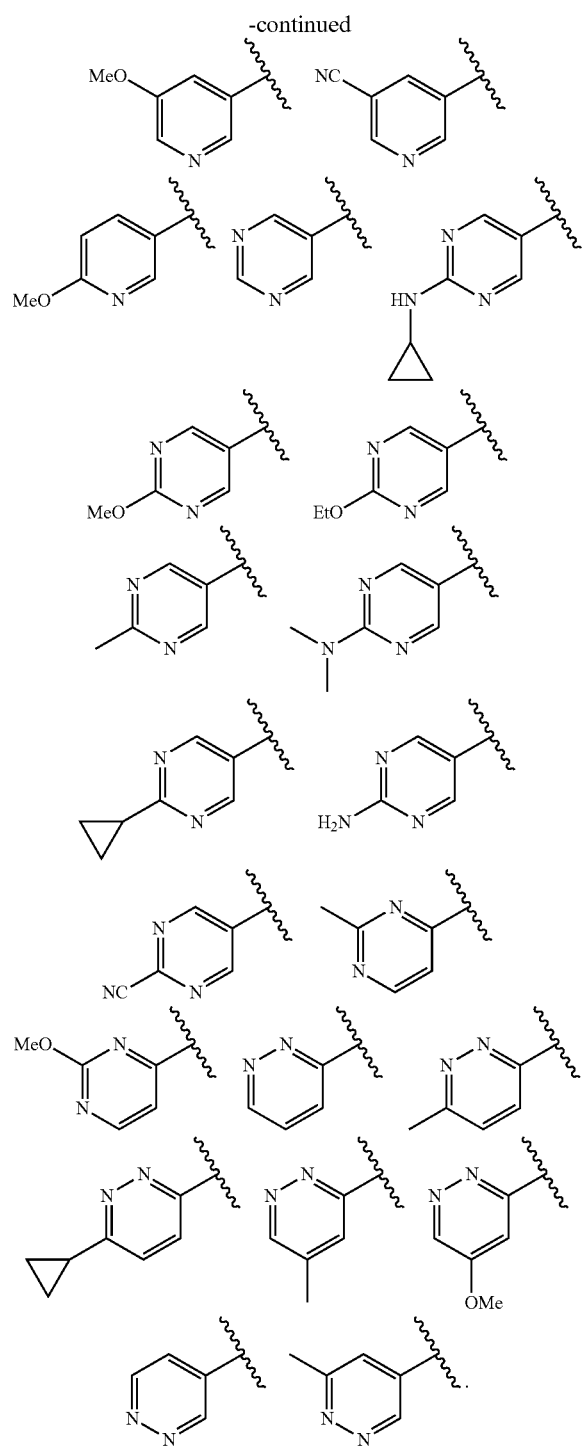

In one embodiment, $R^4$ is hetAr$^4$—O—. In one embodiment, $R^4$ is the structure:

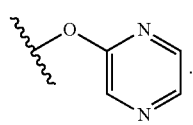 [SMILES: *Oc1cnccn1]

In one embodiment, $R^4$ is Ar$^4$, where Ar$^4$ is phenyl optionally substituted with one or more groups independently selected from (1-6C)alkyl, halogen, CN, CF$_3$, CF$_3$O—, (1-6C)alkoxy, (1-6Calkyl)OC(=O)—, aminocarbonyl, (1-6C)alkylthio, hydroxy(1-6C)alkyl, (1-6C alkyl)SO$_2$—, HOC(=O)— and (1-3C alkoxy)(1-3C alkyl)OC(=O)—. In one embodiment, Ar$^4$ is phenyl optionally substituted with one or more groups independently selected from methyl, F, Cl, CN, methoxy, CH$_3$OC(=O)—, aminocarbonyl, methylaminocarbonyl, dimethylaminocarbonyl, methylthio, CH$_3$SO$_2$—, HOC(=O)— and CH$_3$OCH$_2$CH$_2$OC(=O)—. In one embodiment, Ar$^4$ is phenyl optionally substituted with one or two of said substituents. In one embodiment, Ar$^4$ is selected from the structures:

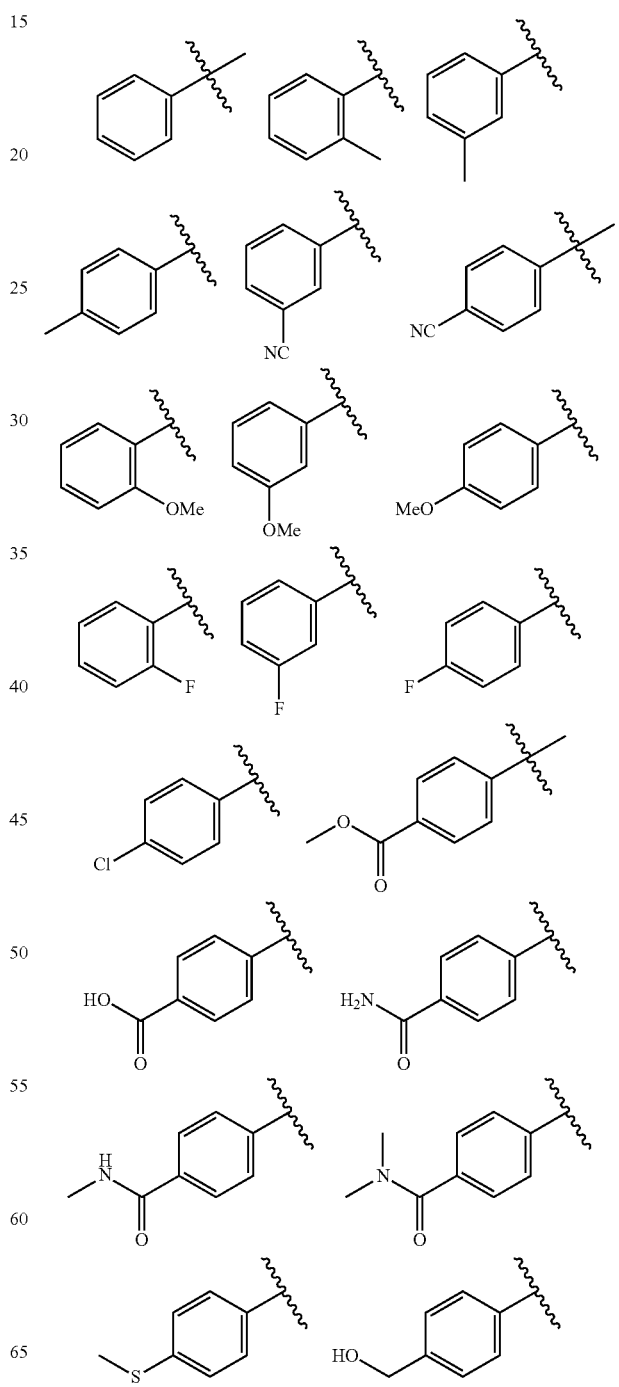

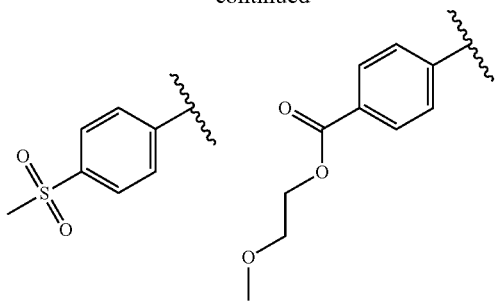

In one embodiment, R⁴ is hetCyc²(O)CH₂, where hetCyc² is a 4-6 membered heterocyclic ring having 1-2 ring heteroatoms independently selected from N and O, wherein hetCyc² is optionally substituted with 1-2 groups independently selected from (1-6C)alkyl, (1-4C alkoxy)carbonyl, and (1-6C)acyl. Examples of hetCyc² include oxetaynyl, tetrahydrofuranyl, tetrahydropyranyl, azetidinyl, pyrrolidinyl, piperidinyl, piperazinyl, morpholinyl, and 1,3-dioxolanyl rings optionally substituted with 1-2 groups independently selected from (1-6C)alkyl, (1-4C alkoxy)carbonyl and (1-6C)acyl. In one embodiment, R⁴ when represented by hetCyc²(O)CH₂ is selected from the structures:

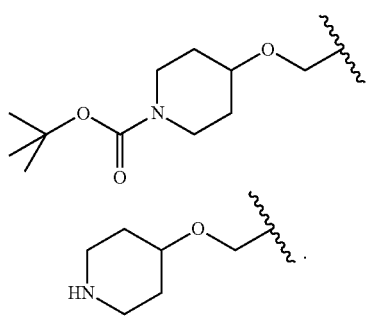

In one embodiment, R⁴ is (1-4C alkoxycarbonyl)(1-6C)alkoxy. In one embodiment, R⁴ is methoxycarbonyl(1-6C)alkoxy or ethylcarbonyl(1-6C)alkoxy. A particular example is ethoxycarbonylmethoxy.

In one embodiment, R⁴ is hydroxycarbonyl(1-6C)alkoxy. In one embodiment, R⁴ is hydroxycarbonylmethoxy.

In one embodiment, R⁴ is aminocarbonyl(1-6C)alkoxy. In one embodiment, R⁴ is H₂NC(=O)(1-6C)alkoxy, (1-6C alkyl)NHC(=O)(1-6C)alkoxy, or di(1-6Calkyl)NC(=O)(1-6C)alkoxy. In one embodiment, R⁴ is H₂NC(=O)CH₂O—, H₂NC(=O)CH₂CH₂O— or CH₃CH₂NC(=O)CH₂O—.

In one embodiment, R⁴ is hetCyc²C(=O)(1-6C)alkoxy, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl, and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O)(1-6C)alkoxy is the structure:

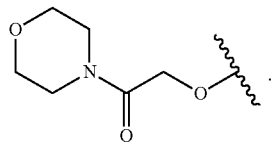 [SMILES: *OCC(=O)N1CCOCC1]

In one embodiment, R⁴ is hydroxy(1-3C alkoxy)(1-6C) alkoxy. In one embodiment, R⁴ is 2-hydroxy-3-methoxypropoxy, having the structure:

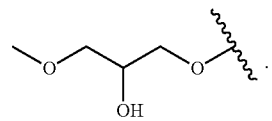 [SMILES: *OCC(O)COC]

In one embodiment, R⁴ is hydroxytrifluoro(1-6C)alkoxy. In one embodiment, R⁴ is 3,3,3-difluoro-2-hydroxypropoxy having the structure:

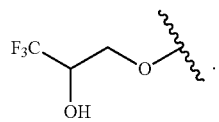

In one embodiment, R⁴ is (1-3C)alkylsulfonamido(1-6C)alkoxy. In one embodiment, R⁴ is methanesulfonamido(1-6C)alkoxy. In one embodiment, R⁴ is 2-methanesulfonamidoethoxy having the structure:

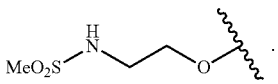

In one embodiment, R⁴ is (1-3C)alkylamido(1-6C)alkoxy. In one embodiment, R⁴ is 2-(methylamido)ethoxy having the structure:

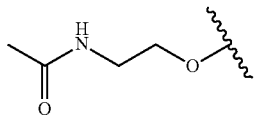 [SMILES: *OCCNC(C)=O]

In one embodiment, R⁴ is di(1-3C alkyl)aminocarboxy. In one embodiment, R⁴ is dimethylaminocarboxy having the structure:

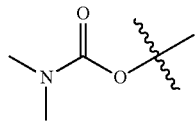

In one embodiment, R⁴ is hetCyc²C(=O)O—, where hetCyc² is a 4-6 membered heterocyclic ring having 1-2 ring heteroatoms independently selected from N and O and optionally substituted with 1-2 groups independently selected from (1-6C)alkyl, (1-4C alkoxy)carbonyl and (1-6C)acyl. In one embodiment, hetCyc² is oxetaynyl, tetrahydrofuranyl, tetrahydropyranyl, azetidinyl, pyrrolidinyl, piperidinyl, piperazinyl, morpholinyl, or 1,3-dioxolanyl optionally substituted with 1-2 groups independently selected from (1-6C)alkyl, (1-4C alkoxy)carbonyl and (1-6C)acyl. In one embodiment, hetCyc² is morpholinyl. In one embodiment, R⁴ when represented by hetCyc²C(=O)O— is the structure:

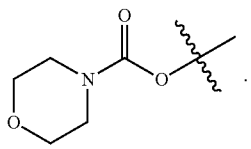

In one embodiment, R⁴ is hydroxydifluoro(1-6C)alkyl. In one embodiment, R⁴ is 2,2-difluoro-2-hydroxyethyl.

In one embodiment, R⁴ is (1-4C alkylcarboxy)(1-6C)alkyl. In one embodiment, R⁴ is methylcarboxy(1-6C)alkyl. In one embodiment, R⁴ is 2-(methylcarboxy)ethyl.

In one embodiment, R⁴ is (1-6C)alkoxycarbonyl. In one embodiment, R⁴ is methoxycarbonyl or ethoxycarbonyl.

In one embodiment, R⁴ is hydroxycarbonyl.

In one embodiment, R⁴ is aminocarbonyl, that is, a RR'NCO— radical where R and R' are independently hydrogen or (1-6C)alkyl as defined herein. In one embodiment, R⁴ is aminocarbonyl, methylaminocarbonyl, dimethylaminocarbonyl, ethylcarbonyl or isopropylaminocarbonyl.

In one embodiment, R⁴ is (1-3C alkoxy)aminocarbonyl. In one embodiment, R⁴ is methoxyaminocarbonyl.

In one embodiment, R⁴ is hetCyc³, where is a 4-7 membered heterocycle having 1-2 ring heteroatoms independently selected from N and O and optionally substituted with one or more substituents independently selected from F, CN, CF₃, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is tetrahydropyranyl, piperidinyl, pyrrolidinyl or azetidinyl optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl. In one embodiment, hetCyc³ is optionally substituted with one or two of said substituents. In one embodiment, hetCyc³ is tetrahydropyranyl, piperidinyl, pyrrolidinyl or azetidinyl optionally substituted with CN, Me, CH₃C(=O)—, MeSO₂—, or CF₃SO₂—. In one embodiment, R⁴ when represented by hetCyc³ is selected from the structures:

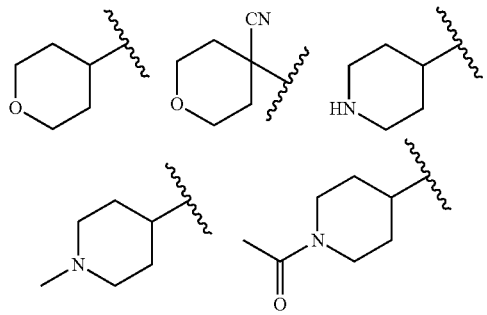

In one embodiment, R⁴ is halogen. In one embodiment, R⁴ is Br.

In one embodiment, R⁴ is CN.

In one embodiment, R⁴ is trifluoromethylsulfonyl.

In one embodiment, R⁴ is hetAr⁵, where hetAr⁵ is a group selected from the structures:

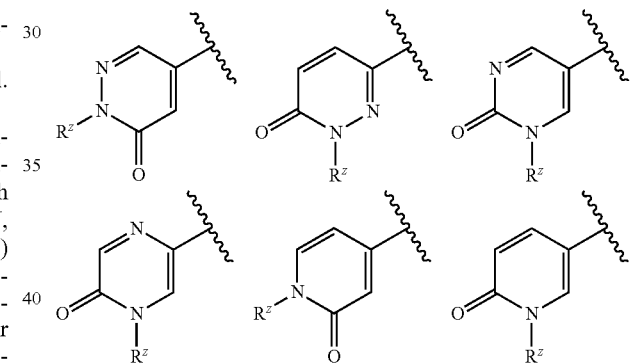

where R^z is (3-4C)cycloalkyl or (1-3C)alkyl (optionally substituted with 1-3 fluoros), wherein each of said hetAr⁵ groups is optionally further substituted with one or more groups independently selected from F and (1-3C)alkyl optionally substituted with 1-3 fluoros.

In one embodiment, R⁴ when represented by hetAr⁵ is selected from the structures:

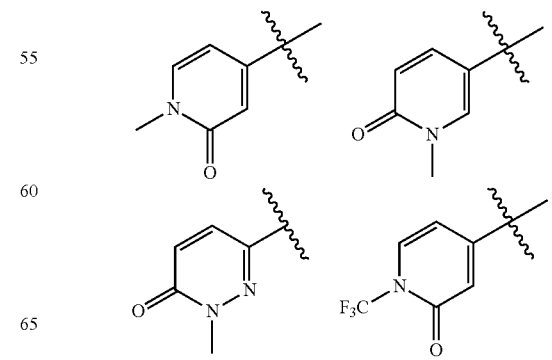

In one embodiment, R⁴ is N-(1-3C alkyl)oxadiazolonyl. In one embodiment, R⁴ is represented by the structures:

In one embodiment, R⁴ is selected from H, (1-6C)alkyl, trifluoro(1-6C)alkyl, hydroxy(1-6C)alkyl, cyano(1-6C)alkyl, (1-3C alkoxy)(1-6C)alkyl, (1-6C)alkoxy, monofluoro(1-6C)alkoxy, cyano(1-6C)alkoxy, hydroxy(1-6C)alkoxy, dihydroxy(2-6C)alkoxy, hetCyc²(1-6C)alkoxy, Ar³(1-6C)alkoxy, (1-4C alkoxy)(1-6C)alkoxy, (1-3C alkylsulfonyl)(1-6C)alkoxy, (3-6C)cycloalkyl, hetAr⁴, hetAr⁴—O—, Ar⁴, and hetAr⁵.

In one embodiment, R⁴ is hetAr⁴, Ar⁴, or hetAr⁵.

In one embodiment, R⁴ is hetAr⁴ or hetAr⁵.

In one embodiment, R⁴ is pyrazolyl optionally substituted with one or more groups independently selected from (1-6C)alkyl, or R⁴ is a hetAr⁵ group having the structure:

where R^z is (3-4C)cycloalkyl or (1-3C)alkyl (optionally substituted with 1-3 fluoros), wherein said hetAr⁵ group is optionally further substituted with one or more groups independently selected from F and (1-3C)alkyl optionally substituted with 1-3 fluoros.

In one embodiment, R⁵ is (1-6C)alkyl. In one embodiment, R⁵ is methyl, ethyl, propyl, isopropyl or butyl.

In one embodiment, R⁵ is monofluoro(1-6C)alkyl, difluoro(1-6C)alkyl, trifluoro(1-6C)alkyl, tetrafluro(2-6C)alkyl or pentafluro(2-6C)alkyl. In one embodiment, R⁵ is fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropane or 2,2,3,3,3-pentafluoropropyl.

In one embodiment, R⁵ is halogen. In one embodiment, R⁵ is F. In one embodiment, R⁵ is Cl. In one embodiment, R⁵ is Br.

In one embodiment, R⁵ is CN.

In one embodiment, R⁵ is (1-4C)alkoxy. In one embodiment, R⁵ is methoxy or ethoxy.

In one embodiment, R⁵ is hydroxy(1-4C)alkyl. In one embodiment, R⁵ is hydroxymethyl or 3-hydroxypropyl.

In one embodiment, R⁵ is (1-4C alkyl)OC(═O)—. In one embodiment, R⁵ is CH₃CH₂OC(═O)—.

In one embodiment, R⁵ is (1-6C)alkylthio. In one embodiment, R⁵ is methylthio (MeS—).

In one embodiment, R⁵ is phenyl optionally substituted with one or more groups independently selected from halogen, (1-6C)alkyl and (1-6C)alkoxy. In one embodiment, R⁵ is phenyl optionally substituted with one or more groups independently selected from F, Cl, methyl, ethyl, methoxy and ethoxy. In one embodiment, R⁵ is phenyl.

In one embodiment, R⁵ is (3-4C)cycloalkyl. In one embodiment, R⁵ is cyclopropyl. In one embodiment, R⁵ is cyclobutyl.

In one embodiment, R⁵ is amino. In one embodiment, R⁵ is NH₂.

In one embodiment, R⁵ is aminocarbonyl. In one embodiment, R⁵ is H₂NC(═O)—.

In one embodiment, R⁵ is trifluoro(1-3C alkyl)amido. In one embodiment, R⁵ is CF₃C(═O)NH—.

In one embodiment, R⁵ is halogen, CN, (1-6C)alkyl, (1-4C)alkoxy, hydroxy(1-4C)alkyl, or phenyl optionally substituted with one or more groups independently selected from halogen, (1-6C)alkyl and (1-6C)alkoxy.

In one embodiment, R⁵ is selected from halogen, and (1-6C)alkyl.

In one embodiment, R⁵ is selected from methyl, Cl and Br.

In one embodiment of Formula I, R⁴ is selected from H, (1-6C)alkyl, trifluoro(1-6C)alkyl, cyano(1-6C)alkyl, (1-3C alkoxy)(1-6C)alkyl, (1-6C)alkoxy, cyano(1-6C)alkoxy, hydroxy(1-6C)alkoxy, (1-4C alkoxy)(1-6C)alkoxy, (3-6C)cycloalkyl, hetAr⁴, Ar⁴, and hetAr⁵; and R⁵ is selected from halogen, CN, (1-6C)alkyl, (1-4C)alkoxy, hydroxy(1-4C)alkyl, (1-6C)alkylthio, and phenyl optionally substituted with one or more groups independently selected from halogen, (1-6C)alkyl and (1-6C)alkoxy.

In one embodiment of Formula I, R⁴ is selected from hetAr⁴, Ar⁴, and hetAr⁵; and R⁵ is selected from (1-6C)alkyl.

In one embodiment of Formula I, R⁴ is selected from hetAr⁴ and hetAr⁵; and R⁵ is selected from (1-6C)alkyl.

In one embodiment of Formula I, R⁴ is hetAr⁴ and R⁵ is selected from (1-6C)alkyl.

In one embodiment of Formula I, R⁴ is pyrazolyl optionally substituted with one or more substituents independently selected from (1-6C)alkyl; and R⁵ is selected from (1-6C)alkyl.

In one embodiment of Formula I, R⁴ is hetAr⁵; and R⁵ is selected from (1-6C)alkyl.

In one embodiment of Formula I, R⁴ is a hetAr⁵ group having the structure:

where R^z is (3-4C)cycloalkyl or (1-3C)alkyl (optionally substituted with 1-3 fluoros), wherein said hetAr⁵ group is optionally further substituted with one or more groups independently selected from F and (1-3C)alkyl optionally substituted with 1-3 fluoros; and R⁵ is selected from (1-6C)alkyl.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl; or $R^4$ and $R^5$ together with the atoms to which they are attached form a 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or $SO_2$.

In one embodiment, $R^4$ and $R^5$ together with the atoms to which they are attached form a 5-6 membered saturated, partially unsaturated or unsaturated carbocyclic ring optionally substituted with one or more substituents independently selected from (1-6C)alkyl. In one embodiment, Ring C when $R^4$ and $R^5$ together with the atoms to which they are attached form a 5-6 membered saturated or unsaturated carbocyclic ring is selected from the structures:

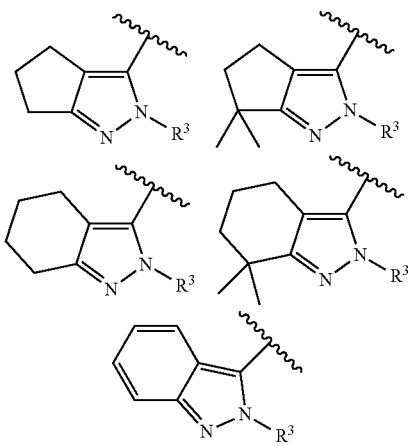

where $R^3$ is as defined for Formula I.

In one embodiment, $R^4$ and $R^5$ together with the atoms to which they are attached form a 5-6 membered saturated carbocyclic ring optionally substituted with one or more substituents independently selected from (1-6C)alkyl, or $R^4$ and $R^5$ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6C)acyl, and said sulfur ring atom is optionally oxidized to S(=O) or $SO_2$.

In one embodiment, $R^4$ and $R^5$ together with the atoms to which they are attached form a 5-6 membered saturated carbocyclic ring optionally substituted with one or more substituents independently selected from (1-6C)alkyl. In one embodiment, Ring C when $R^4$ and $R^5$ together with the atoms to which they are attached form a 5-6 membered saturated carbocyclic ring is selected from the structures:

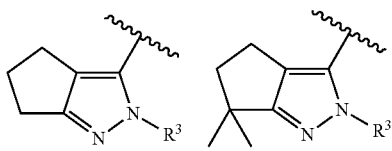

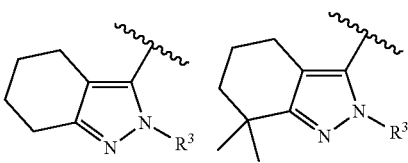

where $R^3$ is as defined for Formula I.

In one embodiment, $R^4$ and $R^5$ together with the atoms to which they are attached form a 5-6 membered saturated, partially unsaturated or unsaturated heterocyclic ring having a ring heteroatom selected from N, O or S, wherein said ring N atom is optionally substituted with (1-6C alkyl)C(=O)O—, (1-6C alkyl)C(=O)—, (1-6C)alkyl or oxo, and said S ring atom is optionally oxidized to S(=O) or $SO_2$. In one embodiment, Ring C when $R^4$ and $R^5$ together with the atoms to which they are attached form a 5-6 membered saturated heterocyclic ring is selected from the structures:

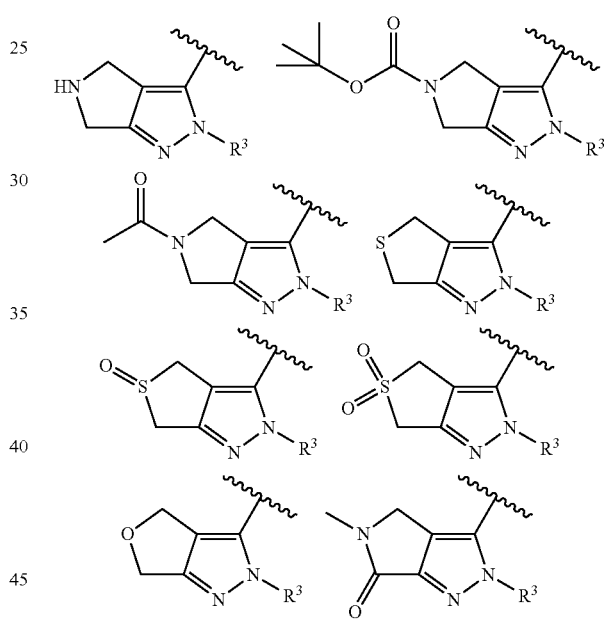

where $R^3$ is as defined for Formula I.

In one embodiment, $R^4$ and $R^5$ together with the atoms to which they are attached form a 5-6 membered saturated heterocyclic ring having a ring heteroatom selected from N, O or S, wherein said ring N atom is optionally substituted with (1-6C alkyl)C(=O)O— or (1-6C alkyl)C(=O)—, and said S ring atom is optionally oxidized to S(=O) or $SO_2$. In one embodiment, Ring C when $R^4$ and $R^5$ together with the atoms to which they are attached form a 5-6 membered saturated heterocyclic ring is selected from the structures:

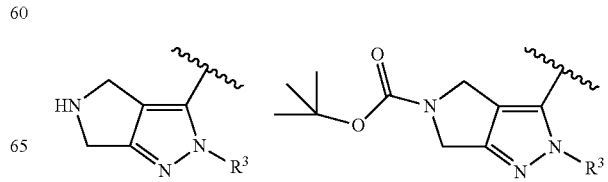

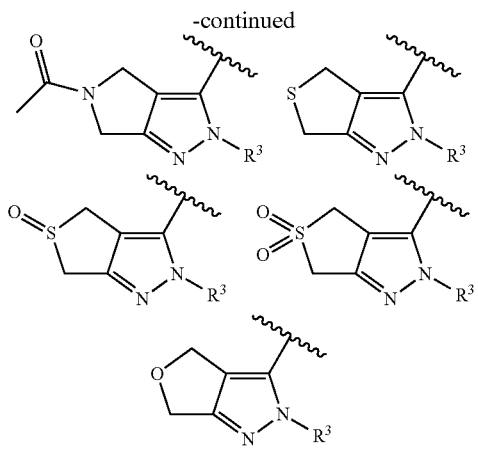

where R³ is as defined for Formula I.
In one embodiment, Ring C is formula C-2

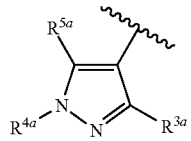

where R³ᵃ, R⁴ᵃ, and R⁵ᵃ are as defined for Formula I.

In one embodiment, R³ᵃ, R⁴ᵃ and R⁵ᵃ are as defined for Formula

In one embodiment, R³ᵃ is hydrogen.

In one embodiment, R³ᵃ is halogen.

In one embodiment, R³ᵃ is (1-6C)alkyl. In one embodiment, R³ᵃ is methyl.

In one embodiment, R³ᵃ is trifluoro(1-6C)alkyl. In one embodiment, R³ᵃ is CF₃.

In one embodiment, R³ᵃ is (3-6C)cycloalkyl. In one embodiment, R³ᵃ is cyclopropyl.

In one embodiment, R³ᵃ is phenyl optionally substituted with one or more substituents independently selected from halogen and (1-6C)alkyl. In one embodiment, R³ᵃ is phenyl, fluorophenyl or methylphenyl, for example include phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embedment, R³ᵃ is phenyl.

In one embodiment, R³ᵃ is a 5-6 membered heteroaryl ring having 1-3 ring heteroatoms independently selected from N, O and S and optionally substituted with one or more groups independently selected from (1-6C)alkyl and halogen. In one embodiment, R³ᵃ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl ring optionally substituted with (1-6C) alkyl or halogen. In one embodiment, R³ᵃ is pyrazolyl, pyridyl or pyridazinyl optionally substituted with one or more groups independently selected from (1-6C)alkyl and halogen. In one embodiment, R³ᵃ is pyrazolyl, pyridyl or pyridazinyl optionally substituted with (1-6C)alkyl or halogen.

In one embodiment, R⁴ᵃ is hydrogen.

In one embodiment, R⁴ᵃ is (1-6C)alkyl. In one embodiment, R⁴ᵃ is methyl, ethyl or isopropyl.

In one embodiment, R⁴ᵃ is trifluoro(1-6C)alkyl. In one embodiment, R⁴ᵃ is 2,2,2-trifluoroethyl.

In one embodiment, R⁴ᵃ is phenyl optionally substituted with one or more groups independently selected from (1-6C) alkyl, halogen, CN, CF₃, CF₃O—, (1-6C)alkoxy, (1-6Calkyl)OC(=O)—, aminocarbonyl, (1-6C)alkylthio, hydroxy(1-6C)alkyl, (1-6C alkyl)SO₂—, HOC(=O)— and (1-3C alkoxy)(1-3C alkyl)OC(=O)—. In one embodiment, R⁴ᵃ is phenyl optionally substituted with one or more groups independently selected from methyl, F, Cl, CN, methoxy, CH₃OC(=O)—, aminocarbonyl, methylaminocarbonyl, dimethylaminocarbonyl, methylthio, CH₃SO₂—, HOC(=O)— or CH₃OCH₂CH₂OC(=O)—. In certain embodiments, R⁴ᵃ is phenyl optionally substituted with one or two of said substituents. In one embodiment, R⁴ᵃ is phenyl.

In one embodiment, R⁴ᵃ is a 5-6 membered heteroaryl ring having 1-3 ring heteroatoms independently selected from N, S and O and optionally substituted with 1-2 substituents independently selected from (1-6C)alkyl, hydroxy (1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, and (1-3C trifluoroalkoxy)(1-3C)trifluoroalkyl. In one embodiment, R⁴ᵃ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl or imidazo[1,2-a]pyridinyl optionally substituted with 1-2 substituents independently selected from (1-6C)alkyl, hydroxy(1-6C) alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, and (1-3C trifluoroalkoxy)(1-3C)trifluoroalkyl. In one embodiment, R⁴ᵃ is pyrazinyl.

In one embodiment, R⁵ᵃ is as defined for Formula I.

In one embodiment, R⁵ᵃ is selected from hydrogen, halogen, (1-6C)alkyl and phenyl.

In one embodiment, R⁵ᵃ is hydrogen.

In one embodiment, R⁵ᵃ is halogen.

In one embodiment, R⁵ᵃ is (1-6C)alkyl. In one embodiment, R⁵ᵃ is methyl.

In one embodiment, R⁵ᵃ is phenyl.

In one embodiment, Ring C is formula C-2, in which R³ᵃ is (1-6C)alkyl, trifluoro(1-6C)alkyl or phenyl; R⁴ᵃ is (1-6C) alkyl, trifluoro(1-6C)alkyl, phenyl or pyrazinyl; and R⁵ᵃ is hydrogen, (1-6C)alkyl or phenyl.

In one embodiment, Ring C is formula C-2, wherein R³ᵃ is (1-6C)alkyl, trifluoro(1-6C)alkyl or phenyl; R⁴ᵃ is (1-6C) alkyl, trifluoro(1-6C)alkyl, phenyl or pyrazinyl; and R⁵ᵃ is (1-6C)alkyl or phenyl.

In another embodiment of the present invention there is provided a compound according to Formula I, which is designated as Formula I-a, wherein:

X is O;

Ring C is formula C-1:

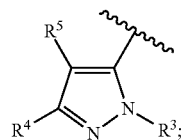

R³ is (1-6C)alkyl, hydroxy(1-6C)alkyl, Ar², hetCyc¹, (3-7C)cycloalkyl, or hetAr²;

$R^4$ is H, OH, (1-6C)alkyl, monofluoro(1-6C)alkyl, difluoro(1-6C)alkyl, trifluoro(1-6C)alkyl, tetrafluoro(2-6C)alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr$^3$(1-6C)alkyl, Ar$^3$(1-6C)alkyl, (1-6C)alkoxy, monofluoro(1-6C)alkoxy, difluoro(1-6C)alkoxy trifluoro(1-6C)alkoxy, tetrafluoro(2-6C)alkoxy, pentafluoro(2-6C)alkoxy cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc$^2$(1-6C)alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C)alkoxy, or (1-3C alkoxy)(1-6C)alkyl], hetAr$^4$, hetAr$^4$—O—, Ar$^4$, hetCyc$^2$(O)CH$_2$—, (1-4C alkoxycarbonyl)(1-6C)alkoxy, hydroxycarbonyl(1-6C)alkoxy, aminocarbonyl(1-6C)alkoxy, hetCyc$^2$C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C)alkylamido(1-6C)alkoxy, di(1-3C alkyl)aminocarboxy, hetCyc$^2$C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc$^3$, halogen, CN, trifluoromethylsulfonyl, N-(1-3C alkyl)oxadiazolonyl, or hetAr$^5$;

$R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, or phenyl optionally substituted with one or more groups independently selected from halogen, (1-6C)alkyl and (1-6C)alkoxy; and $R^1$, $R^2$, Ring A, m, n, p, Ar$^2$, hetCyc$^1$, hetAr$^2$, hetCyc$^2$, hetCyc$^3$, hetAr$^3$, Ar$^a$, hetAr$^4$, herAr$^5$, $R^z$ and Ar$^4$ are as defined for Formula I.

In one embodiment of Formula I-a, $R^3$ is Ar$^2$; $R^4$ is hetAr$^4$, Ar$^4$, or hetAr$^5$; $R^5$ is (1-6C)alkyl; and $R^1$, $R^2$, Ring A, m, n, p, Ar$^2$, hetAr$^4$, herAr$^5$, $R^z$ and Ar$^4$ are as defined for Formula I. In one embodiment of Formula I-a, $R^3$ is phenyl.

In one embodiment of Formula I-a, $R^3$ is Ar$^2$; $R^4$ is hetAr$^4$ or hetAr$^5$; $R^5$ is (1-6C)alkyl; and $R^1$, $R^2$, Ring A, m, n, p, Ar$^2$, hetAr$^4$, hetAr$^5$ and $R^z$ are as defined for Formula I. In one embodiment of Formula I-a, $R^3$ is phenyl.

In one embodiment of Formula I-a, $R^3$ is Ar$^2$; $R^4$ is hetAr$^4$; $R^5$ is (1-6C)alkyl; and $R^1$, $R^2$, Ring A, m, n, p, Ar$^2$, and hetAr$^4$ are as defined for Formula I. In one embodiment of Formula I-a, $R^3$ is phenyl.

In one embodiment of Formula I-a, $R^3$ is Ar$^2$; $R^4$ is hetAr$^4$ or hetAr$^5$; $R^5$ is (1-6C)alkyl; Ring A is formula A-1 or A-2; and m, n, $R^1$, $R^2$, Ar$^2$, hetAr$^4$, hetAr$^5$, and $R^z$ are as defined for Formula I. In one embodiment of Formula I-a, $R^3$ is phenyl.

In one embodiment of Formula I-a, $R^3$ is Ar$^2$; $R^4$ is hetAr$^4$; $R^5$ is (1-6C)alkyl; Ring A is formula A-1 or A-2; and m, n, $R^1$, $R^2$, Ar$^2$ and hetAr$^4$ are as defined for Formula I.

In one embodiment of Formula I-a, $R^3$ is Ar$^2$; $R^4$ is hetAr$^4$ or hetAr$^5$; $R^5$ is (1-6C)alkyl; Ring A is formula A-1 or A-2; $R^1$ is formula R$^1$-1; and m, n, $R^2$, Ar$^2$, hetAr$^4$, hetAr$^5$, and lee are as defined for Formula I. In one embodiment of Formula I-a, $R^3$ is phenyl.

In one embodiment of Formula I-a, $R^3$ is Ar$^2$; $R^4$ is hetAr$^4$; $R^5$ is (1-6C)alkyl; Ring A is formula A-1 or A-2; $R^1$ is formula $R^1$-1; and m, n, $R^2$, Ar$^2$, and hetAr$^4$ are as defined for Formula I. In one embodiment of Formula I-a, $R^3$ is phenyl.

In one embodiment of Formula I-a, $R^3$ is Ar$^2$; $R^4$ is hetAr$^4$; $R^5$ is (1-6C)alkyl; Ring A is formula A-1 or A-2; $R^1$ is formula $R^1$-1; $R^2$ is halogen, (1-3C)alkyl (optionally substituted with 1-3 fluoros), and m, n, Ar$^2$, and hetAr$^4$ are as defined for Formula I. In one embodiment of Formula I-a, $R^3$ is phenyl.

In one embodiment of Formula I-a, $R^3$ is Ar$^2$; $R^4$ is hetAr$^4$; $R^5$ is (1-6C)alkyl; Ring A is formula A-1 or A-2; $R^1$ is selected from the structures:

$R^2$ is halogen, (1-3C)alkyl (optionally substituted with 1-3 fluoros), and m, n, Ar$^2$, hetAr$^4$ and Ar$^4$ are as defined for Formula I. In one embodiment of Formula I-a, $R^3$ is phenyl.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts.

In one embodiment, the compounds of Formula I include the free base form of compounds of Examples 1-49 or pharmaceutically acceptable salts thereof.

In one embodiment, the compounds of Formula I include the compounds of Examples 1-49 as pharmaceutically acceptable salts.

In one embodiment, the compounds of Formula I include the hydrochloride salts of compounds of Examples 1-49.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

II with a corresponding compound having the formula III

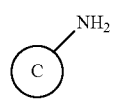

III in the presence carbonyldiimidazole or triphosgene and a base; or (b) for a compound of Formula I where X is S, coupling a corresponding compound having the formula II

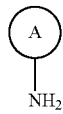

II with a corresponding compound of formula III

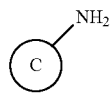

III in the presence di(1H-imidazol-2-yl)methanethione and a base; or (c) for a compound of Formula I where X is O, coupling a corresponding compound having the formula II

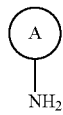

II with a corresponding compound having the formula IV

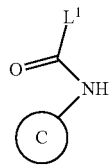

IV where L¹ is a leaving group, in the presence of a base; or (d) for a compound of Formula I where X is O, coupling a corresponding compound having the formula V

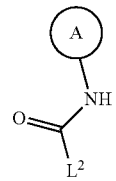

V where L² is a leaving group, with a corresponding compound having the formula III

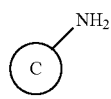

III in the presence of a base; or (e) for a compound of Formula I where X is O, activating a corresponding compound having the formula VI

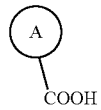

VI with diphenylphosphoryl azide followed by coupling the activated intermediate with a corresponding compound having the formula III

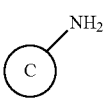

III in the presence a base; or (f) for a compound of Formula I where X is O, coupling a corresponding compound having the formula II

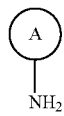

II with a corresponding compound having the formula VII

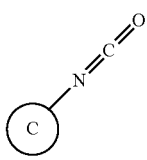

VII in the presence of a base; or (g) for a compound of Formula I where X is O, coupling a corresponding compound having the formula VIII

VIII with a corresponding compound having the formula III

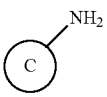

III in the presence of a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed, New York; John Wiley & Sons, Inc., 1991. Examples of amine protecting groups include acyl and alkoxycarbonyl groups, such as t-butoxycarbonyl (BOC) and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, V, VI, VII, and VIII are also provided as further aspects of the invention. In one embodiment, compounds of the formulas II, V, VI, VII, and VIII are useful as intermediates for the preparation of compounds of Formula I.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:

LMNA=Prelamin-A/C;
TFG=TRK-fused gene protein;
TPM3=Tropomyosin alpha-3;
CD74=HLA class II histocompatibility antigen gamma chain;
NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: *Nature Medicine* 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: *Cancer Genetics and Cytogenetics* 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: *Nature Genet.* 45(10): 1141-9 | Chemotherapeutics (e.g. bevacizumab, everolimus, lomustine, temozolomide) |
| Colorectal Carcinoma | Martin-Zanca et al. 1986: *Nature* 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: *Leukemia* 21: 2171-2180 Reuther et al. 2000: *Mol Cell Biol* 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: *Human Mutation* 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: *Cancer Cell* 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: *Clinical & Experimental Metastasis* 17: 307-314 Papatsoris et al 2007: *Expert Opinion on Investigational Drugs* 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: *Gene* 325: 1-15 | Chemotherapeutics (e.g. cyclophosphamide, doxorubicin, vincristine) |
| Pancreatic Carcinoma | Zhang et al 2005: *Oncology Reports* 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: *Journal of Investigative Dermatology* 128(8): 2031 | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas et al 2010: *Journal of Oral and Maxillofacial Surgery* 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: *Asian Pacific Journal of Cancer Prevention* 13: 1511 | Chemotherapeutics (e.g. docetaxel, doxorubucin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating Trypanosoma cruzi infection in a mammal, comprising administering to said mammal in need thereof one or more compounds of Formula I or a pharmaceutically acceptable salt thereof in an amount effective to treat said Trypanosoma cruzi infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansels Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example Trypanosoma cruzi infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or Trypanosoma cruzi infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is Trypanosoma cruzi infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. THF, DCM, toluene, DMF and dioxane were purchased from Aldrich in Sure/Seal™ bottles and used as received.

The reactions set forth below were done generally under a positive pressure of nitrogen or argon (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value<100 nM; B represents an averaged $IC_{50}$ value from 100 to 1,000 nM; and C represents an averaged $IC_{50}$ value from 1,000 to 10,000 nM.

TABLE A

| Example No. | TrkA Enzyme $IC_{50}$ (nM) |
| --- | --- |
| 1 | C |
| 2 | A |
| 3 | A |
| 4 | B |
| 5 | A |
| 6 | A |
| 7 | B |
| 8 | A |

TABLE A-continued

| Example No. | TrkA Enzyme IC$_{50}$ (nM) |
|---|---|
| 9 | A |
| 10 | A |
| 11 | B |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |

Example A-2 p38 Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [Na$^+$] HEPES pH 7.3, 10 mM MgCl$_2$, 100 μM NaVO$_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The IC$_{50}$ values were determined by fitting a four parameter model to the percent of control data. The compounds of Examples 1-49 were tested in this assay, and all compounds were found to be 1000 fold more potent against TrkA than p38α.

Example B

Off-Target Kinase Profiling

A representative compound (Example 15) of the invention was tested for off-target kinase activity at a concentration of 10 μM by Millipore, Inc. in their KinaseProfiler™ service against all the kinases available in their full kinase panel. The compound was run in duplicate at a concentration of ATP near the Km for each individual kinase according to Millipore's specifications. The results are shown in Table B. Data are reported as percent of control (POC) and are the average of the two replicates.

In the KinaseProfiler™ the compound of Example 15 showed remarkable and unexpected selectivity for inhibiting TrkA versus other kinases in the panel. In fact, the compound was largely inactive against off-target kinases at a concentration of 10 μM, and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 15 Avg POC |
|---|---|
| Ab12 | 108 |
| Abl-P | 140.5 |
| AKT1 | 120 |
| AKT2 | 166.5 |
| AKT3 | 119.5 |
| ALK | 105 |
| ALK4 | 113 |
| AMPK(A1/B1/G1) | 149 |
| ARKS | 97.5 |
| AURKA | 113.5 |
| Axl | 107 |
| BLK_m | 118.5 |
| Bmx | 129.5 |
| BrSK1 | 123.5 |
| BrSK2 | 123 |
| BTK | 119.5 |
| CAMK1 | 96 |
| CAMK1d | 103 |
| CAMK2b | 101.5 |
| CAMK2d | 135.5 |
| CAMK2g | 103 |
| CAMK4 | 132 |
| CDK1/cyclinB | 97 |
| CDK2/cyclinA | 112.5 |
| CDK2/cyclinE | 106.5 |
| CDK3/cyclinE | 101 |
| CDK5/p25 | 106 |
| CDK5/p35 | 110 |
| CDK6/cyclinD3 | 111 |
| CDK7/cyclinH/MAT1 | 106 |
| CDK9/cyclinT1 | 112.5 |
| CHK1 | 118 |
| CHK2 | 130 |
| CK1_y | 96.5 |
| CK1delta | 111.5 |
| CK1gamma1 | 99.5 |
| CK1gamma2 | 120 |
| CK1gamma3 | 112.5 |
| CK2 | 94.5 |
| CK2alpha2 | 112.5 |
| CLK2 | 111.5 |
| CLK3 | 105 |
| c-RAF | 98.5 |
| CSK | 139 |
| DAPK1 | 121.5 |
| DAPK2 | 104.5 |
| DAPK3 | 106 |
| DCAMKL2 | 136 |
| DDR2 | 104.5 |
| DMPK | 108.5 |
| DRAK1 | 135.5 |
| DYRK2 | 93.5 |

TABLE B-continued

| Kinase | Example 15 Avg POC |
|---|---|
| eEF-2K | 181 |
| EGFR | 103 |
| EphA1 | 117 |
| EphA2 | 104 |
| EphA3 | 117 |
| EphA4 | 115 |
| EphA5 | 115.5 |
| EphA7 | 103 |
| EphA8 | 127.5 |
| EphB1 | 130 |
| EphB2 | 112.5 |
| EphB3 | 78.5 |
| EphB4 | 132.5 |
| ErbB4 | 118.5 |
| ERK1 | 103.5 |
| ERK2 | 108 |
| FAK | 103.5 |
| FAK2 | 102.5 |
| Fer | 99 |
| Fes | 110 |
| FGFR1 | 111.5 |
| FGFR2 | 108 |
| FGFR3 | 106.5 |
| FGFR4 | 120 |
| Fgr | 118 |
| Flt1 | 97.5 |
| Flt3 | 81 |
| Flt4 | 91 |
| Fms | 94 |
| Fyn | 111.5 |
| GRK5 | 90 |
| GRK6 | 103 |
| GRK7 | 115 |
| GSK3alpha | 131 |
| GSK3beta | 114.5 |
| Haspin | 121.5 |
| Hck | 89 |
| HIPK1 | 118 |
| HIPK2 | 99.5 |
| HIPK3 | 101 |
| IGF-1R | 85 |
| IGF-1R Activated | 102 |
| IKKalpha | 128 |
| IKKbeta | 113.5 |
| IR | 95 |
| IR Activated | 119.5 |
| IRAK1 | 103 |
| IRAK4 | 124.5 |
| IRR | 99.5 |
| ITK | 125 |
| JAK2 | 111.5 |
| JAK3 | 111 |
| JNK1alpha1 | 107 |
| JNK2alpha2 | 92 |
| JNK3 | 104 |
| KDR | 136 |
| KIT | 99.5 |
| Lck | 94.5 |
| LIMK1 | 93.5 |
| LKB1 | 90.5 |
| LOK | 135 |
| Lyn | 84.5 |
| MAP3K5 | 105 |
| MAP4K2 | 112.5 |
| MAPKAP-K2 | 129.5 |
| MAPKAP-K3 | 112.5 |
| MAPKAP-K5 | 92 |
| MARK1 | 107 |
| MARK2 | 101.5 |
| MEK1 | 121.5 |
| MELK | 142.5 |
| Mer | 97.5 |
| Met | 110.5 |
| MINK | 121.5 |
| MICK4_m | 137.5 |
| MKK6 | 124.5 |
| MKK7beta | 140 |
| MKNK2 | 106 |
| MLK1 | 110.5 |
| MRCKalpha | 137 |
| MRCKbeta | 105.5 |
| MSK1 | 132.5 |
| MSK2 | 147 |
| MSSK1 | 122 |
| MST1 | 94.5 |
| MST2 | 101.5 |
| MST3 | 137 |
| mTOR | 102.5 |
| mTOR/FKBP12 | 97.5 |
| MuSK | 100 |
| MYLK | 111.5 |
| NEK11 | 75 |
| NEK2 | 88.5 |
| NEK3 | 120 |
| NEK6 | 111.5 |
| NEK7 | 142 |
| NLK | 117 |
| p38alpha | 100.5 |
| p38beta | 106.5 |
| p38delta | 100.5 |
| p38gamma | 108 |
| p70S6K | 130.5 |
| PAK2 | 101.5 |
| PAK4 | 110.5 |
| PAK5 | 132.5 |
| PAK6 | 148 |
| PASK | 188 |
| PDGFRalpha | 117.5 |
| PDGFRbeta | 134 |
| PDK1 | 116.5 |
| PhKgamma2 | 110.5 |
| Pim-1 | 108 |
| Pim-2 | 142.5 |
| Pim-3 | 105.5 |
| PKAC-alpha | 149 |
| PKCalpha | 104 |
| PKCbetaI | 106 |
| PKCbetaII | 99 |
| PKCdelta | 96 |
| PKCepsilon | 97 |
| PKCeta | 105.5 |
| PKCgamma | 99.5 |
| PKCiota | 68 |
| PKCtheta | 105 |
| PKCzeta | 103 |
| PKD1 | 113.5 |
| PKD2 | 98.5 |
| Plk1 | 89.5 |
| Plk2 | 105 |
| Plk3 | 109 |
| PRK2 | 101.5 |
| PRKG1alpha | 113.5 |
| PRKG1beta | 130 |
| PrKX | 134 |
| PTK5 | 102.5 |
| PTK6 | 124 |
| Ret | 91.5 |
| RIPK2 | 102 |
| ROCK-I | 117.5 |
| ROCK-II | 99 |
| Ron | 108.5 |
| Ros | 105.5 |
| Rse | 109 |
| Rsk1 | 118 |
| Rsk2 | 136.5 |
| Rsk3 | 104 |
| Rsk4 | 105 |
| SGK1 | 124 |
| SGK2 | 117.5 |
| SGK3 | 132 |
| SIK | 137 |
| SRC | 90 |
| SRPK1 | 112.5 |
| SRPK2 | 113.5 |
| STK33 | 104.5 |
| Syk | 100 |

TABLE B-continued

| Kinase | Example 15 Avg POC |
|---|---|
| TAK1 | 95 |
| TAO1 | 113 |
| TAO2 | 126 |
| TAO3 | 95 |
| TBK1 | 110 |
| TEC Activated | 101.5 |
| Tie2 | 160.5 |
| TLK2 | 101 |
| TNK2 | 124 |
| TrkA | 0 |
| TrkB | 105 |
| TSSK1 | 80 |
| TSSK2 | 114.5 |
| Txk | 135.5 |
| ULK2 | 95 |
| ULK3 | 92.5 |
| VRK2 | 94 |
| WNK2 | 122.5 |
| WNK3 | 108.5 |
| Yes | 120.5 |
| ZAP-70 | 141.5 |

Preparation of Synthetic Intermediates

Intermediate X1

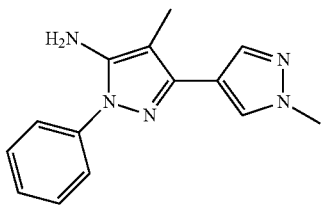 [SMILES: Cc1c(-c2cnn(C)c2)nn(-c2ccccc2)c1N]

1',4-dimethyl-1-phenyl-1H,1'H-[3,4'-bipyrazol]-5-amine

Step A: Preparation of ethyl 1-methyl-1H-pyrazole-4-carboxylate

A solution of ethyl 2-formyl-3-oxopropanoate (100 g, 694 mmol) in EtOH (700 mL) was cooled in an ice bath to 5° C. and methylhydrazine (35.8 mL, 680 mmol) was added dropwise at a rate such that the internal temperature did not exceed 12° C. The ice bath was removed and the reaction mixture was allowed to stir at ambient temperature for 16 hours. The reaction mixture was concentrated and the residue dissolved in $CH_2Cl_2$. The solution was concentrated and residue was dried in vacuum for 48 hours to yield the title compound as an orange oil (106 g, 99% yield). MS (apci) m/z=155.1 (M+H).

Step B: Preparation of 2-methyl-3-(1-methyl-1H-pyrazol-4-yl)-3-oxopropanenitrile A 1M solution of LiHMDS in THF (1440 mL, 1.440 mmol) was cooled to −78° C. and propiononitrile (103 mL, 1440 mmol) was added via a dropping funnel. The mixture was stirred at −78° C. for 90 minutes and a solution of ethyl 1-methyl-1H-pyrazole-4-carboxylate (106 g, 688 mmol) in anhydrous THF (500 mL) was added dropwise via an addition funnel over 45 minutes. The reaction mixture was allowed to slowly warm to ambient temperature and stirred for 16 hours. The solvent was decanted from the formed precipitate and the residual solid was dissolved in warm water. The aqueous mixture was washed with with ether (3×1000 mL) and treated with concentrated HCl to pH 5. The aqueous mixture was extracted with $CH_2Cl_2$ (3×1000 mL) and the combined extracts were dried over $MgSO_4$, filtered and concentrated to yield the title compound as an amber oil (92 g, 82% yield). MS (apci) m/z=162.1 (M−H).

Step C: Preparation of 1',4-dimethyl-1-phenyl-1H,1'H-3,4'-bipyrazol-5-amine

A mixture of 2-methyl-3-(1-methyl-1H-pyrazol-4-yl)-3-oxopropanenitrile (60.0 g, 368 mmol) and phenylhydrazine hydrochloride (58 g, 404 mmol) in absolute ethanol (1 L) was heated at reflux for 17 hours. The reaction mixture was cooled, concentrated and the residual solid was suspended in 1M NaOH (1 L). The solid was collected via vacuum filtration and the product cake washed with water and hexanes. Additional solid precipitated from the filtrate and was collected. The combined solids were crushed and suspended in ether (500 mL). The solid was collected by filtration, washed with hexanes and dried in vacuo to provide the title compound (93 g, 100% yield) as a yellow solid. MS (apci) m/z=254.1 (M+H).

Intermediate X2

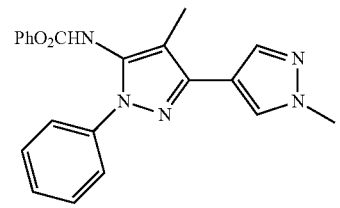

phenyl (1',4-dimethyl-1-phenyl-1H,1'H-[3,4'-bipyrazol]-5-yl)carbamate

A solution of 1',4-dimethyl-1-phenyl-1H,1'H-3,4'-bipyrazol-5-amine (Intermediate X1, 50.0 g, 197 mmol) in EtOAc (1 L) was treated with 2M NaOH (500 mL) and the mixture was stirred for 3 minutes. Phenyl chloroformate (74.3 mL, 592 mmol) was added slowly at rate such that the internal temperature did not exceed 33° C. The reaction mixture was stirred at ambient temperature for 2 hours and additional phenyl chloroformate (10 mL) was added. After 30 minutes the organic layer was separated, washed with saturated NaCl and concentrated in vacuo. The residue was purified by silica column chromatography eluting with 75% EtOAc/hexanes to provide the title compound (60 g, 81% yield) as a cream foam. MS (apci) m/z=374.1

Intermediate X3

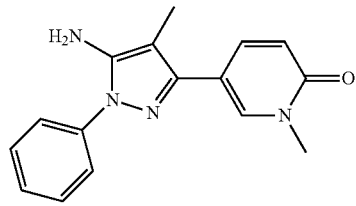 [SMILES: Cc1c(-c2ccc(=O)n(C)c2)nn(-c2ccccc2)c1N]

5-(5-amino-4-methyl-1-phenyl-1H-pyrazol-3-yl)-1-methylpyridin-2(1H)-one

Step A: Preparation of 5-amino-4-methyl-1-phenyl-1H-pyrazol-3(2H)-one

A mixture of ethyl 2-cyanopropanoate (50.5 g, 397 mmol) and phenylhydrazine (39 mL, 397 mmol) in dioxane (100 mL) was heated at 110° C. for 5 days. The mixture was cooled to ambient temperature and was concentrated to ½ volume. The mixture was cooled in ice bath, treated with cold Et₂O and agitated until a granular suspension formed. The solid was collected via vacuum filtration, washed thoroughly with Et₂O and dried in vacuum provide the title compound as a white powder (34.7 g, 46%). MS (apci) m/z=190.1 (M+H).

Step B: Preparation of 3-bromo-4-methyl-1-phenyl-1H-pyrazol-5-amine

To a suspension of 5-amino-4-methyl-1-phenyl-1H-pyrazol-3(2H)-one (1.60 g, 8.46 mmol) in acetonitrile (30 mL) was added phosphorus oxybromide (3.64 g, 12.7 mmol) in one portion. The reaction mixture was stirred at reflux for 3 hours, cooled to ambient temperature and concentrated in vacuum. The residue was treated with CH₂Cl₂ (50 mL) and saturated NaHCO₃ (50 mL) was slowly added. The mixture was stirred for 30 minutes, the organic layer was separated and the aqueous layer was extracted with CH₂Cl₂ (2×50 mL). The combined organic phases were washed with saturated NaCl (20 mL), dried over Na₂SO₄, filtered and concentrated. The residue was purified by silica column chromatography eluting with 2:1 hexanes/EtOAc to afford the title compound (273 mg, 13% yield) as a white solid. MS (apci) m/z=254.0 (M+H).

Step C: Preparation of 5-(5-amino-4-methyl-1-phenyl-1H-pyrazol-3-yl)-1-methylpyridin-2(1H)-one 3-bromo-4-methyl-1-phenyl-1H-pyrazol-5-amine (763 mg, 3.03 mmol), 1-methyl-5-(4,4,5,5-tetramethyl-1,3,2-dioxaborolan-2-yl)pyridin-2(1H) one (1.42 g, 6.05 mmol), K₂CO₃ (1.67 g, 12.1 mmol) and Pd(PPh₃)₄ (350 mg, 0.30 mmol) were combined in toluene (10 mL), water (5 mL) and EtOH (2.5 mL). The reaction mixture was heated to 95° C. in a sealed tube for 16 hours. The mixture was cooled, filtered and the filtrate was concentrated. The residue was partitioned between water (30 mL) and EtOAc (30 mL). The organic layer was removed and the aqueous layer was extracted with EtOAc (2×20 mL). The combined organic phases were washed with saturated NaCl (20 mL), dried over Na₂SO₄, filtered and concentrated. The residue was purified by silica column chromatography eluting with 2% MeOH/DCM to afford the title compound (504 mg, 59% yield) as a yellow foam. MS (apci) m/z=281.2 (M+H).

Intermediate X4

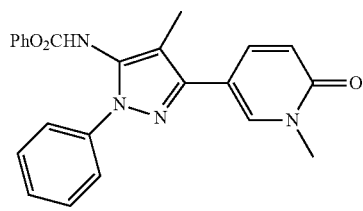

phenyl (4-methyl-3-(1-methyl-6-oxo-1,6-dihydropyridin-3-yl)-1-phenyl-1H-pyrazol-5-yl)carbamate To a suspension of 5-(5-amino-4-methyl-1-phenyl-1H-pyrazol-3-yl)-1-methylpyridin-2(1H)-one (Intermediate X3, 2.80 g, 10.0 mmol) in EtOAc (120 mL) was added 2N NaOH (15.0 mL, 30.0 mmol) followed by phenyl chloroformate (2.50 mL, 20.0 mmol). The mixture was stirred at ambient temperature for 16 hours and was diluted with water (100 mL) and EtOAc (100 mL). The organic layer was removed and the aqueous layer extracted with EtOAc (2×50 mL). The combined organic phases were washed with saturated NaHCO₃ (50 mL) and saturated NaCl (50 mL) and dried over Na₂SO₄. The dried solution was filtered and concentrated to afford the title compound as a pale yellow syrup which was used directly without purification. MS (apci) m/z=401.2 (M+H).

Intermediate X5

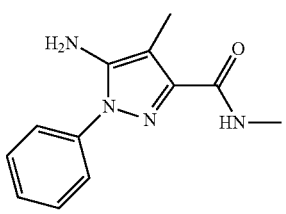 [SMILES: CNC(=O)c1nn(-c2ccccc2)c(N)c1C]

5-amino-N,4-dimethyl-1-phenyl-1H-pyrazole-3-carboxamide

Step A: Preparation of ethyl 5-amino-4-methyl-1-phenyl-1H-pyrazole-3-carboxylate A 1M solution of lithium bis(trimethylsilyl)amide in THF (46.4 mL, 46.4 mmol) was diluted with THF (100 mL) and cooled to −78° C. Propiononitrile (3.08 mL, 53.0 mmol) was added dropwise over 2 minutes and the mixture stirred for 1 hour. Diethyl oxalate (6.00 mL, 44.2 mmol) was added dropwise over 5 minutes and the reaction mixture was stirred at −78° C. for 45 minutes then stirred at 0° C. for 4 hours. The reaction mixture was quenched with H₂O (100 mL) and extracted Et₂O (2×). The aqueous phase was treated with 6M HCl to pH 5 and extracted Et₂O (3×). The combined organic phases were washed with saturated NaCl (100 mL), dried over MgSO₄, filtered and concentrated. The residual yellow syrup was dissolved in EtOH (150 mL), phenylhydrazine hydrochloride (6.15 g, 42.5 mmol) was added and the reaction mixture was heated at reflux for 17 hours. The reaction mixture was cooled and diluted with saturated NaHCO₃ (50 mL) and H₂O (50 mL). The mixture was extracted with CH₂Cl₂ (3×100 mL) and the combined organic extracts were dried over MgSO₄, filtered and concentrated. The residue was purified on a SiO₂ column eluting with a gradient of 0-60% acetone in hexanes to provide the title compound as a yellow solid (7.11 g, 65%). ¹H NMR (CDCl₃) δ 7.58 (m, 2H), 7.49 (m, 2H), 7.40 (m, 1H), 4.41 (q, 2H), 2.21 (s, 311), 1.40 (t, 3H) ppm. MS (apci) m/z=246.1 (M+H).

Step B: Preparation of 5-amino-4-methyl-1-phenyl-1H-pyrazole-3-carboxylic acid

To a solution of ethyl 5-amino-4-methyl-1-phenyl-1H-pyrazole-3-carboxylate (1.52 mg, 6.21 mmol) in 2:1 THF/MeOH (18 mL) was added 2M LiOH (9.31 mL, 18.6 mmol). The reaction mixture was stirred at ambient temperature for 19 hours and was partially concentrated under reduced pressure. The residual aqueous mixture was neutralized with 6M HCl and extracted with 10% MeOH/DCM (3×25 mL). The combined organic extracts were washed with saturated NaCl (50 mL), dried over MgSO$_4$, filtered and concentrated to give the title compound as a yellow solid (1.3 g, 96% yield). MS (apci) m/z=218.1 (M+H).

Step C: Preparation of 5-amino-N,4-dimethyl-1-phenyl-1H-pyrazole-3-carboxamide To a solution of 5-amino-4-methyl-1-phenyl-1H-pyrazole-3-carboxylic acid (223 mg, 1.02 mmol) in acetonitrile (10 mL) were sequentially added DIEA (0.71 mL, 4.10 mmol), methylamine hydrochloride (138 mg, 2.05 mmol), DMF (2 mL) and HATU (428 mg, 1.13 mmol). The reaction mixture was stirred at ambient temperature for 19 hours and partially concentrated under reduced pressure. The residual mixture was purified by reverse-phase column chromatography eluting with 5-60% acetonitrile/water to afford the title compound as a pale yellow solid (182 mg, 77% yield). MS (apci) m/z=231.1 (M+H).

Intermediate X6

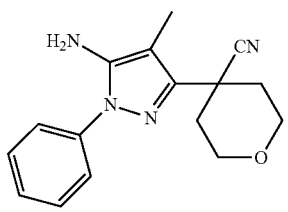 [SMILES: Cc1c(C2(C#N)CCOCC2)nn(-c2ccccc2)c1N]

4-(5-amino-4-methyl-1-phenyl-1H-pyrazol-3-yl)tetrahydro-2H-pyran-4-carbonitrile

Using methyl 4-cyanotetrahydro-2H-pyran-4-carboxylate in Steps B-C of procedure described for synthesis of Intermediate X1, the title compound was prepared as a white solid (53% over 2 steps). $^1$H NMR (CDCl$_3$) δ 7.55-7.46 (m, 4H), 7.34 (t, J=7.4 Hz, 1H), 4.05-4.01 (m, 2H), 3.88 (app dt, J=11.5, 2.0 Hz, 2H), 3.62 (br s, 2H), 2.33-2.19 (m, 4H), 2.11 (s, 3H) ppm.

Intermediate X7

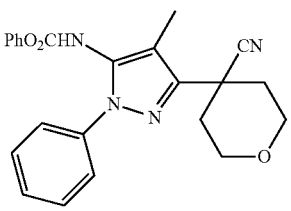

phenyl (3-(4-cyanotetrahydro-2H-pyran-4-yl)-4-methyl-1-phenyl-1H-pyrazol-5-yl)carbamate A fine suspension of 4-(5-amino-4-methyl-1-phenyl-1H-pyrazol-3-yl)tetrahydro-2H-pyran-4-carbonitrile (Intermediate X6, 400 mg, 1.42 mmol) in EtOAc (7 mL) was cooled to 0° C. and 2M NaOH (1700 μL, 3.40 mmol) and phenylchloroformate (213 μL, 1.70 mmol) were added sequentially. The reaction mixture was stirred for 5 minutes at 0° C., and then allowed to warm to ambient temperature and stirred for 3 hours. Additional phenylchloroformate (40 μL) was added and the reaction was stirred for an additional 2 hours. The mixture was washed with H$_2$O (2×), 1M HCl (2×), H$_2$O and saturated NaCl. The organic layer was diluted with an equal volume of hexanes and dried over MgSO$_4$/activated charcoal. The dried solution was eluted through a SiO$_2$ plug, eluting with 50% EtOAc-hexanes. The eluate was concentrated and the residual syrup was treated with 25% Et$_2$O-hexanes. The mixture was sonicated until a granular suspension formed and the suspension was stirred vigorously for 30 minutes. The solid was collected, washed with 25% Et$_2$O-hexanes and dried in vacuum to afford the title compound as a white solid (480 mg, 84%). $^1$H NMR (CDCl$_3$) δ 7.51-7.10 (m, 9H), 6.75 (br s, 1H), 6.51 (s, 1H), 4.07-4.02 (dd, J=9.7, 3.7 Hz, 2H), 3.89 (app dt, J=12.2, 2.3 Hz, 2H), 2.36-2.22 (m, 4H), 2.26 (s, 3H) ppm.

Intermediate X8

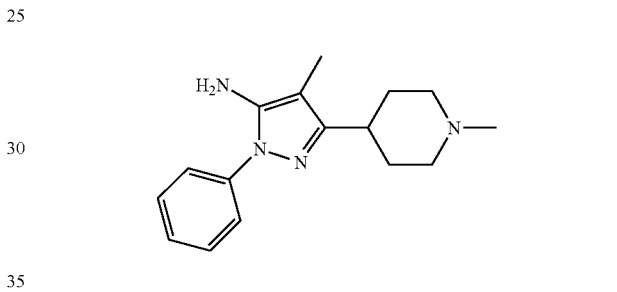

4-methyl-3-(1-methylpiperidin-4-yl)-1-phenyl-1H-pyrazol-5-amine

Step A: Preparation of tert-butyl 4-(5-amino-4-methyl-1-phenyl-1H-pyrazol-3-yl)piperidine-1-carboxylate A 1M solution of LiHMDS (22.0 mL, 22.0 mmol) in dry THF was cooled to −78° C. and propiononitrile (1.73 mL, 24.0 mmol) was added dropwise over 5 minutes. The mixture was stirred at −78° C. for 45 minutes and a solution of 1-tert-butyl 4-ethyl piperidine-1,4-dicarboxylate (5.15 g, 20.0 mmol) in dry THF (20 mL) was added over 5 minutes. The reaction mixture was stirred for 15 hours during which time the temperature slowly increased to ambient during the first 3-4 hours. The reaction mixture was quenched with chilled H$_2$O (100 mL) and mixed. The mixture was extracted with Et$_2$O (3×), the aqueous portion was cooled to 0° C. and 6M HCl was added dropwise to pH 3. The acidified mixture was extracted with EtOAc (3×) and the combined extracts were dried over MgSO$_4$/activated charcoal. The dried solution was filtered through a packed Celite® plug eluting with EtOAc. The filtrate was concentrated to give crude tert-butyl 4-(2-cyanopropanoyl)piperidine-1-carboxylate as a light gold syrup (2.92 g, 55%).

To a solution of the crude tert-butyl 4-(2-cyanopropanoyl)piperidine-1-carboxylate (2.83 g, 10.6 mmol) in absolute EtOH (50 mL) was added phenylhydrazine hydrochloride (1.84 g, 12.8 mmol) and the mixture was stirred at ambient temperature for 2 hours. The reaction mixture was heated at 60° C. for 64 hours, cooled to ambient temperature and concentrated. The residual orange foam was partitioned into H₂O (80 mL) and EtOAc (40 mL) and treated with 1M NaOH to pH 5. The organic layer was separated and the aqueous layer extracted with EtOAc (2×). The combined EtOAc fractions were washed with saturated NaCl, dried over MgSO₄/activated charcoal and diluted with an equal volume of hexanes. The dried solution was eluted through a SiO₂ plug eluting with 50% EtOAc-hexanes. The eluate was concentrated to a yellow foam that was treated with 5% Et₂O-hexanes and agitated to give a granular suspension. The suspension was collected via vacuum filtration, washed with hexanes and dried in vacuum to furnish the title compound as a white powder (2.01 g, 53%). MS (apci) m/z=357.2 (M+H).

Step B: Preparation of 4-methyl-1-phenyl-3-(piperidin-4-yl)-1H-pyrazol-5-amine dihydrochloride To a solution of tert-butyl 4-(5-amino-4-methyl-1-phenyl-1H-pyrazol-3-yl)piperidine-1-carboxylate (1.50 g, 4.21 mmol) in EtOAc (25 mL) was added 4M HCl (15.8 mL, 63.1 mmol) in dioxane and the mixture was stirred at ambient temperature for 3 hours. The reaction mixture was treated with dry MeOH (10 mL) and additional 4M HCl in dioxane (10 mL) and was stirred for 16 hours. The reaction mixture was concentrated, the residual solid was washed EtOAc and dried in vacuum to provide the title compound as a light tan powder (1.40 g, 100%). MS (apci) m/z=257.2 (M+H).

Step C: Preparation of 4-methyl-3-(1-methylpiperidin-4-yl)-1-phenyl-1H-pyrazol-5-amine A fine suspension of 4-methyl-1-phenyl-3-(piperidin-4-yl)-1H-pyrazol-5-amine dihydrochloride (329 mg, 1.00 mmol) in dry CH₃CN (3 mL) was cooled to −10° C. (ice-MeOH bath) and DIEA (574 μL, 3.30 mmol) was added. The mixture was stirred for 5 minutes and the resulting solution was treated with methyl iodide (62.5 μL, 1.00 mmol). The reaction mixture was stirred for 3 hours during which time the bath temperature slowly reached 15° C. The cold reaction mixture was added to H₂O (15 mL) and the mixture treated with 2M NaOH to pH 12. The mixture was extracted with EtOAc (3×) and the combined extracts washed with saturated NaCl. The EtOAc solution was dried over MgSO₄/activated charcoal, filtered through packed Celite® and concentrated to give and oily solid. The solid was treated with Et₂O, mixed for 30 minutes and the suspension filtered. The filtrate was concentrated to provide the title compound as a light tan foam that was dried in vacuum (77 mg, 28%). MS (apci) m/z=271.2 (M+H).

Intermediate Y1

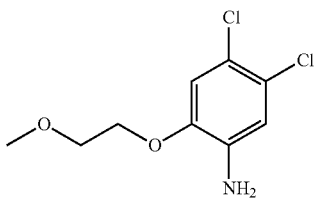

4,5-dichloro-2-(2-methoxyethoxy)aniline

Step A: Preparation of 1,2-dichloro-4-(2-methoxyethoxy)-5-nitrobenzene

A solution of 1,2-dichloro-4-fluoro-5-nitrobenzene (442 mg, 2.00 mmol) in anhydrous 2-methoxyethanol (4 mL) was cooled to 0° C. and sodium hydride (55.6 mg, 2.20 mmol) was added in small portions (vigorous gas evolution). The mixture was stirred at 0° C. for 30 minutes and was treated with 1M HCl (5 mL). The resulting suspension was diluted with H₂O (5 mL) and stirred at ambient temperature for 5 minutes. The solid was collected via vacuum filtration, the product cake was washed with H₂O and dissolved in CH₂Cl₂. The CH₂Cl₂ solution was dried over Na₂SO₄/activated charcoal and filtered through a SiO₂ plug (CH₂Cl₂ for elution). The eluate was concentrated to give the title compound as a light yellow solid that was dried in vacuum (515 mg, 97%). ¹H NMR (CDCl₃) δ 8.00 (s, 1H), 7.26 (s, 1H), 4.25 (dd, J=4.5, 4.5 Hz, 2H), 3.79 (dd, J=4.6, 4.6 Hz, 2H), 3.45 (s, 3H) ppm.

Step B: Preparation of 1,2-dichloro-4-(2-methoxyethoxy)aniline

To a suspension of 2800 Raney Nickel (171 mg, 1.00 mmol, estimated 50 wt. % H₂O) in MeOH (5 mL) was added 1,2-dichloro-4-(2-methoxyethoxy)-5-nitrobenzene (266 mg, 1.00 mmol). The reaction flask was flushed with H₂ gas and the reaction mixture stirred under a balloon atmosphere of H₂ for 21 hours. The reaction flask was flushed with N₂ and the mixture filtered through packed Celite® using MeOH for rinse and elution. The filtrate was concentrated and the residue was dissolved in CH₂Cl₂. The solution was dried over Na₂SO₄/activated charcoal and filtered through a thin pad of SiO₂ eluting with CH₂Cl₂. The filtrate was concentrated to furnish the title compound as a white solid that was dried in vacuum (198 mg, 84%). MS (apci) m/z=236.0 (M+H).

Intermediate Y2

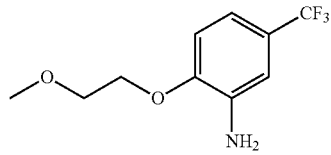 [SMILES: COCCOc1ccc(C(F)(F)F)cc1N]

2-(2-methoxyethoxy)-5-(trifluoromethyl)aniline

Using 1-fluoro-2-nitro-4-(trifluoromethyl)benzene in the procedure described for the synthesis of Intermediate Y1, the title compound was obtained as a white solid (451 mg, 96% over two steps). MS (apci) m/z=236.1 (M+H).

Intermediate Y3

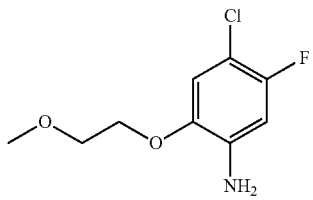

5-chloro-4-fluoro-2-(2-methoxyethoxy)aniline

Using 1-chloro-2,5-difluoro-4-nitrobenzene in the procedure described for the synthesis of Intermediate Y1, the title compound was obtained as a white solid (155 mg, 63% over two steps). MS (apci) m/z=220.1 (M+H).

Intermediate Y4

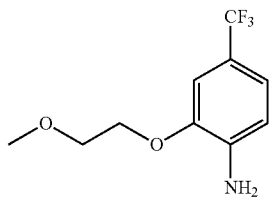

2-(2-methoxyethoxy)-4-(trifluoromethyl)aniline

Step A: Preparation of 2-(2-methoxyethoxy)-1-nitro-4-(trifluoromethyl)benzene

The title compound was prepared using 2-chloro-1-nitro-4-(trifluoromethyl)benzene in Step A of the procedure outlined for Intermediate Y1. The compound was isolated as a white solid (520 mg, 98%). $^1$H NMR (CDCl$_3$) δ 7.89 (d, J=8.4 Hz, 1H), 7.39 (s, 1H), 7.31 (d, J=8.4 Hz, 1H), 4.32 (dd, J=4.5, 4.5 Hz, 2H), 3.81 (dd, J=4.6, 4.6 Hz, 2H), 3.45 (s, 3H) ppm.

Step B: Preparation of 2-(2-methoxyethoxy)-4-(trifluoromethyl)aniline

A mixture of Zn dust (<10 micron, 214 mg, 3.28 mmol) and 2-(2-methoxyethoxy)-1-nitro-4-(trifluoromethyl)benzene (174 mg, 0.656 mmol) in MeOH (3 mL) was cooled to 0° C. and saturated NH$_4$Cl (0.5 mL) was added. The reaction mixture was stirred for 5 minutes and the ice bath was removed. The reaction mixture was stirred at ambient temperature for 16 hours and filtered through packed Celite® (MeOH for rinse and elution). The filtrate was concentrated and the residual solid was treated with 0.5M K$_2$CO$_3$ (10 mL) and extracted with Et$_2$O (3×). The combined extracts were washed with H$_2$O, saturated NaCl and dried over MgSO$_4$. The dried solution was filtered and concentrated to give the title compound as a white solid that was dried in vacuum (154 mg, 100%). $^1$H NMR (CDCl$_3$) δ 7.07 (d, J=8.1 Hz, 1H), 7.00 (s, 1H), 6.71 (d, J=8.2 Hz, 1H), 4.17 (dd, J=4.3, 4.3 Hz, 2H), 3.96 (br s, 2H), 3.76 (dd, J=4.6, 4.6 Hz, 2H), 3.44 (s, 3H) ppm.

Intermediate Y5

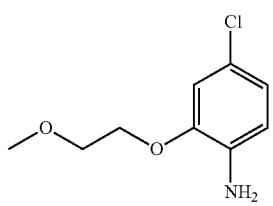

4-chloro-2-(2-methoxyethoxy)aniline

Using 4-chloro-2-fluoro-1-nitrobenzene in the procedure described for the synthesis of Intermediate Y1, the title compound was obtained as a white solid after recrystallization from hexanes (170 mg, 60% over two steps). $^1$H NMR (CDCl$_3$) δ 6.78 (s, 1H), 6.77 (d, J=8.9 Hz, 1H), 6.62 (d, J=8.5 Hz, 1H), 4.12 (dd, J=4.6, 4.6 Hz, 2H), 3.77 (br s, 2H), 3.74 (dd, J=4.7, 4.7 Hz, 2H), 3.44 (s, 3H) ppm.

Intermediate Y6

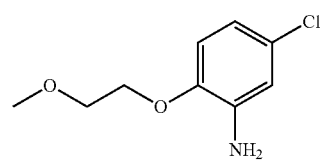

5-chloro-2-(2-methoxyethoxy)aniline

Using 4-chloro-1-fluoro-2-nitrobenzene in the procedure described for Intermediate Y1, the title compound was obtained as a white solid (269 mg, 99% over two steps). In this instance, 50% EtOAc-hexanes was used as the eluent for the SiO$_2$ plug. $^1$H NMR (CDCl$_3$) δ 6.72-6.61 (m, 3H), 4.10 (dd, J=4.6, 4.6 Hz, 2H), 3.87 (br s, 2H), 3.73 (dd, J=4.5, 4.5 Hz, 2H), 3.43 (s, 3H) ppm.

Intermediate Y7

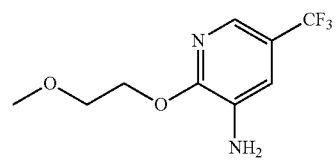 [SMILES: COCCOc1ncc(C(F)(F)F)cc1N]

2-(2-methoxyethoxy)-5-(trifluoromethyl)pyridin-3-amine

Step A: Preparation of 2-(2-methoxyethoxy)-3-nitro-5-(trifluoromethyl)pyridine

To a solution of 3-nitro-5-(trifluoromethyl)pyridin-2(1H)-one (322 mg, 1.50 mmol) in dry DME (10 mL) was added polystyrene-supported PPh$_3$ (754 mg, 1.50 mmol, 1.99 mmol/g) and the mixture was stirred for 10 minutes to allow the resin to swell. The mixture was treated with 2-methoxyethanol (154 µL, 1.95 mmol) followed by DEAD (365 µL, 2.25 mmol) and the reaction mixture was stirred at ambient temperature for 3 hours. The mixture was filtered with thorough washing of the collected resin with CH$_2$Cl$_2$. The filtrate was concentrated to a yellow wax that was partitioned into H$_2$O and Et$_2$O and mixed. The organic layer was separated and the aqueous layer was extracted with Et$_2$O (2×). The Et$_2$O fractions were combined and washed with saturated NaCl, dried over MgSO$_4$ and filtered through a SiO$_2$ plug eluting with Et$_2$O. The eluate was concentrated and the residue purified on a SiO$_2$ column (CH$_2$Cl$_2$ then 25% EtOAc-hexanes) to provide the title compound as a colorless oil (134 mg, 34%). $^1$H NMR (CDCl$_3$) δ 8.66 (s, 8.50 (s, 1H), 4.74 (dd, J=5.5, 4.1 Hz, 2H), 3.83 (dd, J=5.5, 4.2 Hz, 2H), 3.46 (s, 3H) ppm.

Step B: Preparation of 2-(2-methoxyethoxy)-5-(trifluoromethyl)pyridin-3-amine

To a solution of 2-(2-methoxyethoxy)-3-nitro-5-(trifluoromethyl)pyridine (115 mg, 0.432 mmol) in MeOH (2 mL) was added 5% Pd on carbon (92.0 mg, 0.0216 mmol, 50 wt. % H$_2$O) and the reaction vessel was flushed with H$_2$ gas. The reaction mixture was stirred under a balloon atmosphere of H$_2$ for 4.5 hours and was purged with N$_2$ gas. The mixture was filtered through packed Celite® using MeOH for rinsing and elution. The filtrate was concentrated and the residual solid was dissolved in Et$_2$O. The solution was dried over MgSO$_4$, filtered and concentrated to furnish the title compounds as a white solid that dried in vacuum (98 mg, 96%). $^1$H NMR (CDCl$_3$) δ 7.81 (s, 1H), 7.01 (s, 1H), 4.58 (dd, J=4.6, 3.5 Hz, 2H), 3.83 (br s, 2H), 3.78 (dd, J=4.7, 3.4 Hz, 2H), 3.43 (s, 3H) ppm.

Intermediate Y8

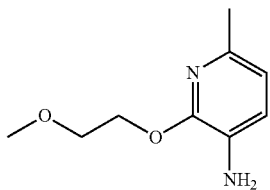

2-(2-methoxyethoxy)-6-methylpyridin-3-amine

Step A: Preparation of 2-(2-methoxyethoxy)-6-methyl-3-nitropyridine

Anhydrous 2-methoxyethanol (3 mL) was cooled to 0° C. and sodium hydride (56.8 mg, 2.25 mmol) was added in small portions (vigorous, spontaneous gas evolution). The mixture was stirred for 5 minutes and 2-chloro-6-methyl-3-nitropyridine (264 mg, 1.50 mmol) was added. The mixture was stirred for 2 hours during which time the bath temp reached 10° C. The cold reaction mixture was treated with H$_2$O (9 mL) and the resulting suspension was stirred at ambient temperature for 5 minutes. The solid was collected, washed with H$_2$O and dried in vacuum to provide the title compounds a brown powder (230 mg, 72%). $^1$H NMR (CDCl$_3$) δ 8.20 (d, J=8.0 Hz, 1H), 6.84 (d, J=8.1 Hz, 1H), 4.64 (dd, J=4.8, 4.8 Hz, 2H), 3.81 (dd, J=4.9, 4.9 Hz, 2H), 3.45 (s, 3H), 2.52 (s, 3H) ppm.

Step B: Preparation of 2-(2-methoxyethoxy)-6-methylpyridin-3-amine

To a solution of 2-(2-methoxyethoxy)-6-methyl-3-nitropyridine (115 mg, 0.542 mmol) in MeOH (2 mL) was added 5% Pd on carbon (115 mg, 0.0271 mmol, 50 wt. % H$_2$O) and the reaction vessel was flushed with H$_2$ gas. The reaction mixture was stirred under a balloon atmosphere of H$_2$ for 6 hours, purged with N$_2$ gas and filtered through packed Celite® (MeOH for rinse and elution). The filtrate was concentrated and the residual solid was dissolved in CH$_2$Cl$_2$. The solution was dried over Na$_2$SO$_4$, filtered and concentrated to provide the title compound as a white solid that dried in vacuum (91 mg, 92%). $^1$H NMR (CDCl$_3$) δ 6.81 (d, J=7.5 Hz, 1H), 6.54 (d, J=7.5 Hz, 1H), 4.52 (dd, J=4.7, 4.7 Hz, 2H), 3.76 (dd, J=4.8, 4.8 Hz, 2H), 3.58 (br s, 2H), 3.43 (s, 3H), 2.33 (s, 3H) ppm.

Intermediate Y9

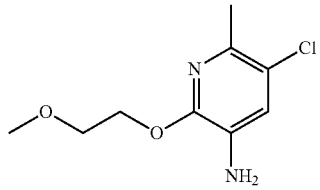

5-chloro-2-(2-methoxyethoxy)-6-methylpyridin-3-amine

Step A: Preparation of 3-chloro-6-(2-methoxyethoxy)-2-methyl-5-nitropyridine

A mixture of 2-(2-methoxyethoxy)-6-methyl-3-nitropyridine (Intermediate Y8, Step A, 100 mg, 0.471 mmol) and N-chlorosuccinimide (83.5 mg, 0.613 mmol) in dry DMF (2.0 mL) was stirred at 50° C. for 60 hours. The reaction mixture was cooled to ambient temperature and was added to chilled half-saturated NaHCO$_3$ (6 mL). The mixture was stirred at ambient temperature for 5 minutes and treated with 1M NaOH to pH 12. The mixture was extracted with Et$_2$O (3×) and the combined extracts washed with H$_2$O and saturated NaCl (2×). The organic fraction was dried over MgSO$_4$, filtered through a SiO$_2$ plug (Et$_2$O elution) and concentrated. The residue was purified on a SiO$_2$ column (10% EtOAc-hexanes) to provide the title compound as a colorless oil (60 mg, 52%). $^1$H NMR (CDCl$_3$) δ 8.27 (s, 1H), 4.63 (dd, J=4.8, 3.6 Hz, 2H), 3.80 (dd, J=4.8, 3.6 Hz, 2H), 3.45 (s, 3H), 2.59 (s, 3H) ppm.

Step B: Preparation of 5-chloro-2-(2-methoxyethoxy)-6-methylpyridin-3-amine

A mixture of 2800 Raney Nickel (39.6 mg, 0.231 mmol, estimated 50 wt. % H$_2$O) and 3-chloro-6-(2-methoxyethoxy)-2-methyl-5-nitropyridine (57.0 mg, 0.231 mmol) in MeOH (2 mL) was flushed with H$_2$ gas and stirred under a balloon atmosphere of H$_2$ for 4 hours. The reaction mixture was purged with N$_2$ gas, filtered through packed Celite® (MeOH rinse and elution) and concentrated. The residue was dissolved in CH$_2$Cl$_2$ and dried over Na$_2$SO$_4$. The solution was filtered, concentrated and the residual white solid dried in vacuum to provide the title compound (49 mg, 98%). MS (apci) m/z=217.1 (M+H).

Intermediate Y10

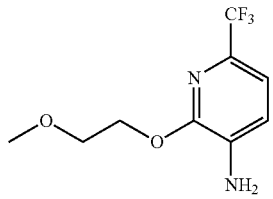

2-(2-methoxyethoxy)-6-(trifluoromethyl)pyridin-3-amine

Step A: Preparation of 2-(2-methoxyethoxy)-3-nitro-6-(trifluoromethyl)pyridine

Anhydrous 2-methoxyethanol (3 mL) was cooled to 0° C. and sodium hydride (39.3 mg, 1.56 mmol) was added in small portions (vigorous, spontaneous gas evolution). The mixture was stirred for 5 minutes and 2-chloro-3-nitro-6-(trifluoromethyl)pyridine (235 mg, 1.04 mmol) was added. The mixture was stirred for 2 hours during which time the bath temperature reached 10° C. The cold reaction mixture was treated with H$_2$O (15 mL) and the resulting emulsion stirred at ambient temperature for 15 minutes. The mixture was extracted with Et$_2$O (3×) and the combined extracts were washed with H$_2$O (2×), saturated NaCl and dried over MgSO$_4$. The dried solution was eluted through a SiO$_2$ plug (Et$_2$O elution) and concentrated. The residual light gold oil was dried in vacuum to provide the title compound (270 mg, 98%). $^1$H NMR (CDCl$_3$) δ 8.38 (d, J=8.0 Hz, 1H), 7.41 (d, J=8.0 Hz, 1H), 4.71 (dd, J=4.7, 4.7 Hz, 2H), 3.82 (dd, J=4.7, 4.7 Hz, 2H), 3.45 (s, 3H) ppm.

Step B: Preparation of 2-(2-methoxyethoxy)-6-(trifluoromethyl)pyridin-3-amine

A mixture of 2800 Raney Nickel (96.6 mg, 0.564 mmol, estimated 50 wt. % H$_2$O) and 2-(2-methoxyethoxy)-3-nitro-6-(trifluoromethyl)pyridine (150 mg, 0.564 mmol) in MeOH (3 mL) was flushed with H$_2$ gas and stirred under a balloon atmosphere of H$_2$ for 15 hours. Additional Raney Nickel (~100 mg) was added and the reaction mixture was stirred under a H$_2$ balloon for 2 hours. The reaction mixture was purged with N$_2$, filtered through packed Celite® (MeOH rinse and elution) and concentrated. The residual solid was dissolved in CH$_2$Cl$_2$, dried over Na$_2$SO$_4$, filtered and concentrated. The residual white solid was dried in vacuum to provide the title compound (128 mg, 96%). $^1$H NMR (CDCl$_3$) δ 7.10 (d, J=7.8 Hz, 1H), 6.87 (d, J=7.8 Hz, 1H), 4.58 (dd, J=4.7, 4.7 Hz, 2H), 4.03 (br s, 2H), 3.77 (dd, J=4.7, 4.7 Hz, 2H), 3.43 (s, 3H) ppm.

Intermediate Y11

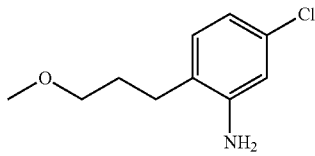

5-chloro-2-(3-methoxypropyl)aniline

Step A: Preparation of 1-chloro-4-(3-methoxypropyl)benzene

A suspension of sodium hydride (0.444 g, 17.6 mmol) in dry THF (25 mL) was cooled to 0° C. and 3-(4-chlorophenyl)propan-1-ol (2.00 g, 11.7 mmol) was added. The mixture was stirred for 5 minutes, allowed to reach ambient temperature and stirred for 15 minutes. The mixture was cooled to 0° C. and methyl iodide (0.879 mL, 14.1 mmol) was added. The reaction mixture was stirred for 5 minutes, allowed to reach ambient temperature and stirred for 7 hours. The reaction mixture was slowly poured into 1M HCl (30 mL) containing crushed ice (30 mL) and mixed. The mixture was extracted with Et$_2$O (3×) and the combined extracts were washed with H$_2$O (2×), saturated NaCl and dried over MgSO$_4$/activated charcoal. The dried solution was eluted through a SiO$_2$ plug (Et$_2$O elution) and concentrated to provide the title compound as a colorless oil (2.13 g, 98%). $^1$H NMR (CDCl$_3$) δ 7.24 (d, J=8.3 Hz, 2H), 7.11 (d, J=8.2 Hz, 2H), 3.36 (t, J=6.3 Hz, 2H), 3.33 (s, 3H), 2.66 (t, J=7.4 Hz, 2H), 1.85 (m, 2H) ppm.

Step B: Preparation of 4-chloro-1-(3-methoxypropyl)-2-nitrobenzene

Nitronium tetrafluoroborate (615 mg, 4.40 mmol) in dry CH$_2$Cl$_2$ (25 mL) was cooled to −78° C. and 1-chloro-4-(3-methoxypropyl)benzene (739 mg, 4.00 mmol) was added. The reaction mixture was stirred for 4 hours during which time the temperature slowly reached 0° C. The reaction mixture was stirred at 0° C. for 30 minutes and treated with saturated NaHCO$_3$ (20 mL) The mixture was allowed to reach ambient temperature and mixed for 30 minutes. The organic layer was separated, washed with H$_2$O and dried over Na$_2$SO$_4$. The dried solution was eluted through a SiO$_2$ plug (CH$_2$Cl$_2$) and concentrated. The residual oil was purified on a SiO$_2$ column (10% EtOAc-hexanes) to furnish the title compound as a colorless oil (330 mg, 36%). $^1$H NMR (CDCl$_3$) δ 7.90 (s, 1H), 7.49 (d, J=8.3 Hz, 1H), 7.32 (d, J=8.3 Hz, 1H), 3.40 (t, J=6.1 Hz, 2H), 3.34 (s, 3H), 2.95 (t, J=7.6 Hz, 2H), 1.91 (m, 2H) ppm.

Step C: Preparation of 5-chloro-2-(3-methoxypropyl)aniline

A mixture of 2800 Raney Nickel (239 mg, 1.39 mmol, estimated 50 wt. % H$_2$O) and 4-chloro-1-(3-methoxypropyl)-2-nitrobenzene (320 mg, 1.39 mmol) in MeOH (4 mL) was flushed with H$_2$ gas and stirred under a balloon atmosphere of H$_2$ for 15 hours. The reaction mixture was purged with N$_2$ gas, filtered through packed Celite® (MeOH rinse and elution) and concentrated. The residue was dissolved in CH$_2$Cl$_2$, dried over Na$_2$SO$_4$, filtered and concentrated. The residual syrup was purified on a SiO$_2$ column (CH$_2$Cl$_2$) to secure the title compound as a colorless oil (161 mg, 58%). $^1$H NMR (CDCl$_3$) δ 6.93 (d, J=8.2 Hz, 1H), 6.67 (d, J=10.1 Hz, 1H), 6.66 (s, 1H), 3.94 (br s, 2H), 3.37 (t, J=5.9 Hz, 2H), 3.35 (s, 3H), 2.55 (t, J=7.2 Hz, 2H), 1.84 (m, 2H) ppm.

Intermediate Y12

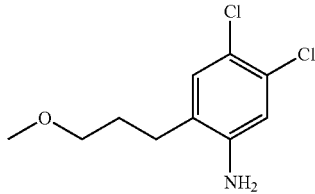

4,5-dichloro-2-(3-methoxypropyl)aniline

Step A: Preparation of 3-(3,4-dichlorophenyl)propan-1-ol

To 1M BH$_3$-THF complex in THF (200 mL, 200 mmol) was added 3-(3,4-dichlorophenyl)propanoic acid (11.0 g, 50.0 mmol) in portions over 5 minutes (gas evolution). The mixture was stirred at ambient temperature for 15 minutes and was heated at reflux for 17 hours. The reaction mixture was cooled to ambient temperature and cooled in an ice bath. The mixture was slowly quenched with cold 6M HCl (100 mL) and the mixture stirred at ambient temperature for 1 hour. The THF was removed in vacuum, the remaining aqueous mixture diluted with H₂O (200 mL) and extracted with Et₂O (3×). The extracts were combined, washed with H₂O and saturated NaCl and dried over MgSO₄. The dried solution was eluted through a SiO₂ plug (Et₂O) and concentrated. The residual oil was purified on a SiO₂ column (20% EtOAc-hexanes) to furnish the title compound as a colorless oil (9.45 g, 92%). $^1$H NMR (CDCl₃) δ 7.34 (d, J=7.4 Hz, 1H), 7.29 (s, 1H), 7.03 (d, J=7.5 Hz, 1H), 3.66 (t, J=6.3 Hz, 2H), 2.68 (t, J=7.4 Hz, 2H), 1.86 (m, 2H), 1.53 (s, 1H) ppm.

Step B: Preparation of 1,2-dichloro-4-(3-methoxypropyl)benzene

To a solution of 3-(3,4-dichlorophenyl)propan-1-ol (9.34 g, 45.5 mmol) in dry THF (90 mL) was added sodium hydride (1.73 g, 68.3 mmol) and the mixture was stirred at ambient temperature for 15 minutes. Methyl iodide (3.42 mL, 54.7 mmol) was added and the reaction mixture was stirred for 15 hours. The reaction mixture was slowly quenched with cold 0.5 M HCl (250 mL) and was concentrated to an aqueous mixture. The mixture was extracted with Et₂O (3×) and the combined extracts were washed with H₂O (2×), saturated NaCl and dried over MgSO₄/activated charcoal. The dried solution was eluted through a SiO₂ plug (Et₂O elution) and concentrated to provide the title compound as a colorless oil after drying in vacuum (9.64 g, 97%). $^1$H NMR (CDCl₃) δ 7.31 (d, J=8.2 Hz, 1H), 7.28 (s, 1H), 7.02 (d, J=8.9 Hz, 1H), 3.37 (t, J=6.2 Hz, 2H), 3.34 (s, 3H), 2.65 (t, J=7.2 Hz, 2H), 1.85 (m, 2H) ppm.

Step C: Preparation of 1,2-dichloro-4-(3-methoxypropyl)-5-nitrobenzene

Nitronium tetrafluoroborate (6.74 g, 48.2 mmol) in dry CH₂Cl₂ (200 mL) was cooled to −15° C. (ice/MeOH bath) and 1,2-dichloro-4-(3-methoxypropyl)benzene (9.60 g, 43.8 mmol) in dry CH₂Cl₂ (25 mL) was added. The mixture was stirred for 4 hours during which time the temperature slowly rose to ambient. The reaction mixture was treated with cold, saturated NaHCO₃ (100 mL) and H₂O (100 mL) and mixed for 30 minutes. The organic layer was separated, washed with H₂O and dried over Na₂SO₄. The dried solution was eluted through a SiO₂ plug (CH₂Cl₂) and concentrated. The residual light yellow oil was dried in vacuum to provide the crude title compound containing approximately 15% of a minor nitro isomer (11.1 g, 96%). $^1$H NMR (CDCl₃) δ 8.05 (s, 1H), 7.48 (s, 1H), 3.41 (t, J=6.0 Hz, 2H), 3.34 (s, 3H), 2.96 (dd, J=7.6, 6.3 Hz, 2H), 1.91 (m, 2H) ppm.

Step D: Preparation of 4,5-dichloro-2-(3-methoxypropyl)aniline

A mixture of 2800 Raney Nickel (2.92 g, 17.0 mmol, estimated 50 wt. % H₂O) and crude 1,2-dichloro-4-(3-methoxypropyl)-5-nitrobenzene (11.1 g, 34.0 mmol) in MeOH (140 mL) was flushed with H₂ gas and stirred under a balloon atmosphere of H₂ for 20 hours. The mixture was purged with N₂ gas, filtered through packed Celite® (MeOH rinse and elution) and concentrated. The residual solid was dissolved in CH₂Cl₂, dried over Na₂SO₄/activated charcoal, filtered and concentrated. The crude product was purified on a SiO₂ column (CH₂Cl₂ then 30% EtOAc-hexanes for elution). The purified solid was washed with hexanes and dried in vacuum to afford the title compound as a white solid. Additional product crystallized from the hexanes washes as long colorless needles (7.40 g, 93% combined yield). $^1$H NMR (CDCl₃) δ 7.06 (s, 1H), 6.73 (s, 1H), 3.93 (br s, 2H), 3.37 (t, J=5.8 Hz, 2H), 3.35 (s, 3H), 2.53 (t, J=7.3 Hz, 2H), 1.83 (m, 2H) ppm.

Intermediate Y13

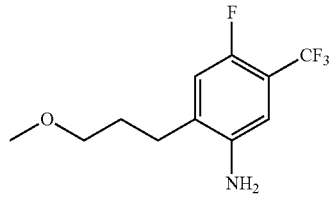 [SMILES: COCCCc1cc(F)c(C(F)(F)F)cc1N]

4-fluoro-2-(3-methoxypropyl)-5-(trifluoromethyl)aniline

Utilizing 3-(3-fluoro-4-(trifluoromethyl)phenyl)propanoic acid in the procedure described for the preparation of Intermediate Y12, the title compound was obtained as a white solid (562 mg, 49% over 4 steps). $^1$H NMR (CDCl₃) δ 6.87 (d, J=10.9 Hz, 1H), 6.82 (d, J=6.2 Hz, 1H), 3.91 (br s, 2H), 3.38 (t, J=5.8 Hz, 2H), 3.36 (s, 3H), 2.61 (t, J=7.3 Hz, 2H), 1.87 (m, 2H) ppm.

Intermediate Z1

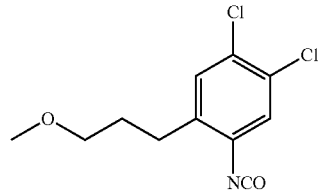

1,2-dichloro-4-isocyanato-5-(3-methoxypropyl)benzene

To a solution of triphosgene (1.88 g, 6.21 mmol) in dry CH₂Cl₂ (50 mL) was added a solution of 4,5-dichloro-2-(3-methoxypropyl)aniline (Intermediate Y12, 4.00 g, 17.1 mmol) and DIEA (5.41 mL, 31.1 mmol) in dry CH₂Cl₂ (30 mL) dropwise over 1.5 hours. The mixture was stirred for 2 hours and concentrated. The residual solid was stirred vigorously in dry Et₂O for 3 hours, filtered through packed Celite® (Et₂O elution) and the filtrate concentrated to provide the title compound as a light bronze oil (4.04 g, 100%). $^1$H NMR (CDCl₃) δ 7.28 (s, 1H), 7.20 (s, 1H), 3.39 (t, J=6.1 Hz, 2H), 3.35 (s, 3H), 2.68 (t, J=7.4 Hz, 2H), 1.85 (m, 2H) ppm.

Intermediate X9

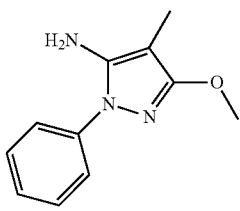

3-methoxy-4-methyl-1-phenyl-1H-pyrazol-5-amine

To a fine suspension of 5-amino-4-methyl-1-phenyl-1H-pyrazol-3(2H)-one (Intermediate X3, Step A, 300 mg, 1.59 mmol) in 2:1 $CH_2Cl_2$-MeOH (6.0 mL) was added 2M $TMSCHN_2$ (951 μL, 1.90 mmol) in hexanes followed by additional MeOH (1.0 mL). The reaction mixture was stirred at ambient temperature for 2 hours and additional 2M $TMSCHN_2$ in hexanes (1.0 mL) was added. The reaction mixture was for 2 hours and was concentrated. The residual syrup was partitioned into $H_2O$ and 50% EtOAc-hexanes and stirred for 15 minutes. The organic layer was removed and the aqueous layer was extracted with 50% EtOAc-hexanes (2x). The combined organic fractions were washed with saturated NaCl and dried over $MgSO_4$/activated charcoal. The organic mixture was eluted through a $SiO_2$ plug eluting with 50% EtOAc-hexanes and concentrated to give the title compound as a white solid after drying in vacuum (153 mg, 47%). $^1$H NMR ($CDCl_3$) δ 7.60-7.32 (m, 5H), 3.94 (s, 3H), 3.59 (br s, 2H), 1.83 (s, 3H) ppm.

Intermediate X10

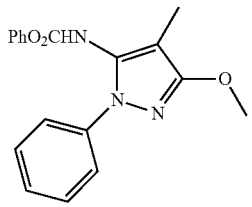

phenyl (3-methoxy-4-methyl-1-phenyl-1H-pyrazol-5-yl)carbamate

A solution of 3-methoxy-4-methyl-1-phenyl-1H-pyrazol-5-amine (Intermediate X9, 140 mg, 0.689 mmol) in EtOAc (3.0 mL) was cooled to 0° C. and NaOH (689 μL, 1.38 mmol) was added followed by phenylchloroformate (129 μL, 1.03 mmol). The reaction mixture was stirred for 5 minutes, then allowed to reach ambient temperature and stirred for 3 hours. The mixture was diluted with hexanes (3 mL) and washed with $H_2O$, 1M HCl, $H_2O$ and saturated NaCl. The organic portion was dried over $MgSO_4$/activated charcoal and filtered through a $SiO_2$ plug eluting with 50% EtOAc-hexanes. The eluate was concentrated and the residual colorless syrup was dried in vacuum. The syrup was dissolved in dry $Et_2O$ and concentrated to a white foam. The foam was sonicated under hexanes until a fine granular suspension formed. The solvent was decanted, the residual solid washed with hexanes and dried in vacuum to provide the title compound as a white solid (185 mg, 83%). $^1$H NMR ($CDCl_3$) δ 7.68-7.02 (m, 9H), 6.89-6.67 (m, 1H), 6.47 (s, 1H), 3.79 (s, 3H), 1.96 (s, 3H) ppm.

Intermediate X11

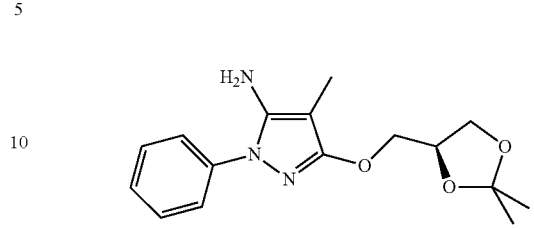

(S)-3-((2,2-dimethyl-1,3-dioxolan-4-yl)methoxy)-4-methyl-1-phenyl-1H-pyrazol-5-amine A mixture of 5-amino-4-methyl-1-phenyl-1H-pyrazol-3(2H)-one (Intermediate X3, Step A, 1.04 g, 5.50 mmol), powdered potassium carbonate (2.07 g, 15.0 mmol) and cesium iodide (1.43 g, 5.50 mmol) in dry DMF (5 mL) was stirred at ambient temperature for 5 minutes. (R)-4-(chloromethyl)-2,2-dimethyl-1,3-dioxolane (0.768 g, 5.00 mmol) was added and the reaction mixture was stirred at 120° C. for 24 hours. The mixture was cooled to ambient temperature, diluted with cold $H_2O$ (12 mL) and extracted with 50% EtOAc-hexanes (3x). The combined extracts were washed with saturated NaCl, dried over $MgSO_4$/activated carbon and filtered through a $SiO_2$ plug capped with a layer of $MgSO_4$ (50% EtOAc-hexanes for elution). The filtrate was concentrated to give the title compound as a light gold syrup (515 mg, 34%). MS (apci) m/z=304.2 (M+H).

Intermediate X12

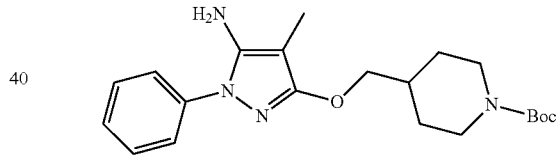

tert-butyl 4-(((5-amino-4-methyl-1-phenyl-1H-pyrazol-3-yl)oxy)methyl)piperidine-1-carboxylate A mixture of 5-amino-4-methyl-1-phenyl-1H-pyrazol-3(2H)-one (Intermediate X3 Step A, 1.00 g, 5.29 mmol), tert-butyl 4-(bromomethyl)piperidine-1-carboxylate (1.62 g, 5.81 mmol) and potassium carbonate (1.83 g, 13.2 mmol) in dry DMF (10 mL) was heated at 70° C. for 48 hours. The mixture was cooled to ambient temperature and was added to an ice/water mixture (60 mL) and stirred until all of the suspended $K_2CO_3$ was dissolved. The mixture was extracted with 50% EtOAc/hexanes and the combined extracts were washed with $H_2O$ and saturated NaCl and dried over $MgSO_4$/activated charcoal. The solution was eluted through a thin $SiO_2$ plug (50% EtOAc/hexanes for elution) and concentrated. The residue was purified on a $SiO_2$ column (10%, 20% EtOAc-hexanes). This provided the title compound as a white foam upon drying in vacuum (971 mg, 48%). MS (apci) m/z=387.2 (M+H).

The intermediate compounds in Table 1-a were prepared according the method used for the synthesis of Intermediate X12 using the appropriate alkylating agent and solvents for the $SiO_2$ plug and column chromatography if necessary.

TABLE 1-a

| Intermediate # | Structure | Name | MS (apci) m/z |
|---|---|---|---|
| X13 | 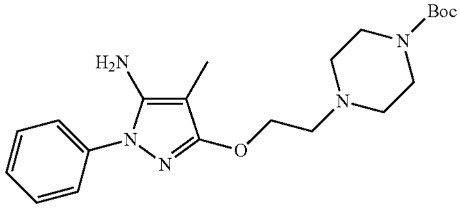 [SMILES: Cc1c(OCCN2CCN(C(=O)OC(C)(C)C)CC2)nn(-c2ccccc2)c1N] | tert-butyl 4-(2-((5-amino-4-methyl-1-phenyl-1H-pyrazol-3-yl)oxy)ethyl)piperazine-1-carboxylate | 402.2 (M + H) |
| X14 | 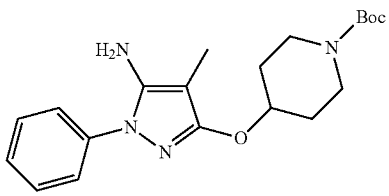 [SMILES: Cc1c(OC2CCN(C(=O)OC(C)(C)C)CC2)nn(-c2ccccc2)c1N] | tert-butyl 4-((5-amino-4-methyl-1-phenyl-1H-pyrazol-3-yl)oxy)piperidine-1-carboxylate | 373.2 (M + H) |
| X15 | 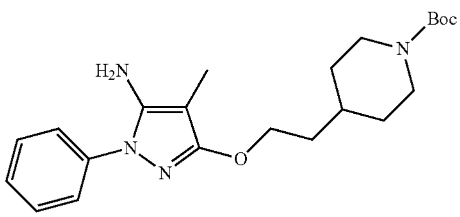 | tert-butyl 4-(2-((5-amino-4-methyl-1-phenyl-1H-pyrazol-3-yl)oxy)ethyl)piperidine-1-carboxylate | 401.2 (M + H) |
| X16 | 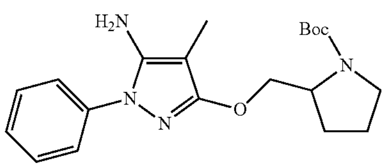 [SMILES: Cc1c(OCC2CCCN2C(=O)OC(C)(C)C)nn(-c2ccccc2)c1N] | tert-butyl 2-(((5-amino-4-methyl-1-phenyl-1H-pyrazol-3-yl)oxy)methyl)pyrrolidine-1-carboxylate | 373.2 (M + H) |
| X17 | 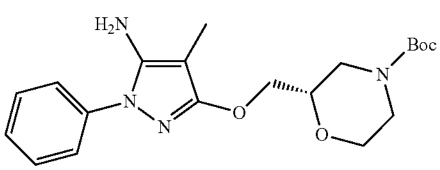 [SMILES: Cc1c(OC[C@@H]2CN(C(=O)OC(C)(C)C)CCO2)nn(-c2ccccc2)c1N] | (S)-tert-butyl 2-(((5-amino-4-methyl-1-phenyl-1H-pyrazol-3-yl)oxy)methyl)morpholine-4-carboxylate | 389.2 (M + H) |
| X18 | 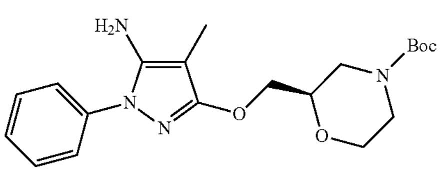 [SMILES: Cc1c(OC[C@H]2CN(C(=O)OC(C)(C)C)CCO2)nn(-c2ccccc2)c1N] | (R)-tert-butyl 2-(((5-amino-4-methyl-1-phenyl-1H-pyrazol-3-yl)oxy)methyl)morpholine-4-carboxylate | 389.2 (M + H) |
| X19 | 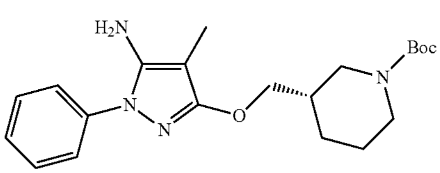 [SMILES: Cc1c(OC[C@H]2CCCN(C(=O)OC(C)(C)C)C2)nn(-c2ccccc2)c1N] | (S)-tert-butyl 3-(((5-amino-4-methyl-1-phenyl-1H-pyrazol-3-yl)oxy)methyl)piperidine-1-carboxylate | 387.2 (M + H) |
| X20 | 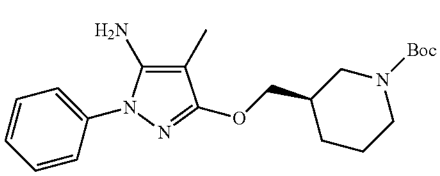 [SMILES: Cc1c(OC[C@@H]2CCCN(C(=O)OC(C)(C)C)C2)nn(-c2ccccc2)c1N] | (R)-tert-butyl 3-(((5-amino-4-methyl-1-phenyl-1H-pyrazol-3-yl)oxy)methyl)piperidine-1-carboxylate | 387.2 (M + H) |

TABLE 1-a-continued

| Intermediate # | Structure | Name | MS (apci) m/z |
|---|---|---|---|
| X21 | 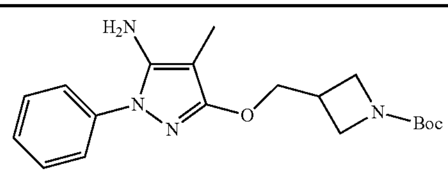 | tert-butyl 3-(((5-amino-4-methyl-1-phenyl-1H-pyrazol-3-yl)oxy)methyl)azetidine-1-carboxylate | 359.2 (M + H) |
| X22 | 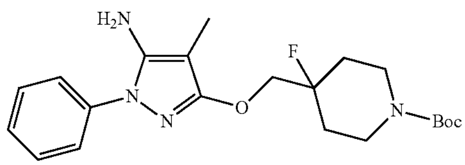 [SMILES: Cc1c(OCC2(F)CCN(C(=O)OC(C)(C)C)CC2)nn(-c2ccccc2)c1N] | tert-butyl 4-(((5-amino-4-methyl-1-phenyl-1H-pyrazol-3-yl)oxy)methyl)-4-fluoropiperidine-1-carboxylate | 405.3 (M + H) |

Intermediate X23

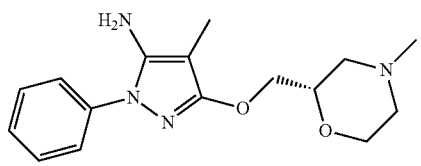 [SMILES: Cc1c(OC[C@@H]2CN(C)CCO2)nn(-c2ccccc2)c1N]

(S)-4-methyl-3-((4-methylmorpholin-2-yl)methoxy)-1-phenyl-1H-pyrazol-5-amine

Step A: Preparation of (S)-4-methyl-3-(morpholin-2-ylmethoxy)-1-phenyl-1H-pyrazol-5-amine (S)-tert-butyl 2-(((5-amino-4-methyl-1-phenyl-1H-pyrazol-3-yl)oxy)methyl)morpholine-4-carboxylate (Intermediate X17, 332 mg, 0.855 mmol) was dissolved in chilled 5M HCl in iPrOH (10 mL) and the solution was stirred at ambient temperature for 2 hours. The mixture was concentrated and the residual white solid was washed with Et$_2$O and dried in vacuum. The solid was dissolved in H$_2$O (5 mL) and the solution was adjusted to pH 13 with the addition of 2M NaOH. The solution was saturated with NaCl(s) and EtOAc (5 mL) was added. The biphasic mixture was stirred for 1 hour, the organic layer was removed and the aqueous portion extracted with EtOAc (2×). The combined EtOAc fractions were dried over MgSO$_4$, filtered and concentrated. The resulting colorless syrup was dried in vacuum to provide the title compound as a white foam (220 mg, 89%). MS (apci) m/z=289.2 (M+H).

Step B: (S)-4-methyl-3-((4-methylmorpholin-2-yl)methoxy)-1-phenyl-1H-pyrazol-5-amine A mixture of (S)-4-methyl-3-(morpholin-2-ylmethoxy)-1-phenyl-1H-pyrazol-5-amine (218 mg, 0.756 mmol) and NaBH(OAc)$_3$ (506 mg, 2.27 mmol) in 1,2-DCE (4 mL) was cooled to 0° C. and 37% aqueous formaldehyde (62.5 µL, 0.832 mmol) was added. The mixture was stirred for 15 hours during which time the solution gradually reached ambient temperature. The mixture was treated with chilled 1.0M NaOH (8 mL) and stirred for 30 minutes. NaCl(s) was added to saturation and the organic layer was removed. The aqueous potion was extracted with CH$_2$Cl$_2$ and the combined organic fractions were dried over Na$_2$SO$_4$/activated charcoal. The solution was filtered through a SiO$_2$ plug capped with a layer of MgSO$_4$, eluting with CH$_2$Cl$_2$, EtOAc then 5% (9:1 MeOH/NH$_4$OH)/EtOAc to provide the title compound as a colorless waxy solid that was dried in vacuum (155 mg, 68%). MS (apci) m/z=303.2 (M+H).

The intermediate compounds of Table 1-b were prepared according the method used for the synthesis of Intermediate X23 using the appropriate Boc-protected amine intermediate and solvents for the SiO$_2$ plug and column chromatography if necessary.

TABLE 1-b

| Intermediate # | Structure | Name | MS (apci) m/z |
|---|---|---|---|
| X24 | 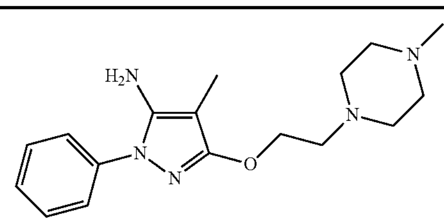 | 4-methyl-3-(2-(4-methylpiperazin-1-yl)ethoxy)-2-phenyl-1H-pyrazol-5-amine | 316.2 (M + H) |

TABLE 1-b-continued

| Intermediate # | Structure | Name | MS (apci) m/z |
|---|---|---|---|
| X25 | 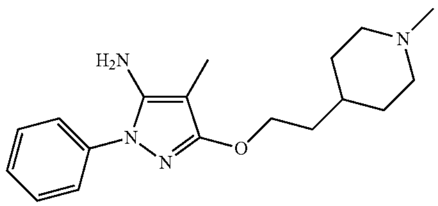 [SMILES: Cc1c(OCCC2CCN(C)CC2)nn(-c2ccccc2)c1N] | 4-methyl-3-(2-(1-methylpiperidin-4-yl)ethoxy)-1-phenyl-1H-pyrazol-5-amine | 315.2 (M + H) |
| X26 | 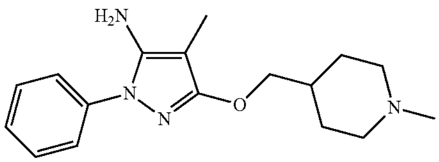 [SMILES: Cc1c(OCC2CCN(C)CC2)nn(-c2ccccc2)c1N] | 4-methyl-3-((1-methylpiperidin-4-yl)methoxy)-1-phenyl-1H-pyrazol-5-amine | 301.2 (M + H) |
| X27 | 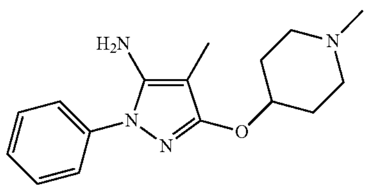 [SMILES: Cc1c(OC2CCN(C)CC2)nn(-c2ccccc2)c1N] | 4-methyl-3-((1-methylpiperidin-4-yl)oxy)-1-phenyl-1H-pyrazol-5-amine | 287.2 (M + H) |
| X28 | 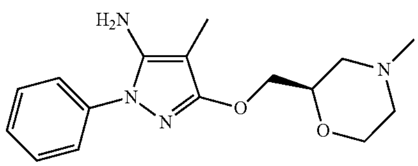 [SMILES: Cc1c(OC[C@H]2CN(C)CCO2)nn(-c2ccccc2)c1N] | (R)-4-methyl-3-((4-methylmorpholin-2-yl)methoxy)-1-phenyl-1H-pyrazol-5-amine | 303.2 (M + H) |
| X29 | 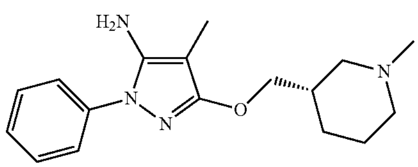 | (S)-4-methyl-3-((1-methylpiperidin-3-yl)methoxy)-1-phenyl-1H-pyrazol-5-amine | 301.2 (M + H) |
| X30 | 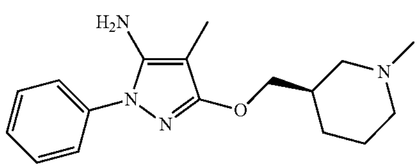 [SMILES: Cc1c(OC[C@@H]2CCCN(C)C2)nn(-c2ccccc2)c1N] | (R)-4-methyl-3-((1-methylpiperidin-3-yl)methoxy)-1-phenyl-1H-pyrazol-5-amine | 301.2 (M + H) |

Intermediate X31

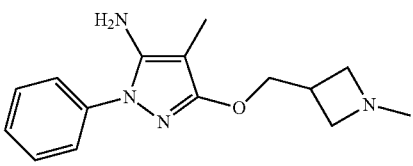 [SMILES: Cc1c(OCC2CN(C)C2)nn(-c2ccccc2)c1N]

4-methyl-3-((1-methylazetidin-3-yl)methoxy)-1-phenyl-1H-pyrazol-5-amine

Step A: Preparation of 3-(azetidin-3-ylmethoxy)-4-methyl-1-phenyl-1H-pyrazol-5-amine A solution of tert-butyl 3-(((5-amino-4-methyl-1-phenyl-1H-pyrazol-3-yl)oxy)methyl)azetidine-1-carboxylate (Intermediate X21, 840 mg, 2.34 mmol) in dry CH$_2$Cl$_2$ (7 mL) was cooled to 0° C. and TFA (14.0 mL, 187 mmol) was added. The mixture was stirred for 16 hours during which time the solution reached ambient temperature. The mixture was concentrated and the residual syrup was dried in vacuum. Dry Et$_2$O was added and the mixture was sonicated and stirred until a granular suspension formed. The solvent was decanted from the settled solid and the solid was washed with Et$_2$O and dried in vacuum to afford a light beige powder. The powder was partitioned into chilled 0.5M NaOH (20 mL) and CH$_2$Cl$_2$ (15 mL) and mixed. NaCl(s) was added to saturation, the organic layer removed and the aqueous layer was extracted with CH$_2$Cl$_2$. The combined organic portions were dried over Na$_2$SO$_4$/activated charcoal, filtered through packed Celite® and concentrated. The residual light gold syrup was dried in vacuum to afford the title compound (410 mg, 68%). MS (apci) m/z=259.2 (M+H).

Step B: Preparation of 4-methyl-3-(1-methylazetidin-3-yl)methoxy)-1-phenyl-1H-pyrazol-5-amine Using 3-(azetidin-3-ylmethoxy)-4-methyl-1-phenyl-1H-pyrazol-5-amine in Step B of the procedure outlined for the preparation of Intermediate X23, the title compound was obtained as a light gold foam (430 mg, 100%). MS (apci) m/z=273.1 (M+H).

Intermediate X32

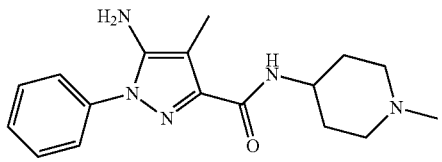 [SMILES: Cc1c(C(=O)NC2CCN(C)CC2)nn(-c2ccccc2)c1N]

5-amino-4-methyl-N-(1-methylpiperidin-4-yl)-1-phenyl-1H-pyrazole-3-carboxamide

To a solution of 5-amino-4-methyl-1-phenyl-1H-pyrazole-3-carboxylic acid (Intermediate X5, Step B, 217 mg, 1.00 mmol) and HATU (418 mg, 1.10 mmol) in dry DMF (3 mL) was added 1-methylpiperidin-4-amine (137 mg, 1.20 mmol) followed by DIEA (348 µL, 2.00 mmol) dropwise over 1 minute. The mixture was stirred at ambient temperature for 5.5 hours, poured into chilled H$_2$O (15 mL) and treated with 1M NaOH to pH=12. The mixture was saturated with NaCl(s) and extracted with EtOAc (4×). The combined organic extracts were dried over MgSO$_4$, filtered through packed Celite® and concentrated. The residual tacky white solid was washed thoroughly with Et$_2$O and dried in vacuum to furnish the product as a granular white solid (330 mg, 105%). MS (apci) m/z=314.2 (M+H).

Intermediate X33

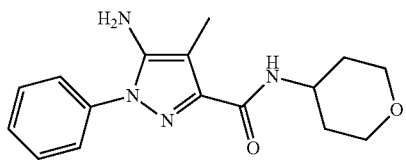 [SMILES: Cc1c(C(=O)NC2CCOCC2)nn(-c2ccccc2)c1N]

5-amino-4-methyl-1-phenyl-N-(tetrahydro-2H-pyran-4-yl)-1H-pyrazole-3-carboxamide To a solution of 5-amino-4-methyl-1-phenyl-1H-pyrazole-3-carboxylic acid (Intermediate X5, Step B, 210 mg, 0.967 mmol) and HBTU (403 mg, 1.06 mmol) in dry DMF (3 mL) was added tetrahydro-2H-pyran-4-amine (117 mg, 1.16 mmol) followed by DIEA (337 µL, 1.93 mmol) dropwise over 2 minutes. The mixture was stirred at ambient temperature for 8 hours and was poured into chilled H$_2$O (15 mL) 1M HCl was added to pH=5 and the mixture extracted with EtOAc (3×). The combined extracts were washed with saturated NaHCO$_3$ and dried over MgSO$_4$. The solution was filtered through a thin SiO$_2$ plug and concentrated to give the product as a white foam that was dried in vacuum (271 mg, 93%). MS (apci) m/z=301.2 (M+H).

Intermediate Y14

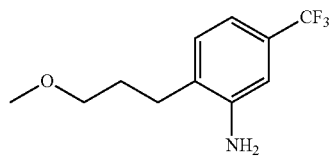 [SMILES: COCCCc1ccc(C(F)(F)F)cc1N]

2-(3-methoxypropyl)-5-(trifluoromethyl)aniline

Utilizing 3-(4-(trifluoromethyl)phenyl)propanoic acid in the procedure described for the preparation of Intermediate Y12, the title compound was obtained as a colorless oil (610 mg, 64% over 4 steps). $^1$H NMR (CDCl$_3$) δ 7.11 (d, J=7.8 Hz, 1H), 6.94 (d, J=67.8 Hz, 1H), 6.88 (s, 1H), 4.03 (br s, 2H), 3.38 (t, J=5.9 Hz, 2H), 3.36 (s, 3H), 2.63 (t, J=7.3 Hz, 2H), 1.87 (m, 2H) ppm.

Intermediate Y15

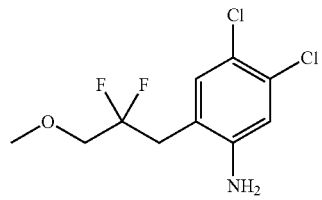 [SMILES: COCC(F)(F)Cc1cc(Cl)c(Cl)cc1N]

4,5-dichloro-2-(2,2-difluoro-3-methoxypropyl)aniline

Step A: Preparation of 1,2-dichloro-4(2,2-difluoro-3-methoxypropyl)benzene: To a solution of 1-(3,4-dichlorophenyl)-3-methoxypropan-2-one (466 mg, 2.00 mmol) in dry CH$_2$Cl$_2$ (10 mL) was added Deoxo-Fluor® (737 µL, 4.00 mmol) and the mixture was stirred at ambient temperature for 24 hours. The reaction mixture was cooled to 0° C. and was slowly treated with saturated NaHCO$_3$ (10 mL). The mixture was stirred for 1 hour during which time the temperature reached ambient. The mixture was diluted with H$_2$O (10 mL), the organic layer removed and the aqueous extracted with CH$_2$Cl$_2$ (2×). The combined organic fractions were diluted with 1 equal volume of hexanes, dried over Na$_2$SO$_4$ and eluted through a SiO$_2$ plug (50% CH$_2$Cl$_2$-hexanes for elution). The eluate was concentrated and the residue was dried in vacuum to provide the title compound as a viscous, colorless oil (484 mg, 95%). $^1$H NMR (CDCl$_3$) δ 7.39 (s, 1H), 7.39 d, J=8.2 Hz, 1H), 7.13 (d, J=8.2 Hz, 1H), 3.46 (t, J=12 Hz, 2H), 3.44 (s, 3H), 3.18 (t, J=16 Hz, 2H) ppm.

Step B: Preparation of 1,2-dichloro-4-(2,2-difluoro-3-methoxypropyl)-5-nitrobenzene A suspension of nitronium tetrafluoroborate (275 mg, 1.96 mmol) in dry CH$_2$Cl$_2$ (10 mL) was cooled to −20° C. (ice/MeOH bath) and 1,2-dichloro-4-(2,2-difluoro-3-methoxypropyl)benzene (464 mg, 1.64 mmol) in dry CH$_2$Cl$_2$ (6 mL) was added. The mixture was stirred for 16 hours during which time the solution slowly reached ambient temperature. The reaction was quenched with cold saturated NaHCO₃ (10 mL) and H₂O (10 mL) and mixed for 30 minutes. The organic layer was removed, washed with H₂O and dried over Na₂SO₄. The solution was eluted through a SiO₂ plug (CH₂Cl₂) and concentrated to provide the title compound as a viscous, yellow-green oil that was dried in vacuum (385 mg, 78%). ¹H NMR (CDCl₃) δ 8.07 (s, 1H), 7.57 (s, 1H), 3.71 (t, J=17 Hz, 2H), 3.56 (t, J=12 Hz, 2H), 3.42 (s, 3H) ppm.

Step C: Preparation of 4,5-dichloro-2-(2,2-difluoro-3-methoxypropyl)aniline

A mixture of 2800 Raney® Nickel (213 mg, 1.24 mmol, est. 50% wt. H₂O) and 1,2-dichloro-4-(2,2-difluoro-3-methoxypropyl)-5-nitrobenzene (382 mg, 1.26 mmol) in MeOH (15 mL) was purged with H₂ and stirred under an atmosphere of H₂ for 7 hours. The mixture was purged with N₂, filtered through packed Celite® (MeOH rinse-elution) and concentrated. The residue was dissolved in CH₂Cl₂ and dried over Na₂SO₄/activated charcoal. The solution was filtered through a SiO₂ plug (CH₂Cl₂ than 50% EtOAc-hexanes for elution) and concentrated. The residual gold syrup was purified on a SiO₂ column (CH₂Cl₂) to provide the title compound as a white solid (340 mg, 100%). ¹H NMR (CDCl₃) δ 7.18 (s, 1H), 6.80 (s, 1H), 4.18 (br s, 2H), 3.48 (t, J=12 Hz, 2H), 3.47 (s, 3H), 3.12 (t, J=16 Hz, 2H) ppm.

Intermediate Z2

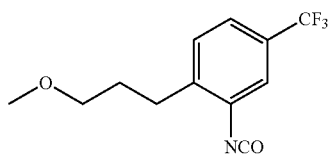

2-isocyanato-1-(3-methoxypropyl)-4-(trifluoromethyl)benzene

To a solution of triphosgene (348 mg, 1.15 mmol) in dry CH₂Cl₂ (5.0 mL) was added a solution of 4,5-dichloro-2-(3-methoxypropyl)aniline (Intermediate Y14, 620 mg, 2.53 mmol) and DIEA (800 µL, 4.59 mmol) in dry CH₂Cl₂ (5.0 mL) dropwise over 1 hour. The mixture was stirred for 2 hours and concentrated. The residue was sonicated in hexanes, stirred vigorously 15 minutes, filtered and concentrated to yield the title compound as a light gold oil (610 mg, 100%). ¹H NMR (CDCl₃) δ 7.41-7.25 (m, 3H), 3.40 (t, J=6.2 Hz, 2H), 3.36 (s, 3H), 2.79 (t, J=7.4 Hz, 2H), 1.92-1.85 (m, 2H) ppm.

Intermediate Z3

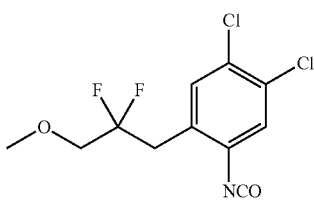

1,2-dichloro-4-(2,2-difluoro-3-methoxypropyl)-5-isocyanatobenzene

To a solution of triphosgene (119 mg, 0.394 mmol) in dry CH₂Cl₂ (2 mL) was added 4,5-dichloro-2-(2,2-difluoro-3-methoxypropyl)aniline (Intermediate Y15, 293 mg, 1.08 mmol) and DIEA (344 µL, 1.97 mmol) in dry CH₂Cl₂ (2 mL) dropwise over 1 hour. The mixture was stirred for 2 hours and was concentrated to a white, oily solid. The solid was sonicated in dry hexanes and the suspension stirred vigorously for 30 minutes. The suspension was filtered through packed Celite® (hexanes elution) and the filtrate was concentrated to provide the title compound as a viscous colorless oil (300 mg, 103%). ¹H NMR (CDCl₃) δ 7.42 (s, 1H), 7.26 (s, 1H), 3.55 (t, J=12 Hz, 2H), 3.47 (s, 3H), 3.26 (t, J=17 Hz, 2H) ppm.

Table 1 provides a list of commercially available pyrazole intermediates can be used in the synthesis of compounds described in the Examples.

TABLE 1

| Pyrazole | Vendor/Catalog # | CAS # |
|---|---|---|
| | Oakwood, 021512 | 126208-61-5 |
| | Array BioPharma, A1075-0 | N/A |
| | Maybridge, GK03066 | 1192-21-8 |
| | Ryan Scientific, EN300-14400 | 89399-92-8 |
| | Oakwood, 021516 | N/A |
| | Alfa Aesar, AAB20095-06 | 118430-73-2 |
| | Aldrich, 532223 | 3524-32-1 |

TABLE 1-continued

| Pyrazole | Vendor/Catalog # | CAS # |
|---|---|---|
| (3-tert-butyl-1-(pyridin-3-yl)-1H-pyrazol-5-amine) | Accela ChemBio Chem Co, SY003755 | 876299-97-7 |
| (1-(4-fluorophenyl)-3-tert-butyl-1H-pyrazol-5-amine) | ChemImpex, 18122 | 778611-16-8 |
| (3-cyclopropyl-1-phenyl-1H-pyrazol-5-amine) | Oakwood, 017105 | 175137-45-8 |
| (1,3-diphenyl-1H-pyrazol-5-amine) | Alfa Aesar, AAB20464-06 | 5356-71-8 |
| (3-methyl-1-phenyl-1H-pyrazol-5-amine) | Aldrich, 541001 | 1131-18-6 |
| (1-methyl-3-phenyl-1H-pyrazol-5-amine) | Alfa Aesar, AAA15754-06 | 10199-50-5 |
| (1-phenyl-1H-pyrazol-5-amine) | TCI America, A0174 | 826-85-7 |
| (3-tert-butyl-1-(2-fluorophenyl)-1H-pyrazol-5-amine) | Oakwood, 023890 | N/A |
| (3-tert-butyl-1-(3-fluorophenyl)-1H-pyrazol-5-amine) | J & W Pharmalab, 68-0035S | 1187931-80-1 |
| (3-cyclopentyl-1-phenyl-1H-pyrazol-5-amine) | VWR, EN300-09508 | N/A |
| (2-methyl-2,4,5,6-tetrahydrocyclopenta[c]pyrazol-3-amine) | ChemBridge, 4019184 | 885529-68-0 |
| (1,3-dimethyl-4-phenyl-1H-pyrazol-5-amine) | ChemBridge, 4001950 | N/A |
| (3-tert-butyl-1-(2-methylphenyl)-1H-pyrazol-5-amine) | ChemImpex, 19156 | 337533-96-7 |
| (3-tert-butyl-1-(3-methylphenyl)-1H-pyrazol-5-amine) | ChemImpex, 19155 | 898537-77-4 |
| (1-methyl-4-phenyl-1H-pyrazol-5-amine) | ChemBridge, 4006072 | N/A |
| (5-amino-3-methyl-1-phenyl-1H-pyrazole-4-carbonitrile) | Oakwood, 005982 | 5346-56-5 |
| (1-phenyl-3-(trifluoromethyl)-1H-pyrazol-5-amine) | ChemImpex, 18771 | 182923-55-3 |
| (5-cyclopropyl-2-methyl-2H-pyrazol-3-amine) | Maybridge, KM00278 | 118430-74-3 |
| (2-methyl-5-(thiophen-2-yl)-2H-pyrazol-3-amine) | Maybridge, KM00835 | 118430-78-7 |

TABLE 1-continued

| Pyrazole | Vendor/Catalog # | CAS # |
|---|---|---|
| (H2N-pyrazole-N-methyl-pyridin-2-yl) | ChemBridge, 4015288 | N/A |
| (H2N-pyrazole-N-methyl-pyridin-3-yl) | ChemBridge, 4015289 | N/A |
| (N-methyl-pyrazole-NH2, 4-fluorophenyl) | Matrix, 020274 | N/A |
| (N-methyl-pyrazole-NH2, 4-methoxyphenyl) | Matrix, 019183 | N/A |
| (NH2-pyrazole-N-methyl, 4-chlorophenyl) | Maybridge, KM 04038 | 126417-82-1 |
| (NH2-pyrazole-N-methyl, 3-methyl, 4-phenyl) | ChemBridge, 4001950 | N/A |
| (NH2-pyrazole, cyano, cyanomethyl, N-phenyl) | Lancaster, AAA17470-06 | 7152-40-1 |

TABLE 1-continued

| Pyrazole | Vendor/Catalog # | CAS # |
|---|---|---|
| (NH2-pyrazole-methyl-ethyl-N-phenyl) | ChemBridge, 4010196 | 91642-97-6 |
| (NH2-pyrazole-CO2Et-N-phenyl) | VWR, AAA13296-14 | 16078-71-0 |

N/A = Not available

Intermediate P1

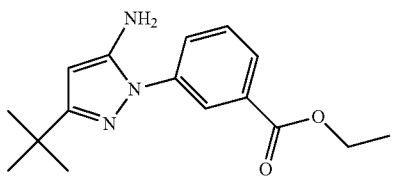 [SMILES: CCOC(=O)c1cccc(-n2nc(C(C)(C)C)cc2N)c1]

Ethyl 3-(5-amino-3-tert-butyl-1H-pyrazol-1-yl)benzoate

To a suspension of ethyl 3-hydrazinylbenzoate hydrochloride (500 mg, 2.31 mmol) in EtOH (20 mL) was added 4,4-dimethyl-3-oxopentanenitrile (318 mg, 2.54 mmol). The reaction mixture was heated to reflux for 18 hours, then cooled to ambient temperature and concentrated in vacuo. The crude product was purified by silica column chromatography, eluting with 0-5% MeOH/DCM to yield the product as a yellow oil (154 mg, 23% yield). MS (apci) m/z=288.2 (M+H).

The compounds in Table 2 were prepared by the method as described for Intermediate P1, substituting 4,4-dimethyl-3-oxopentanenitrile with the appropriate cyanoketone and ethyl 3-hydrazinylbenzoate hydrochloride with the appropriate hydrazine.

TABLE 2

| Intermediate # | Structure | Data |
|---|---|---|
| P2 | (phenyl-N-pyrazole-NH, dimethyl) | MS (apci) m/z = 188.2 (M + H) |

TABLE 2-continued

| Intermediate # | Structure | Data |
|---|---|---|
| P3 | 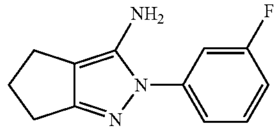 [SMILES: Nc1c2c(nn1-c1cccc(F)c1)CCC2] | MS (apci) m/z = 218.1 (M + H) |
| P4 | 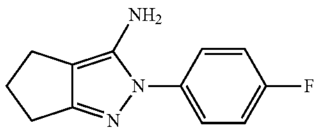 [SMILES: Nc1c2c(nn1-c1ccc(F)cc1)CCC2] | MS (apci) m/z = 218.2 (M + H) |
| P5 | 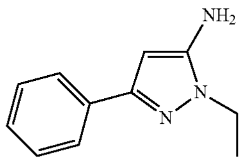 | MS (apci) m/z = 188.2 (M + H) |
| P6 | 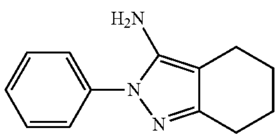 [SMILES: Nc1c2c(nn1-c1ccccc1)CCCC2] | MS (apci) m/z = 214.2 (M + H) |
| P7 | 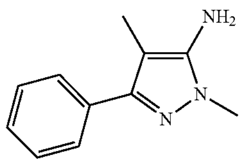 | MS (apci) m/z = 188.2 (M + H) |
| P8 | 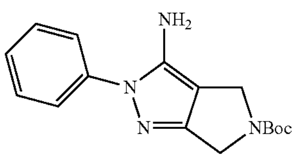 [SMILES: CC(C)(C)OC(=O)N1Cc2nn(-c3ccccc3)c(N)c2C1] | MS (apci) m/z = 301.0 (M + H) |
| P9 | 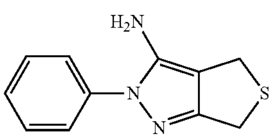 [SMILES: Nc1c2c(nn1-c1ccccc1)CSC2] | MS (apci) m/z = 218.1 (M + H) |
| P10 | 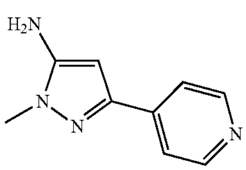 | MS (apci) m/z = 175.2 (M + H) |
| P11 | 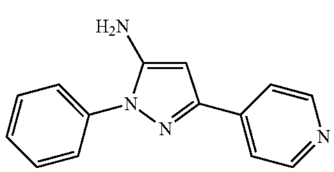 [SMILES: Nc1cc(-c2ccncc2)nn1-c1ccccc1] | MS (apci) m/z = 237.3 (M + H) |
| P12 | 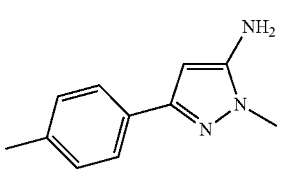 | MS (apci) m/z = 188.2 (M + H) |

TABLE 2-continued

| Intermediate # | Structure | Data |
| --- | --- | --- |
| P13 | 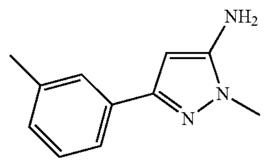 | MS (apci) m/z = 188.2 (M + H) |
| P14 | 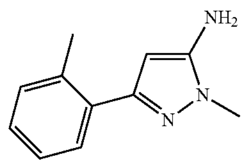 | MS (apci) m/z = 188.2 (M + H) |
| P15 | 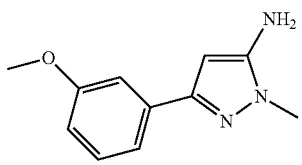 | MS (apci) m/z = 204.2 (M + H) |
| P16 | 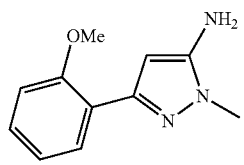 | MS (apci) m/z = 204.2 (M + H) |
| P17 | 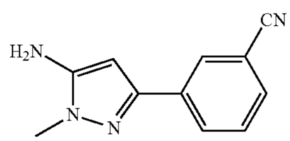 | MS (apci) m/z = 199.0 (M + H) |
| P18 | 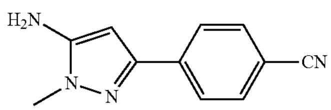 | MS (apci) m/z = 199.1 (M + H) |
| P19 | 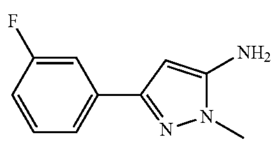 | MS (apci) m/z = 192.2 (M + H) |
| P20 | 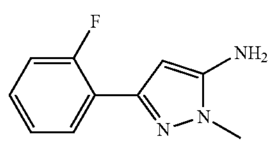 | MS (apci) m/z = 192.2 (M + H) |
| P21 | 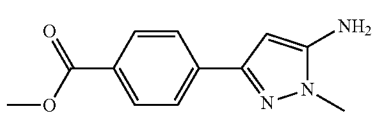 [SMILES: COC(=O)c1ccc(-c2cc(N)n(C)n2)cc1] | MS (apci) m/z = 232.2 (M + H) |
| P22 | 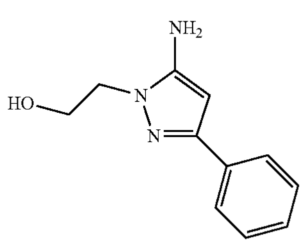 [SMILES: Nc1cc(-c2ccccc2)nn1CCO] | MS (apci) m/z = 204.2 (M + H) |

TABLE 2-continued

| Intermediate # | Structure | Data |
|---|---|---|
| P23 | 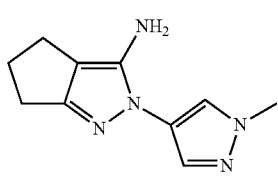 | MS (apci) m/z = 206.1 (M + H) |

Intermediate P101

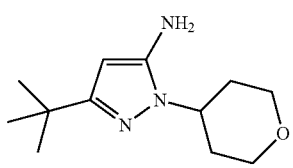 [SMILES: CC(C)(C)c1cc(N)n(C2CCOCC2)n1]

2-(1-methyl-1H-pyrazol-4-yl)-2,4,5,6-tetrahydrocyclopenta-[c]pyrazol-3-amine

Step A: Preparation of di-tert-butyl 1-(1-methyl-1H-pyrazol-4-yl)hydrazine-1,2-dicarboxylate To a solution of 4-bromo-1-methyl-1H-pyrazole (1.93 mL, 18.6 mmol) in ether (37.3 mL) cooled to −78° C. was added nBuLi (23.3 mL, 37.3 mmol). After stirring at −78° C. for 30 minutes, a solution of di-t-butyl azodicarboxylate (4.29 g, 18.6 mmol) in Et$_2$O (37.3 mL, 18.6 mmol) was added dropwise. After 1 hour, the reaction mixture was warmed up to −20° C. and quenched with ice. After warming to ambient temperature, the mixture was filtered and rinsed with Et$_2$O. The resulting solid was taken up in a mixture of DCM and water, and the mixture was phase separated. The organic layer was dried with MgSO$_4$, filtered and concentrated in vacuo to afford the first batch of product as a white solid (1.64 g, 28% yield). A second batch of product was recovered from the filtrate by silica column chromatography, eluting with 40-60% hexanes/EtOAc (0.51 g, 8.8% yield). MS (apci) m/z=313.0 (M+H).

Step B: Preparation of 2-(1-methyl-1H-pyrazol-4-yl)-2,4,5,6-tetrahydrocyclopenta-[c]pyrazol-3-amine To a solution of di-tert-butyl 1-(1-methyl-1H-pyrazol-4-yl)hydrazine-1,2-dicarboxylate (103 mg, 0.330 mmol) in EtOH (1.65 mL, 0.330 mmol) was added concentrated HCl (137 μL, 1.65 mmol). The mixture was stirred at ambient temperature for 5 minutes, then cooled in an ice bath followed by addition of 2-oxocyclopentanecarbonitrile (36.0 mg, 0.330 mmol). After stirring for 5 minutes, the reaction mixture was warmed to ambient temperature overnight. The reaction mixture was concentrated and partitioned in water and DCM. After phase-separation, the aqueous layer was basified (pH 10) and then extracted with DCM (3×10 mL). The combined organic extracts were dried with MgSO$_4$, filtered and concentrated in vacuo. The crude material was purified by reverse-phase column chromatography, eluting with 0-100% acetonitrile/water to afford the product as a yellow solid (4.5 mg, 6.7% yield). MS (apci) m/z=204.1 (M+H).

Intermediate P102

3-tert-butyl-1-(tetrahydro-2H-pyran-4-yl)-1H-pyrazol-5-amine

Step A: Preparation of (tetrahydro-2H-pyran-4-yl)hydrazine hydrochloride

A suspension of dihydro-2H-pyran-4(3H)-one (2.00 g, 20.0 mmol) and tert-butyl hydrazinecarboxylate (2.64 g, 20.0 mmol) in hexanes (20.0 mL) was refluxed for 2 hours. After cooling, BH$_3$-THF complex (20.0 mL, 20.0 mmol) was added and the reaction mixture was stirred for 1 hour. The mixture was then treated with 4 N HCl in dioxane (20.0 mL, 79.9 mmol), followed by 3 drops of water. After stirring at ambient temperature for 1 hour, the reaction mixture was filtered and rinsed with EtOAc to afford the product as a solid (2.39 g, 78.4% yield). MS (apci) m/z=117.0 (M+H).

Step B: Preparation of 3-tert-butyl-1-(tetrahydro-2H-pyran-4-yl)-1H-pyrazol-5-amine Prepared by the method as described in for the preparation of Intermediate P1, substituting (tetrahydro-2H-pyran-4-yl)hydrazine dihydrochloride for ethyl 3-hydrazinylbenzoate hydrochloride to yield the product as a yellow oil (0.472 g, 99.9% yield). MS (apci) m/z=224.1 (M+H).

Intermediate P103

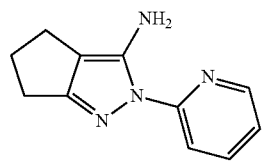 [SMILES: Nc1c2c(nn1-c1ccccn1)CCC2]

2-(pyridin-2-yl)-2,4,5,6-tetrahydrocyclopenta[c]pyrazol-3-amine

Step A: Preparation of 2-(2-(pyridin-2-yl)hydrazono)cyclopentane-carbonitrile A solution of 2-hydrazinylpyridine (0.200 g, 1.83 mmol) and 2-oxocyclopentanecarbonitrile (0.200 g, 1.83 mmol) in MeOH (9.16 mL) was treated with concentrated HCl (0.764 mL, 9.16 mmol) and refluxed for 16 hours. The reaction mixture was concentrated in vacuo, and then partitioned in water and DCM. After phase-separation, the aqueous layer was washed with DCM, basified (saturated NaHCO$_3$, pH 10), and extracted with DCM. The combined organic layers were dried with MgSO$_4$, filtered and concentrated. The crude material was purified by silica column chromatography, eluting with 100% EtOAc to afford the product (0.289 g, 78.6% yield). MS (apci) m/z=201.2 (M+H).

Step B: Preparation of 2-(pyridin-2-yl)-2,4,5,6-tetrahydrocyclopenta[c]pyrazol-3-amine A solution of 2-(2-(pyridin-2-yl)hydrazono)cyclopentanecarbonitrile (0.243 g, 1.21 mmol) in EtOH (6.06 mL, 1.21 mmol) was treated with 6 M HCl (0.202 mL, 1.21 mmol) and refluxed for 3 days. After removal of the solvent, the crude residue was diluted in water, basified (saturated NaHCO$_3$, pH 10) and extracted with DCM. The combined organic layers were dried with MgSO$_4$, filtered and concentrated. The crude material was purified by silica column chromatography, eluting with 50% EtOAc/hexanes to afford the product (0.198 g, 81.6% yield). MS (apci) m/z=201.2 (M+H).

Intermediate P104

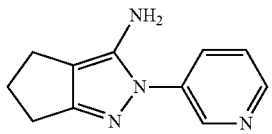 [SMILES: Nc1c2c(nn1-c1cccnc1)CCC2]

2-(pyridin-3-yl)-2,4,5,6-tetrahydrocyclopenta[c]pyrazol-3-amine

Prepared by the method described above for Intermediate P103, substituting 3-hydrazinylpyridine for 2-hydrazinyl pyridine to afford the title product. MS (apci) m/z=201.1 (M+H).

Intermediate P105

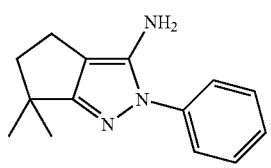 [SMILES: CC1(C)CCc2c1nn(-c1ccccc1)c2N]

6,6-dimethyl-2-phenyl-2,4,5,6-tetrahydrocyclopenta[c]pyrazol-3-amine

Step A: Preparation of 5-chloro-2,2-dimethylpentanenitrile

Isobutyronitrile (1.38 g, 20.0 mmol) and 1-bromo-3-chloropropane (3.46 g, 22.0 mmol) were sequentially added to a 1 M solution of lithium bis(trimethylsilyl)amide (20.0 mL, 20.0 mmol) while stirring. After stirring at 70° C. for 16 hours, the reaction mixture was quenched with water then extracted with DCM. The combined organic layers were dried with MgSO$_4$, filtered and concentrated in vacuo to afford 5-chloro-2,2-dimethylpentanenitrile (2.91 g, 100% yield). $^1$H NMR (CDCl$_3$) δ 3.57-3.61 (m, 2H), 1.94-2.02 (m, 2H), 1.67-1.72 (m, 2H), 1.37 (s, 6H).

Step B: Preparation of 2,2-dimethylhexanedinitrile

A suspension of 5-chloro-2,2-dimethylpentanenitrile (2.91 g, 20.0 mmol) and NaCN (1.57 g, 32.0 mmol) in DMF (20.0 mL) and water (1 mL) was heated at 100° C. for 16 hours. After cooling, the reaction mixture was diluted with water and refluxed for 30 minutes, then cooled, poured into water and stirred for 3 hours. The solution was then extracted with Et$_2$O. The combined Et$_2$O extracts were washed with H$_2$O, dried with MgSO$_4$, filtered and concentrated in vacuo to afford the product (2.20 g, 80.7% yield). $^1$H NMR (CDCl$_3$) δ 2.42-2.47 (m, 2H), 1.83-1.92 (m, 2H), 1.67-1.72 (m, 2H), 1.39 (s, 6H).

Step C: Preparation of 3,3-dimethyl-2-oxocyclopentanecarbonitrile

A suspension of KOtBu (0.511 g, 4.55 mmol) in toluene (18.4 mL) was treated a toluene (2.0 mL) solution of 2,2-dimethylhexanedinitrile (1.00 g, 7.34 mmol) and heated at 80° C. for 2 hours. The reaction mixture was then cooled to ambient temperature and quenched with water. The mixture was separated and the organic layer was stirred in 2 N HCl (20 mL) for 16 hours. The mixture was separated and the organic layer dried with MgSO$_4$, filtered and concentrated in vacuo to a yellow-white solid. The crude solid was purified by silica column chromatography, eluting with 10-40% EtOAc/hexanes, to afford the product (0.250 g, 24.8% yield). $^1$H NMR (CDCl$_3$) δ 3.20-3.26 (m, 1H), 2.38-2.47 (m, 1H), 2.14-2.25 (m, 1H), 1.97-2.05 (m, 1H), 1.74-1.83 (m, 1H), 1.14 (s, 6H).

Step D: Preparation of 6,6-dimethyl-2-phenyl-2,4,5,6-tetrahydrocyclopenta[c] pyrazol-3-amine Prepared by the method as described for Intermediate P1, substituting phenylhydrazine for ethyl 3-hydrazinylbenzoate hydrochloride and 3,3-dimethyl-2-oxocyclopentanecarbonitrile for 4,4-dimethyl-3-oxopentanenitrile to afford the product (0.192 g, 46.2% yield) as a yellow solid. MS (apci) m/z=228.2 (M+H).

Intermediate P106

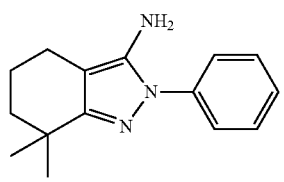 [SMILES: CC1(C)CCCc2c1nn(-c1ccccc1)c2N]

7,7-dimethyl-2-phenyl-4,5,6,7-tetrahydro-2H-indazol-3-amine

Step A: Preparation of 2,2-dimethylheptanedinitrile

Prepared by the method as described for Intermediate P105, Steps A and B, substituting 1-bromo-4-chlorobutane for 1-bromo-3-chloropropane to yield the product (2.21 g, 73.7% yield). ¹H NMR (CDCl₃) δ 2.37-2.42 (m, 2H), 1.53-1.77 (m, 6H), 1.36 (s, 6H).

Step B: Preparation of 3,3-dimethyl-2-oxocyclohexanecarbonitrile

A suspension of KOtBu (0.463 g, 4.13 mmol) in toluene (16.6 mL) was treated with a solution of 2,2-dimethylheptanedinitrile (1.00 g, 6.66 mmol) in toluene (2.0 mL) and heated at 80° C. for 48 hours. After cooling to ambient temperature, the reaction mixture was quenched with water and phase-separated, and the organic layer was stirred with 2 N HCl (20 mL) for 16 hours. After phase-separation, the organic layer was dried with MgSO₄, filtered and concentrated in vacuo. The crude material was purified by silica column chromatography, eluting with 10-20% EtOAc/hexanes to afford the product (0.374 g, 37.2% yield). ¹H NMR (CDCl₃) δ 3.72-3.78 (m, 1H), 2.42-2.50 (m. 1H), 1.78-2.04 (m, 4H), 1.60-1.70 (m, 1H), 1.21 (s, 3H), 1.16 (s, 3H).

Step C: Preparation of 7,7-dimethyl-2-phenyl-4,5,6,7-tetrahydro-2H-indazol-3-amine Prepared by the method as described for Intermediate P1, substituting phenylhydrazine for ethyl 3-hydrazinylbenzoate hydrochloride and 3,3-dimethyl-2-oxocyclohexanecarbonitrile for 4,4-dimethyl-3-oxopentanenitrile to yield the product as an off-white solid (0.490 g, 54.2% yield, 66% purity). MS (apci) m/z=242.2 (M+H).

Intermediate P107

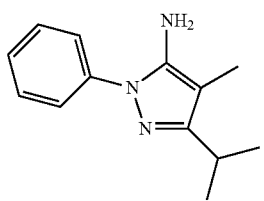 [SMILES: Cc1c(C(C)C)nn(-c2ccccc2)c1N]

3-isopropyl-4-methyl-1-phenyl-1H-pyrazol-5-amine

Step A: Preparation of 2,4-dimethyl-3-oxopentanenitrile

To a solution of propiononitrile (518 mg, 9.40 mmol) in THF (50 mL, 7.83 mmol) at −78° C. under N₂ was slowly added lithium bis(trimethylsilyl)amide (1M in THF) (7.83 mL, 7.83 mmol). After 30 minutes, methyl isobutyrate (0.898 mL, 7.83 mmol) was added dropwise, and the reaction mixture was warmed to 0° C. A yellow precipitate formed, the reaction mixture was stirred for 1 hour, then diluted with H₂O (50 mL) to dissolve the solids. The mixture was extracted with Et₂O (25 mL), and the basic aqueous phase was acidified with 2M HCl (5 mL) and extracted with Et₂O (2×50 mL) The combined organic phases were washed with brine (50 mL), dried with MgSO₄, filtered, and concentrated to afford the product (421 mg, 42.9% yield)

Step B: Preparation of 3-isopropyl-4-methyl-1-phenyl-1H-pyrazol-5-amine

Prepared by the method as described for Intermediate P1, substituting phenyl hydrazine for ethyl 3-hydrazinylbenzoate hydrochloride and 4,4-dimethyl-3-oxopentanenitrile with 2,4-dimethyl-3-oxopentanenitrile to yield the product as a yellow syrup (0.587 g, 81.1% yield). MS (apci) m/z=216.2 (M+H).

Intermediate P108

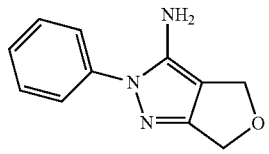 [SMILES: Nc1c2c(nn1-c1ccccc1)COC2]

2-phenyl-4,6-dihydro-2H-furo[3,4-c]pyrazol-3-amine

Step A: Preparation of 4-oxotetrahydrofuran-3-carbonitrile

To a suspension of KOtBu (996.6 mg, 8.881 mmol) in THF (640.4 mg, 8.881 mmol) cooled to 0° C. was added dropwise methyl 2-hydroxyacetate (675.7 µL, 8.881 mmol) and stirred for 10 minutes. The acrylonitrile (589.1 µL, 8.881 mmol) was then added and the reaction stirred at ambient temperature. After 3 hours, the reaction was diluted with H₂O (50 mL), then extracted with Et₂O (25 mL) to remove any starting ester. The basic aqueous phase was acidified with 2M HCl (5 mL), then extracted with Et₂O (2×50 mL) The combined organic phases were dried with MgSO₄, filtered, and concentrated to afford a light brown oil (446 mg, 45.2% yield). ¹H NMR (CDCl₃) δ 4.63 (t, 1H), 4.24 (t, 1H), 4.14 (d, 1H), 4.02 (d, 1H), 3.57 (t, 1H).

Step B: Preparation of 2-phenyl-4,6-dihydro-2H-furo[3,4-c]pyrazol-3-amine

Prepared by the method as described for Intermediate P1, substituting phenyl hydrazine for ethyl 3-hydrazinylbenzoate hydrochloride and 4,4-dimethyl-3-oxopentanenitrile with 4-oxotetrahydrofuran-3-carbonitrile to yield the product as a reddish-brown syrup (182 mg, 22.5% yield). MS (apci) m/z=202.1 (M+H).

Intermediate P109

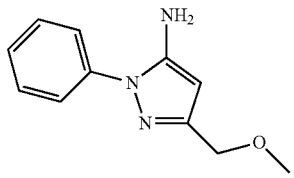

3-(methoxymethyl)-1-phenyl-1H-pyrazol-5-amine

Step A: Preparation of 4-methoxy-3-oxobutanenitrile

To a solution of methyl 2-methoxyacetate (0.4753 mL, 4.803 mmol) in THF (20 mL, 4.803 mmol) at −78° C. under N₂ was added acetonitrile (0.3033 mL, 5.763 mmol), followed by lithium bis(trimethylsilyl)amide (1M in THF) (4.803 mL, 4.803 mmol). After stirring 1 hour, the reaction mixture was warmed to 0° C. and stirred for 1 hour. The reaction mixture was then diluted with H₂O (25 mL), washed with Et₂O (25 mL), then neutralized with 2 M HCl (1.5 mL). This was extracted with Et₂O (2×25 mL) and the combined organic phases were washed with brine (25 mL), dried with MgSO₄, filtered, and concentrated to afford the product (169 mg, 31.1% yield). $^1$H NMR (CDCl₃) δ 4.09 (s, 2H), 3.66 (s, 2H), 3.46 (s, 3H)

Step B: Preparation of 3-(methoxymethyl)-1-phenyl-1H-pyrazol-5-amine

Prepared by the method as described for Intermediate P1, substituting phenyl hydrazine for ethyl 3-hydrazinylbenzoate hydrochloride and 4,4-dimethyl-3-oxopentanenitrile with 4-methoxy-3-oxobutanenitrile to yield the product as a pale yellow residue (6.0 mg, 2.0% yield). MS (apci) m/z=204.0 (M+H).

Intermediate P110

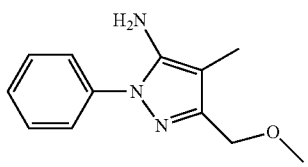 [SMILES: COCc1nn(-c2ccccc2)c(N)c1C]

3-(methoxymethyl)-4-methyl-1-phenyl-1H-pyrazol-5-amine

Prepared according to the method as described for Intermediate P109, replacing acetonitrile with propionitrile to afford the product as an orange residue. MS (apci) m/z=218.0 (M+H).

Intermediate P111

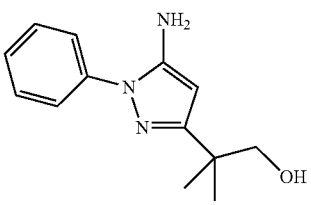 [SMILES: CC(C)(CO)c1cc(N)n(-c2ccccc2)n1]

2-(5-amino-1-phenyl-1H-pyrazol-3-yl)-2-methylpropan-1-ol

Step A: Preparation of methyl 3-(tert-butyldimethylsilyloxy)-2,2-dimethylpropanoate Methyl 3-hydroxy-2,2-dimethylpropanoate (1.000 g, 7.567 mmol), TBDMS-Cl (1.140 g, 7.567 mmol) and imidazole (0.5666 g, 8.323 mmol) were dissolved in DMF (5 mL, 7.567 mmol) and stirred at ambient temperature overnight. The reaction mixture was diluted with H₂O (25 mL) and extracted with EtOAc (2×25 mL). The combined organic phases were washed with brine (25 mL), dried with MgSO₄, filtered and concentrated to afford the product (1.92 g, 103% yield). $^1$H NMR (CDCl₃) δ 3.66 (s, 3H), 3.57 (s, 2H), 1.15 (s, 6H), 0.87 (s, 9H), 0.02 (s, 6H).

Step B: Preparation of 5-(tert-butyldimethylsilyloxy)-4,4-dimethyl-3-oxopentanenitrile Prepared according to the method described for Intermediate P109, replacing methyl 2-methoxyacetate with methyl 3-(tert-butyldimethylsilyloxy)-2,2-dimethylpropanoate to afford the product as a pale yellow residue. $^1$H NMR (CDCl₃) δ 3.70 (s, 2H), 3.55 (s, 2H), 1.15 (s, 6H), 0.89 (s, 9H), 0.06 (s, 6H).

Step C: Preparation of 2-(5-amino-1-phenyl-1H-pyrazol-3-yl)-2-methylpropan-1-ol

Prepared by the method as described for Intermediate P1, substituting phenyl hydrazine for ethyl 3-hydrazinylbenzoate hydrochloride and 4,4-dimethyl-3-oxopentanenitrile with methyl 3-(tert-butyldimethylsilyloxy)-2,2-dimethylpropanoate to yield the product as yellow syrup (74 mg, 66% yield). MS (apci) m/z=232.2 (M+H).

Intermediate P112

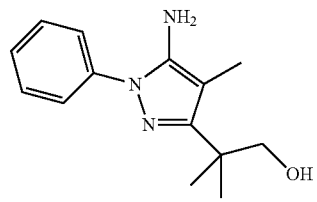 [SMILES: Cc1c(C(C)(C)CO)nn(-c2ccccc2)c1N]

2-(5-amino-4-methyl-1-phenyl-1H-pyrazol-3-yl)-2-methylpropan-1-ol

Prepared according to the method described for Intermediate P111, replacing acetonitrile with propionitrile to afford the product as a yellow residue. MS (apci) m/z=246.2 (M+H).

Intermediate P113

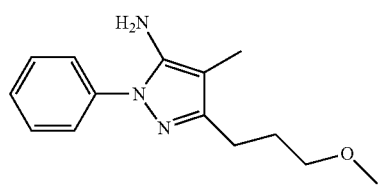 [SMILES: COCCCc1nn(-c2ccccc2)c(N)c1C]

3-(3-methoxypropyl)-4-methyl-1-phenyl-1H-pyrazol-5-amine

Prepared according to the method described for Intermediate P109, replacing methyl 2-methoxyacetate with methyl 4-methoxybutanoate and replacing acetonitrile with propionitrile in Step A to afford the product as an orange-brown syrup. MS (apci) m/z=246.1 (M+H).

Intermediate P114

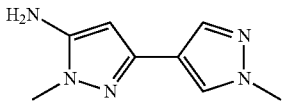

1,1'-dimethyl-1H,1'H-3,4'-bipyrazol-5-amine

Step A: Preparation of 3-(1-methyl-1H-pyrazol-4-yl)-3-oxopropanenitrile

A solution of ethyl 1-methyl-1H-pyrazole-4-carboxylate (500 mg, 3.24 mmol), toluene (7.50 mL, 70.4 mmol), and acetonitrile (346 μL, 6.49 mmol) was treated in one portion with KOtBu (1092 mg, 9.73 mmol) to give a hazy solution. The reaction was allowed to stir at ambient temperature for one hour, and was determined to be complete by HPLC analysis. The mixture was treated with water (7.5 mL) and stirred for 1 minute, then acidified with 3M HCl (3027 μL, 9.08 mmol) to pH 5.5-6. The aqueous layer was extracted with ethyl acetate (3×5 mL) and the combined organic extracts were concentrated in vacuo to give a yellow viscous oil, which completely solidified upon placing under high vacuum to afford the product (102 mg, 21.1% yield). $^1$H NMR (CDCl$_3$) δ 8.02 (s, 1H), 7.94 (s, 1H), 3.98 (s, 3H), 3.82 (s, 2H).

Step B: Preparation of 1,1'-dimethyl-1H,1'H-3,4'-bipyrazol-5-amine

Prepared by the method as described for Intermediate P1, substituting methyl hydrazine for ethyl 3-hydrazinylbenzoate hydrochloride and replacing 4,4-dimethyl-3-oxopentanenitrile with 3-(1-methyl-1H-pyrazol-4-yl)-3-oxopropanenitrile to yield the product as an ivory white solid (45 mg, 44.6% yield). MS (apci) m/z=178.1 (M+H).

Intermediate P115

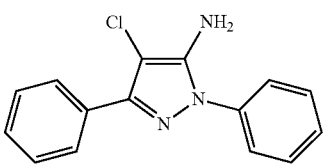 [SMILES: Nc1c(Cl)c(-c2ccccc2)nn1-c1ccccc1]

4-chloro-1,3-diphenyl-1H-pyrazol-5-amine

To a solution of 1,3-diphenyl-1H-pyrazol-5-amine (Table 1; 0.100 g, 0.425 mmol) in acetonitrile (2 mL) was added N-chlorosuccinimide (0.0568 g, 0.425 mmol). The pale yellow solution was stirred at ambient temperature for 3 hours, then concentrated in vacuo and purified by silica column chromatography eluting with 20% EtOAc/Hexanes to afford the product as a light brown oil (0.10 g, 87% yield). MS (apci) m/z=270.0 (M+H).

Intermediate P116

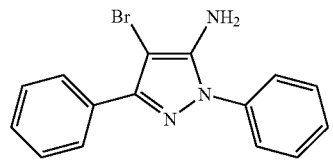

4-bromo-1,3-diphenyl-1H-pyrazol-5-amine

Prepared according to the procedure described for Intermediate P115, substituting N-chloro succinimide with N-bromo-succinimide. MS (apci) m/z=313.9 (M+H).

Intermediate P117

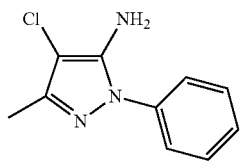

4-chloro-3-methyl-1-phenyl-1H-pyrazol-5-amine

Prepared according to the procedure described for Intermediate P115, substituting 1,3-diphenyl-1H-pyrazol-5-amine with 3-methyl-1-phenyl-1H-pyrazol-5-amine. MS (apci) m/z=207.9 (M+H).

Intermediate P118

4-bromo-3-methyl-1-phenyl-1H-pyrazol-5-amine

Prepared according to the procedure described for Intermediate P117, substituting N-chloro succinimide with N-bromo-succinimide. MS (apci) m/z=251.9 (M+H).

Intermediate P119

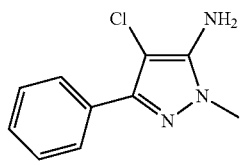

4-chloro-1-methyl-3-phenyl-1H-pyrazol-5-amine

Prepared according to the procedure described for Intermediate P115, substituting 1,3-diphenyl-1H-pyrazol-5- amine with 1-methyl-3-phenyl-1H-pyrazol-5-amine (Table 1). MS (apci) m/z=208.0 (M+H).

Intermediate P120

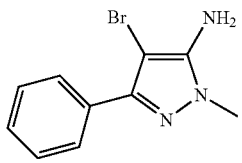

4-bromo-1-methyl-3-phenyl-1H-pyrazol-5-amine

Prepared according to the procedure described for Intermediate P119, substituting N-chloro succinimide with N-bromo-succinimide. MS (apci) m/z=251.9 (M+H).

Intermediate P121

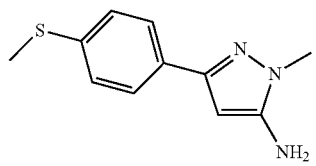

1-methyl-3-(4-(methylthio)phenyl)-1H-pyrazol-5-amine

Step A: Preparation of 3-(4-(methylthio)phenyl)-3-oxopropanenitrile

To a suspension of NaH (60% in mineral oil) (154 mg, 3.84 mmol) in dioxane (25.0 mL, 2.74 mmol) was added acetonitrile (0.217 mL, 4.12 mmol). The reaction mixture was stirred at ambient temperature for 30 minutes, then treated with methyl 4-(methylthio)benzoate (500 mg, 2.74 mmol) and heated to reflux for 15 hours. The suspension was cooled, then diluted with water (25 mL) and washed with $Et_2O$ (25 mL). The aqueous layer was neutralized with 2M HCl (1.8 mL) and extracted with $Et_2O$ (2×25 mL) The combined organic phases were washed with brine (25 mL), dried with $MgSO_4$, filtered and concentrated in vacuo. The resultant residue was purified by silica column chromatography eluting with 0-5% MeOH/DCM to afford the product (317 mg, 60.4% yield). $^1$H NMR ($CDCl_3$) δ 7.82 (d, 2H), 7.30 (d, 2H), 4.02 (s, 2H), 2.54 (s, 3H).

Step B: Preparation of 1-methyl-3-(4-(methylthio)phenyl)-1H-pyrazol-5-amine

Prepared by the method as described in Intermediate P1, substituting methylhydrazine for ethyl 3-hydrazinylbenzoate hydrochloride and substituting 3-(4-(methylthio)phenyl)-3-oxopropanenitrile for 4,4-dimethyl-3-oxopentanenitrile to yield the product as a yellow solid (0.307 g, 96.7% yield). MS (apci) m/z=220.0 (M+H).

Intermediate P122

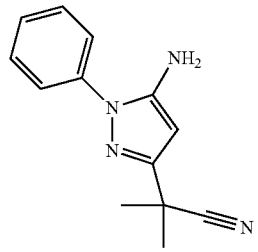 [SMILES: CC(C)(C#N)c1cc(N)n(-c2ccccc2)n1]

2-(5-amino-1-phenyl-1H-pyrazol-3-yl)-2-methylpropanenitrile

Prepared according to the procedure for Intermediate P121, substituting methyl 4-(methylthio)benzoate with ethyl 2-cyano-2-methylpropanoate in Step A and phenyl hydrazine hydrochloride for methyl hydrazine in Step B. MS (apci) m/z=227.1 (M+H).

Intermediate P123

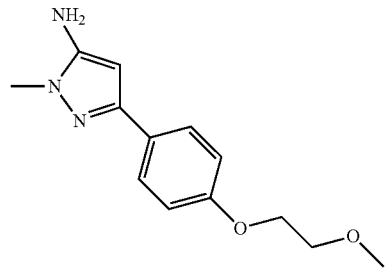

3-(4-(2-methoxyethoxy)phenyl)-1-methyl-1H-pyrazol-5-amine

Step A: Preparation of 3-(4-(benzyloxy)phenyl)-3-oxopropanenitrile

Prepared according to the procedure described for Intermediate P121, substituting methyl 4-(methylthio)benzoate with methyl 4-(benzyloxy)benzoate in Step A. $^1$H NMR ($CDCl_3$) δ 7.90 (d, 2H), 7.42 (m, 4H), 7.37 (m, 1H), 7.05 (d, 2H), 5.16 (s, 2H), 4.00 (s, 2H).

Step B: Preparation of 3-(4-(benzyloxy)phenyl)-1-methyl-1H-pyrazol-5-amine

Prepared by the method as described for Intermediate P1, substituting methylhydrazine for ethyl 3-hydrazinylbenzoate hydrochloride and 3-(4-(benzyloxy)phenyl)-3-oxopropanenitrile for 4,4-dimethyl-3-oxopentanenitrile to yield the product as a yellow solid. MS (apci) m/z=280.1 (M+H).

Step C: Preparation of 4-(5-amino-1-methyl-1H-pyrazol-3-yl)phenol

To a solution of 3-(4-(benzyloxy)phenyl)-1-methyl-1H-pyrazol-5-amine (47 mg, 0.17 mmol) in EtOH (5.0 mL) was added 5% Pd/C (9.0 mg, 0.0084 mmol) and stirred under a H₂ balloon for 17 hours. The reaction mixture was filtered through Celite®, rinsed with EtOH and concentrated in vacuo to afford the product (28 mg, 88% yield). MS (apci) m/z=190.1 (M+H).

Step D: Preparation of 3-(4-(2-methoxyethoxy)phenyl)-1-methyl-1H-pyrazol-5-amine To a solution of 4-(5-amino-1-methyl-1H-pyrazol-3-yl)phenol (14 mg, 0.074 mmol) in DMSO (0.50 mL, 7.0 mmol) was added Cs₂CO₃ (48 mg, 0.15 mmol) and 1-bromo-2-methoxyethane (9.7 μL, 0.10 mmol). The reaction mixture was stirred for 16 hours, then diluted with water (10 mL) and extracted with DCM (3×10 mL) The combined organic extracts were washed with brine (10 mL), dried with MgSO₄, filtered and concentrated to afford the crude product (22 mg, 120% yield). The crude product was used without purification in subsequent steps. MS (apci) m/z=248.0 (M+H).

Intermediate P124

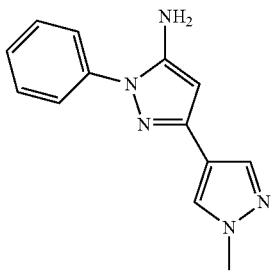 [SMILES: Cn1cc(-c2cc(N)n(-c3ccccc3)n2)cn1]

1'-methyl-1-phenyl-1H,1'H-3,4'-bipyrazol-5-amine

Prepared according to the procedure described for Intermediate P114, substituting methylhydrazine with phenylhydrazine in Step B. MS (apci) m/z=240.0 (M+H).

Intermediate P125

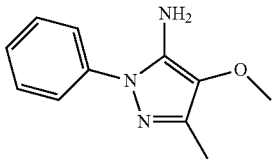

4-methoxy-3-methyl-1-phenyl-1H-pyrazol-5-amine

Prepared according to the procedure for Intermediate P121, substituting methyl 4-(methylthio)benzoate with ethyl acetate and substituting acetonitrile with 2-methoxyacetonitrile in Step A and phenyl hydrazine hydrochloride for methyl hydrazine in Step B. MS (apci) m/z=204.0 (M+H).

Intermediate P126

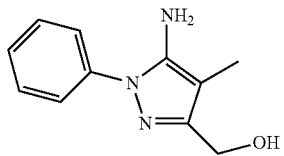

(5-amino-4-methyl-1-phenyl-1H-pyrazol-3-yl)methanol

Prepared according to the procedure for Intermediate P112, substituting methyl 3-hydroxy-2,2-dimethylpropanoate with ethyl 2-hydroxyacetate in Step A. MS (apci) m/z=204.1 (M+H).

Intermediate P127

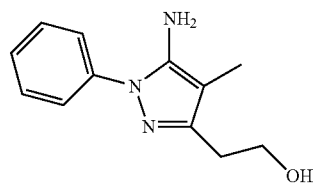 [SMILES: Cc1c(CCO)nn(-c2ccccc2)c1N]

2-(5-amino-4-methyl-1-phenyl-1H-pyrazol-3-yl)ethanol

Prepared according to the procedure for Intermediate P112, substituting methyl 3-hydroxy-2,2-dimethylpropanoate with methyl 3-hydroxypropanoate in Step A. MS (apci) m/z=218.0 (M+H).

Intermediate P128

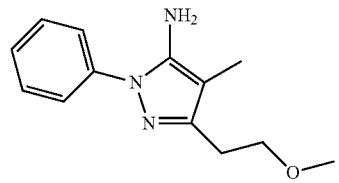 [SMILES: COCCc1nn(-c2ccccc2)c(N)c1C]

3-(2-methoxyethyl)-4-methyl-1-phenyl-1H-pyrazol-5-amine

Step A: Preparation of 5-methoxy-2-methyl-3-oxopentanenitrile

To a suspension of NaNH₂ (50 wt % suspension in toluene) (330 mg, 4.23 mmol) in THF (25 mL, 4.23 mmol) under N₂ at −78° C. was added propiononitrile (0.448 mL, 6.35 mmol), and the reaction mixture was stirred for 30 minutes. Methyl 3-methoxypropanoate (0.495 mL, 4.23 mmol) was added and the reaction mixture was stirred at −78° C. for 1 hour, then at 0° C. for 2.5 hours. The reaction mixture was diluted with H₂O (25 mL) and washed with Et₂O (25 mL). The basic aqueous phase was neutralized with 2M HCl (1.6 mL), then extracted with Et$_2$O (3×25 mL). The combined organic phases were washed with brine (25 mL), dried with MgSO$_4$, filtered, and concentrated to afford the crude product as a pale greenish oil (171 mg). The crude mixture was taken directly to the next step.

Step B: Preparation of 3-(2-methoxyethyl)-4-methyl-1-phenyl-1H-pyrazol-5-amine

Prepared by the method as described for Intermediate P1, substituting 5-methoxy-2-methyl-3-oxopentanenitrile for 4,4-dimethyl-3-oxopentanenitrile and substituting phenylhydrazine hydrochloride for ethyl 3-hydrazinylbenzoate hydrochloride to yield the product as a yellow solid (56 mg, 20% yield). MS (apci) m/z=232.0 (M+H).

Intermediate P129

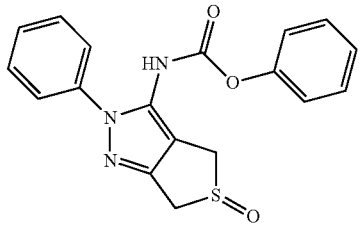 [SMILES: O=C(Nc1c2c(nn1-c1ccccc1)CS(=O)C2)Oc1ccccc1]

Phenyl (5-oxido-2-phenyl-4,6-dihydro-2H-thieno[3,4-c]pyrazol-3-yl)carbamate

A THF (4 mL) solution of phenyl 2-phenyl-4,6-dihydro-2H-thieno[3,4-c]pyrazol-3-ylcarbamate (Intermediate P130, Step B; 50 mg, 0.15 mmol) was cooled to −50° C. with an external dry-ice/MeCN bath and treated with a THF (2 mL) solution of 3-chlorobenzoperoxoic acid (33 mg, 0.13 mmol). After stirring for 1 hour, the mixture was quenched with Na$_2$S$_2$O$_3$ and water, extracted with EtOAc, washed with NaHCO$_3$ and brine, dried with MgSO$_4$, filtered, and concentrated to give the product which was directly used in next step without further purification. MS (apci) m/z=354.1 (M+H).

Intermediate P130

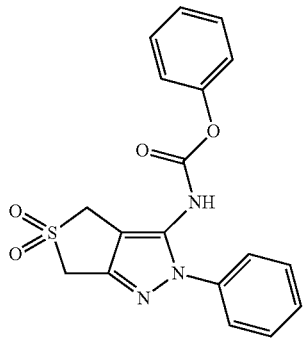 [SMILES: O=C(Nc1c2c(nn1-c1ccccc1)CS(=O)(=O)C2)Oc1ccccc1]

Phenyl (5,5-dioxido-2-phenyl-4,6-dihydro-2H-thieno[3,4-c]pyrazol-3-yl)carbamate

Step A: Preparation of 2-phenyl-4,6-dihydro-2H-thieno[3,4-c]pyrazol-3-amine

A suspension of 4-oxotetrahydrothiophene-3-carbonitrile (1.00 g, 7.86 mmol) and phenylhydrazine hydrochloride (1.25 g, 8.65 mmol) in absolute EtOH (40 mL) was refluxed for 2 hours. After removal of solvent under reduced pressure, the white solid residue was triturated with 1 N NaOH (40 mL). The solid was collected by filtration, washed with 0.1 N NaOH, water, and hexanes (approx. 10 mL each) then dried on high vacuum to yield the product as white solid (1.6 g, 95% yield). MS (apci pos) m/z=218.1 (M+H).

Step B: Preparation of phenyl 2-phenyl-4,6-dihydro-2H-thieno[3,4-c]pyrazol-3-ylcarbamate To a suspension of 2-phenyl-4,6-dihydro-2H-thieno[3,4-c]pyrazol-3-amine (500 mg, 2.30 mmol) in EtOAc (10 mL) was added NaOH (2M aq, 2.3 mL, 4.60 mmol), followed by dropwise addition of phenyl carbonochloridate (0.400 mL, 3.22 mmol). After stirring at ambient temperature for 2 hours, another portion of phenyl carbonochloridate (0.16 mL, 1.3 mmol) was added dropwise, and the reaction was stirred at ambient temperature for 15 hours. The reaction mixture was diluted with EtOAc (20 mL) and phase-separated. The organic phase was washed with H$_2$O, brine (25 mL each), then dried with Na$_2$SO$_4$, filtered and concentrated. The crude material was purified by reverse-phase column chromatography, eluting with 5-70% acetonitrile/water to yield the product as white solid (0.5 g, 64% yield). MS (apci pos) m/z=338.1 (M+H).

Step C: Preparation of phenyl (5,5-dioxido-2-phenyl-4,6-dihydro-2H-thieno[3,4-c]pyrazol-3-yl)carbamate To a turbid solution of phenyl 2-phenyl-4,6-dihydro-2H-thieno[3,4-c]pyrazol-3-ylcarbamate (50 mg, 0.15 mmol) in DCM (1.5 mL) at 0° C. was added MCPBA (91 mg, 0.37 mmol, 70-75% water complex), and the mixture was stirred at ambient temperature for 10 min. The mixture was then diluted with DCM (3 mL) and washed with saturated aqueous NaHCO$_3$ (3×2 mL) and saturated aqueous Na$_2$S$_2$O$_3$ (3×2 mL) The organic layer was dried with MgSO$_4$, filtered and concentrated under reduced pressure to yield the title product as light yellowish foamy solid (31 mg, 57% yield, 95% pure). MS (apci pos) m/z=371.0 (M+H).

Intermediate P132

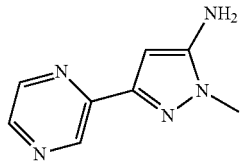

1-methyl-3-(pyrazin-2-yl)-1H-pyrazol-5-amine

Step A: Preparation of 3-oxo-3-(pyrazin-2-yl)propanenitrile

To a suspension of NaH (60% in mineral oil, 81.1 mg, 2.03 mmol) in dioxane (15 mL) was added acetonitrile (0.114 mL, 2.17 mmol), followed by methyl pyrazine-2-carboxylate (200 mg, 1.45 mmol) and the reaction heated to reflux for 2.5 hours. The reaction mixture was cooled to ambient temperature and diluted with H$_2$O (25 mL) and extracted with Et$_2$O (25 mL) The aqueous phase was neutralized with 2M aqueous HCl (0.7 mL), then extracted with 10% MeOH/DCM (3×25 mL). The combined organic phases were washed with brine (25 mL), dried with MgSO₄, filtered, and concentrated to yield the crude product as an orange syrup (134 mg, 62.9% yield). $^1$H NMR (CDCl₃) δ 9.32 (d, 1H), 8.87 (d, 1H), 8.68 (dd, 1H), 4.34 (s, 2H).

Step B: Preparation of 1-methyl-3-(pyrazin-2-yl)-1H-pyrazol-5-amine

To a suspension of 3-oxo-3-(pyrazin-2-yl)propanenitrile (67.0 mg, 0.455 mmol) in EtOH (5 mL) was added methylhydrazine (0.024 mL, 0.455 mmol). The reaction mixture was refluxed for 15 hours, then concentrated in vacuo. The crude product was purified by silica column chromatography, eluting with 0-5% MeOH/DCM to yield the product as a brown residue (33 mg, 41% yield). MS (apci) m/z=176.2 (M+H).

Intermediate P133

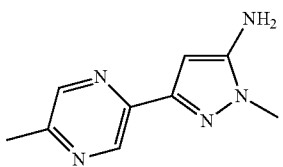

1-methyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate and propionitrile with acetonitrile to afford 3-(5-methylpyrazin-2-yl)-3-oxopropanenitrile. In Step B, phenylhydrazine was replaced by methylhydrazine to afford the title pyrazole. MS (apci) m/z=190.2 (M+H).

Intermediate P134

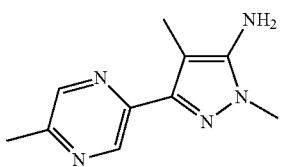

1,4-dimethyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate to afford 2-methyl-3-(5-methylpyrazin-2-yl)-3-oxopropanenitrile. In Step B, phenylhydrazine was replaced by methylhydrazine to afford the title compound. MS (apci) m/z=204.1 (M+H).

Intermediate P135

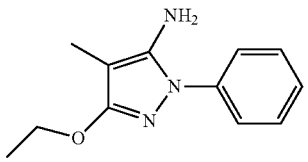 [SMILES: CCOc1nn(-c2ccccc2)c(N)c1C]

3-ethoxy-4-methyl-1-phenyl-1H-pyrazol-5-amine

Step A: Preparation of 5-amino-4-methyl-1-phenyl-1H-pyrazol-3(2H)-one

A mixture of ethyl 2-cyanopropanoate (5.0 g, 46 mmol) and phenylhydrazine (5.9 g, 46 mmol) in dioxane (10 mL) was heated at 110° C. for 17 hours. The crude material was cooled to ambient temperature, concentrated, and triturated with cold EtOH and Et₂O. The resultant solid was filtered, washed with Et₂O, and dried under vacuum to give the product as a white solid (3.4 g, 39% yield). MS (apci) m/z=190.0 (M−H).

Step B: Preparation of 3-ethoxy-4-methyl-1-phenyl-1H-pyrazol-5-amine

To a suspension of 5-amino-4-methyl-1-phenyl-1H-pyrazol-3(2H)-one (10.0 g, 52.9 mmol) in DMF (100 mL) was added K₂CO₃ (14.6 g, 106 mmol) and bromoethane (4.34 mL, 58.1) at ambient temperature. After stirring for 17 hours, the reaction mixture was treated with EtOAc and washed with water (3×, to obtain the N-alkylation product) and brine, dried with MgSO₄, filtered, and concentrated to give the product (5.35 g, 47% yield). MS (apci) m/z=218.1 (M+H).

The compounds in Table 3 were prepared by the method as described for Intermediate P135, substituting bromoethane with the appropriate alkyl halide or alkyl methanesulfonate.

TABLE 3

| Intermediate # | Structure | Data |
|---|---|---|
| P200 | ![structure] | MS (apci) m/z = 248.1 (M + H) |

TABLE 3-continued

| Intermediate # | Structure | Data |
| --- | --- | --- |
| P201 | 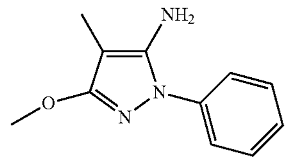 | MS (apci) m/z = 204.1 (M + H) |
| P202 | 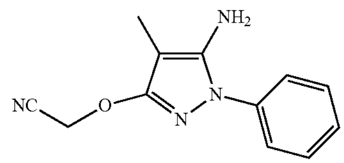 [SMILES: Cc1c(OCC#N)nn(-c2ccccc2)c1N] | MS (apci) m/z = 229.0 (M + H) |
| P203 | 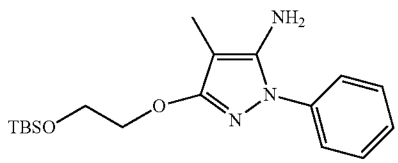 [SMILES: Cc1c(OCCO[Si](C)(C)C(C)(C)C)nn(-c2ccccc2)c1N] | MS (apci) m/z = 348.1 (M + H) |
| P204 | 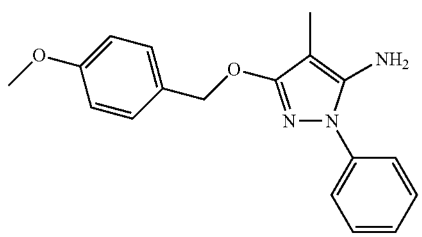 [SMILES: COc1ccc(COc2nn(-c3ccccc3)c(N)c2C)cc1] | MS (apci) m/z = 310.0 (M + H) |
| P205 | 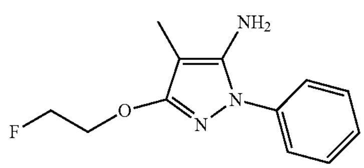 [SMILES: Cc1c(OCCF)nn(-c2ccccc2)c1N] | MS (apci) m/z = 236.1 (M + H) |
| P206 | 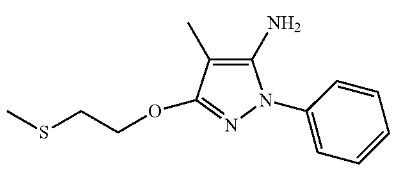 | MS (apci) m/z = 264.0 (M + H) |
| P207 | 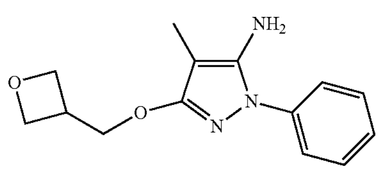 [SMILES: Cc1c(OCC2COC2)nn(-c2ccccc2)c1N] | MS (apci) m/z = 260.1 (M + H) |
| P208 | 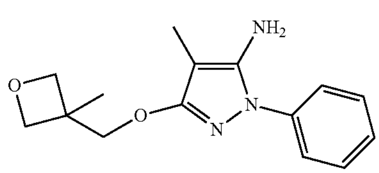 | MS (apci) m/z = 274.1 (M + H) |
| P209 | 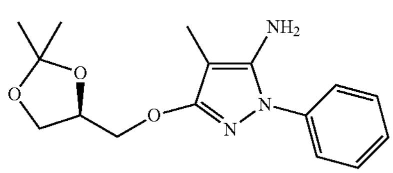 [SMILES: Cc1c(OC[C@H]2COC(C)(C)O2)nn(-c2ccccc2)c1N] | MS (apci) m/z = 304.1 (M + H) |

TABLE 3-continued

| Intermediate # | Structure | Data |
|---|---|---|
| P210 | 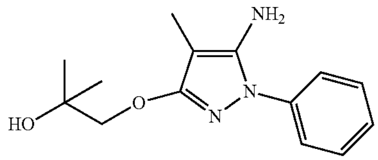 [SMILES: Cc1c(OCC(C)(C)O)nn(-c2ccccc2)c1N] | MS (apci) m/z = 262.1 (M + H) |
| P211 | 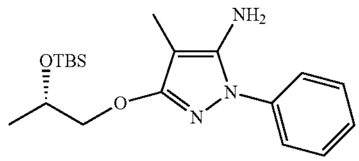 [SMILES: Cc1c(OC[C@H](C)O[Si](C)(C)C(C)(C)C)nn(-c2ccccc2)c1N] | MS (apci) m/z = 362.0 (M + H) |
| P212 | 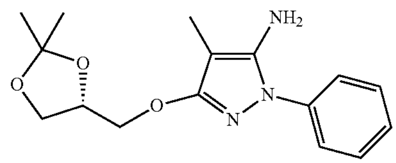 [SMILES: Cc1c(OC[C@@H]2COC(C)(C)O2)nn(-c2ccccc2)c1N] | MS (apci) m/z = 304.1 (M + H) |

Intermediate P136

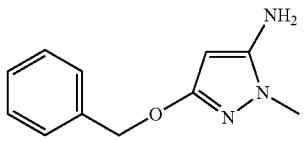

3-(benzyloxy)-1-methyl-1H-pyrazol-5-amine

Step A: Preparation of 5-amino-1-methyl-4-phenyl-1H-pyrazol-3(2H)-one

To a suspension of ethyl 2-cyano-2-phenylacetate (2.56 g, 13.3 mmol) in EtOH (10 mL) was added dropwise methylhydrazine (1.09 mL, 19.9 mmol). The reaction was heated at 85° C. for 15 hours. The reaction mixture was cooled to 0° C. and filtered. The resultant solid was washed with cold EtOH (20 mL) and Et₂O (20 mL) to give the desired product (2.10 g, 83.7% yield). MS (apci) m/z=190.2 (M+H)

Step B: Preparation of 3-(benzyloxy)-1-methyl-1H-pyrazol-5-amine

A suspension of 5-amino-1-methyl-1H-pyrazol-3(2H)-one (0.35 g, 3.1 mmol), Benzyl chloride (0.43 g, 3.4 mmol), and K₂CO₃ (1.3 g, 9.3 mmol) in DMF (4 mL) was heated at 70° C. for 17 hours. After cooling, the reaction mixture was treated with EtOAc, washed with water and brine, dried with MgSO₄, and concentrated in vacuo. The crude product was purified by silica column chromatography eluting with 2-6% MeOH/DCM to afford the title compound (0.16 g, 25% yield). MS (apci) m/z=204.0 (M+H).

Intermediate P137

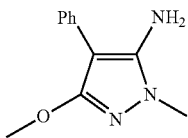

3-methoxy-1-methyl-4-phenyl-1H-pyrazol-5-amine

To a suspension of 5-amino-1-methyl-4-phenyl-1H-pyrazol-3(2H)-one (Step A of the preparation of Intermediate P136; 208 mg, 1.10 mmol) and K₂CO₃ (456 mg, 3.30 mmol) in DMF (5 mL) was added dropwise iodomethane (172 mg, 1.21 mmol). The reaction mixture was stirred for 15 hours. The solvent was removed under reduced pressure and the residue was purified by silica column chromatography eluting with 33% EtOAc/Hexanes to give the title pyrazole (66.0 mg, 30.4% yield). MS (apci) m/z=204.1 (M+H).

Intermediate P138

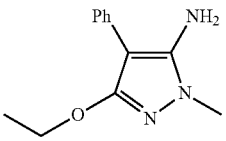 [SMILES: CCOc1nn(C)c(N)c1-c1ccccc1]

3-ethoxy-1-methyl-4-phenyl-1H-pyrazol-5-amine

Prepared as described in Intermediate P137, replacing iodomethane with iodoethane in Step B to afford the title compound. MS (apci) m/z=218.2 (M+H).

Intermediate P139

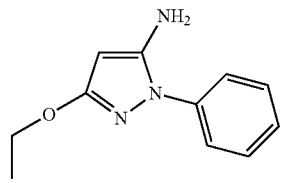

3-ethoxy-1-phenyl-1H-pyrazol-5-amine

Prepared according to the procedure described for Intermediate 135, substituting ethyl-2-cyanopropanoate with-ethyl-2-cyanoacetate in Step A. MS (apci) m/z=204.0 (M+H).

The compounds in the following Table were prepared by the method as described for Intermediate P135, substituting bromoethane with the appropriate alkyl halide, alkyl methanesulfonate or epoxide.

| Intermediate # | Structure | MS (apci) m/z |
| --- | --- | --- |
| P140 | 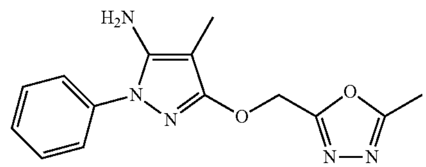 [SMILES: Cc1nnc(COc2nn(-c3ccccc3)c(N)c2C)o1] | 286.1 (M + H) |
| P141 | 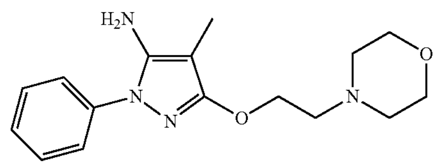 [SMILES: Cc1c(OCCN2CCOCC2)nn(-c2ccccc2)c1N] | 303.1 (M + H) |
| P142 | 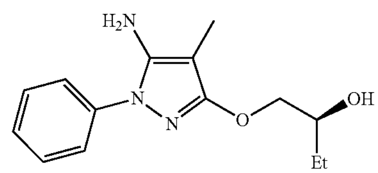 [SMILES: CC[C@H](O)COc1nn(-c2ccccc2)c(N)c1C] | 262.1 (M + H) |
| P143 | 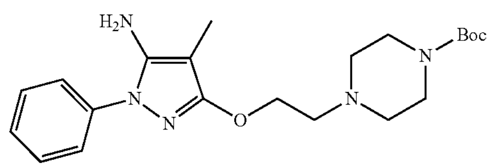 [SMILES: Cc1c(OCCN2CCN(C(=O)OC(C)(C)C)CC2)nn(-c2ccccc2)c1N] | 402.2 (M + H) |
| P144 | 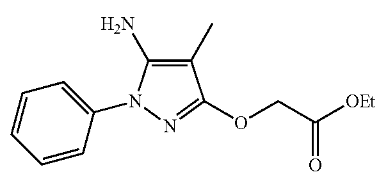 [SMILES: CCOC(=O)COc1nn(-c2ccccc2)c(N)c1C] | 276.1 (M + H) |
| P145 | 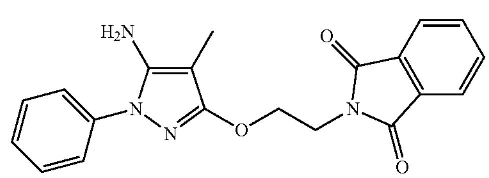 [SMILES: Cc1c(OCCN2C(=O)c3ccccc3C2=O)nn(-c2ccccc2)c1N] | 363.1 (M + H) |
| P146 | 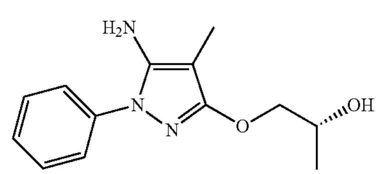 [SMILES: Cc1c(OC[C@@H](C)O)nn(-c2ccccc2)c1N] | 248.1 (M + H) |

| Intermediate # | Structure | MS (apci) m/z |
|---|---|---|
| P147 | 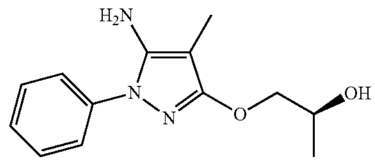 [SMILES: Cc1c(OC[C@H](C)O)nn(-c2ccccc2)c1N] | 248.1 (M + H) |
| P148 | 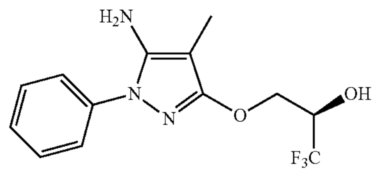 [SMILES: Cc1c(OC[C@@H](O)C(F)(F)F)nn(-c2ccccc2)c1N] | 302.1 (M + H) |
| P149 | 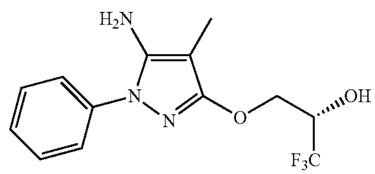 [SMILES: Cc1c(OC[C@H](O)C(F)(F)F)nn(-c2ccccc2)c1N] | 302.1 (M + H) |
| P150 | 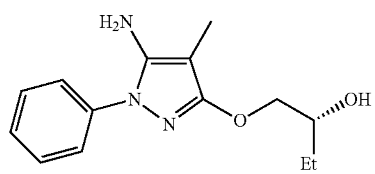 [SMILES: CC[C@@H](O)COc1nn(-c2ccccc2)c(N)c1C] | 262.1 (M + H) |

Intermediate 151

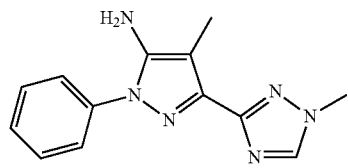 [SMILES: Cc1c(-c2ncn(C)n2)nn(-c2ccccc2)c1N]

1'-(2-methoxyethyl)-1-phenyl-1H,1'H-[3,4'-bipyrazol]-5-amine

Step A: Preparation of methyl 1-methyl-1H-1,2,4-triazole-3-carboxylate

To a stirred suspension of NaH (60% oil dispersion, 0.346 g, 8.66 mmol) in DMF (20 mL) was added dropwise a solution of methyl 1H-1,2,4-triazole-3-carboxylate (1.00 g, 7.87 mmol) in DMF (20 mL) at 0° C. under nitrogen. The reaction mixture was stirred at 0° C. for 1 hour. MeI (0.982 mL, 15.7 mmol) was added dropwise. The reaction mixture was stirred at ambient temperature overnight. The reaction was poured into cold water and extracted with EtOAc. The combined organic layers were washed with brine, dried and concentrated. The residue was purified by column chromatography (3:1 hexanes/EtOAc) to give the title compound (0.380 g, 34% yield) as a white solid. MS (apci) m/z=142.1 (M+H).

Step B: Preparation of 1'-(2-methoxyethyl)-1-phenyl-1H,1'H-[3,4'-bipyrazol]-5-amine Prepared according to the method described for Intermediate P109, using methyl 1-methyl-1H-1,2,4-triazole-3-carboxylate as a replacement for methyl 2-methoxyacetate, and substituting propionitrile for acetonitrile in Step A. MS (apci) m/z=255.1 (M+H).

Intermediate 152

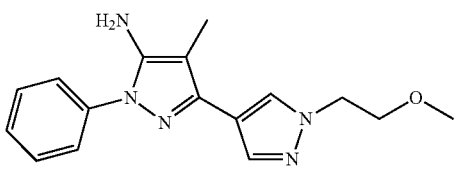 [SMILES: COCCn1cc(-c2nn(-c3ccccc3)c(N)c2C)cn1]

1'-(2-methoxyethyl)-4-methyl-1-phenyl-1H,1'H-[3,4'-bipyrazol]-5-amine

Prepared according to the method described for Intermediate P109, using ethyl 1-(2-methoxyethyl)-1H-pyrazole-4- carboxylate as a replacement for methyl 2-methoxyacetate, and substituting propionitrile for acetonitrile in Step A.

Intermediate 153

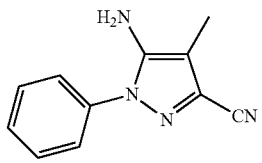

5-amino-4-methyl-1-phenyl-1H-pyrazole-3-carbonitrile

To a stirred solution of aniline (2.02 g, 21.7 mmol) in 6 N HCl (22 mL) was added dropwise a solution of NaNO₂ (1.50 g, 21.7 mmol) in water (20 mL) at 0-5° C. The reaction mixture was stirred at 0° C. for 15 minutes. Acetic acid (10 mL) was added. This solution was added dropwise to a stirred solution of ethyl 2,3-dicyanobutanoate (Prepared according to the procedure described in *Bioorganic & Medicinal Chemistry*, 2004, 12, 3345-3356, 3.60 g, 21.7 mmol) in acetic acid (12 mL) and water (18 mL) at 0° C. After stirring for 1 hour, concentrated ammonium hydroxide (50 mL) was added dropwise followed by THF (50 mL). The reaction was stirred at ambient temperature overnight. The organic layer was separated. The aqueous layer was extracted with EtOAc. The combined organic layers were washed with brine, dried and concentrated. The residue was purified by flash chromatography on silica gel (3:1 hexanes/EtOAc) to give the title compound (2.95 g, 69% yield). MS (apci) m/z=198.9 (M+H).

Intermediate 155

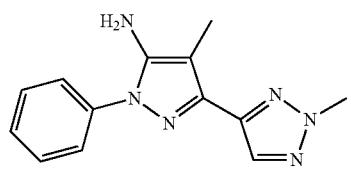 [SMILES: Cc1c(-c2cnn(C)n2)nn(-c2ccccc2)c1N]

4-methyl-3-(2-methyl-2H-1,2,3-triazol-4-yl)-1-phenyl-1H-pyrazol-5-amine

Step A: Preparation of ethyl 2-methyl-2H-1,2,3-triazole-4-carboxylate

A mixture of ethyl 2H-1,2,3-triazole-4-carboxylate (2.00 g, 14.2 mmol), K₂CO₃ (3.53 g, 25.5 mmol) and methyl iodide (3.54 mL, 56.7 mmol) in acetonitrile (40 mL) was stirred at 50° C. under nitrogen overnight. After cooling to ambient temperature, the mixture was filtered through Celite®. The filtrate was concentrated in vacuo. The residue was purified by flash chromatography on silica gel (4:1 hexane/EtOAc) to give the title compound (0.780 g, 35% yield). MS (apci) m/z=156.0 (M+H).

Step B: Preparation of 4-methyl-3-(2-methyl-2H-1,2,3-triazol-4-yl)-1-phenyl-1H-pyrazol-5-amine Prepared according to the method described for Intermediate P109 using ethyl 2-methyl-2H-1,2,3-triazole-4-carboxylate as a replacement for methyl 2-methoxyacetate, and substituting propionitrile for acetonitrile in Step A. MS (apci) m/z=254.9 (M+H).

Intermediate 156

3-bromo-4-methyl-1-phenyl-1H-pyrazol-5-amine

To a stirred solution of 5-amino-4-methyl-1-phenyl-1H-pyrazol-3(2H)-one (Intermediate P135, Step A, 1.00 g, 5.29 mmol) in MeCN (20 mL) was added POBr₃ (2.27 g, 7.93 mmol). The reaction mixture was heated at reflux for 3 hours. The reaction was concentrate in vacuo. The residue was taken up in DCM. Saturated aqueous NaHCO₃ solution was carefully added. The aqueous layer was extracted with DCM. The combined organic layers were washed with brine, dried and concentrated. The residue was purified by flash chromatography on silica gel (1:2 hexane/EtOAc to give the title compound (0.23 g, 17% yield). MS (apci) m/z=251.8 (M+H).

Intermediate 157

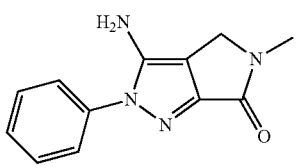 [SMILES: CN1Cc2c(nn(-c3ccccc3)c2N)C1=O]

3-amino-5-methyl-2-phenyl-4,5-dihydropyrrolo[3,4-c]pyrazol-6(2H)-one

Step A: Preparation of ethyl 5-amino-4-((methylamino)methyl)-1-phenyl-1H-pyrazole-3-carboxylate To a stirred solution of ethyl 5-amino-4-formyl-1-phenyl-1H-pyrazole-3-carboxylate (Prepared according to the procedure described in *J. Heterocyclic Chemistry*, 2010, 47, p. 287-291, 142 mg, 0.548 mmol) in DCM (3 mL) was added 2.0 M MeNH₂ in THF (0.822 mL, 1.64 mmol). Two drops of acetic acid was added. The reaction mixture was stirred at ambient temperature overnight. MeOH (0.4 mL) was added followed by NaBH₄ (31 mg, 0.82 mmol) portionwise. The reaction was quenched by the slow addition of water. The mixture was extracted with DCM. The combined organic layers were washed with brine, dried and concentrated. The crude was used in the next step without further purification. MS (apci) m/z=275.0 (M+H).

Step B: Preparation of 3-amino-5-methyl-2-phenyl-4,5-dihydropyrrolo[3,4-c]pyrazol-6(2H)-one To a stirred solution of ethyl 5-amino-4-((methylamino)methyl)-1-phenyl-1H-pyrazole-3-carboxylate (crude, 65 mg, 0.24 mmol) in MeOH (0.5 mL) and THF (0.5 mL) was added 2 N NaOH (0.24 mL, 0.47 mmol). The reaction mixture was stirred at ambient temperature for 4 hours and then concentrated in vacuo. To the residue was added water. The pH was adjusted to 4-5 using 1 N HCl. Water was evaporated under reduced pressure. The crude acid (58 mg) was dissolved in DMF (3 mL). Et$_3$N (66 μL, 0.47 mmol) was added followed by EDCI (90 mg, 0.47 mmol) and HOBt (32 mg, 0.24 mmol). The reaction mixture was stirred at ambient temperature overnight and then partitioned between EtOAc and water. The aqueous layer was extracted with EtOAc. The combined organic layers were washed with water and brine, dried and concentrated. The residue was purified by flash chromatography on silica gel (2% MeOH in DCM) to give the title compound (15 mg, 28%) as a white solid. MS (apci) m/z=228.9 (M+H).

Intermediate 158

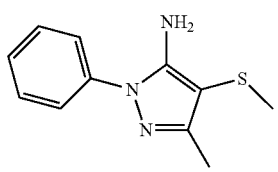

3-methyl-4-(methylthio)-1-phenyl-1H-pyrazol-5-amine

Prepared according to the method described for Intermediate P109, replacing methyl 2-methoxyacetate with ethyl acetate and replacing acetonitrile with 2-(methylthio)acetonitrile in Step A to afford the product as a brown oil. MS (apci) m/z=220.1 (M+H).

Intermediate 159

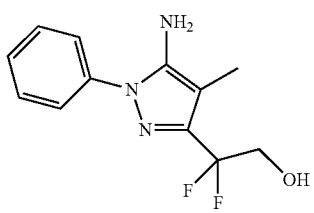 [SMILES: Cc1c(C(F)(F)CO)nn(-c2ccccc2)c1N]

2-(5-amino-4-methyl-1-phenyl-1H-pyrazol-3-yl)-2,2-difluoroethanol

Prepared according to the method described for Intermediate P111, replacing acetonitrile with propionitrile and replacing methyl 3-hydroxy-2,2-dimethylpropanoate with ethyl 2,2-difluoro-3-hydroxypropanoate to afford the product as a pale yellow solid. MS (apci) m/z=254.1 (M+H).

Intermediate 160

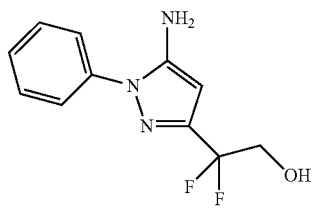 [SMILES: Nc1cc(C(F)(F)CO)nn1-c1ccccc1]

2-(5-amino-1-phenyl-1H-pyrazol-3-yl)-2,2-difluoroethanol

Prepared according to the method described for Intermediate P111, replacing methyl 3-hydroxy-2,2-dimethylpropanoate with ethyl 2,2-difluoro-3-hydroxypropanoate to afford the product as a pale yellow solid. MS (apci) m/z=240.0 (M+H).

Intermediate 161

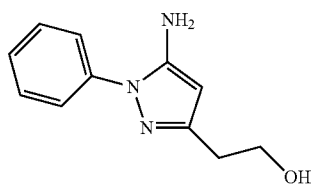 [SMILES: Nc1cc(CCO)nn1-c1ccccc1]

2-(5-amino-1-phenyl-1H-pyrazol-3-yl)ethanol

Prepared according to the method described in Intermediate P111, replacing methyl 3-hydroxy-2,2-dimethylpropanoate with methyl 3-hydroxypropanoate in Step A. MS (apci) m/z=204.1 (M+H).

Intermediate 162

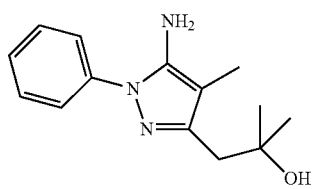 [SMILES: Cc1c(CC(C)(C)O)nn(-c2ccccc2)c1N]

1-(5-amino-4-methyl-1-phenyl-1H-pyrazol-3-yl)-2-methylpropan-2-ol

Step A: Preparation of ethyl 3-hydroxy-3-methylbutanoate

To a solution of lithium bis(trimethylsilyl)amide (1M in THF) (100 mL, 100 mmol) in THF (100 mL) under N$_2$ and cooled to −78° C. was added ethyl acetate (9.74 mL, 100 mmol). The reaction mixture was stirred for 30 minutes, and then acetone (8.81 mL, 120 mmol) was added. The reaction mixture was stirred for 10 minutes, and then quenched with HCl (2M aqueous, 70 mL, 140 mmol) and allowed to warm to ambient temperature. The reaction mixture was extracted with EtOAc (2×150 mL). The organic phases were combined and washed with saturated aqueous NaHCO$_3$ (2×50 mL), dried (MgSO$_4$), filtered and concentrated to afford the product as a yellow oil (12.8 g, 88% yield). $^1$H NMR (CDCl$_3$) δ 4.18 (q, 3H), 2.49 (s, 2H), 1.29 (m, 9H).

Step B: Preparation of 5-hydroxy-5-methyl-3-oxohexanenitrile

To a solution of propionitrile (1.77 mL, 30.5 mmol) in THF (100 mL) under N$_2$ at −78° C. was added lithium bis(trimethylsilyl)amide (1M in THF) (27.9 mL, 27.9 mmol). Stirred 1 hour, then ethyl 3-hydroxy-3-methylbutanoate (1.86 g, 12.7 mmol) was added. The reaction mixture was stirred at −78° C. for 1 hour, then stirred at 0° C. for 1.5 hours, then diluted with H$_2$O (100 mL) and extracted with Et$_2$O (50 mL). The phases were separated and the basic aqueous phase was neutralized with HCl (6M aqueous, 4.5 mL), then extracted with Et$_2$O (3×75 mL). The combined organic phases were washed with brine (75 mL), dried (MgSO$_4$), filtered, and concentrated to afford the product as a pale yellow oil (1.24 g, 63% yield). $^1$H NMR (CDCl$_3$) δ 3.54 (m, 1H), 2.89 (s, 2H), 1.50 (d, 3H), 1.32 (s, 3H), 1.31 (s, 3H).

Step C: Preparation of 1-(5-amino-4-methyl-1-phenyl-1H-pyrazol-3-yl)-2-methylpropan-2-ol To a suspension of phenylhydrazine (0.793 mL, 7.99 mmol) and HCl (5-6M in iPrOH, 1.60 mL, 7.99 mmol) in EtOH (25 mL) was added a solution of 5-hydroxy-2,5-dimethyl-3-oxohexanenitrile (1.24 g, 7.99 mmol) in EtOH (25 mL). The reaction mixture was refluxed for 17 hours, then cooled to ambient temperature, diluted with saturated aqueous NaHCO$_3$ (10 mL), extracted 10:90 MeOH/DCM (3×25 mL), and the combined organic phases were dried (MgSO$_4$), filtered and concentrated. Purified by silica column chromatography eluting with 0-75% acetone/hexanes to afford the title compound as an orange oil (1.13 g, 58% yield). MS (apci) m/z=246.1 (M+H).

The following pyrazole intermediates were prepared according to the method used for the preparation of Intermediate 162, Steps B and C, using the appropriate starting material. For the preparation of Intermediates 168 and 169, the starting material (purchased from Oakwood) was a mixture of cis and trans diastereomers.

| Intermediate # | Structure | Name | MS (apci) m/z |
|---|---|---|---|
| 163 | 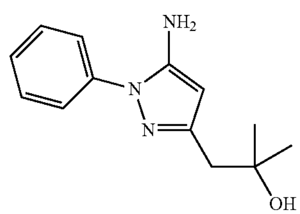 [SMILES: CC(C)(O)Cc1cc(N)n(-c2ccccc2)n1] | 1-(5-amino-1-phenyl-1H-pyrazol-3-yl)-2-methylpropan-2-ol | 232.1 (M + H) |
| 164 | 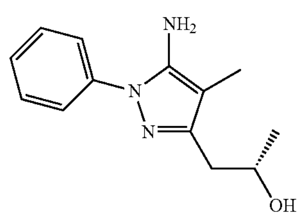 [SMILES: Cc1c(C[C@H](C)O)nn(-c2ccccc2)c1N] | (S)-1-(5-amino-4-methyl-1-phenyl-1H-pyrazol-3-yl)propan-2-ol | 232.1 (M + H) |
| 165 | 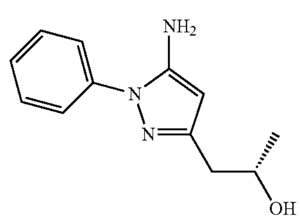 [SMILES: C[C@H](O)Cc1cc(N)n(-c2ccccc2)n1] | (S)-1-(5-amino-1-phenyl-1H-pyrazol-3-yl)propan-2-ol | 218.1 (M + H) |
| 166 | 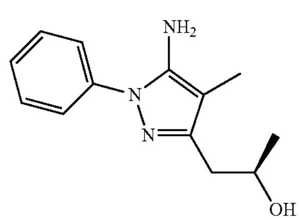 [SMILES: Cc1c(C[C@@H](C)O)nn(-c2ccccc2)c1N] | (R)-1-(5-amino-4-methyl-1-phenyl-1H-pyrazol-3-yl)propan-2-ol | 232.1 (M + H) |

| Intermediate # | Structure | Name | MS (apci) m/z |
|---|---|---|---|
| 167 | 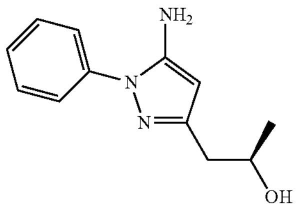 [SMILES: C[C@@H](O)Cc1cc(N)n(-c2ccccc2)n1] | (R)-1-(5-amino-1-phenyl-1H-pyrazol-3-yl)propan-2-ol | 218.1 (M + H) |
| 168 | 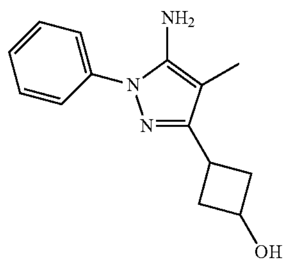 [SMILES: Cc1c(C2CC(O)C2)nn(-c2ccccc2)c1N] | 3-(5-amino-4-methyl-1-phenyl-1H-pyrazol-3-yl)cyclobutanol | 244.1 (M + H) |
| 169 | 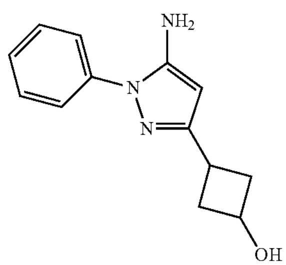 [SMILES: Nc1cc(C2CC(O)C2)nn1-c1ccccc1] | 3-(5-amino-1-phenyl-1H-pyrazol-3-yl)cyclobutanol | 230.1 (M + H) |

Intermediate 170 ethyl 5-amino-4-methyl-1-phenyl-1H-pyrazole-3-carboxylate

Prepared according to the method described for Intermediate P109, replacing methyl 2-methoxyacetate with diethyl oxalate and replacing acetonitrile with propionitrile in Step A to afford the product as a yellow solid. MS (apci) m/z=246.1 (M+H).

Intermediate 171

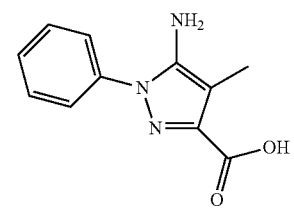 [SMILES: Cc1c(C(=O)O)nn(-c2ccccc2)c1N]

5-amino-4-methyl-1-phenyl-1H-pyrazole-3-carboxylic acid

To a solution of ethyl 5-amino-4-methyl-1-phenyl-1H-pyrazole-3-carboxylate (Intermediate 170, 1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried (MgSO$_4$), filtered and concentrated to give the title compound as a yellow solid (1.3 g, 96% yield) MS (apci) m/z=218.1 (M+H).

Intermediate 172

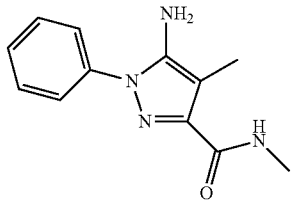 [SMILES: CNC(=O)c1nn(-c2ccccc2)c(N)c1C]

5-amino-N,4-dimethyl-1-phenyl-1H-pyrazole-3-carboxamide

To a solution of 5-amino-4-methyl-1-phenyl-1H-pyrazole-3-carboxylic acid (Intermediate 171, 223 mg, 1.02 mmol) in acetonitrile (10 mL) were added DIEA (0.71 mL, 4.10 mmol), methanamine hydrochloride (138 mg, 2.05 mmol), DMF (2 mL), and then HATU (428 mg, 1.13 mmol). The reaction mixture was stirred at ambient temperature for 19 hours and then partially concentrated under reduced pressure. The mixture was purified by reverse-phase column chromatography, eluting with 5-60% acetonitrile/water to afford the title compound as a pale yellow solid (182 mg, 77% yield). MS (apci) m/z=231.1 (M+H).

Intermediate 173

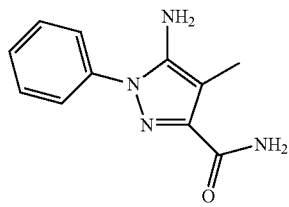 [SMILES: Cc1c(C(N)=O)nn(-c2ccccc2)c1N]

5-amino-4-methyl-1-phenyl-1H-pyrazole-3-carboxamide

A solution of 5-amino-4-methyl-1-phenyl-1H-pyrazole-3-carbonitrile (150 mg, 0.757 mmol) in concentrated H$_2$SO$_4$ (0.5 mL) was stirred at ambient temperature for 17 hours. The reaction mixture was cooled and neutralized by the addition of aqueous NaOH (2M, 11 mL), then extracted 10% MeOH/DCM (5×10 mL), and the combined organic extracts were washed with brine, dried (MgSO$_4$), filtered and concentrated under reduced pressure to afford the title compound as a white solid (151 mg, 95% yield). MS (apci) m/z=239.1 (M+Na).

Intermediate 174

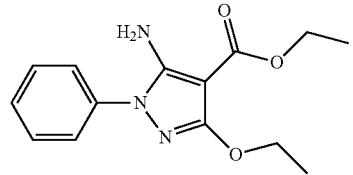 [SMILES: CCOC(=O)c1c(OCC)nn(-c2ccccc2)c1N]

ethyl 5-amino-3-ethoxy-1-phenyl-1H-pyrazole-4-carboxylate

Step A: Preparation of diethyl 2-cyanomalonate

To a suspension of NaH (60 wt % in mineral oil, 499 mg, 12.49 mmol) in THF (100 mL) under N$_2$ at 0° C. was added diethyl malonate (1.90 mL, 12.49 mmol). The ice bath was removed and the reaction mixture was stirred at ambient temperature for 30 minutes, then cooled to 0° C. and cyanic bromide (5M in MeCN, 2.5 mL, 12.49 mmol) was added. The reaction mixture was stirred at ambient temperature for 19 hours, then diluted with H$_2$O (50 mL), extracted with Et$_2$O (50 mL). The aqueous phase was neutralized with HCl (2M aq, 3 mL) then extracted with DCM (2×50 mL). The combined DCM extracts were dried (MgSO$_4$), filtered, and concentrated to afford the product as a yellow oil (837 mg, 36% yield). 1H NMR (CDCl$_3$) δ 4.46 (s, 1H), 4.35 (q, 4H), 1.35 (t, 6H).

Step B: Preparation of ethyl 5-amino-3-ethoxy-1-phenyl-1H-pyrazole-4-carboxylate Prepared according to the method described for Intermediate P135, replacing ethyl 2-cyanopropanoate with diethyl 2-cyanomalonate in Step A to afford the product as a brown syrup (400 mg, 32% yield). MS (apci) m/z=276.1 (M+H).

Intermediate 175

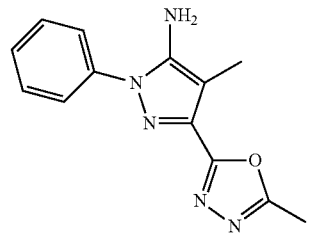 [SMILES: Cc1nnc(-c2nn(-c3ccccc3)c(N)c2C)o1]

4-methyl-3-(5-methyl-1,3,4-oxadiazol-2-yl)-1-phenyl-1H-pyrazol-5-amine

Step A: Preparation of N'-acetyl-5-amino-4-methyl-1-phenyl-1H-pyrazole-3-carbohydrazide To a solution of 5-amino-4-methyl-1-phenyl-1H-pyrazole-3-carboxylic acid (Intermediate 171, 93 mg, 0.428 mmol) in DCM (5 mL) and DIEA (0.149 mL, 0.856 mmol) was added isobutyl carbonochloridate (0.061 mL, 0.471 mmol). The reaction mixture was stirred at ambient temperature for 1 hour, then acetohydrazide (48 mg, 0.642 mmol) was added. The reaction mixture was stirred at ambient temperature for 18 hours, then diluted with H$_2$O (10 mL), extracted DCM (2×10 mL), dried (MgSO$_4$), filtered and concentrated under reduced pressure to afford the product as a pale yellow solid (119 mg, 101% yield). MS (apci) m/z=274.1 (M+H).

Step B: Preparation of 4-methyl-3-(5-methyl-1,3,4-oxadiazol-2-yl)-1-phenyl-1H-pyrazol-5-amine A mixture of N'-acetyl-5-amino-4-methyl-1-phenyl-1H-pyrazole-3-carbohydrazide (117 mg, 0.428 mmol) and POCl$_3$ (0.5 mL) was heated in a pressure tube to 90° C. for 1 hour. The reaction mixture was transferred to a separatory funnel with EtOAc (5 mL), then diluted with saturated aqueous NaHCO$_3$ (20 mL), extracted with EtOAc (2×15 mL), dried (MgSO$_4$), filtered and concentrated. The residue was purified by silica column chromatography eluting with 0-75% acetone/hexanes to afford the title compound as a yellow solid (19.6 mg, 18% yield). MS (apci) m/z=256.1 (M+H).

Intermediate 176

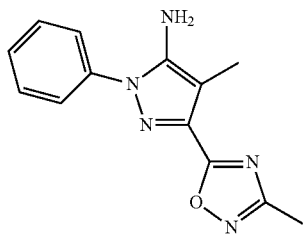 [SMILES: Cc1noc(-c2nn(-c3ccccc3)c(N)c2C)n1]

4-methyl-3-(3-methyl-1,2,4-oxadiazol-5-yl)-1-phenyl-1H-pyrazol-5-amine

To a suspension of NaH (60% in mineral oil, 36 mg, 0.897 mmol) in THF (5 mL) under N$_2$ was added N-hydroxyacetimidamide (66 mg, 0.897 mmol). The reaction mixture was heated to reflux for 1 hour, then cooled to ambient temperature and ethyl 5-amino-4-methyl-1-phenyl-1H-pyrazole-3-carboxylate (Intermediate 170, 200 mg, 0.815 mmol) was added. The reaction mixture was heated to reflux for 18 hours, then cooled to ambient temperature and additional NaH (60% in mineral oil, 18 mg, 0.449 mmol) was added. The reaction mixture was heated to reflux for 4 hours, then diluted with H$_2$O (10 mL), extracted DCM (2×15 mL), and the combined organic extracts were dried (MgSO$_4$), filtered and concentrated under reduced pressure. The residue was purified by silica column chromatography eluting with 0-50% acetone/hexanes to afford the title compound as an orange solid (84 mg, 40% yield). MS (apci) m/z=256.1 (M+H).

Intermediate 177

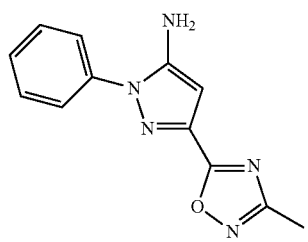 [SMILES: Cc1noc(-c2cc(N)n(-c3ccccc3)n2)n1]

3-(3-methyl-1,2,4-oxadiazol-5-yl)-1-phenyl-1H-pyrazol-5-amine

Prepared according to the method described in Intermediate 176, replacing ethyl 5-amino-4-methyl-1-phenyl-1H-pyrazole-3-carboxylate with ethyl 5-amino-1-phenyl-1H-pyrazole-3-carboxylate (Nanjing Chemlin Chemical Co.) to afford the product as a tan solid (83 mg, 53% yield). MS (apci) m/z=242.1 (M+H).

Intermediate 178

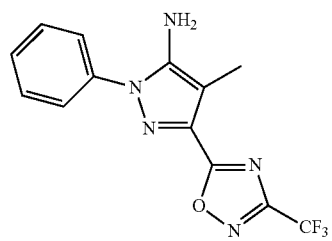 [SMILES: Cc1c(-c2nc(C(F)(F)F)no2)nn(-c2ccccc2)c1N]

4-methyl-1-phenyl-3-(3-(trifluoromethyl)-1,2,4-oxadiazol-5-yl)-1H-pyrazol-5-amine Step A: Preparation of 2,2,2-trifluoro-N'-hydroxyacetimidamide To a suspension of hydroxylamine hydrochloride (5.45 g, 78.4 mmol) in MeOH (100 mL) was added NaOMe (25 wt % solution in MeOH, 17.9 mL, 78.4 mmol) and the mixture stirred at ambient temperature for 10 minutes, then filtered and the solid was washed with MeOH. The filtrate was cooled to 0° C. and then 2,2,2-trifluoroacetonitrile (7.45 g, 78.4 mmol) gas was bubbled into the solution over 30 minutes. The reaction mixture was then allowed to warm to ambient temperature for 19 hours. The solution was concentrated under reduced pressure to 50 mL and the solids were filtered. The filtrate was concentrated, re-suspended in cold MeOH, and filtered. The filtrate was concentrated, again re-suspended in cold MeOH, and filtered. The filtrate was concentrated to give the product as a waxy white solid (6.7 g, 67% yield). $^1$H NMR (CD$_3$CN) δ 8.32 (s, 1H), 5.25 (br s, 2H). $^{19}$F NMR (CD$_3$CN) δ −71.8 (s).

Step B: Preparation of 4-methyl-1-phenyl-3-(3-(trifluoromethyl)-1,2,4-oxadiazol-5-yl)-1H-pyrazol-5-amine To a suspension of NaH (60% in mineral oil, 356 mg, 0.897 mmol) in THF (5 mL, 0.815 mmol) under N$_2$ was added 2,2,2-trifluoro-N'-hydroxyacetimidamide (115 mg, 0.897 mmol). The reaction mixture was heated to reflux for 1 hour, then cooled to ambient temperature and powdered 4A molecular sieves (200 mg) and ethyl 5-amino-4-methyl-1-phenyl-1H-pyrazole-3-carboxylate (Intermediate 170; 200 mg, 0.815 mmol) were added and heated to reflux. The reaction mixture was heated to reflux for 18 hours, then filtered, diluted with H$_2$O (15 mL), extracted DCM (2×25 mL), and the combined organic extracts were washed with brine (25 mL), dried (MgSO$_4$), filtered and concentrated under reduced pressure. The residue was purified by silica column chromatography eluting with 0-50% acetone/hexanes to afford the title compound as a white solid (44 mg, 17% yield). MS (apci) m/z=310.1 (M+H).

Intermediate 179

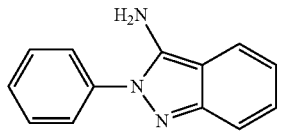 [SMILES: Nc1c2ccccc2nn1-c1ccccc1]

2-phenyl-2H-indazol-3-amine

Step A: Preparation of 1-(2-iodophenyl)-2-phenyldiazene

To a solution of 2-iodoaniline (1.00 g, 4.57 mmol) in acetic acid (46 mL) was added nitrosobenzene (0.880 g, 8.22 mmol) and the mixture was heated at 85° C. for 16 hours. The mixture was cooled to ambient temperature, poured into water and slowly treated with saturated NaHCO$_3$ until basic. The mixture was extracted with EtOAc (3×) and the combined extracts were washed with water, saturated NaCl and dried over MgSO$_4$. The solution was filtered, concentrated and the residue purified by reverse phase chromatography to provide the title compound as a red solid (0.880 g, 63% yield). $^1$H NMR (CDCl$_3$) δ 7.23-7.39 (m, 3H), 7.64 (d, 1H), 7.56-7.51 (m, 3H), 7.45 (t, 1H), 7.1 (t, 1H).

Step B: 2-(phenyldiazenyl)benzonitrile

To a solution of 1-(2-iodophenyl)-2-phenyldiazene (0.44 g, 1.4 mmol) in 1-propanol (14 mL) was added CuCN (0.900 g, 10.0 mmol) and the reaction was heated at reflux for 16 hours. The mixture was cooled to ambient temperature, filtered and the collected solid washed with CH$_2$Cl$_2$. The combined filtrate and washes were concentrated to provide the title compound as red-orange solid that was dried in vacuum (0.280 g, 95% yield). $^1$H NMR (CDCl$_3$) δ 8.03-8.06 (m, 2H), 7.88 (dd, 2H), 7.71 (t, 1H), 7.54-7.58 (m, 4H).

Step C: 2-phenyl-2H-indazol-3-amine

A mixture of 2-(phenyldiazenyl)benzonitrile (0.28 g, 1.35 mmol) and SnCl$_2$ dihydrate (0.562 mL, 6.76 mmol) in EtOH (14 mL) was heated at reflux for 16 hours. The mixture was cooled to ambient temperature and concentrated. The residue was diluted with EtOAc and water and filtered. The aqueous layer was removed and the EtOAc layer was washed with water. The combined aqueous fractions were basified with saturated NaHCO$_3$ and extracted with CH$_2$Cl$_2$ (2×). The combined organic layers were dried over MgSO$_4$, filtered and concentrated to provide the title compound as a light purple solid that was dried in vacuum (0.241 g, 85% yield). $^1$H NMR (CDCl$_3$) δ 7.69 (d, 2H), 7.52-7.58 (m, 3H), 7.47 (d, 2H), 7.26 (t, 1H), 6.90 (t, 1H), 4.28 (br s, 2H).

Intermediate 180

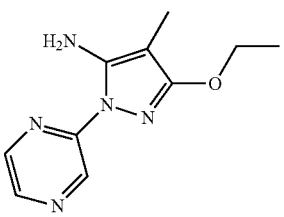 [SMILES: CCOc1nn(-c2cnccn2)c(N)c1C]

3-ethoxy-4-methyl-1-(pyrazin-2-yl)-1H-pyrazol-5-amine

Step A: 5-amino-4-methyl-1-(pyrazin-2-yl)-1H-pyrazol-3(2H)-one

To a mixture of 2-hydrazinylpyrazine (0.551 g, 5.00 mmol) and ethyl 2-cyanopropanoate (0.669 g, 5.00 mmol) in abs. EtOH (10 mL) was added 3M NaOEt in EtOH (0.167 mL, 0.501 mmol) and the mixture was heated at reflux for 64 hours. The mixture was concentrated and the residual yellow-brown solid was treated with EtOAc (30 mL) and sonicated. The resulting tan suspension was stirred vigorously for 8 hours. The solid was collected via vacuum filtration, washed with EtOAc and dried in vacuum to afford the title compound as a light tan powder (682 mg, 71%). $^1$H NMR (DMSO d$_6$) δ 10.3 (br s, 1H), 8.82 (s, 11-1), 8.30 (d, 2H), 6.55 (s, 2H), 1.71 (s, 3H).

Step B: 3-ethoxy-4-methyl-1-(pyrazin-2-yl)-1H-pyrazol-5-amine

A mixture of 5-amino-4-methyl-1-(pyrazin-2-yl)-1H-pyrazol-3(2H)-one (382 mg, 2.00 mmol) and powdered K$_2$CO$_3$ (552 mg, 4.00 mmol) in dry DMF (3.0 mL) was stirred at ambient temperature for 10 minutes. The mixture was cooled to 0° C. and bromoethane (229 mg, 2.10 mmol) was added. The mixture was allowed to reach ambient temperature and was stirred 24 hours. The reaction mixture poured into cold H$_2$O (12 mL), allowed to reach ambient temperature and was extracted with EtOAc (3×). The combined extracts were washed with saturated NaCl (2×), dried over MgSO$_4$ and activated carbon. The dried solution was diluted with and equal volume of hexanes and filtered through a SiO$_2$ plug capped with a MgSO$_4$ layer eluting with 50% EtOAc-hexanes. The filtrate was concentrated and the residual yellow solid was washed with hexanes (3×) and dried in vacuum to afford the title compound as a light yellow crystalline solid (195 mg, 45%). $^1$H NMR (CDCl$_3$) δ 9.10 (s, 1H), 8.23 (s, 1H), 8.14 (s, 1H), 5.50 (br s, 21H), 4.33 (q, 2H), 1.80 (s, 3H), 1.42 (t, 3H).

Intermediate 181

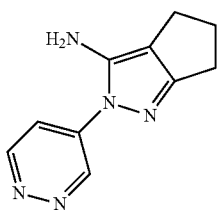 [SMILES: Nc1c2c(nn1-c1ccnnc1)CCC2]

2-(pyridazin-4-yl)-2,4,5,6-tetrahydrocyclopenta[c]pyrazol-3-amine

A suspension of 4-hydrazinylpyridazine hydrobromide (0.368 g, 1.93 mmol) in absolute EtOH (5 mL) was treated with 2-oxocyclopentanecarbonitrile (0.191 g, 1.75 mmol) and the mixture was heated at reflux for 22 hours. The mixture was cooled to ambient temperature and was concentrated to an orange solid. The solid was suspended in 1M NaOH and stirred for 10 minutes. The solid was collected, washed thoroughly with $H_2O$ and $Et_2O$ and dried in vacuum to furnish title compound as a tan powder (0.323 g, 92%). MS (apci) m/z=202.1 (M+H).

Intermediate 182

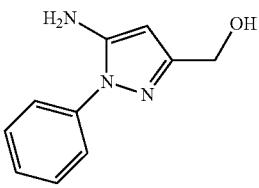 [SMILES: Nc1cc(CO)nn1-c1ccccc1]

(5-amino-1-phenyl-1H-pyrazol-3-yl)methanol

Step A: Ethyl 2-(tert-butyldimethylsilyloxy)acetate

A mixture of ethyl 2-hydroxyacetate (3.00 g, 28.8 mmol), TBDMS-Cl (5.21 g, 34.6 mmol) and imidazole (2.55 g, 37.5 mmol) was stirred at ambient temperature for 60 hours. The mixture was concentrated and the residue was purified by $SiO_2$ chromatography eluting with 10% EtOAc-hexanes to provide the title compound as a colorless oil (4.12 g, 65%). $^1$H NMR (CDCl$_3$) δ 4.12 (s, 2H), 4.09 (q, 2H), 1.17 (t, 3H), 0.18 (s, 9H), 0.00 (s, 6H).

Step B: (5-amino-1-phenyl-1H-pyrazol-3-yl)methanol

A solution of acetonitrile (0.526 mL, 10.1 mmol) in dry THF (20.4 mL, 9.16 mmol) was cooled to −78° C. and 2.5M nBuLi in hexanes (4.21 mL, 10.5 mmol) was added dropwise. The reaction mixture was stirred for 15 minutes and ethyl 2-(tert-butyldimethylsilyloxy)acetate (2.00 g, 9.16 mmol) was added. The reaction mixture was allowed to warm to ambient temperature and was stirred for 2 hours. The reaction mixture was diluted with ice water and was concentrated. The residual aqueous mixture was acidified to pH=5 and extracted with EtOAc (3×). The combined organics were washed with brine, dried over MgSO$_4$, filtered and concentrated. The residual brown oil was dissolved in MeOH (23 mL) and phenyl hydrazine (0.907 mL, 9.14 mmol) was added. The mixture was treated with concentrated HCl (3.81 mL, 45.7 mmol) and heated at reflux for 18 hours. Upon cooling, the mixture was concentrated and the residue was partitioned into in $H_2O$ and $CH_2Cl_2$. The mixture was filtered and the organic layer was removed from the filtrate. The aqueous portion was washed with $CH_2Cl_2$ and was treated with saturated NaHCO$_3$ until basic. The aqueous mixture was extracted with $CH_2Cl_2$ (3×) and the combined organic fractions were dried over MgSO$_4$, filtered and concentrated. The residue was purified by silica column chromatography using 70-100% EtOAc/hexanes gradient elution followed by 0-5% MeOH/EtOAc. The product pools were combined and concentrated to give the title compound as a yellow foam (0.760 g, 44% yield). MS (apci) m/z=190.1 (M+H).

Intermediate 183

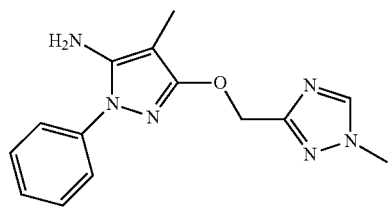 [SMILES: Cc1c(OCc2ncn(C)n2)nn(-c2ccccc2)c1N]

4-methyl-3-((1-methyl-1H-1,2,4-triazol-3-yl)methoxy)-1-phenyl-1H-pyrazol-5-amine The title compound was prepared by the method as described for Intermediate P135, substituting bromoethane with 3-(chloromethyl)-1-methyl-1H-1,2,4-triazole hydrochloride. The product was isolated as a gold syrup (110 mg, 27%). MS (apci) m/z=285.1 (M+H).

Intermediate 184

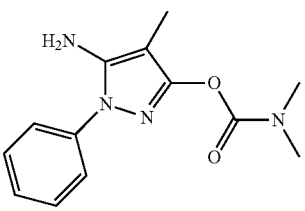 [SMILES: Cc1c(OC(=O)N(C)C)nn(-c2ccccc2)c1N]

5-amino-4-methyl-1-phenyl-1H-pyrazol-3-yl dimethylcarbamate

A mixture of 5-amino-4-methyl-1-phenyl-1H-pyrazol-3(2H)-one (Intermediate P135 Step A, 0.378 g, 2.00 mmol) and powdered K$_2$CO$_3$ (0.553 g, 4.00 mmol) in dry DMF (4 mL) was stirred at ambient temperature for 5 minutes. Dimethylcarbamoyl chloride (0.206 mL, 2.20 mmol) was added and the mixture was stirred for 6 hours. The mixture was poured into chilled H$_2$O (40 mL) and was extracted with EtOAc (3×). The combined extracts were washed with saturated NaCl (2×), dried over MgSO₄ and filtered through a SiO₂ plug capped with a MgSO₄ layer (EtOAc elution). The filtrate was concentrated and the residue dried in vacuum to give the title compound as a light gold syrup (0.507 g, 97%). MS (apci) m/z=261.1 (M+H).

Intermediate 185

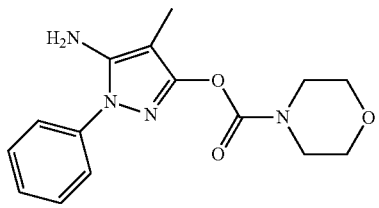 [SMILES: Cc1c(OC(=O)N2CCOCC2)nn(-c2ccccc2)c1N]

5-amino-4-methyl-1-phenyl-1H-pyrazol-3-yl morpholine-4-carboxylate

The title compound was prepared using morpholine-4-carbonyl chloride in the procedure outlined for 5-amino-4-methyl-1-phenyl-1H-pyrazol-3-yl dimethylcarbamate (Intermediate 184). The compound was isolated as a light yellow wax (0.285 g, 47%). ¹H NMR (CDCl₃) δ 7.54 (d, 2H), 7.43 (t, 2H), 7.31 (t, 1H), 3.66-3.78 (m, 8H), 3.57 (br s, 2H), 1.85 (s, 3H).

Intermediate 186

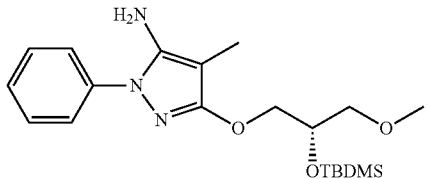 [SMILES: COC[C@@H](COc1nn(-c2ccccc2)c(N)c1C)O[Si](C)(C)C(C)(C)C]

(S)-3-(2-((tert-butyldimethylsilyl)oxy)-3-methoxypropoxy)-4-methyl-1-phenyl-1H-pyrazol-5-amine Step A: (S)-1-(5-amino-4-methyl-1-phenyl-1H-pyrazol-3-yloxy)-3-methoxypropan-2-ol A mixture of 5-amino-4-methyl-1-phenyl-1H-pyrazol-3(2H)-one (P135 Step A, 1.21 g, 6.40 mmol) and powdered K₂CO₃ (1.77 g, 12.8 mmol) in dry DMF (12 mL) was stirred at ambient temperature for 10 minutes. (S)-2-(methoxymethyl)oxirane (0.622 mL, 6.72 mmol) was added and the mixture was stirred at 80° C. for 6 hours. The mixture was cooled to ambient temperature, poured into chilled H₂O (25 mL) and extracted with EtOAc (3×). The combined extracts were washed with saturated NaCl (2×), dried over MgSO₄ and filtered through a SiO₂ plug capped with a layer of MgSO₄ eluting with EtOAc. The filtrate was concentrated to give the title compound as a colorless, viscous oil (701 mg, 40%). MS (apci) m/z=278.1 (M+H).

Step B: (S)-3-(2-((tert-butyldimethylsilyl)oxy)-3-methoxypropoxy)-4-methyl-1-phenyl-1H-pyrazol-5-amine To a solution of TBDMS-Cl (725 mg, 4.81 mmol) and imidazole (390 mg, 5.72 mmol) in dry DMF (7.0 mL) was added (S)-1-(5-amino-4-methyl-1-phenyl-1H-pyrazol-3-yloxy)-3-methoxypropan-2-ol (635 mg, 2.29 mmol) in dry DMF (2 mL). The mixture stirred at ambient temperature for 2.5 hours. The mixture added to H₂O (70 mL), mixed for 5 minutes and extracted with Et₂O (3×). The combined extracts were washed with saturated NaCl (2×) and dried over MgSO₄. The dried solution was filtered through a SiO₂ plug capped with a layer of MgSO₄ (Et₂O elution). The filtrate was concentrated to give the title compound as a colorless oil that was dried in vacuum (940 mg, 105%). MS (apci) m/z=392.2 (M+H). ¹H NMR (CDCl₃) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 187

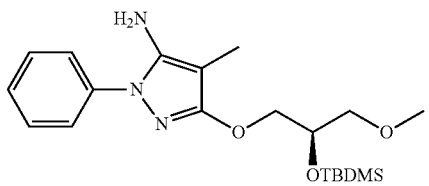 [SMILES: COC[C@H](COc1nn(-c2ccccc2)c(N)c1C)O[Si](C)(C)C(C)(C)C]

(R)-3-(2-((tert-butyldimethylsilyl)oxy)-3-methoxypropoxy)-4-methyl-1-phenyl-1H-pyrazol-5-amine The title compound was prepared using the procedure described for (S)-3-(2-((tert-butyldimethylsilyl)oxy)-3-methoxypropoxy)-4-methyl-1-phenyl-1H-pyrazol-5-amine (Intermediate 186) substituting (S)-2-(methoxymethyl)oxirane with (R)-2-(methoxymethyl)oxirane in Step A. The product was obtained as a colorless syrup (921 mg, 38% over 2 steps). MS (apci) m/z=392.2 (M+H). ¹H NMR (CDCl₃) δ 7.50 (d, 2H), 7.40 (t, 2H), 7.23 (t, 1H), 4.09-4.30 (m, 3H), 3.57 (br s, 2H), 3.38-3.44 (m, 2H), 3.32 (s, 3H), 1.83 (s, 3H), 0.88 (s, 9H), 0.11 (s, 6H).

Intermediate 188

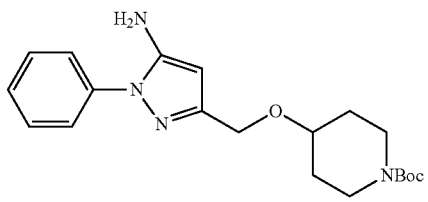 [SMILES: CC(C)(C)OC(=O)N1CCC(OCc2cc(N)n(-c3ccccc3)n2)CC1]

tert-butyl 4-((5-amino-1-phenyl-1H-pyrazol-3-yl)methoxy)piperidine-1-carboxylate Step A: tert-butyl 4-(2-ethoxy-2-oxoethoxy)piperidine-1-carboxylate A solution of tert-butyl 4-hydroxypiperidine-1-carboxylate (2.00 g, 9.94 mmol) in dry THF (25 mL) was cooled to 0° C. and KOtBu (1.12 g, 9.94 mmol) was added. The mixture was allowed to reach ambient temperature and was stirred for 10 minutes. The mixture was cooled to 0° C. and ethyl 2-bromoacetate (1.65 mL, 14.9 mmol) was added dropwise. The reaction was allowed to reach ambient temperature and was stirred for 17 hours. The mixture was partitioned into in H$_2$O and EtOAc, mixed and the organic layer was removed. The organic layer was dried over MgSO$_4$, filtered and concentrated. The residual thick yellow oil was purified by silica chromatography using a 10-25% EtOAc/hexanes gradient elution to afford the title compound as a colorless oil (0.967 g, 34% yield). $^1$H NMR (CDCl$_3$) δ 4.22 (q, 2H), 4.12 (s, 2H), 3.67-3.84 (m, 2H), 3.52-3.63 (m, 1H), 3.05-3.11 (m, 2H), 1.81-1.90 (m, 2H), 1.53-1.62 (m, 2H), 1.45 (s, 9H), 1.29 (t, 3H).

Step B: tert-butyl 4-((5-amino-1-phenyl-1H-pyrazol-3-yl)methoxy)piperidine-1-carboxylate A solution of diisopropylamine (1.08 mL, 7.74 mmol) in dry THF (5 mL) was cooled to 0° C. and 2.5M nBuLi in hexanes (2.96 mL, 7.41 mmol) was slowly added. The mixture was stirred at 0° C. for 10 minutes and was cooled to −78° C. Acetonitrile (0.404 mL, 7.74 mmol) was added and the mixture was stirred for 15 minutes. A solution of tert-butyl 4-(2-ethoxy-2-oxoethoxy)piperidine-1-carboxylate (0.967 g, 3.37 mmol) in THF (2.5 mL) was added and the mixture was stirred at −78° C. for 1 hour. The mixture was allowed to reach ambient temperature, was quenched with ice water and concentrated. The residual aqueous mixture was neutralized with 2M HCl and was extracted with CH$_2$Cl$_2$ (3×). The combined organic fractions were dried over MgSO$_4$, filtered and concentrated to provide the crude cyanoketone as a yellow oil that was used immediately in the next step.

Step C: tert-butyl 4-((5-amino-1-phenyl-1H-pyrazol-3-yl)methoxy)piperidine-1-carboxylate The crude oil obtained in Step B was dissolved in EtOH (17 mL) and phenylhydrazine (0.396 mL, 3.99 mmol) was added. The mixture was heated at 60° C. for 60 hours, was cooled to ambient temperature and was concentrated. The residue was partitioned into EtOAc and water, mixed and the organic layer removed. The aqueous layer was extracted with EtOAc (2×) and the combined EtOAc portions were dried over MgSO$_4$, filtered and concentrated. The residual orange oil was purified by silica chromatography using a 10-100% EtOAc/hexanes gradient elution. The pooled product fractions were concentrated and the residual yellow-orange oil was re-purified by reverse phase HPLC using a 0-100% acetonitrile/water gradient to provide the title compound as an orange foam (0.264 g, 21% yield). MS (apci) m/z=373.2 (M+H).

Intermediate 189

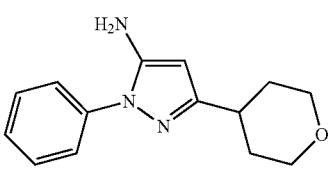 [SMILES: Nc1cc(C2CCOCC2)nn1-c1ccccc1]

1-phenyl-3-(tetrahydro-2H-pyran-4-yl)-1H-pyrazol-5-amine

Step A: 3-oxo-3-(tetrahydro-2H-pyran-4-yl)propanenitrile

A 1M solution of LHMDS in dry THF (26.3 mL, 26.3 mmol) was cooled to −78° C. and acetonitrile (1.43 mL, 27.5 mmol) was added dropwise over 2 minutes. The mixture was stirred at −78° C. for 1 hour and a solution of methyl tetrahydro-2H-pyran-4-carboxylate (3.41 mL, 25.0 mmol) in dry THF (12 mL) was added. The mixture was stirred for 1 hour, the dry ice bath was removed and the mixture allowed to reach ambient temperature. The mixture was poured into chilled H$_2$O (250 mL) and was extracted with Et$_2$O (3×). The aqueous portion was cooled to 0° C. and 6M HCl was added dropwise to pH=3 (starting pH=12). The mixture was extracted with EtOAc (3×) and the combined extracts were dried over MgSO$_4$. The solution eluted through a SiO$_2$ plug eluting with EtOAc. The filtrate was concentrated to give the title compound as a colorless oil (2.52 g, 66%). $^1$H NMR (CDCl$_3$) δ 3.99-4.06 (m, 2H), 3.54 (s, 2H), 3.46 (t, 2H), 2.76-2.86 (m, 1H), 1.70-1.86 (m, 4H).

Step B: 1-phenyl-3-(tetrahydro-2H-pyran-4-yl)-1H-pyrazol-5-amine

To a solution of 3-oxo-3-(tetrahydro-2H-pyran-4-yl)propanenitrile (2.30 g, 12.8 mmol) in absolute EtOH (35 mL) was added phenylhydrazine hydrochloride (2.21 g, 15.3 mmol) and the mixture was heated at reflux until complete by TLC (5 hours). The mixture was cooled to ambient temperature and was concentrated. The residue was partitioned in H$_2$O (75 mL) and EtOAc (40 mL). 2M NaOH was added to pH=5 with vigorous mixing, the organic layer was removed and the aqueous was extracted with EtOAc (2×). The combined EtOAc fractions were washed with H$_2$O and saturated NaCl. The solution was diluted with an equal volume of hexanes, dried over MgSO$_4$/activated carbon and eluted through a SiO$_2$ plug eluting with 50% EtOAc-hexanes. The filtrate was concentrated to give a gold syrup. The syrup was treated with Et$_2$O and stirred until a fine, granular suspension formed. The solid was collected, washed with Et$_2$O and dried in vacuum to furnish the title compound as a white solid (2.01 g, 65%). $^1$H NMR (CDCl$_3$) δ 7.55 (d, 2H), 7.46 (t, 2H), 7.32 (t, 1H), 5.49 (s, 1H), 4.00-4.08 (m, 2H), 3.97 (br s, 2H), 3.52 (dt, 2H), 2.86 (m, 1H) 1.73-1.93 (m, 4H).

The following compounds were prepared according to the method used for the preparation of 1-phenyl-3-(tetrahydro-2H-pyran-4-yl)-1H-pyrazol-5-amine (Intermediate 189) using either acetonitrile or propiononitrile in Step A in conjunction with the appropriate ester.

| Intermediate # | Structure | Data |
|---|---|---|
| 190 | 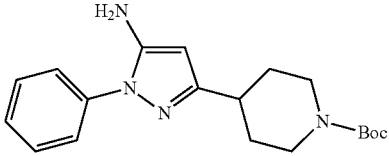 [SMILES: CC(C)(C)OC(=O)N1CCC(c2cc(N)n(-c3ccccc3)n2)CC1] | MS (apci) m/z = 343.1 (M + H) |
| 191 | 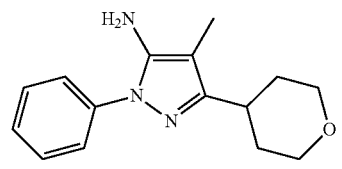 [SMILES: Cc1c(C2CCOCC2)nn(-c2ccccc2)c1N] | MS (apci) m/z = 258.0 (M + H) |
| 192 | 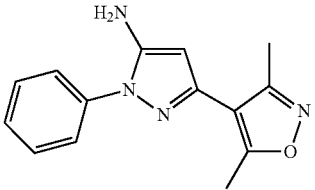 [SMILES: Cc1noc(C)c1-c1cc(N)n(-c2ccccc2)n1] | $^1$H NMR (CDCl$_3$) δ 7.62 (d, 2H), 7.50 (t, 2H), 7.37 (t, 1H), 5.72 (s, 1H), 3.91 (br s, 2H), 2.58 (s, 3H), 2.44 (s, 3H). |
| 193 | 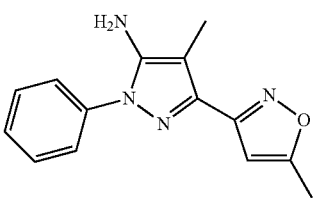 [SMILES: Cc1cc(-c2nn(-c3ccccc3)c(N)c2C)no1] | $^1$H NMR (CDCl$_3$) δ 7.60 (d, 2H), 7.49 (t, 2H), 7.37 (t, 1H), 6.45 (s, 1H), 3.67 (br s, 2H), 2.45 (s, 3H), 2.24 (s, 3H). |
| 194 | 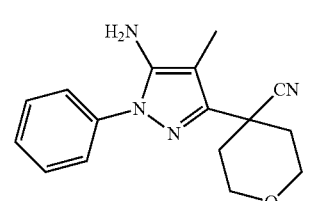 | $^1$H NMR (CDCl$_3$) δ 7.45-7.56 (m, 4H), 7.35 (t, 1H), 4.00-4.06 (m, 2H), 3.88 (dt, 2H), 3.62 (br s, 2H), 2.18-2.34 (m, 4H), 2.11 (s,3H). |
| 195 | 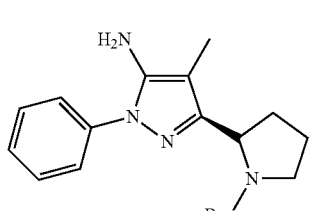 | MS (apci) m/z = 343.2 (M + H) |
| 196 | 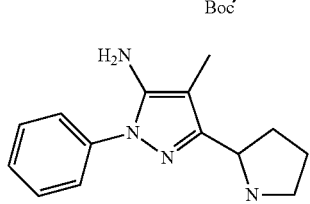 | MS (apci) m/z = 343.2 (M + H) |
| 197 | 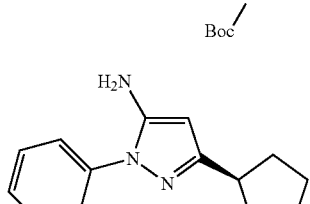 | MS (apci) m/z = 329.2 (M + H) |

| Intermediate # | Structure | Data |
|---|---|---|
| 198 | 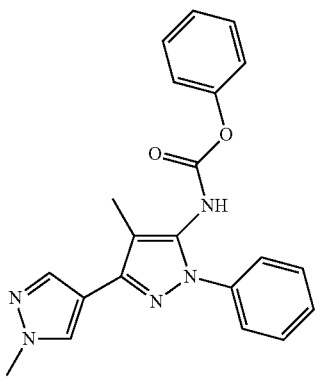 | MS (apci) m/z = 329.2 (M + H) |

Intermediate 199

Phenyl 1',4-dimethyl-1-phenyl-1H,1'H-3,4'-bipyrazol-5-ylcarbamate

Step A: ethyl 1-methyl-1H-pyrazole-4-carboxylate

To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield tan orange oil. LC/MS and $^1$H NMR showed essentially pure ethyl 1-methyl-1H-pyrazole-4-carboxylate (106 g, 99.1%).

Step B: 2-methyl-3-(1-methyl-1H-pyrazol-4-yl)-3-oxopropanenitrile

To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with with ether (3×1000 mL). The aqueous phase was then pH-adjusted to 5 (pH paper) using concentrated HCl and saturated bicarbarbonate solution The aqueous layer was extracted with DCM (3×1000 mL). The combined organic extracts were dried over MgSO$_4$ filtered and concentrated to yield the 2-methyl-3-(1-methyl-1H-pyrazol-4-yl)-3-oxopropanenitrile as an amber oil (92 g, 82%). MS (apci) m/z=162.1 (M−H).

Step C: 1',4-dimethyl-1-phenyl-1H,1'H-3,4'-bipyrazol-5-amine

A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected filtration, washed with hexanes and air dried under vacuum to provide 1',4-dimethyl-1-phenyl-1H,1'H-3,4'-bipyrazol-5-amine (93 g, 100%).

Step D: phenyl 1',4-dimethyl-1-phenyl-1H,1'H-3,4'-bipyrazol-5-ylcarbamate

In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated in vacuo. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 200

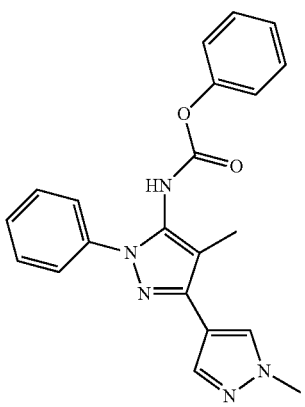 [SMILES: Cc1c(-c2cnn(C)c2)nn(-c2ccccc2)c1NC(=O)Oc1ccccc1]

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 201

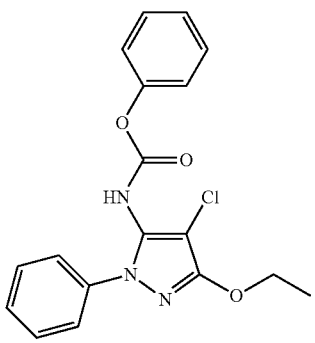 [SMILES: CCOc1nn(-c2ccccc2)c(NC(=O)Oc2ccccc2)c1Cl]

phenyl (4-chloro-3-ethoxy-1-phenyl-1H-pyrazol-5-yl)carbamate

Step A: Preparation of phenyl (3-ethoxy-1-phenyl-1H-pyrazol-5-yl)carbamate

To a suspension of 3-ethoxy-1-phenyl-1H-pyrazol-5-amine (Intermediate P139, 169 mg, 0.832 mmol) in EtOAc (5 mL) at 0° C. was added 2.0 M aqueous NaOH solution (1.25 mL, 2.50 mmol), followed by dropwise addition of phenyl carbonochloridate (0.178 mL, 1.41 mmol). The reaction was stirred at ambient temperature for 15 hours. The reaction mixture was diluted with EtOAc and phase-separated. The organic layer was washed with water and brine, dried over MgSO$_4$, and concentrated. The residue was purified by flash chromatography on silica gel (6:1 hexanes: EtOAc) to give the title compound (219 mg, 81% yield). MS (apci) m/z=324.1 (M+H).

Step B: Preparation of phenyl (4-chloro-3-ethoxy-1-phenyl-1H-pyrazol-5-yl)carbamate To a solution of phenyl 3-ethoxy-1-phenyl-1H-pyrazol-5-ylcarbamate (92 mg, 0.28 mmol) and pyridinium 4-methylbenzenesulfonate (7.2 mg, 0.028 mmol) in DCM (2 mL) was added N-chlorosuccinimide (42 mg, 0.31 mmol) at ambient temperature. The mixture was stirred at ambient temperature for 2 days and then concentrated under reduced pressure. The residue was purified by flash chromatography on silica gel (9:1, hexanes/EtOAc) to give the title compound (76 mg, 75% yield). MS (apci) m/z=358.1 (M+H).

Intermediate 203

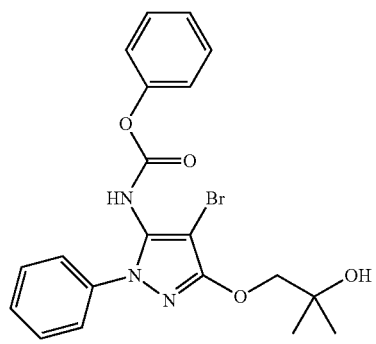

Phenyl (4-bromo-3-(2-hydroxy-2-methylpropoxy)-1-phenyl-1H-pyrazol-5-yl)carbamate Step A: Preparation of 5-amino-1-phenyl-1H-pyrazol-3(2H)-one Prepared according to the method described for Intermediate P1, replacing 4,4-dimethyl-3-oxopentanenitrile with ethyl 2-cyanoacetate, and substituting phenylhydrazine for ethyl 3-hydrazinylbenzoate hydrochloride. MS (apci) m/z=176.0 (M+H).

Step B: Preparation of 1-((5-amino-1-phenyl-1H-pyrazol-3-yl)oxy)-2-methylpropan-2-ol A mixture of 5-amino-1-phenyl-1H-pyrazol-3(2H)-one (0.330 g, 1.88 mmol), 2,2-dimethyloxirane (0.143 g, 1.98 mmol) and K$_2$CO$_3$ (0.521 g, 3.77 mmol) in DMA (5 mL) was heated at 80° C. for 3 days. After cooling, the reaction mixture was diluted with EtOAc, washed with water and brine and dried over MgSO$_4$. The mixture was filtered through a pad of SiO₂ eluting with EtOAc to yield the title compound. MS (apci) m/z=248.1 (M+H).

Step C: Preparation of phenyl (3-(2-hydroxy-2-methylpropoxy)-1-phenyl-1H-pyrazol-5-yl)carbamate Prepared according to the method described for Intermediate 201. Step A using 1-((5-amino-1-phenyl-1H-pyrazol-3-yl)oxy)-2-methylpropan-2-ol as a replacement for 3-ethoxy-1-phenyl-1H-pyrazol-5-amine. MS (apci) m/z=368.1 (M+H).

Step D: Preparation of phenyl (4-bromo-3-(2-hydroxy-2-methylpropoxy)-1-phenyl-1H-pyrazol-5-yl)carbamate Prepared according to the method described for Intermediate 201, Step B using N-bromosuccinimide as a replacement for N-chlorosuccinimide, and substituting phenyl (3-(2-hydroxy-2-methylpropoxy)-1-phenyl-1H-pyrazol-5-yl)carbamate for phenyl 3-ethoxy-1-phenyl-1H-pyrazol-5-ylcarbamate. MS (apci) m/z=446.1 (M+H).

The following compounds prepared according to the method describe for the preparation of Intermediate 200, using the appropriate amino pyrazole intermediate.

| Intermediate # | Structure | Name | Data |
| --- | --- | --- | --- |
| 204 | 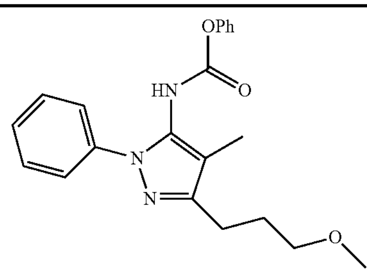 | phenyl 3-(3-methoxypropyl)-4-methyl-1-phenyl-1H-pyrazol-5-ylcarbamate | MS (apci) m/z = 366.1 (M + H). |
| 205 | 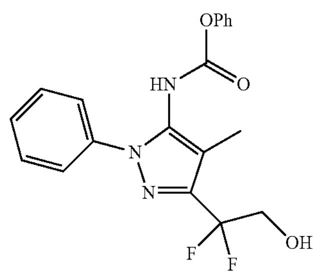 [SMILES: Cc1c(C(F)(F)CO)nn(-c2ccccc2)c1NC(=O)Oc1ccccc1] | phenyl 3-(1,1-difluoro-2-hydroxyethyl)-4-methyl-1-phenyl-1H-pyrazol-5-ylcarbamate | MS (apci) m/z = 374.1 (M + H). |
| 206 | 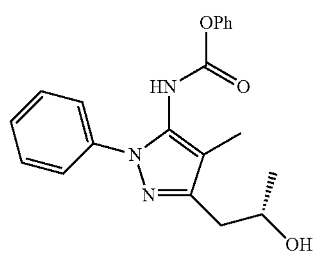 [SMILES: Cc1c(C[C@H](C)O)nn(-c2ccccc2)c1NC(=O)Oc1ccccc1] | (S)-phenyl 3-(2-hydroxypropyl)-4-methyl-1-phenyl-1H-pyrazol-5-ylcarbamate | MS (apci) m/z = 352.1 (M + H). |
| 207 | 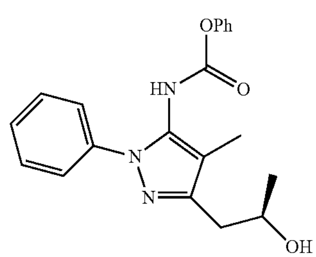 [SMILES: Cc1c(C[C@@H](C)O)nn(-c2ccccc2)c1NC(=O)Oc1ccccc1] | (R)-phenyl 3-(2-hydroxypropyl)-4-methyl-1-phenyl-1H-pyrazol-5-ylcarbamate | MS (apci) m/z = 352.1 (M + H). |
| 208 | 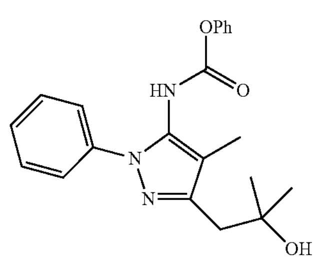 [SMILES: Cc1c(CC(C)(C)O)nn(-c2ccccc2)c1NC(=O)Oc1ccccc1] | phenyl 3-(2-hydroxy-2-methylpropyl)-4-methyl-1-phenyl-1H-pyrazol-5-ylcarbamate | MS (apci) m/z = 366.2 (M + H). |

-continued

| Intermediate # | Structure | Name | Data |
|---|---|---|---|
| 209 | 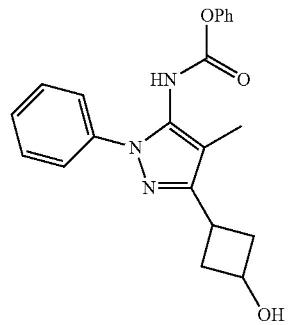 [SMILES: Cc1c(C2CC(O)C2)nn(-c2ccccc2)c1NC(=O)Oc1ccccc1] | phenyl 3-(3-hydroxycyclobutyl)-4-methyl-1-phenyl-1H-pyrazol-5-ylcarbamate | MS (apci) m/z = 364.2 (M + H). |
| 210 | 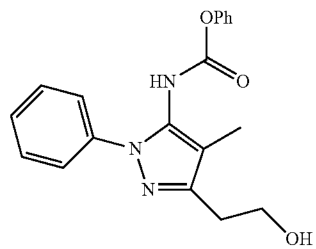 [SMILES: Cc1c(CCO)nn(-c2ccccc2)c1NC(=O)Oc1ccccc1] | phenyl 3-(2-hydroxyethyl)-4-methyl-1-phenyl-1H-pyrazol-5-ylcarbamate | MS (apci) m/z = 338.1 (M + H). |
| 211 | 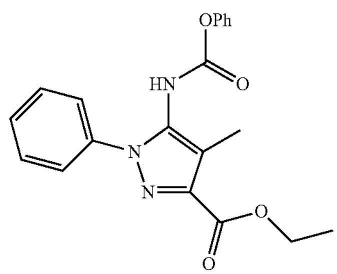 [SMILES: CCOC(=O)c1nn(-c2ccccc2)c(NC(=O)Oc2ccccc2)c1C] | ethyl 4-methyl-5-(phenoxycarbonylamino)-1-phenyl-1H-pyrazole-3-carboxylate | MS (apci) m/z = 366.1 (M + H). |
| 212 | 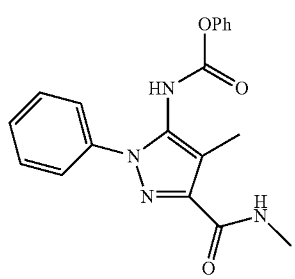 [SMILES: CNC(=O)c1nn(-c2ccccc2)c(NC(=O)Oc2ccccc2)c1C] | phenyl 4-methyl-3-(methylcarbamoyl)-1-phenyl-1H-pyrazol-5-ylcarbamate | MS (apci) m/z = 351.1 (M + H). |
| 213 | 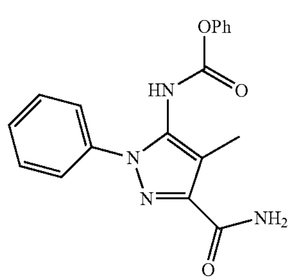 [SMILES: Cc1c(C(N)=O)nn(-c2ccccc2)c1NC(=O)Oc1ccccc1] | phenyl 3-carbamoyl-4-methyl-1-phenyl-1H-pyrazol-5-ylcarbamate | MS (apci) m/z = 337.1 (M + H). |

| Intermediate # | Structure | Name | Data |
|---|---|---|---|
| 214 | 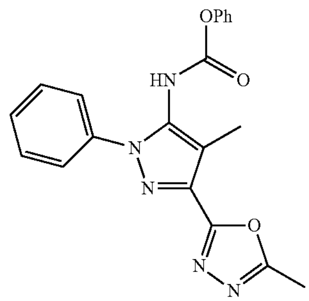 [SMILES: Cc1nnc(-c2nn(-c3ccccc3)c(NC(=O)Oc3ccccc3)c2C)o1] | phenyl (4-methyl-3-(5-methyl-1,3,4-oxadiazol-2-yl)-1-phenyl-1H-pyrazol-5-yl)carbamate | MS (apci) m/z = 376.1 (M + H). |
| 215 | 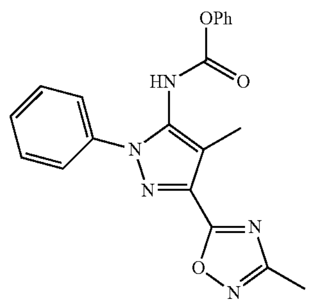 [SMILES: Cc1noc(-c2nn(-c3ccccc3)c(NC(=O)Oc3ccccc3)c2C)n1] | phenyl 4-methyl-3-(3-methyl-1,2,4-oxadiazol-5-yl)-1-phenyl-1H-pyrazol-5-ylcarbamate | MS (apci) m/z = 376.1 (M + H). |
| 216 | 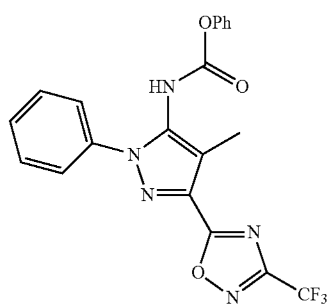 [SMILES: Cc1c(-c2nc(C(F)(F)F)no2)nn(-c2ccccc2)c1NC(=O)Oc1ccccc1] | phenyl 4-methyl-1-phenyl-3-(3-(trifluoromethyl)-1,2,4-oxadiazol-5-yl)-1H-pyrazol-5-ylcarbamate | MS (apci) m/z = 430.1 (M + H). |
| 217 | 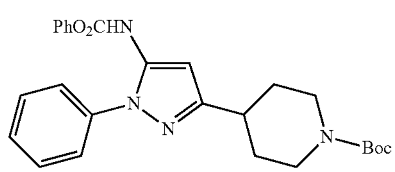 | tert-butyl 4-(5-((phenoxycarbonyl)amino)-1-phenyl-1H-pyrazol-3-yl)piperidine-1-carboxylate | MS (apci) m/z = 463.3 (M + H) |
| 218 | 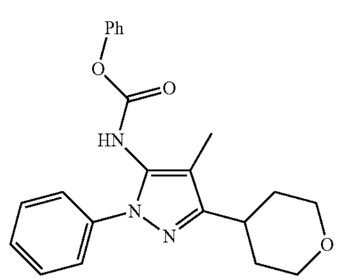 [SMILES: Cc1c(C2CCOCC2)nn(-c2ccccc2)c1NC(=O)Oc1ccccc1] | phenyl (4-methyl-1-phenyl-3-(tetrahydro-2H-pyran-4-yl)-1H-pyrazol-5-yl)carbamate | MS (apci) m/z = 378.2 (M + H) |

| Intermediate # | Structure | Name | Data |
|---|---|---|---|
| 219 | 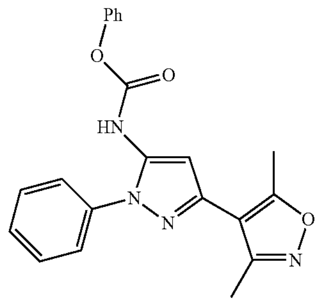 [SMILES: Cc1noc(C)c1-c1cc(NC(=O)Oc2ccccc2)n(-c2ccccc2)n1] | phenyl (3-(3,5-dimethylisoxazol-4-yl)-1-phenyl-1H-pyrazol-5-yl)carbamate | $^1$H NMR (CDCl$_3$) δ 7.56-7.64 (m, 4H), 7.48-7.52 (m, 1H), 7.40 (t, 2H), 7.26 (t, 2H), 7.16 (br s, 2H), 6.71 (br s, 1H), 2.60 (s, 3H) 2.46 (s, 3H) |
| 220 | 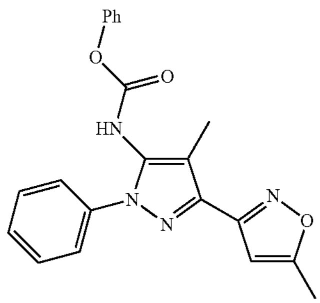 [SMILES: Cc1cc(-c2nn(-c3ccccc3)c(NC(=O)Oc3ccccc3)c2C)no1] | phenyl (4-methyl-3-(5-methylisoxazol-3-yl)-1-phenyl-1H-pyrazol-5-yl)carbamate | $^1$HNMR (CDCl$_3$) δ 7.54 (d, 2H), 7.49 (t, 2H), 7.41 (t, 1H), 7.33 (br s, 2H), 7.20 (br s, 1H), 7.08 (br s, 1H), 6.74 (br s, 1H), 6.66 (br s, 1H), 6.48 (s, 1H), 2.45 (s, 3H) 2.34 (s, 3H) |
| 221 | 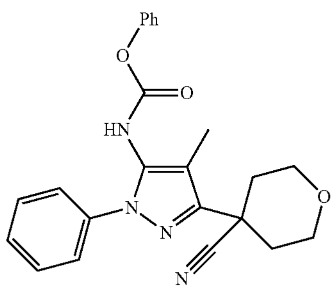 [SMILES: Cc1c(C2(C#N)CCOCC2)nn(-c2ccccc2)c1NC(=O)Oc1ccccc1] | phenyl (3-(4-cyanotetrahydro-2H-pyran-4-yl)-4-methyl-1-phenyl-1H-pyrazol-5-yl)carbamate | $^1$HNMR (CDCl$_3$) δ 7.06-7.56 (m, 9H), 6.75 (br s, 1H), 6.51 (s, 1H), 4.04 (d, 2H) 3.89 (t, 2H), 2.20-2.39 (m, 4H), 2.28 (s, 3H) |
| 222 | 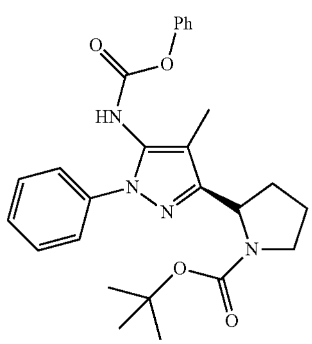 | (R)-tert-butyl 2-(4-methyl-5-((phenoxycarbonyl)amino)-1-phenyl-1H-pyrazol-3-yl)pyrrolidine-1-carboxylate | MS (apci) m/z = 463.2 (M + H) |
| 223 | 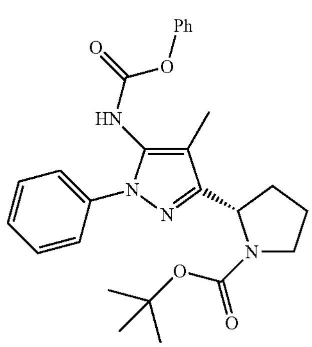 [SMILES: Cc1c([C@@H]2CCCN2C(=O)OC(C)(C)C)nn(-c2ccccc2)c1NC(=O)Oc1ccccc1] | (S)-tert-butyl 2-(4-methyl-5-((phenoxycarbonyl)amino)-1-phenyl-1H-pyrazol-3-yl)pyrrolidine-1-carboxylate | MS (apci) m/z = 463.2 (M + H) |

-continued

| Intermediate # | Structure | Name | Data |
|---|---|---|---|
| 224 | 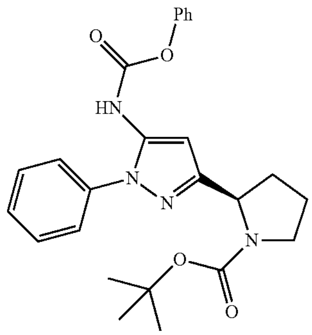 [SMILES: CC(C)(C)OC(=O)N1CCC[C@@H]1c1cc(NC(=O)Oc2ccccc2)n(-c2ccccc2)n1] | (R)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 225 | 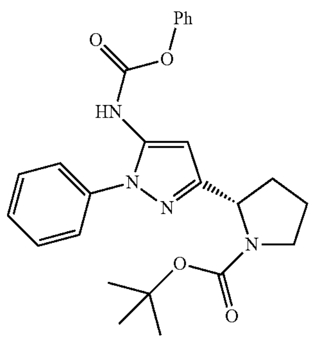 | (S)-tert-butyl 2-(5-((phenoxycarbonyl)amino)-1-phenyl-1H-pyrazol-3-yl)pyrrolidine-1-carboxylate | MS (apci) m/z = 449.2 (M + H) |
| 226 | 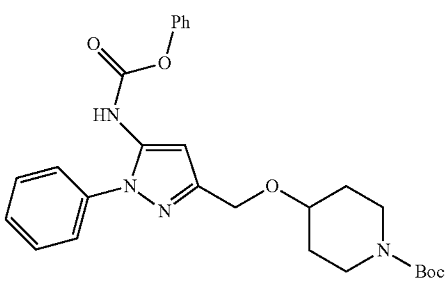 [SMILES: CC(C)(C)OC(=O)N1CCC(OCc2cc(NC(=O)Oc3ccccc3)n(-c3ccccc3)n2)CC1] | tert-butyl 4-((5-((phenoxycarbonyl)amino)-1-phenyl-1H-pyrazol-3-yl)methoxy)piperidine-1-carboxylate | MS (apci) m/z = 493.2 (M + H) |
| 227 | 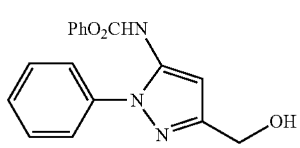 | phenyl(3-(hydroxymethyl)-1-phenyl-1H-pyrazol-5-yl)carbamate | MS (apci) m/z 310.1 (M + H) |

Intermediate 228

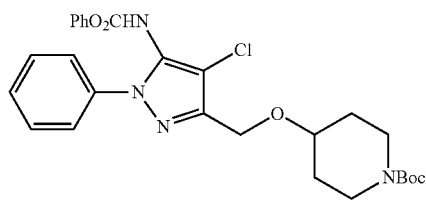

tert-butyl 4-((4-chloro-5-((phenoxycarbonyl)amino)-1-phenyl-1H-pyrazol-3-yl)methoxy)piperidine-1-carboxylate To a suspension of tert-butyl 4-((5-(phenoxycarbonylamino)-1-phenyl-1H-pyrazol-3-yl)methoxy)piperidine-1-carboxylate (Intermediate 226), 98.5 mg, 0.200 mmol) in DCM (2.0 mL) was added pyridinium 4-methylbenzenesulfonate (PPTS) (5.03 mg, 0.020 mmol) and N-chlorosuccinimide (40.1 mg, 0.300 mmol). The resulting solution was stirred at ambient temperature for 8 days. The mixture was diluted with water and $CH_2Cl_2$, the organic layer was separated and the aqueous was extracted with $CH_2Cl_2$ (2×). The combined organic fractions were dried over $MgSO_4$, filtered and concentrated. The residue was purified by silica chromatography using 30-40% EtOAc/hexanes gradient elution to afford the title compound as an orange oil (73.5 mg, 70% yield). MS (apci) m/z=527.2 (M+H).

Intermediate 229

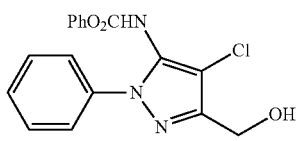

Phenyl (4-chloro-3-(hydroxymethyl)-1-phenyl-1H-pyrazol-5-yl)carbamate

Prepared from phenyl 3-(hydroxymethyl)-1-phenyl-1H-pyrazol-5-ylcarbamate (Intermediate 227) using the procedure outlined for the preparation of tert-butyl 4-((4-chloro-5-((phenoxycarbonyl)amino)-1-phenyl-1H-pyrazol-3-yl)methoxy)piperidine-1-carboxylate (Intermediate 228). In this instance, the compound was isolated a white solid (108 mg, 28%). MS (apci) m/z=344.0 (M+H).

Intermediate 230

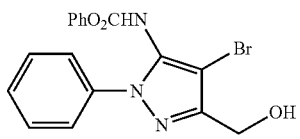

Phenyl (4-bromo-3-(hydroxymethyl)-1-phenyl-1H-pyrazol-5-yl)carbamate

To a suspension of phenyl 3-(hydroxymethyl)-1-phenyl-1H-pyrazol-5-ylcarbamate (Intermediate 227, 100 mg, 0.323 mmol) in $CH_2Cl_2$ (1.6 mL) was added pyridinium 4-methylbenzenesulfonate (PPTS) (8.12 mg, 0.0323 mmol) and N-bromosuccinimide (86.3 mg, 0.485 mmol). The reaction mixture was stirred for 16 hours at ambient temperature. The resulting suspension was filtered and the collected solid washed briefly with $CH_2Cl_2$ and dried in vacuum to afford the title compound a white solid (48.5 mg, 39%). MS (apci) m/z=388.0 (M+H).

The following pyrazole intermediates were made according to the methods described for the preparation of Intermediate 228, 229 or 230.

| Intermediate | Structure | Name | MS (apci) m/z |
|---|---|---|---|
| 231 | 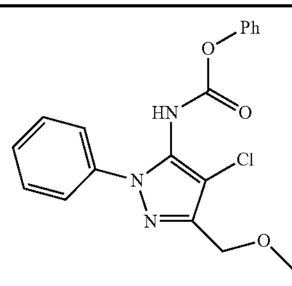 | phenyl (4-chloro-3-(methoxymethyl)-1-phenyl-1H-pyrazol-5-yl)carbamate | 358.1 (M + H) |
| 232 | 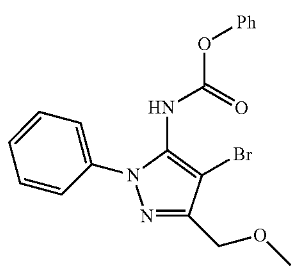 [SMILES: COCc1nn(-c2ccccc2)c(NC(=O)Oc2ccccc2)c1Br] | phenyl (4-bromo-3-(methoxymethyl)-1-phenyl-1H-pyrazol-5-yl)carbamate | 402.2 (M + H) |

-continued

| Intermediate | Structure | Name | MS (apci) m/z |
|---|---|---|---|
| 233 | 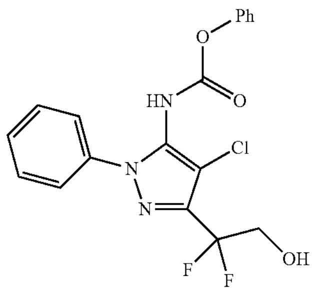 [SMILES: O=C(Nc1c(Cl)c(C(F)(F)CO)nn1-c1ccccc1)Oc1ccccc1] | phenyl (4-chloro-3-(1,1-difluoro-2-hydroxyethyl)-1-phenyl-1H-pyrazol-5-yl)carbamate | 394.1 (M + H) |
| 234 | 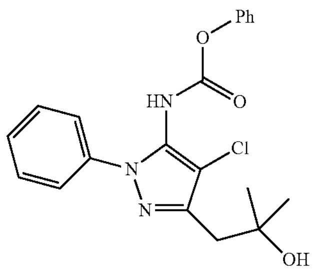 [SMILES: CC(C)(O)Cc1nn(-c2ccccc2)c(NC(=O)Oc2ccccc2)c1Cl] | phenyl (4-chloro-3-(2-hydroxy-2-methylpropyl)-1-phenyl-1H-pyrazol-5-yl)carbamate | 386.1 (M + H) |
| 235 | 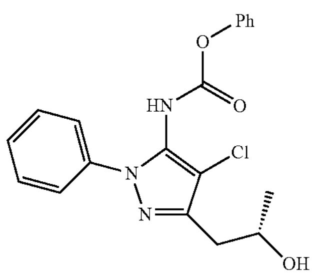 [SMILES: C[C@H](O)Cc1nn(-c2ccccc2)c(NC(=O)Oc2ccccc2)c1Cl] | (S)-phenyl (4-chloro-3-(2-hydroxypropyl)-1-phenyl-1H-pyrazol-5-yl)carbamate | 372.1 (M + H) |
| 236 | 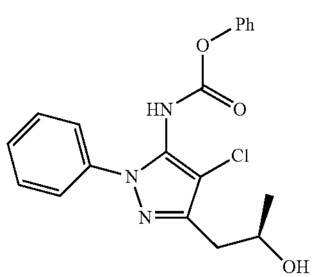 [SMILES: C[C@@H](O)Cc1nn(-c2ccccc2)c(NC(=O)Oc2ccccc2)c1Cl] | (R)-phenyl (4-chloro-3-(2-hydroxypropyl)-1-phenyl-1H-pyrazol-5-yl)carbamate | 372.1 (M + H) |
| 237 | 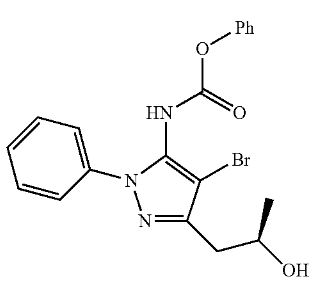 | (R)-phenyl (4-bromo-3-(2-hydroxypropyl)-1-phenyl-1H-pyrazol-5-yl)carbamate | 416.0 (M + H) |

-continued

| Intermediate | Structure | Name | MS (apci) m/z |
|---|---|---|---|
| 238 | 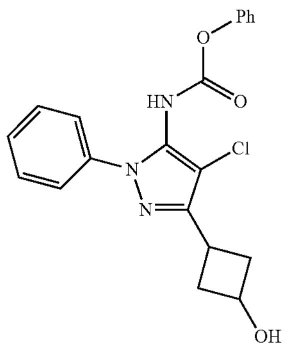 [SMILES: O=C(Nc1c(Cl)c(C2CC(O)C2)nn1-c1ccccc1)Oc1ccccc1] | phenyl (4-chloro-3-(3-hydroxycyclobutyl)-1-phenyl-1H-pyrazol-5-yl)carbamate | 384.1 (M + H) |
| 239 | 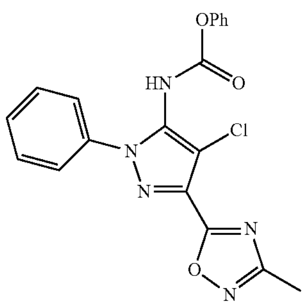 | phenyl 4-chloro-3-(3-methyl-1,2,4-oxadiazol-5-yl)-1-phenyl-1H-pyrazol-5-ylcarbamate | 396.0 (M + H) |
| 240 | 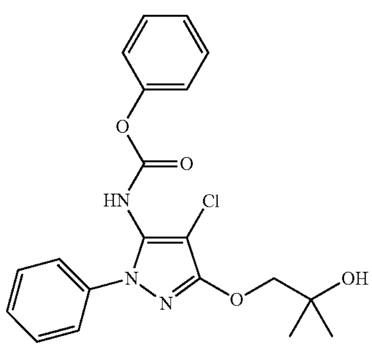 | phenyl (4-chloro-3-(2-hydroxy-2-methylpropoxy)-1-phenyl-1H-pyrazol-5-yl)carbamate | 446.1 (M + H) |
| 241 | 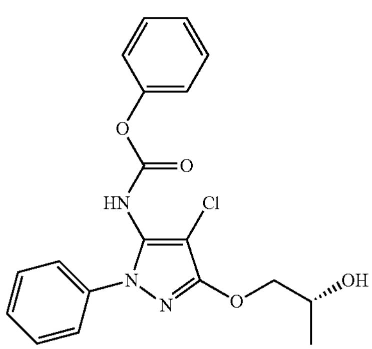 | phenyl (4-chloro-3-(2-hydroxy-2-methylpropoxy)-1-phenyl-1H-pyrazol-5-yl)carbamate | 388.1 (M + H) |

| Intermediate | Structure | Name | MS (apci) m/z |
|---|---|---|---|
| 242 | 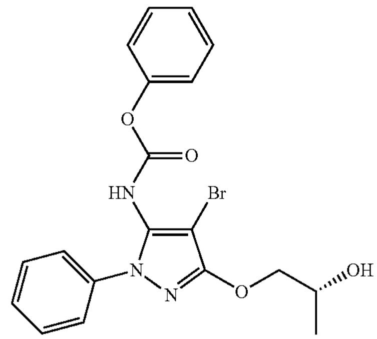 [SMILES: C[C@@H](O)COc1nn(-c2ccccc2)c(NC(=O)Oc2ccccc2)c1Br] | phenyl (4-bromo-3-(2-hydroxy-2-methylpropoxy)-1-phenyl-1H-pyrazol-5-yl)carbamate | 433.0 (M + H) |
| 243 | 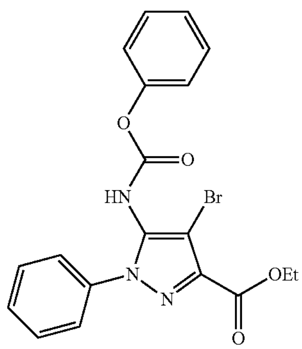 [SMILES: CCOC(=O)c1nn(-c2ccccc2)c(NC(=O)Oc2ccccc2)c1Br] | ethyl 4-bromo-5-((phenoxycarbonyl)amino)-1-phenyl-1H-pyrazole-3-carboxylate | 430.0 (M + H) |

Intermediate 245

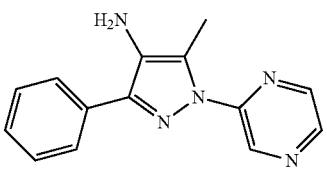 [SMILES: Cc1c(N)c(-c2ccccc2)nn1-c1cnccn1]

5-methyl-3-phenyl-1-(pyrazin-2-yl)-1H-pyrazol-4-amine

Step A: 2-(5-methyl-4-nitroso-3-phenyl-1H-pyrazol-1-yl)pyrazine

To a solution of 2-hydrazinylpyrazine (0.485 g, 4.40 mmol) in HOAc (6 mL) was added (2-(hydroxyimino)-1-phenylbutane-1,3-dione (0.765 g, 4.00 mmol) in small portions over 2 minutes. The mixture was stirred for 5 minutes and the resulting light orange suspension was stirred at 60° C. for 6 hours. EtOH (1 mL) was added and the mixture was heated at 60° C. for an additional 6 hours. The resulting dark green suspension was cooled to ambient temperature and the mixture was diluted with H$_2$O (30 mL). The green suspension was stirred for 1 hour and the solid was collected via vacuum filtration. The collected solid was washed with H$_2$O and dried in vacuum. The solid was suspended in EtOH (25 mL) and concentrated HCl (500 μL) was added. The mixture was heated at reflux for 20 hours, cooled to ambient temperature and diluted with chilled H$_2$O (75 mL). The mixture was treated with 1M NaOH to pH=7 and was extracted with Et$_2$O (3×). The combined extracts were washed with saturated NaCl and dried over MgSO$_4$. The dried solution was filtered through packed Celite® and concentrated. The residual green-yellow solid was purified on a SiO$_2$ column using step gradient elution (25% CH$_2$Cl$_2$, 50% EtOAc/hexanes) to furnish the title compound as a turquoise solid (325 mg, 31%). MS (apci) m/z=266.1 (M+H).

Step B: 5-methyl-3-phenyl-1-(pyrazin-2-yl)-1H-pyrazol-4-amine

To a mixture of 2-(5-methyl-4-nitroso-3-phenyl-1H-pyrazol-1-yl)pyrazine (325 mg, 1.04 mmol) and Zn dust (340 mg, 5.21 mmol) in EtOH (10 mL) was added concentrated HCl (95.5 μL, 1.15 mmol). The mixture was stirred at ambient temperature for 17 hours, then at 65° C. for 3 hours. The mixture was cooled to ambient temperature and was filtered through packed Celite® eluting with MeOH. The eluent was concentrated, and the residue was treated with H$_2$O and mixed. The resulting orange suspension treated with 2M HCl to pH=1 and the mixture was extracted with Et$_2$O (3×). The aqueous portion was treated with 2M NaOH to pH=8 and extracted with EtOAc (3×). The combined EtOAc extracts were washed with saturated NaCl and dried over MgSO$_4$/activated carbon. The solution was eluted through a SiO$_2$ plug eluting with EtOAc. The eluent was concentrated to give the title compound as a light yellow wax (33 mg, 13%). MS (esi) m/z=252.2 (M+H).

Intermediate 246

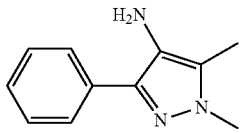

1,5-dimethyl-3-phenyl-1H-pyrazol-4-amine

Step A:
1,5-dimethyl-4-nitroso-3-phenyl-1H-pyrazole

To a solution of methylhydrazine (0.484 g, 10.5 mmol) in HOAc (10 mL) was added 2-(hydroxyimino)-1-phenylbutane-1,3-dione (2.01 g, 10.5 mmol) in small portions over 5 minutes. The reaction mixture was heated at 60° C. for 1 hour and was cooled to ambient temperature. Et$_2$O (50 mL) and H$_2$O (10 mL) were added to the mixture followed by slow addition of saturated Na$_2$CO$_3$ until pH=8 was obtained. The organic layer was removed and the aqueous layer was extracted with Et$_2$O (2×). The combined organic fractions were dried over Na$_2$SO$_4$, filtered and concentrated. The residue was purified by silica gel chromatography (1:5 EtOAc/hexanes) to give the title compound as a green solid (1.32 g, 63%). MS (apci) m/z=202.1 (M+H).

Step B: 1,5-dimethyl-3-phenyl-1H-pyrazol-4-amine

To a solution of 1,5-dimethyl-4-nitroso-3-phenyl-1H-pyrazole (1.32 g, 6.60 mmol) in MeOH (50 mL) was added Pd(OH)$_2$ on carbon (200 mg, 20 wt %, 0.286 mmol) and the reaction mixture was shaken under 50 psi of H$_2$ for 3 hours at ambient temperature. The reaction mixture was evacuated, purged with N$_2$ filtered through a pad of Celite® with MeOH elution. The eluent was concentrated and the residue dried in vacuum to provide the title compound as a tan solid (1.23 g, 100%). MS (apci) m/z=188.1 (M+H).

Intermediate 247

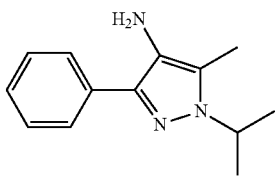 [SMILES: Cc1c(N)c(-c2ccccc2)nn1C(C)C]

1-isopropyl-5-methyl-3-phenyl-1H-pyrazol-4-amine

The title compound was prepared according to the method described for Intermediate 246, using isopropylhydrazine hydrochloride in place of methylhydrazine in Step A to provide 620 mg (57%) of the title compound over 2 steps. MS (apci) m/z=216.1 (M+H).

Intermediate 248

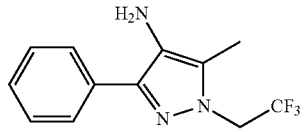 [SMILES: Cc1c(N)c(-c2ccccc2)nn1CC(F)(F)F]

5-methyl-3-phenyl-1-(2,2,2-trifluoroethyl)-1H-pyrazol-4-amine

Step A: 5-methyl-4-nitroso-3-phenyl-1-(2,2,2-trifluoroethyl)-1H-pyrazole

The title compound was prepared using (2,2,2-trifluoroethyl)hydrazine in place of methylhydrazine in Step A of the procedure described for the preparation of 1,5-dimethyl-3-phenyl-1H-pyrazol-4-amine (Intermediate 246). The compound was isolated as a green solid (999 mg, 71%). $^1$H NMR (CDCl$_3$) δ 7.60-7.73 (m, 5H), 4.70 (q, 2H), 2.27 (t, 3H).

Step B: 5-methyl-3-phenyl-1-(2,2,2-trifluoroethyl)-1H-pyrazol-4-amine

To a mixture of 5-methyl-4-nitroso-3-phenyl-1-(2,2,2-trifluoroethyl)-1H-pyrazole (50 mg, 0.186 mmol) and Zn dust (60.7 mg, 0.929 mmol) in EtOH (0.4 mL) was added concentrated HCl (17.0 μL, 0.204 mmol) and the mixture was heated at reflux for 3 hours. The mixture was cooled to ambient temperature and was diluted with MeOH and filtered. The filtrate was concentrated and the residue was diluted in water. The aqueous mixture was treated with saturated NaHCO$_3$ until pH=10 was achieved. The mixture was extracted with DCM (3×) and the combined extracts were dried over Na$_2$SO$_4$, filtered and concentrated afford the title compound as a yellow oil (47.1 mg, 99.4% yield). MS (apci) m/z=256.1 (M+H).

Intermediate 249

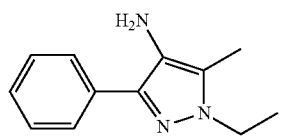

1-ethyl-5-methyl-3-phenyl-1H-pyrazol-4-amine

Step A:
1-ethyl-5-methyl-4-nitroso-3-phenyl-1H-pyrazole

The title compound was prepared according to the procedure described for the preparation of Intermediate 246, using ethylhydrazine oxalate in place of methylhydrazine in Step A. 1-Ethyl-5-methyl-4-nitroso-3-phenyl-1H-pyrazole was isolated as a green oil (288 mg, 26%). $^1$H NMR (CDCl$_3$) δ 8.19 (d, 2H), 7.46-7.50 (m, 3H), 4.15 (q, 2H), 2.43 (s, 3H), 1.50 (t, 3H). The minor regioisomer, 1-ethyl-3-methyl-4-nitroso-5-phenyl-1H-pyrazole, was also obtained as a blue-green solid (165 mg, 15%). $^1$H NMR (CDCl$_3$) δ 7.71 (dd, 2H), 7.59 (m, 3H), 4.17 (q, 2H), 2.28 (s, 3H), 1.51 (t, 3H).

Step B: 1-ethyl-5-methyl-3-phenyl-1H-pyrazol-4-amine

Prepared according to the procedure described for the preparation of Intermediate 248, using 1-ethyl-5-methyl-4-nitroso-3-phenyl-1H-pyrazole in Step B. the title compound was isolated as a light purple solid (281 mg, 104%). MS (apci) m/z=202.1 (M+H).

Intermediate 250

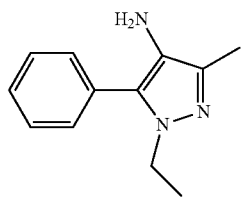

1-ethyl-3-methyl-5-phenyl-1H-pyrazol-4-amine

Prepared according to the procedure described for the preparation of Intermediate 249, using 1-ethyl-3-methyl-4-nitroso-5-phenyl-1H-pyrazole in Step A. The title compound was prepared according to Step B. The compound was isolated as a colorless oil (82.4 mg, 52.5%) after purification by reverse-phase chromatography. MS (apci) m/z=202.1 (M+H).

Intermediate 251

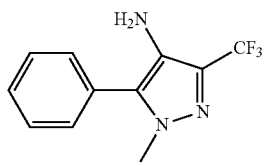 [SMILES: Cn1nc(C(F)(F)F)c(N)c1-c1ccccc1]

1-methyl-5-phenyl-3-(trifluoromethyl)-1H-pyrazol-4-amine

Step A: 4,4,4-trifluoro-2-(hydroxyimino)-1-phenylbutane-1,3-dione

A solution of 4,4,4-trifluoro-1-phenylbutane-1,3-dione (5.00 g, 23.1 mmol) in HOAc (46.3 mL) was chilled to 10° C. and sodium nitrite (1.84 g, 26.6 mmol) in water (6.0 mL) was added. The mixture was stirred at ambient temperature for 90 minutes and was diluted with $H_2O$ (150 mL). The mixture was extracted with $Et_2O$ (3×) and the combined organic fractions were carefully washed with saturated $NaHCO_3$ until pH=9. The $Et_2O$ solution was washed with $H_2O$ and saturated NaCl and was dried over $MgSO_4$. The dried solution was filtered and concentrated to afford the title compound as a yellow foam (4.21 g, 74.2% yield). MS (apci) m/z=244.1 (M−H).

Step B: 4-nitroso-3-phenyl-5-(trifluoromethyl)-1H-pyrazole

A solution of hydrazine monohydrate (0.204 g, 4.08 mmol) in EtOH (5 mL) was cooled to 0° C. and 4,4,4-trifluoro-2-(hydroxyimino)-1-phenylbutane-1,3-dione (1.00 g, 4.08 mmol) in EtOH (15 mL) was added. The reaction mixture was stirred at ambient temperature for 3 hours, excess powdered $MgSO_4$ was added and the mixture was heated at 60° C. for 16 hours. The mixture was cooled to ambient temperature, filtered and concentrated to afford the crude title compound as a green solid (78.7 mg, 8.0%) that was taken directly to the next step. MS (apci) m/z=240.0 (M−H).

Step C: 1-methyl-5-phenyl-3-(trifluoromethyl)-1H-pyrazol-4-amine

To a solution of 4-nitroso-3-phenyl-5-(trifluoromethyl)-1H-pyrazole (78.7 mg, 0.326 mmol) in DMF (1.6 mL) was added NaH (14.4 mg, 0.359 mmol) and the mixture was stirred at ambient temperature for 30 minutes. The mixture was treated with methyl iodide (40.6 µL, 0.653 mmol) and stirred for 17 hours. The reaction mixture was directly purified by reverse phase HPLC using 20-100% acetonitrile/water gradient elution to provide a light blue solid (40.2 mg). The solid was dissolved in EtOH (0.35 mL) and was subjected to the reduction procedure described in Step B of the preparation of 5-methyl-3-phenyl-1-(2,2,2-trifluoroethyl)-1H-pyrazol-4-amine (Intermediate 248). The title compound was obtained as white solid (25.1 mg, 66.1%).

Intermediate 252

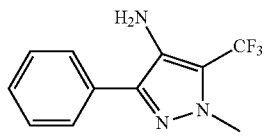 [SMILES: Cn1nc(-c2ccccc2)c(N)c1C(F)(F)F]

1-methyl-3-phenyl-5-(trifluoromethyl)-1H-pyrazol-4-amine

Step A: 1-methyl-4-nitroso-3-phenyl-5-(trifluoromethyl)-1H-pyrazole

To a solution of methylhydrazine (0.214 mL, 4.08 mmol) in EtOH (20 mL) was added 4,4,4-trifluoro-2-(hydroxyimino)-1-phenylbutane-1,3-dione (Intermediate 251, Step A; 1.00 g, 4.079 mmol). The reaction mixture was stirred at ambient temperature for 1 hour and excess $MgSO_4$ was added. The mixture was stirred at 60° C. for 48 hours and was cooled to ambient temperature. The mixture was filtered and the filtrate concentrated to a green residue. The residue was purified by silica gel chromatography using a 10-30% EtOAc/hexanes gradient for elution to provide the title compound as a green solid (482 mg, 46%). $^1$H NMR (CDCl$_3$) δ 7.89 (d, 2H), 7.45-7.52 (m, 3H), 4.15 (s, 3H).

Step B: 1-methyl-3-phenyl-5-(trifluoromethyl)-1H-pyrazol-4-amine

Prepared from 1-methyl-4-nitroso-3-phenyl-5-(trifluoromethyl)-1H-pyrazole according to the method described for the preparation of Intermediate 248, Step B. The title compound was obtained as white solid (309 mg, 68%). $^1$H NMR (CDCl$_3$) δ 7.65 (d, 2H), 7.45 (t, 2H), 7.35 (t, 1H), 3.93 (s, 3H), 3.52 (br s, 2H).

Synthetic Examples

Example 1

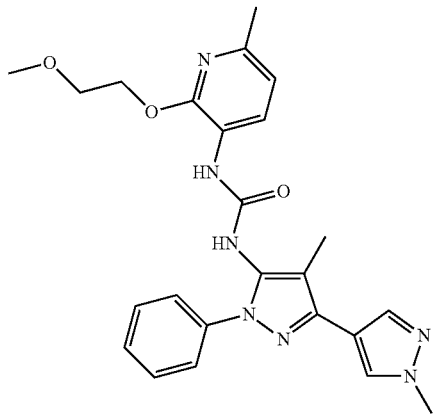

1-(1',4-dimethyl-1-phenyl-1H,1'H-[3,4'-bipyrazol]-5-yl)-3-(2-(2-methoxyethoxy)-6-methylpyridin-3-yl) urea To a mixture of phenyl (1',4-dimethyl-1-phenyl-1H,1'H-[3,4'-bipyrazol]-5-yl)carbamate (Intermediate X2, 94.0 mg, 0.252 mmol) and 2-(2-methoxyethoxy)-6-methylpyridin-3-amine (Intermediate Y8, 50.5 mg, 0.277 mmol) in dry DMA (1.0 mL) was added DIEA (87.7 μL, 0.503 mmol) and the solution was stirred at 50° C. for 15 hours. The reaction mixture was cooled to ambient temperature, added to chilled $H_2O$ (6 mL) and the resulting white suspension was mixed for 5 minutes. The solid was collected, washed with $H_2O$ and stirred in $CH_2Cl_2$ for 15 minutes. The cloudy solution was dried over $Na_2SO_4$, filtered and concentrated. The residue was purified on a $SiO_2$ column ($CH_2Cl_2$, 50%, 100% EtOAc-hexanes step gradient elution) to provide the title compound as a white solid (94 mg, 81%). $^1H$ NMR ($CDCl_3$) δ 8.19 (d, J=8.0 Hz, 1H), 7.91 (s, 1H), 7.80 (s, 1H), 7.53 (d, J=7.6 Hz, 2H), 7.41 (t, J=8.0 Hz, 2H), 7.33 (d, J=7.0 Hz, 1H), 7.27 (s, 1H), 6.66 (d, J=7.9 Hz, 1H), 6.58 (s, 1H), 4.41 (dd, J=4.6, 4.6 Hz, 2H), 3.97 (s, 3H), 3.55 (dd, J=4.7, 4.7 Hz, 2), 3.19 (s, 3H), 2.34 (s, 3H), 2.21 (s, 3H) ppm. MS (apci) m/z=462.2 (M+H).

The compounds of Table 1 were prepared according the method used for the synthesis of Example 1 using appropriate starting materials and eluent for column chromatography.

TABLE 1

| Ex. # | Structure | Name | Data |
|---|---|---|---|
| 2 | 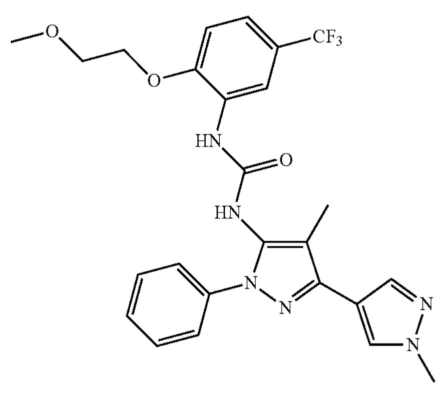 | 1-(1',4-dimethyl-1-phenyl-1H,1'H-[3,4'-bipyrazol]-5-yl)-3-(2-(2-methoxyethoxy)-5-(trifluoromethyl)phenyl)urea | MS (apci) m/z = 515.2 (M + H) |
| 3 | 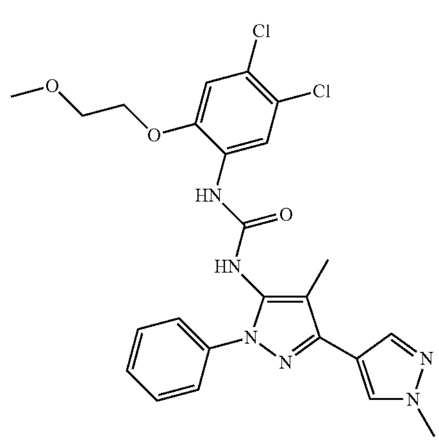 | 1-(4,5-dichloro-2-(2-methoxyethoxy)phenyl)-3-(1',4-dimethyl-1-phenyl-1H,1'H-[3,4'-bipyrazol]-5-yl)urea | MS (apci) m/z = 515.1 (M + H) |

TABLE 1-continued

| Ex. # | Structure | Name | Data |
|---|---|---|---|
| 4 | 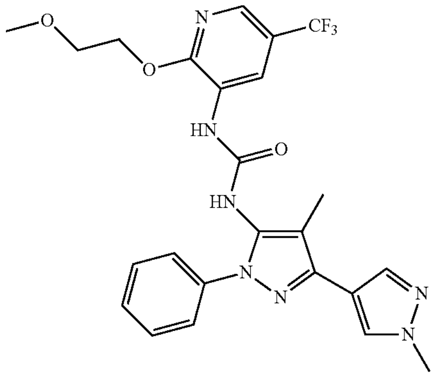 | 1-(1',4-dimethyl-1-phenyl-1H,1'H-[3,4'-bipyrazol]-5-yl)-3-(2-(2-methoxyethoxy)-5-(trifluoromethyl)pyridin-3-yl)urea | MS (apci) m/z = 514.2 (M − H) |
| 5 | 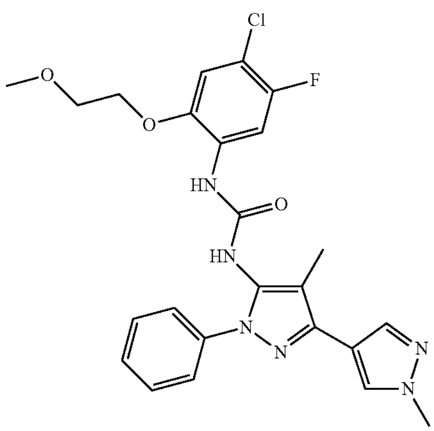 | 1-(4-chloro-5-fluoro-2-(2-methoxyethoxy)phenyl)-3-(1',4-dimethyl-1-phenyl-1H,1'H-[3,4'-bipyrazol]-5-yl)urea | MS (apci) m/z = 499.1 (M + H) |
| 6 | 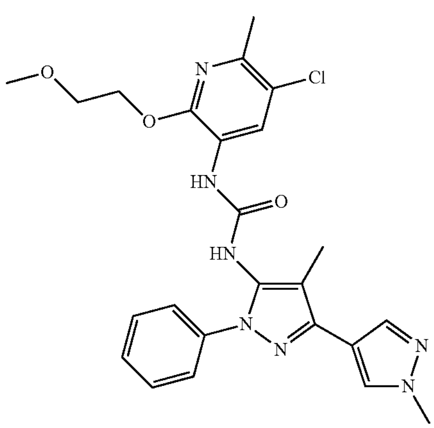 | 1-(5-chloro-2-(2-methoxyethoxy)-6-methylpyridin-3-yl)-3-(1',4-dimethyl-1-phenyl-1H,1'H-[3,4'-bipyrazol]-5-yl)urea | MS (apci) m/z = 494.2 (M − H) |

TABLE 1-continued

| Ex. # | Structure | Name | Data |
|---|---|---|---|
| 7 | 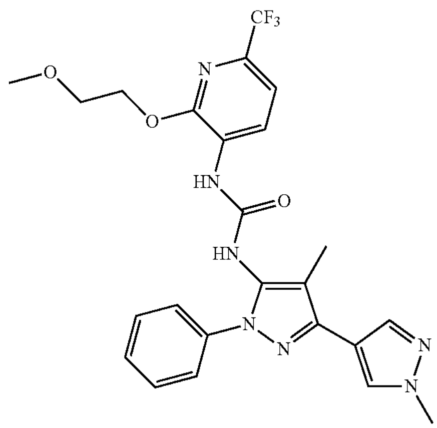 | 1-(1',4-dimethyl-1-phenyl-1H,1'H-[3,4'-bipyrazol]-5-yl)-3-(2-(2-methoxyethoxy)-6-(trifluoromethyl)pyridin-3-yl)urea | MS (apci) m/z = 516.2 (M + H) |
| 8 | 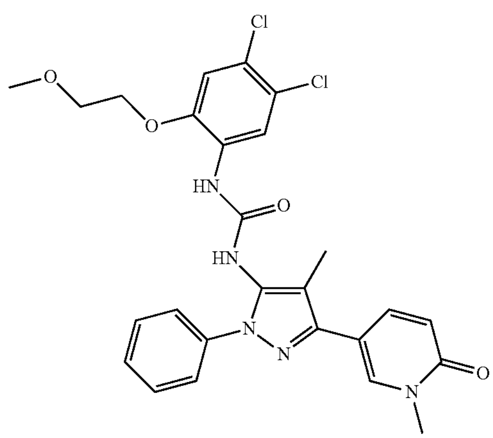 | 1-(4,5-dichloro-2-(2-methoxyethoxy)phenyl)-3-(4-methyl-3-(1-methyl-6-oxo-1,6-dihydropyridin-3-yl)-1-phenyl-1H-pyrazol-5-yl)urea | MS (apci) m/z = 540.1 (M − H) |
| 9 | 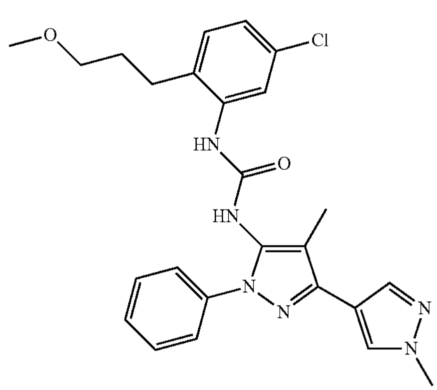 | 1-(5-chloro-2-(3-methoxypropyl)phenyl)-3-(1',4-dimethyl-1-phenyl-1H,1'H-[3,4'-bipyrazol]-5-yl)urea | MS (apci) m/z = 479.2 (M + H) |

TABLE 1-continued

| Ex. # | Structure | Name | Data |
|---|---|---|---|
| 10 | 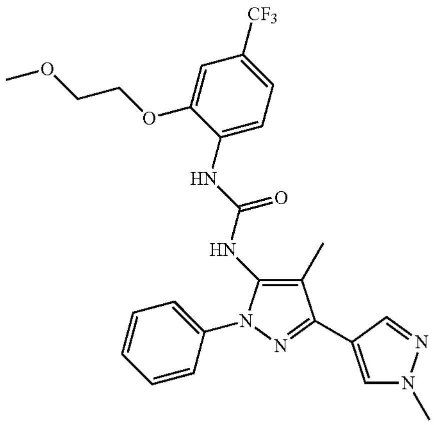 | 1-(1',4-dimethyl-1-phenyl-1H,1'H-[3,4'-bipyrazol]-5-yl)-3-(2-(2-methoxyethoxy)-4-(trifluoromethyl)phenyl)urea | MS (apci) m/z = 515.2 (M + H) |
| 11 | 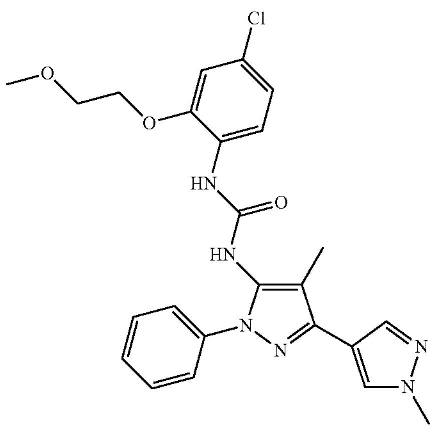 | 1-(4-chloro-2-(2-methoxyethoxy)phenyl)-3-(1',4-dimethyl-1-phenyl-1H,1'H-[3,4'-bipyrazol]-5-yl)urea | MS (apci) m/z = 481.1 (M + H) |
| 12 | 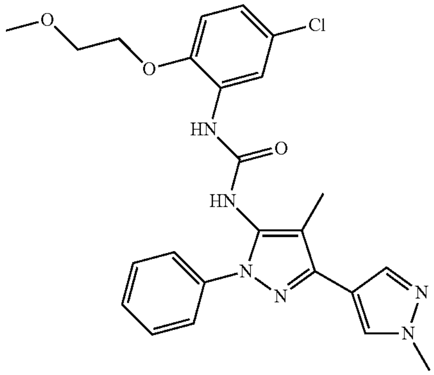 | 1-(5-chloro-2-(2-methoxyethoxy)phenyl)-3-(1',4-dimethyl-1-phenyl-1H,1'H-[3,4'-bipyrazol]-5-yl)urea | MS (apci) m/z = 481.2 (M + H) |

TABLE 1-continued

| Ex. # | Structure | Name | Data |
|---|---|---|---|
| 13 | 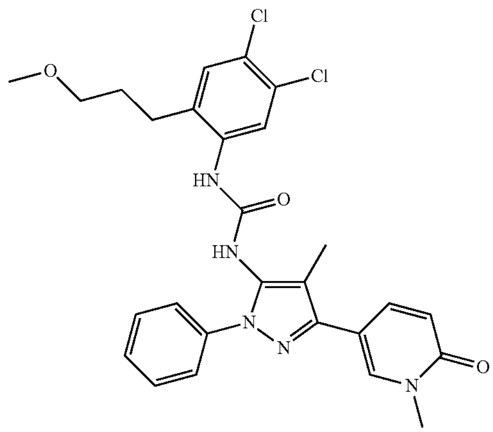 [SMILES: COCCCc1cc(Cl)c(Cl)cc1NC(=O)Nc1c(C)c(-c2ccc(=O)n(C)c2)nn1-c1ccccc1] | 1-(4,5-dichloro-2-(3-methoxypropyl)phenyl)-3-(4-methyl-3-(1-methyl-6-oxo-1,6-dihydropyridin-3-yl)-1-phenyl-1H-pyrazol-5-yl)urea | MS (apci) m/z = 538.2 (M − H) |
| 14 | 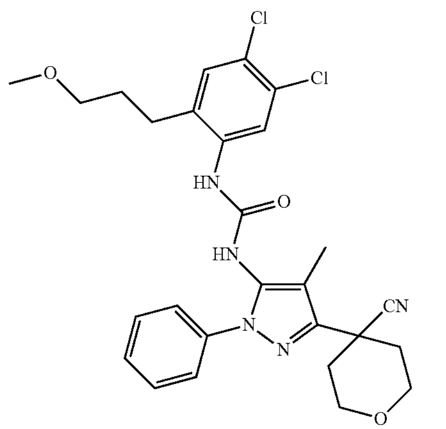 [SMILES: COCCCc1cc(Cl)c(Cl)cc1NC(=O)Nc1c(C)c(C2(C#N)CCOCC2)nn1-c1ccccc1] | 1-(3-(4-cyanotetrahydro-2H-pyran-4-yl)-4-methyl-1-phenyl-1H-pyrazol-5-yl)-3-(4,5-dichloro-2-(3-methoxypropyl)phenyl) urea | MS (apci) m/z = 542.2 (M + H) |

Example 15

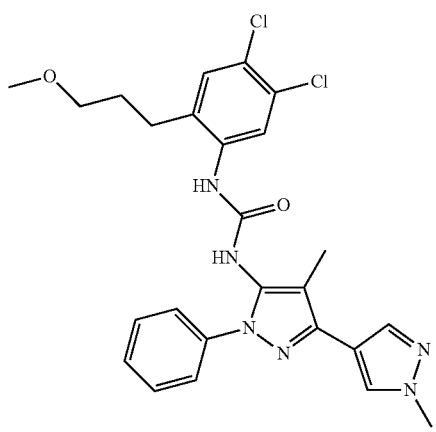

1-(4,5-dichloro-2-(3-methoxypropyl)phenyl)-3-(1',4-dimethyl-1-phenyl-1H,1'H-[3,4'-bipyrazol]-5-yl)urea A mixture of 1',4-dimethyl-1-phenyl-1H,1'H-[3,4'-bipyrazol]-5-amine (Intermediate X1, 114 mg, 0.450 mmol) and 1,2-dichloro-4-isocyanato-5-(3-methoxypropyl)benzene (Intermediate Z1, 140 mg, 0.484 mmol) in dry dioxane (2.0 mL) was stirred at ambient temperature for 64 hours. The resulting thick slurry was diluted with dioxane (2 mL), the solid collected and washed with dioxane and Et₂O. The solid was treated with warm acetone and sonicated for 5 minutes. The cooled suspension was collected, washed with acetone and dried in vacuum to afford the title compound a white solid (78 mg, 34%). MS (apci) m/z=513.1 (M+H).

Example 16

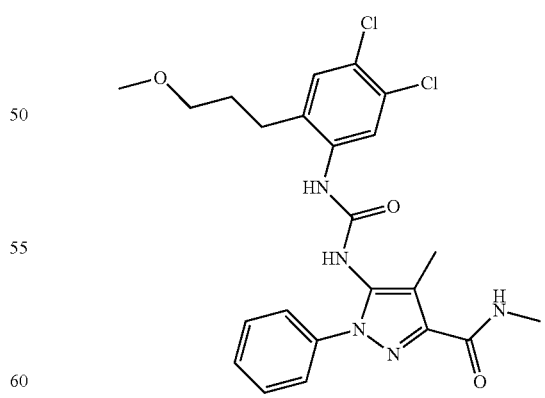

5-(3-(4,5-dichloro-2-(3-methoxypropyl)phenyl) ureido)-N,4-dimethyl-1-phenyl-1H-pyrazole-3-carboxamide To a solution of 5-amino-N,4-dimethyl-1-phenyl-1H-pyrazole-3-carboxamide (Intermediate X5, 34.6 mg, 0.150 mmol) in dry dioxane (1.0 mL) was added 1,2-dichloro-4-isocyanato-5-(3-methoxypropyl)benzene (Intermediate Z1, 43.4 mg, 0.150 mmol) and the reaction mixture was stirred at ambient temperature for 6 hours. The reaction mixture was heated at 45° C. for 16 hours then at 60° C. for 2 hours. The reaction mixture was cooled to ambient temperature and the suspended solid was collected via vacuum filtration. The collected solid was washed with dioxane and Et$_2$O and dried in vacuum to afford the title compound as a white solid. Additional pure product precipitated out of the wash filtrates (41 mg, 56% combined yield). MS (apci) m/z=488.1 (M–H).

Example 17

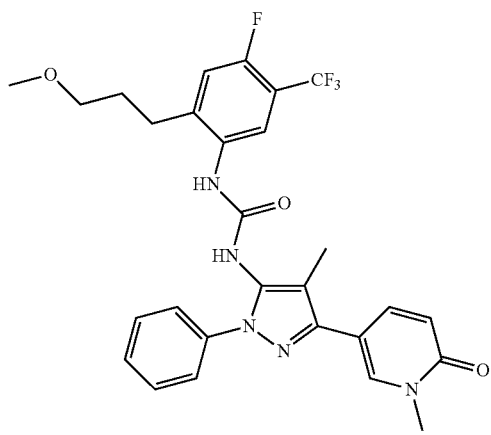

1-(4-fluoro-2-(3-methoxypropyl)-5-(trifluoromethyl)phenyl)-3-(4-methyl-3-(1-methyl-6-oxo-1,6-dihydropyridin-3-yl)-1-phenyl-1H-pyrazol-5-yl)urea Step A: To a solution of triphosgene (110 mg, 0.362 mmol) in dry CH$_2$Cl$_2$ (3 mL) was added a solution of 4-fluoro-2-(3-methoxypropyl)-5-(trifluoromethyl)aniline (Intermediate Y13, 250 mg, 0.995 mmol) and DIEA (315 µL, 1.81 mmol) in dry CH$_2$Cl$_2$ (3 mL) dropwise over 1 hour. The mixture was stirred for 2.5 hours and concentrated. The residual solid was stirred vigorously in hexanes for 2 hours, the suspension was filtered and the filtrate was concentrated. The residual light gold oil was dried in vacuum to provide crude 1-fluoro-4-isocyanato-5-(3-methoxypropyl)-2-(trifluoromethyl)benzene.

Step B: To a solution of 5-(5-amino-4-methyl-1-phenyl-1H-pyrazol-3-yl)-1-methylpyridin-2(1H)-one (Intermediate X3, 64.7 mg, 0.231 mmol) in dry dioxane (1.2 mL) was added the crude 1-fluoro-4-isocyanato-5-(3-methoxypropyl)-2-(trifluoromethyl)benzene (64.0 mg, 0.115 mmol) and the mixture was stirred at ambient temperature for 5 hours then at 60° C. for 2 hours. The reaction mixture was cooled to ambient temperature and was concentrated. The residue was purified on a SiO$_2$ column (CH$_2$Cl$_2$, 50% EtOAc-hexanes, EtOAc, 5% MeOH/EtOAc step gradient elution). The purified material was washed with Et$_2$O and dried in vacuum to furnish the title compound as a light tan powder (17 mg, 27%). MS (apci) m/z=556.2 (M–H).

Example 18

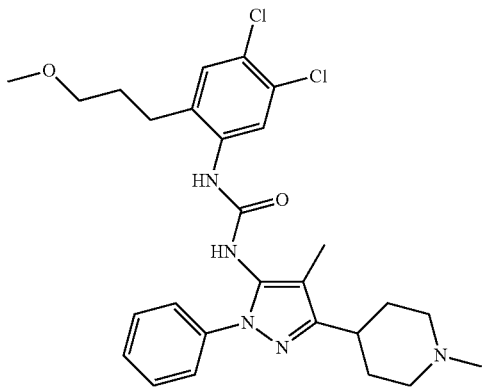

1-(4,5-dichloro-2-(3-methoxypropyl)phenyl)-3-(4-methyl-3-(1-methylpiperidin-4-yl)-1-phenyl-1H-pyrazol-5-yl)urea To a solution of 4-methyl-3-(1-methylpiperidin-4-yl)-1-phenyl-1H-pyrazol-5-amine (Intermediate X8, 33.8 mg, 0.125 mmol) in dry dioxane (1.0 mL) was added 1,2-dichloro-4-isocyanato-5-(3-methoxypropyl)benzene (Intermediate Z1, 36.1 mg, 0.125 mmol) and the reaction mixture was stirred at 45° C. for 6 hours. The reaction mixture was cooled to ambient temperature and was diluted with dry Et$_2$O (2 mL). The resulting white suspension was filtered and the filtrate concentrated. The residue was purified on a SiO$_2$ column (EtOAc then 10% (9:1 MeOH/NH$_4$OH)/EtOAc) to produce a colorless glass. The glass was sonicated under 5% Et$_2$O-hexanes until white granular suspension formed. The solvent was decanted and the residual solid was washed with hexanes and dried in vacuum to afford the title compound as a white solid (25 mg, 38%). MS (apci) m/z=530.2 (M+H).

Example 19

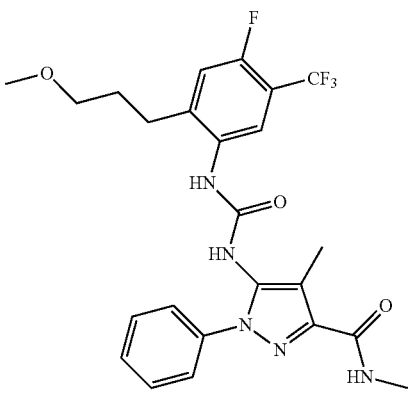

5-(3-(4-fluoro-2-(3-methoxypropyl)-5-(trifluoromethyl)phenyl)ureido)-N,4-dimethyl-1-phenyl-1H-pyrazole-3-carboxamide Using 5-amino-N,4-dimethyl-1-phenyl-1H-pyrazole-3-carboxamide (Intermediate X5) in the procedure outlined for Example 17, the title compound was obtained as a white solid (7.5 mg, 9.3%) after purification by SiO$_2$ column chromatography (CH$_2$Cl$_2$, 50% EtOAc-hexanes, EtOAc step gradient). MS (apci) m/z=508.2 (M+H).

Example 20

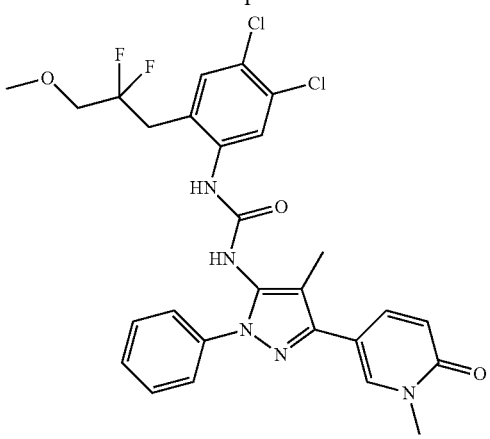

1-(4,5-dichloro-2-(2,2-difluoro-3-methoxypropyl)phenyl)-3-(4-methyl-3-(1-methyl-6-oxo-1,6-dihydropyridin-3-yl)-1-phenyl-1H-pyrazol-5-yl)urea To a solution of 5-(5-amino-4-methyl-1-phenyl-1H-pyrazol-3-yl)-1-methylpyridin-2(1H)-one (Intermediate X3, 42.0 mg, 0.150 mmol) and DIEA (31.3 µL, 0.180 mmol) in dry DMA (0.75 mL) was added carbonyldiimidazole (28.1 mg, 0.165 mmol) and the mixture was stirred at ambient temperature for 2 hours and then at 50° C. for 5 hours. The mixture was cooled to ambient temperature and 4,5-dichloro-2-(2,2-difluoro-3-methoxypropyl)aniline (Intermediate Y15, 40.5 mg, 0.150 mmol) was added. The mixture was stirred at 40° C. for 16 hours, cooled to ambient temperature, diluted with 0.5 M HCl (2 mL) and stirred for 10 minutes. The resulting white suspension was collected and the solid washed with 0.5M HCl, $H_2O$ and $Et_2O$. The solid was treated with 1:1 $CH_2Cl_2$-acetone and sonicated for 5 minutes. The cloudy solution was dried over $Na_2SO_4$, filtered and concentrated. The residual solid was purified on a $SiO_2$ column (0%, 3%, 6% MeOH/$CH_2Cl_2$ step gradient elution), dissolved in MeOH, filtered and concentrated to provide the title compound as a white solid (8.0 mg, 9.3%). MS (apci) m/z=574.2 (M–H).

Example 21

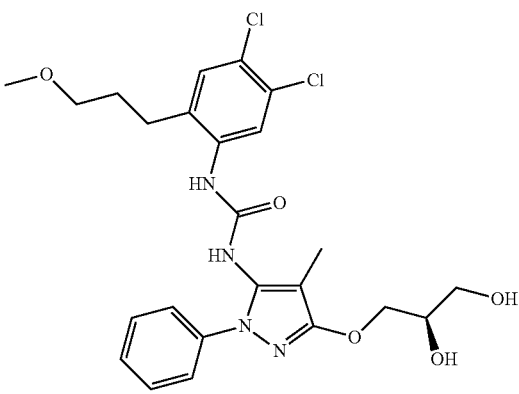 [SMILES: COCCCc1cc(Cl)c(Cl)cc1NC(=O)Nc1c(C)c(OC[C@H](O)CO)nn1-c1ccccc1]

(R)-1-(4,5-dichloro-2-(3-methoxypropyl)phenyl)-3-(3-(2,3-dihydroxypropoxy)-4-methyl-1-phenyl-1H-pyrazol-5-yl)urea Step A: Preparation of (S)-1-(4,5-dichloro-2-(3-methoxypropyl)phenyl)-3-(3-((2,2-dimethyl-1,3-dioxolan-4-yl)methoxy)-4-methyl-1-phenyl-1H-pyrazol-5-yl)urea A mixture of (S)-3-((2,2-dimethyl-1,3-dioxolan-4-yl)methoxy)-4-methyl-1-phenyl-1H-pyrazol-5-amine (Intermediate X11, 41.0 mg, 0.135 mmol) and 1,2-dichloro-4-isocyanato-5-(3-methoxypropyl)benzene (Intermediate Z1, 38.7 mg, 0.149 mmol) in dry dioxane (1.0 mL) was stirred at ambient temperature for 24 hours then at 50° C. for 6 hours. The mixture was cooled to ambient temperature, concentrated and the residue purified on a $SiO_2$ column ($CH_2Cl_2$, 25%, 50% EtOAc-hexanes step gradient) to provide the title compound as a white solid (41 mg, 54%). MS (apci) m/z=563.2 (M+H).

Step B: Preparation of (R)-1-(4,5-dichloro-2-(3-methoxypropyl)phenyl)-3-(3-(2,3-dihydroxypropoxy)-4-methyl-1-phenyl-1H-pyrazol-5-yl)urea To a solution of (S)-1-(4,5-dichloro-2-(3-methoxypropyl)phenyl)-3-(3-((2,2-dimethyl-1,3-dioxolan-4-yl)methoxy)-4-methyl-1-phenyl-1H-pyrazol-5-yl)urea (40.0 mg, 0.071 mmol) in THF (2 mL) was added 1M HCl (2 mL) and the mixture was stirred at ambient temperature for 6 hours. The mixture was concentrated to an aqueous suspension and treated with 2M NaOH to pH=7. The resulting suspension was collected and washed thoroughly with $H_2O$ and $Et_2O$. The solid was dissolved in MeOH and concentrated to provide the title compound as a white solid after drying in vacuum (35 mg, 94%). MS (apci) m/z=521.2 (M–H).

Example 22

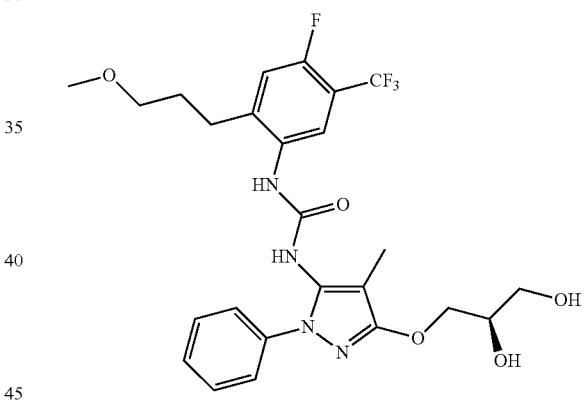

(R)-1-(3-(2,3-dihydroxypropoxy)-4-methyl-1-phenyl-1H-pyrazol-5-yl)-3-(4-fluoro-2-(3-methoxypropyl)-5-(trifluoromethyl)phenyl)urea Step A: Preparation of ((S)-1-(3-((2,2-dimethyl-1,3-dioxolan-4-yl)methoxy)-4-methyl-1-phenyl-1H-pyrazol-5-yl)-3-(4-fluoro-2-(3-methoxypropyl)-5-(trifluoromethyl)phenyl)urea To a solution of (S)-3-((2,2-dimethyl-1,3-dioxolan-4-yl)methoxy)-4-methyl-1-phenyl-1H-pyrazol-5-amine (Intermediate X11, 34.0 mg, 0.112 mmol) and DIEA (23.4 µL, 0.134 mmol) in dry DMA (0.60 mL) was added CDI (21.0 mg, 0.123 mmol) and the mixture was stirred at ambient temperature for 6 hours and then at 50° C. for 16 hours. Additional CDI (5 mg) was added and the mixture was heated at 50° C. for 5 hours. The mixture was cooled to ambient temperature and 4-fluoro-2-(3-methoxypropyl)-5-(trifluoromethyl)aniline (Intermediate Y13, 33.8 mg, 0.134 mmol) was added. The mixture was stirred at 50° C. for 19 hours, cooled to ambient temperature and then treated with H₂O and 50% EtOAc-hexane. 1M HCl was added to pH=3 and the organic layer was removed. The aqueous layer was extracted with 50% EtOAc-hexane (2×) and the combined organic fractions were washed with H₂O, saturated NaCl (2×) and dried over MgSO₄. The solution was filtered, concentrated and the residue purified on a SiO₂ column (CH₂Cl₂, 25%, 50% EtOAc-hexanes step gradient) to furnish the title compound as a white solid (28 mg, 34%). MS (apci) m/z=581.3 (M+H).

Step B: Preparation of (R)-1-(3-(2,3-dihydroxypropoxy)-4-methyl-1-phenyl-1H-pyrazol-5-yl)-3-(4-fluoro-2-(3-methoxypropyl)-5-(trifluoromethyl)phenyl)urea To a solution of (S)-1-(3-((2,2-dimethyl-1,3-dioxolan-4-yl)methoxy)-4-methyl-1-phenyl-1H-pyrazol-5-yl)-3-(4-fluoro-2-(3-methoxypropyl)-5-(trifluoromethyl)phenyl)urea (25 mg, 0.034 mmol) in THF (1.5 mL) was added 1M HCl (1.5 mL) and the mixture was stirred at ambient temperature for 4 hours. The mixture was concentrated to an aqueous suspension and treated with 2M NaOH to pH=5. The suspension was collected and the solid was washed thoroughly with H₂O and Et₂O. The solid was dissolved in EtOAc, filtered through a Celite® plug capped with packed MgSO₄ (EtOAc elution) and concentrated to provide the title compound as a white (14 mg, 75%). MS (apci) m/z=539.2 (M−H).

Example 23

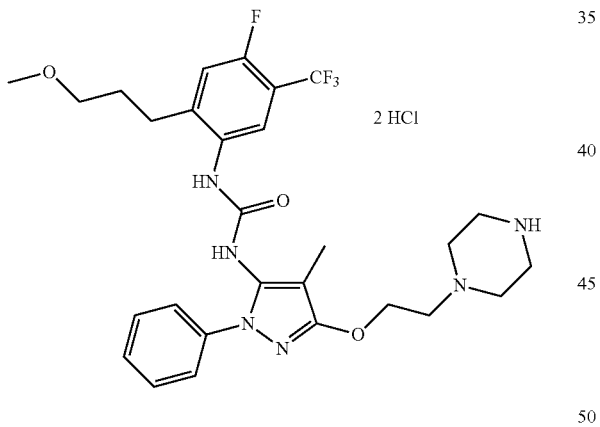

(S)-1-(4,5-dichloro-2-(3-methoxypropyl)phenyl)-3-(4-methyl-3-(morpholin-2-ylmethoxy)-1-phenyl-1H-pyrazol-5-yl)urea dihydrochloride Step A: Preparation of tert-butyl 4-(2-((5-(3-(4-fluoro-2-(3-methoxypropyl)-5-(trifluoromethyl)phenyl)ureido)-4-methyl-1-phenyl-1H-pyrazol-3-yl)oxy)ethyl)piperazine-1-carboxylate To a solution of tert-butyl 4-(2-((5-amino-4-methyl-1-phenyl-1H-pyrazol-3-yl)oxy)ethyl)piperazine-1-carboxylate (Intermediate X13, 100 mg, 0.249 mmol) and DIEA (52.1 µL, 0.299 mmol) in dry THF (1.5 mL) was added CDI (46.8 mg, 0.274 mmol) and the mixture was stirred for at 50° C. for 17 hours. The mixture was cooled to ambient temperature and 4-fluoro-2-(3-methoxypropyl)-5-(trifluorom-ethyl)aniline (Intermediate Y13, 75.1 mg, 0.299 mmol) was added. The reaction mixture was stirred at 50° C. for 7 hours, cooled to ambient temperature and diluted with H₂O and 50% EtOAc-hexane. The organic layer was removed and the aqueous portion was extracted with 50% EtOAc-hexane. The combined organic fractions were washed with H₂O and saturated NaCl and dried over MgSO₄/activated charcoal. The solution was filtered and concentrated, and the residue was purified on a SiO₂ column (CH₂Cl₂, 25%, 50%, 100% EtOAc-hexane). The resulting waxy solid was recrystallized from Et₂O to give the title compound as a white solid (35 mg, 21%). MS (apci) m/z=679.3 (M+H).

Step B: Preparation of (S)-1-(4,5-dichloro-2-(3-methoxypropyl)phenyl)-3-(4-methyl-3-(morpholin-2-ylmethoxy)-1-phenyl-1H-pyrazol-5-yl)urea dihydrochloride To a solution of tert-butyl 4-(2-((5-(3-(4-fluoro-2-(3-methoxypropyl)-5-(trifluoromethyl)phenyl)ureido)-4-methyl-1-phenyl-1H-pyrazol-3-yl)oxy)ethyl)piperazine-1-carboxylate (31 mg, 0.0451 mmol) in EtOAc (1.0 mL) was added chilled 5M HCl in iPrOH (902 µL, 4.51 mmol) and the mixture was stirred at ambient temperature for 2.5 hours. The mixture was concentrated and the residual colorless syrup was dried in vacuum. The residue was treated with 50% EtOAc-hexanes and then sonicated. The resulting white suspension was stirred for 15 minutes. The solvent was decanted to provide the title compound as a white solid after drying in vacuum (28 mg, 97%). MS (apci) m/z=579.3 (M+H).

Example 24

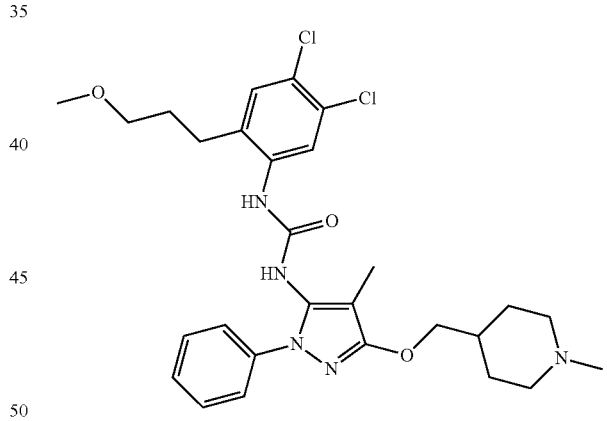

(1-(4,5-dichloro-2-(3-methoxypropyl)phenyl)-3-(4-methyl-3-methylpiperidin-4-yl)methoxy)-1-phenyl-1H-pyrazol-5-yl)urea To a solution of 4-methyl-3-methylpiperidin-4-yl)methoxy)-1-phenyl-1H-pyrazol-5-amine (Intermediate X26, 130 mg, 0.389 mmol) in dry dioxane (3 mL) was added 1,2-dichloro-4-isocyanato-5-(3-methoxypropyl)benzene (Intermediate Z1, 122 mg, 0.467 mmol) and the mixture was stirred at 40° C. for 24 hours. The mixture was concentrated and the residue purified on a SiO₂ column (CH₂Cl₂, EtOAc, 5% (9:1MeOH/NH₄OH)/EtOAc). The resulting solid was washed with Et₂O and dried in vacuum to provide the title compound as a white solid (115 mg, 66%). MS (apci) m/z=560.2 (M+H).

The compounds of Table 4 were prepared according the method used for the synthesis of Example 24 using appropriate starting materials, solvent and eluent for column chromatography.

TABLE 4

| Ex # | Structure | Name | Data |
|---|---|---|---|
| 25 | 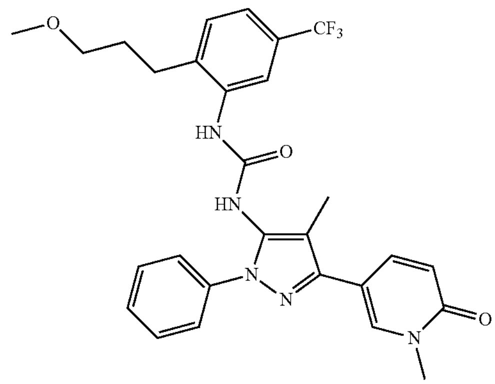 [SMILES: COCCCc1ccc(C(F)(F)F)cc1NC(=O)Nc1c(C)c(-c2ccc(=O)n(C)c2)nn1-c1ccccc1] | 1-(2-(3-methoxypropyl)-5-(trifluoromethyl)phenyl)-3-(4-methyl-3-(1-methyl-6-oxo-1,6-dihydropyridin-3-yl)-1-phenyl-1H-pyrazol-5-yl)urea | MS (apci) m/z = 540.2 (M + H) |
| 26 | 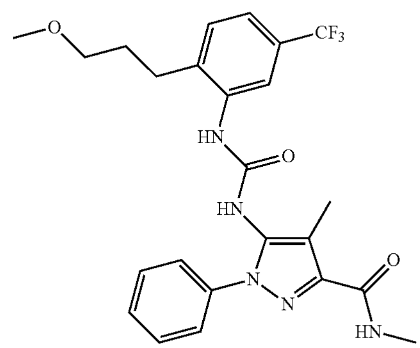 | 5-(3-(2-(3-methoxypropyl)-5-(trifluoromethyl)phenyl)ureido)-N,4-dimethyl-1-phenyl-1H-pyrazole-3-carboxamide | MS (apci) m/z = 490.2 (M + H) |
| 27 | 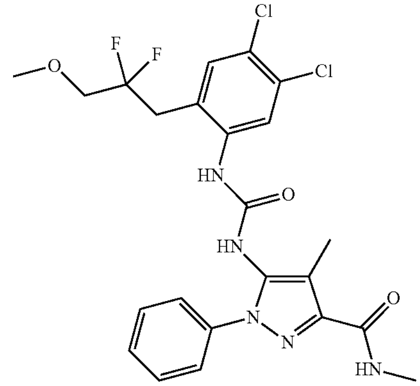 | 5-(3-(4,5-dichloro-2-(2,2-difluoro-3-methoxypropyl)phenyl)ureido)-N,4-dimethyl-1-phenyl-1H-pyrazole-3-carboxamide | MS (apci) m/z = 526.1 (M + H) |

TABLE 4-continued
| Ex # | Structure | Name | Data |
|---|---|---|---|
| 28 | 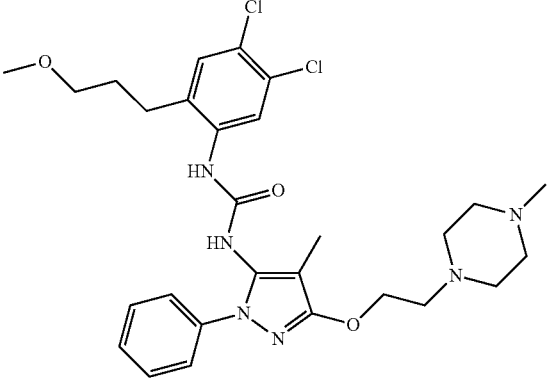 | 1-(4,5-dichloro-2-(3-methoxypropyl)phenyl)-3-(4-methyl-3-(2-(4-methylpiperazin-1-yl)ethoxy)-1-phenyl-1H-pyrazol-5-yl)urea | MS (apci) m/z = 575.2 (M + H) |
| 29 | 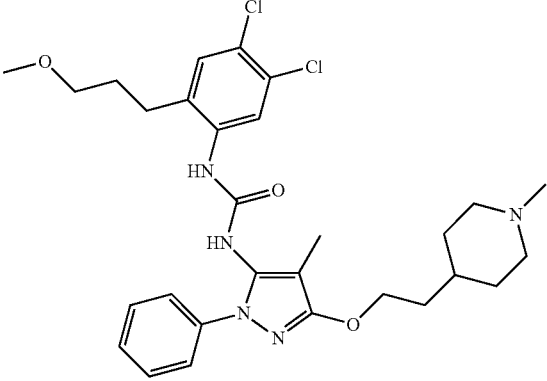 | 1-(4,5-dichloro-2-(3-methoxypropyl)phenyl)-3-(4-methyl-3-(2-(1-methylpiperidin-4-yl)ethoxy)-1-phenyl-1H-pyrazol-5-yl)urea | MS (apci) m/z = 574.2 (M + H) |
| 30 | 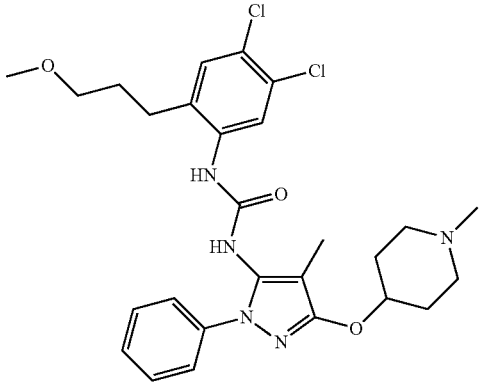 | 1-(4,5-dichloro-2-(3-methoxypropyl)phenyl)-3-(4-methyl-3-((1-methylpiperidin-4-yl)oxy)-1-phenyl-1H-pyrazol-5-yl)urea | MS (apci) m/z = 546.2 (M + H) |

TABLE 4-continued

| Ex # | Structure | Name | Data |
|---|---|---|---|
| 31 | 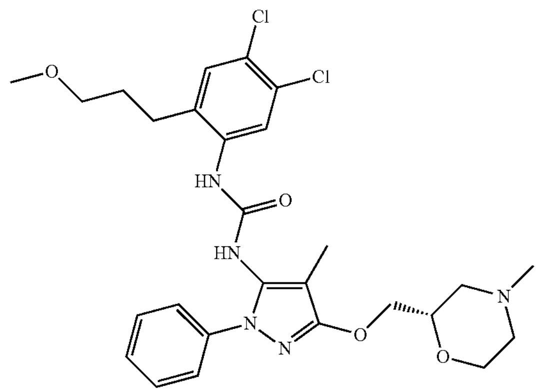 | (S)-1-(4,5-dichloro-2-(3-methoxypropyl)phenyl)-3-(4-methyl-3-((4-methylmorpholin-2-yl)methoxy)-1-phenyl-1H-pyrazol-5-yl)urea | MS (apci) m/z = 562.2 (M + H) |
| 32 | 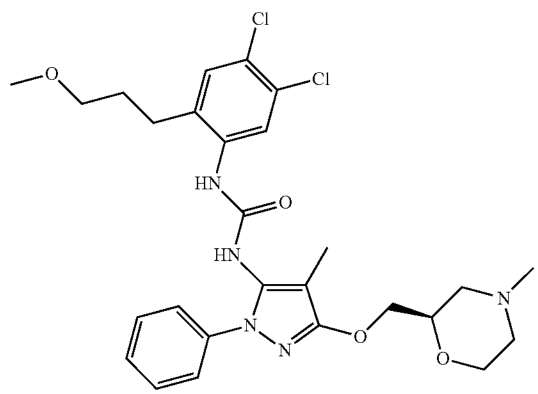 | (R)-1-(4,5-dichloro-2-(3-methoxypropyl)phenyl)-3-(4-methyl-3-((4-methylmorpholin-2-yl)methoxy)-1-phenyl-1H-pyrazol-5-yl)urea | MS (apci) m/z = 562.2 (M + H) |
| 33 | 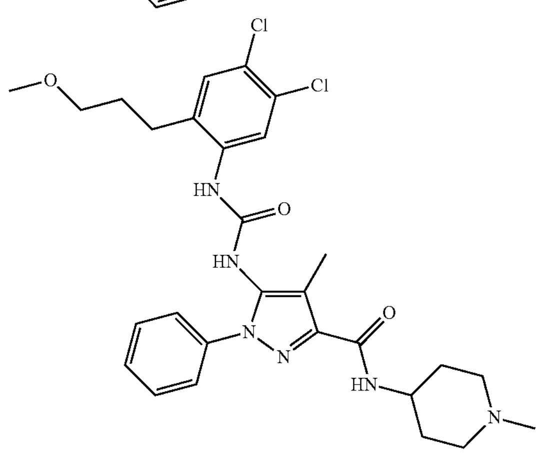 | 5-(3-(4,5-dichloro-2-(3-methoxypropyl)phenyl)ureido)-4-methyl-N-(1-methylpiperidin-4-yl)-1-phenyl-1H-pyrazole-3-carboxamide | MS (apci) m/z = 573.2 (M + H) |
| 34 | 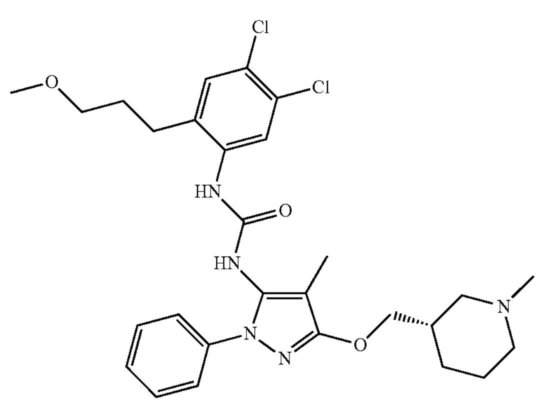 | (S)-1-(4,5-dichloro-2-(3-methoxypropyl)phenyl)-3-(4-methyl-3-((1-methylpiperidin-3-yl)methoxy)-1-phenyl-1H-pyrazol-5-yl)urea | MS (apci) m/z = 560.2 (M + H) |

TABLE 4-continued

| Ex # | Structure | Name | Data |
|---|---|---|---|
| 35 | 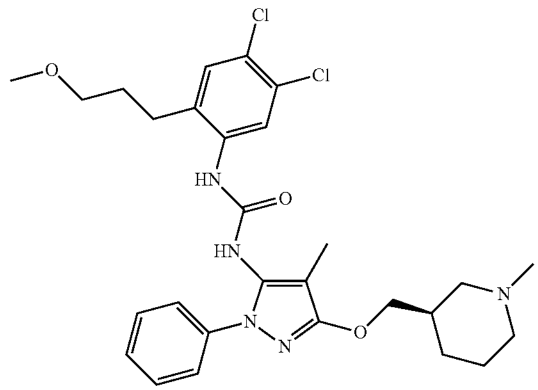 | (R)-1-(4,5-dichloro-2-(3-methoxypropyl)phenyl)-3-(4-methyl-3-((1-methylpiperidin-3-yl)methoxy)-1-phenyl-1H-pyrazol-5-yl)urea | MS (apci) m/z = 560.2 (M + H) |
| 36 | 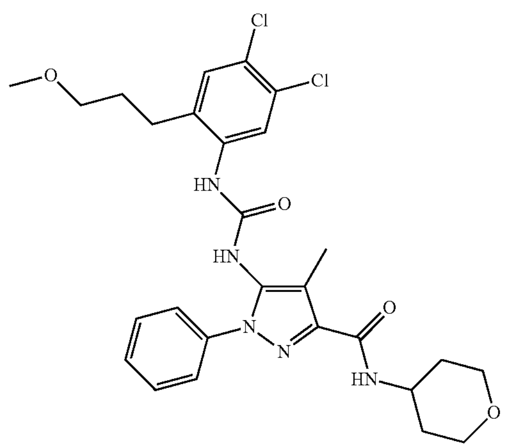 [SMILES: COCCCc1cc(Cl)c(Cl)cc1NC(=O)Nc1c(C)c(C(=O)NC2CCOCC2)nn1-c1ccccc1] | 5-(3-(4,5-dichloro-2-(3-methoxypropyl)phenyl)ureido)-4-methyl-1-phenyl-N-(tetrahydro-2H-pyran-4-yl)-1H-pyrazole-3-carboxamide | MS (apci) m/z = 558.2 (M − H) |
| 37 | 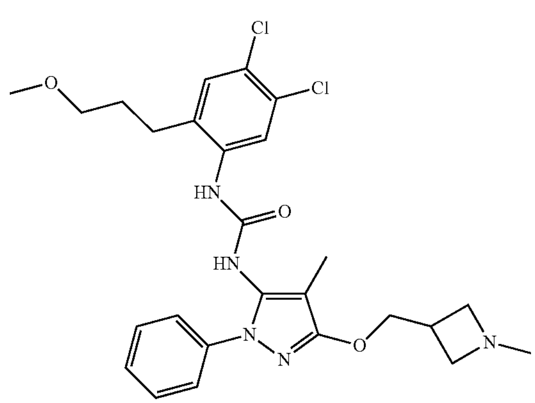 | 1-(4,5-dichloro-2-(3-methoxypropyl)phenyl)-3-(4-methyl-3-((1-methylazetidin-3-yl)methoxy)-1-phenyl-1H-pyrazol-5-yl)urea | MS (apci) m/z = 532.2 (M + H) |

Example 38

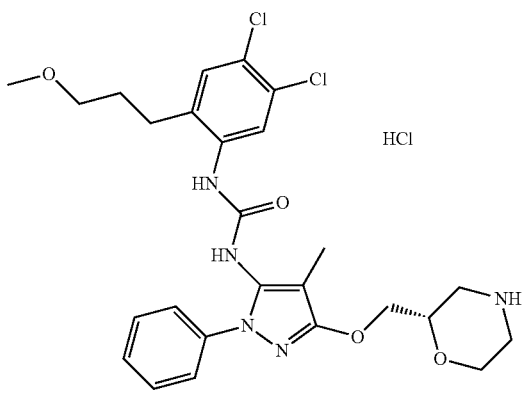 [SMILES: COCCCc1cc(Cl)c(Cl)cc1NC(=O)Nc1c(C)c(OC[C@@H]2CNCCO2)nn1-c1ccccc1 ; Cl]

(S)-1-(4,5-dichloro-2-(3-methoxypropyl)phenyl)-3-(4-methyl-3-(morpholin-2-ylmethoxy)-1-phenyl-1H-pyrazol-5-yl)urea hydrochloride Step A: Preparation of (S)-tert-butyl 2-(((5-(3-(4,5-dichloro-2-(3-methoxypropyl)phenyl)ureido)-4-methyl-1-phenyl-1H-pyrazol-3-yl)oxy)methyl)morpholine-4-carboxylate To a solution of (S)-tert-butyl 2-(((5-amino-4-methyl-1-phenyl-1H-pyrazol-3-yl)oxy)methyl)morpholine-4-carboxylate (Intermediate X17, 64.7 mg, 0.150 mmol) in dry dioxane (1.0 mL) was added 1,2-dichloro-4-isocyanato-5-(3-methoxypropyl)benzene (Intermediate Z1, 46.8 mg, 0.180 mmol) and the mixture was stirred at ambient temperature for 24 hours. The reaction mixture was concentrated and the residue was purified on a $SiO_2$ column ($CH_2Cl_2$, 20%, 40% EtOAc-hexanes step gradient elution) to provide the title compound as a white solid (58 mg, 60%). MS (apci) m/z=646.2 (M−H).

Step B: Preparation of (S)-1-(4,5-dichloro-2-(3-methoxypropyl)phenyl)-3-(4-methyl-3-(morpholin-2-ylmethoxy)-1-phenyl-1H-pyrazol-5-yl)urea hydrochloride (S)-tert-butyl 2-(((5-(3-(4,5-dichloro-2-(3-methoxypropyl)phenyl)ureido)-4-methyl-1-phenyl-1H-pyrazol-3-yl)oxy)methyl)morpholine-4-carboxylate (58 mg, 0.080 mmol) was dissolved in chilled 5M HCl in iPrOH (3 mL) and the solution was stirred at ambient temperature for 2 hours. The reaction mixture was concentrated and the residue dried to a colorless glass. The glass was sonicated under 50% EtOAc-hexanes until a fine white suspension formed. The solvent was decanted, and the remaining solid was washed with 50% EtOAc-hexanes and dried in vacuum to give the title compound as a white powder (42 mg, 89%). MS (apci) m/z=548.2 (M+H).

The compounds of Table 5 were prepared according the method used for the synthesis of Example 38 using appropriate starting materials, solvent and eluent for column chromatography.

TABLE 5

| Ex # | Structure | Name | Data |
|---|---|---|---|
| 39 | 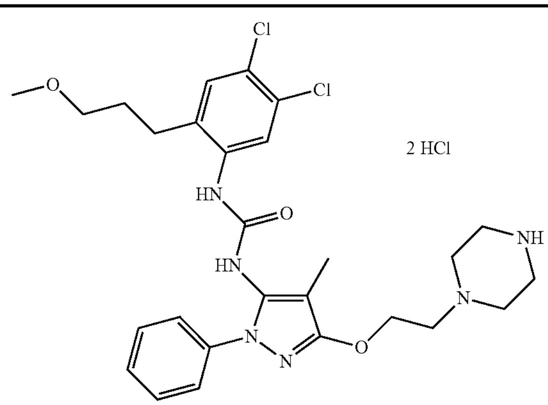 | 1-(4,5-dichloro-2-(3-methoxypropyl)phenyl)-3-(4-methyl-1-phenyl-3-(2-(piperazin-1-yl)ethoxy)-1H-pyrazol-5-yl)urea dihydrochloride | MS (apci) m/z = 561.2 (M + H) |
| 40 | 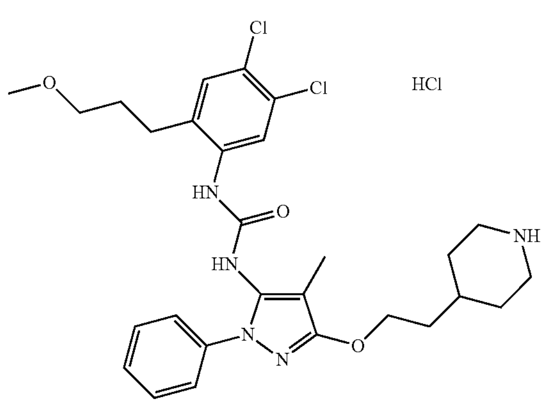 [SMILES: COCCCc1cc(Cl)c(Cl)cc1NC(=O)Nc1c(C)c(OCCC2CCNCC2)nn1-c1ccccc1 ; Cl] | 1-(4,5-dichloro-2-(3-methoxypropyl)phenyl)-3-(4-methyl-1-phenyl-3-(2-(piperidin-4-yl)ethoxy)-1H-pyrazol-5-yl)urea hydrochloride | MS (apci) m/z = 560.2 (M + H) |

TABLE 5-continued

| Ex # | Structure | Name | Data |
|---|---|---|---|
| 41 | 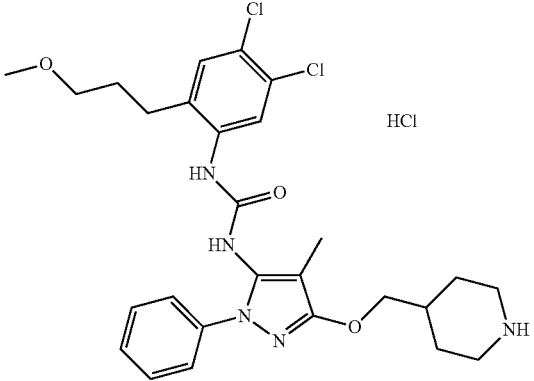 [SMILES: COCCCc1cc(Cl)c(Cl)cc1NC(=O)Nc1c(C)c(OCC2CCNCC2)nn1-c1ccccc1 ; Cl] | 1-(4,5-dichloro-2-(3-methoxypropyl)phenyl)-3-(4-methyl-1-phenyl-3-(piperidin-4-ylmethoxy)-1H-pyrazol-5-yl)urea hydrochloride | MS (apci) m/z = 546.2 (M + H) |
| 42 | 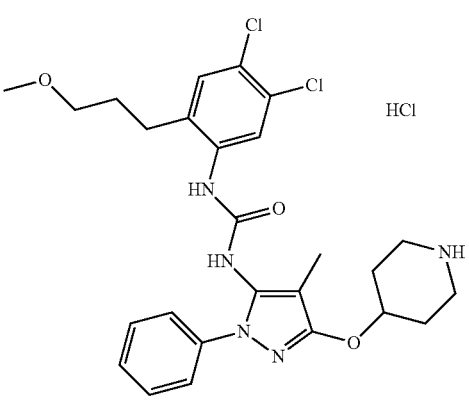 [SMILES: COCCCc1cc(Cl)c(Cl)cc1NC(=O)Nc1c(C)c(OC2CCNCC2)nn1-c1ccccc1 ; Cl] | 1-(4,5-dichloro-2-(3-methoxypropyl)phenyl)-3-(4-methyl-1-phenyl-3-(piperidin-4-yloxy)-1H-pyrazol-5-yl)urea hydrochloride | MS (apci) m/z = 532.2 (M + H) |
| 43 | 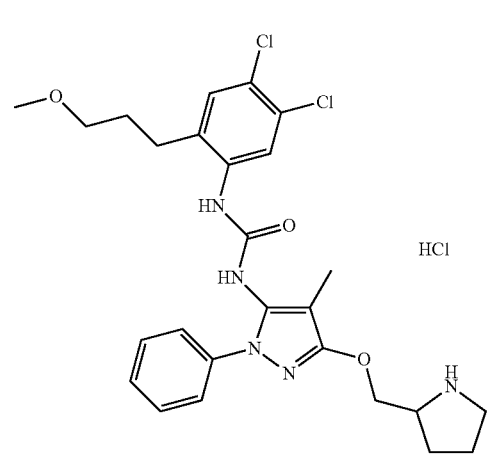 [SMILES: COCCCc1cc(Cl)c(Cl)cc1NC(=O)Nc1c(C)c(OCC2CCCN2)nn1-c1ccccc1 ; Cl] | 1-(4,5-dichloro-2-(3-methoxypropyl)phenyl)-3-(4-methyl-1-phenyl-3-(pyrrolidin-2-ylmethoxy)-1H-pyrazol-5-yl)urea hydrochloride | MS (apci) m/z = 532.2 (M + H) |

TABLE 5-continued

| Ex # | Structure | Name | Data |
|---|---|---|---|
| 44 | 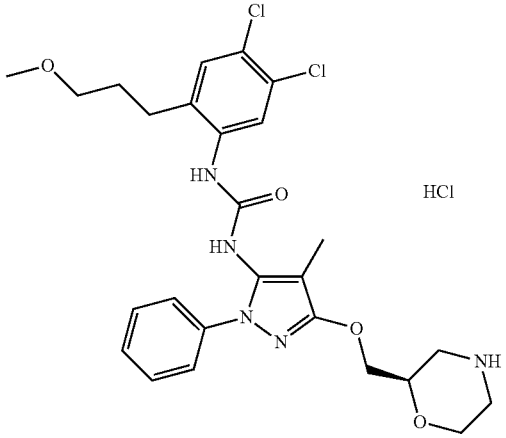 [SMILES: COCCCc1cc(Cl)c(Cl)cc1NC(=O)Nc1c(C)c(OC[C@H]2CNCCO2)nn1-c1ccccc1 ; Cl] | (R)-1-(4,5-dichloro-2-(3-methoxypropyl)phenyl)-3-(4-methyl-3-(morpholin-2-ylmethoxy)-1-phenyl-1H-pyrazol-5-yl)urea hydrochloride | MS (apci) m/z = 548.2 (M + H) |
| 45 | 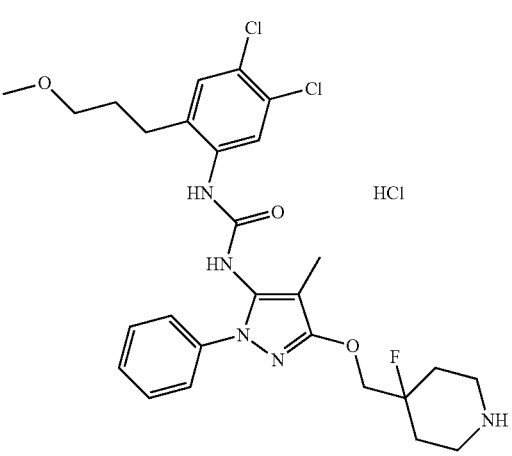 [SMILES: COCCCc1cc(Cl)c(Cl)cc1NC(=O)Nc1c(C)c(OCC2(F)CCNCC2)nn1-c1ccccc1 ; Cl] | 1-(4,5-dichloro-2-(3-methoxypropyl)phenyl)-3-(3-((4-fluoropiperidin-4-yl)methoxy)-4-methyl-1-phenyl-1H-pyrazol-5-yl)urea hydrochloride | MS (apci) m/z = 564.2 (M + H) |
| 46 | 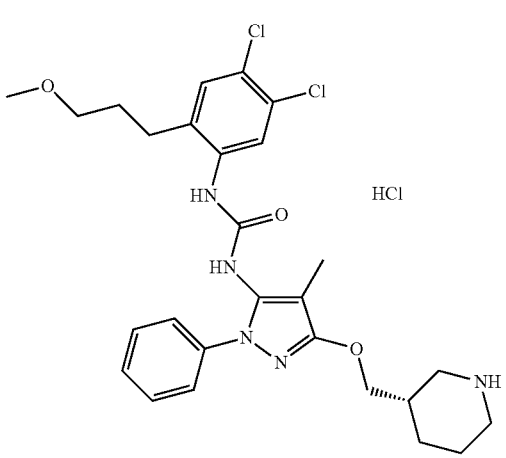 [SMILES: COCCCc1cc(Cl)c(Cl)cc1NC(=O)Nc1c(C)c(OC[C@H]2CCCNC2)nn1-c1ccccc1 ; Cl] | (S)-1-(4,5-dichloro-2-(3-methoxypropyl)phenyl)-3-(4-methyl-1-phenyl-3-(piperidin-3-ylmethoxy)-1H-pyrazol-5-yl)urea hydrochloride | MS (apci) m/z = 546.2 (M + H) |

TABLE 5-continued

| Ex # | Structure | Name | Data |
|---|---|---|---|
| 47 | 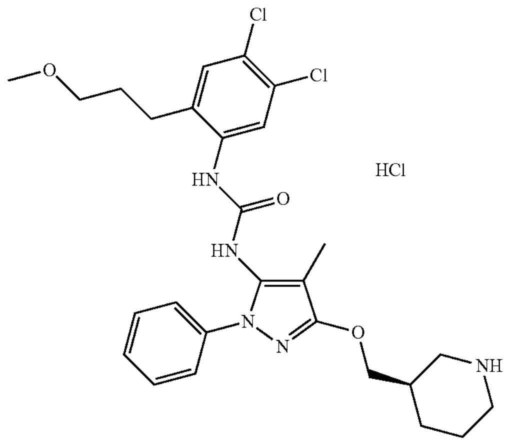 [SMILES: COCCCc1cc(Cl)c(Cl)cc1NC(=O)Nc1c(C)c(OC[C@@H]2CCCNC2)nn1-c1ccccc1 ; Cl] | (R)-1-(4,5-dichloro-2-(3-methoxypropyl)phenyl)-3-(4-methyl-1-phenyl-3-(piperidin-3-ylmethoxy)-1H-pyrazol-5-yl)urea hydrochloride | MS (apci) m/z = 546.2 (M + H) |

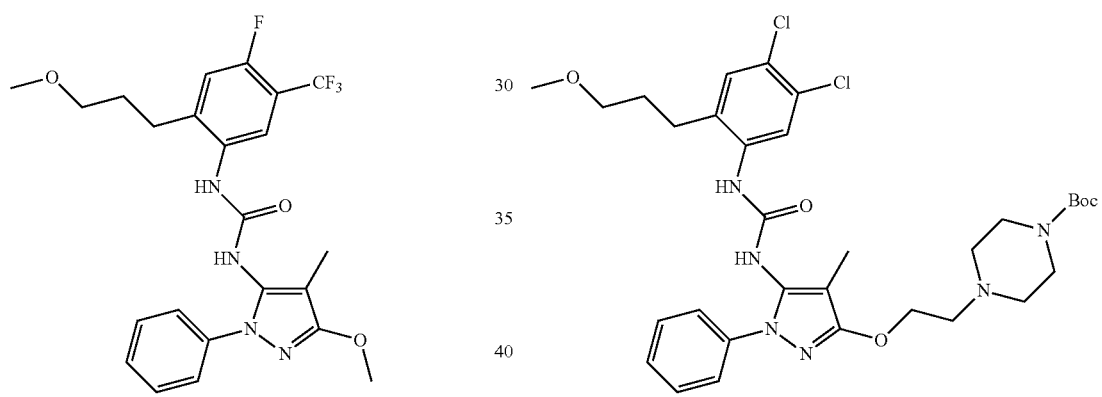

Example 48

1-(4-fluoro-2-(3-methoxypropyl)-5-(trifluoromethyl)phenyl)-3-(3-methoxy-4-methyl-1-phenyl-1H-pyrazol-5-yl)urea To a mixture of phenyl (3-methoxy-4-methyl-1-phenyl-1H-pyrazol-5-yl)carbamate (Intermediate X10, 16.0 mg, 0.0495 mmol) and 4-fluoro-2-(3-methoxypropyl)-5-(trifluoromethyl)aniline (Intermediate Y13, 13.7 mg, 0.0544 mmol) in dry THF (0.5 mL) was added DIEA (17.2 μL, 0.0990 mmol) and the solution was stirred at 40° C. for 16 hours. The reaction mixture was cooled to ambient temperature and washed with H₂O, 1M NaOH and H₂O. The organic layer was dried over Na₂SO₄, filtered and concentrated. The crude residue was purified by silica chromatography (CH₂Cl₂ followed by 25% to 50% EtOAc-hexanes) to yield the title product as a white solid (5 mg, 21%). MS (apci) m/z=481.2 (M+H).

Example 49 tert-butyl 4-(2-((5-(3-(4,5-dichloro-2-(3-methoxypropyl)phenyl)ureido)-4-methyl-1-phenyl-1H-pyrazol-3-yl)oxy)ethyl)piperazine-1-carboxylate A mixture of tert-butyl 4-(2-((5-amino-4-methyl-1-phenyl-1H-pyrazol-3-yl)oxy)ethyl)piperazine-1-carboxylate (Intermediate X13, 60.2 mg, 0.150 mmol) and 1,2-dichloro-4-isocyanato-5-(3-methoxypropyl)benzene (Intermediate Z1, 42.9 mg, 0.165 mmol) in dry dioxane (1.0 mL) was stirred at 50° C. for 18 hours. After cooling to ambient temperature, the reaction mixture was concentrated and the residue was purified on silica chromatography (DCM followed by 25% and 50% EtOAc in hexanes, then 100% EtOAc) to yield the title product as white solid, which was triturated with ether and dried (40 mg, 40%). MS (apci) m/z=661.2 (M+H).

What is claimed is:
1. A compound of Formula I-2:

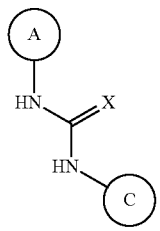

I-2 or a stereoisomer, tautomer, or pharmaceutically acceptable salt, solvate or prodrug thereof, wherein:
Ring A is formula A-1

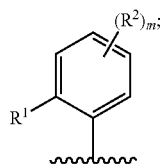

A-1 m is 1 or 2;
$R^1$ is formula $R^1$-1, $R^1$-2 or $R^1$-3

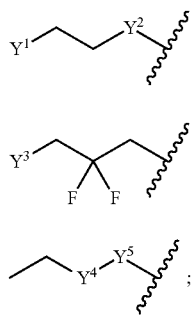

$R^1$-1

$R^1$-2

$R^1$-3

$Y^1$ is $CH_3CH_2$—, $CF_3CH_2$—, $CH_3O$—, $F_3CO$—, $F_2CHO$—, $FCH_2O$—, $CH_3S$—, $F_3CS$—, $F_2CHS$—, or $FCH_2S$—;
$Y^2$ is O, S, NH, MeN— or $CH_2$;
$Y^3$ is $CH_3O$—, $CH_3S$—, MeNH— or $Me_2N$—;
$Y^4$ is $CH_2$ and $Y^5$ is S or O, or $Y^4$ is S or O and $Y^5$ is $CH_2$;
$R^2$ is halogen or (1-3C)alkyl (optionally substituted with 1-3 fluoros);
X is O, S, NH or N—CN;
Ring C is formula C-1

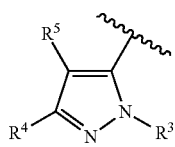

C-1

$R^3$ is $Ar^2$;
$Ar^2$ is phenyl;
$R^4$ is (1-6C)alkoxy, dihydroxy(2-6C)alkoxy, hetCyc$^2$(1-6C)alkoxy, hetAr$^4$, aminocarbonyl, hetCyc$^3$, or hetAr$^5$;

hetCyc$^2$ is a 4-6 membered heterocyclic ring having 1-2 ring heteroatoms independently selected from N and O and optionally substituted with (1-6C)alkyl, (1-4C alkylcarboxy)(1-6C)alkyl, or halogen;
hetCyc$^3$ is a 4-7 membered heterocycle having 1-2 ring heteroatoms independently selected from N and O and optionally substituted with CN or (1-6C)alky;
hetAr$^4$ is a 5-6 membered heteroaryl ring having 1-3 ring nitrogen heteroatoms and optionally substituted with (1-6C)alkyl;
hetAr$^5$ is

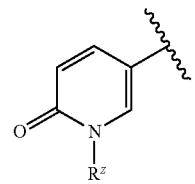

where $R^z$ is (1-3C)alkyl (optionally substituted with 1-3 fluoros);
and
$R^5$ is (1-6C)alkyl.
2. A compound according to claim 1, wherein X is O.
3. A compound according to claim 1, wherein $R^1$ is formula $R^1$-1.
4. A compound according to claim 3, wherein $R^1$ is selected from the structures:

5. The compound according to claim 1, wherein $R^4$ is hetAr$^4$ or hetAr$^5$.
6. The compound according to claim 5, wherein $R^4$ is hetAr$^4$.
7. The compound according to claim 6, wherein $R^4$ is pyrazolyl optionally substituted with one or more groups independently selected from (1-6C)alkyl.
8. A compound according to claim 1, selected from
1-(1',4-dimethyl-1-phenyl-1H,1'H-[3,4'-bipyrazol]-5-yl)-3-(2-(2-methoxyethoxy)-5-(trifluoromethyl)phenyl) urea;
1-(4,5-dichloro-2-(2-methoxyethoxy)phenyl)-3-(1',4-dimethyl-1-phenyl-1H,1'H-[3,4'-bipyrazol]-5-yl)urea;
1-(4-chloro-5-fluoro-2-(2-methoxyethoxy)phenyl)-3-(1',4-dimethyl-1-phenyl-1H,1'H-[3,4'-bipyrazol]-5-yl) urea;
1-(4,5-dichloro-2-(2-methoxyethoxy)phenyl)-3-(4-methyl-3-(1-methyl-6-oxo-1,6-dihydropyridin-3-yl)-1-phenyl-1H-pyrazol-5-yl)urea;
1-(5-chloro-2-(3-methoxypropyl)phenyl)-3-(1',4-dimethyl-1-phenyl-1H,1'H-[3,4'-bipyrazol]-5-yl)urea;
1-(1',4-dimethyl-1-phenyl-1H,1'H-[3,4'-bipyrazol]-5-yl)-3-(2-(2-methoxyethoxy)-4-(trifluoromethyl)phenyl) urea;
1-(4-chloro-2-(2-methoxyethoxy)phenyl)-3-(1',4-dimethyl-1-phenyl-1H,1'H-[3,4'-bipyrazol]-5-yl)urea;
1-(5-chloro-2-(2-methoxyethoxy)phenyl)-3-(1',4-dimethyl-1-phenyl-1H,1'H-[3,4'-bipyrazol]-5-yl)urea;

1-(4,5-dichloro-2-(3-methoxypropyl)phenyl)-3-(4-methyl-3-(1-methyl-6-oxo-1,6-dihydropyridin-3-yl)-1-phenyl-1H-pyrazol-5-yl)urea;
1-(3-(4-cyanotetrahydro-2H-pyran-4-yl)-4-methyl-1-phenyl-1H-pyrazol-5-yl)-3-(4,5-dichloro-2-(3-methoxypropyl)phenyl)urea;
1-(4,5-dichloro-2-(3-methoxypropyl)phenyl)-3-(1',4-dimethyl-1-phenyl-1H,1'H-[3,4'-bipyrazol]-5-yl)urea;
5-(3-(4,5-dichloro-2-(3-methoxypropyl)phenyl)ureido)-N,4-dimethyl-1-phenyl-1H-pyrazole-3-carboxamide;
1-(4-fluoro-2-(3-methoxypropyl)-5-(trifluoromethyl)phenyl)-3-(4-methyl-3-(1-methyl-6-oxo-1,6-dihydropyridin-3-yl)-1-phenyl-1H-pyrazol-5-yl)urea;
1-(4,5-dichloro-2-(3-methoxypropyl)phenyl)-3-(4-methyl-3-(1-methylpiperidin-4-yl)-1-phenyl-1H-pyrazol-5-yl)urea;
5-(3-(4-fluoro-2-(3-methoxypropyl)-5-(trifluoromethyl)phenyl)ureido)-N,4-dimethyl-1-phenyl-1H-pyrazole-3-carboxamide;
1-(4,5-dichloro-2-(2,2-difluoro-3-methoxypropyl)phenyl)-3-(4-methyl-3-(1-methyl-6-oxo-1,6-dihydropyridin-3-yl)-1-phenyl-1H-pyrazol-5-yl)urea;
(R)-1-(4,5-dichloro-2-(3-methoxypropyl)phenyl)-3-(3-(2,3-dihydroxypropoxy)-4-methyl-1-phenyl-1H-pyrazol-5-yl)urea;
(R)-1-(3-(2,3-dihydroxypropoxy)-4-methyl-1-phenyl-1H-pyrazol-5-yl)-3-(4-fluoro-2-(3-methoxypropyl)-5-(trifluoromethyl)phenyl)urea;
(S)-1-(4,5-dichloro-2-(3-methoxypropyl)phenyl)-3-(4-methyl-3-(morpholin-2-ylmethoxy)-1-phenyl-1H-pyrazol-5-yl)urea;
(1-(4,5-dichloro-2-(3-methoxypropyl)phenyl)-3-(4-methyl-3-((1-methylpiperidin-4-yl)methoxy)-1-phenyl-1H-pyrazol-5-yl)urea;
1-(2-(3-methoxypropyl)-5-(trifluoromethyl)phenyl)-3-(4-methyl-3-(1-methyl-6-oxo-1,6-dihydropyridin-3-yl)-1-phenyl-1H-pyrazol-5-yl)urea,
5-(3-(2-(3-methoxypropyl)-5-(trifluoromethyl)phenyl)ureido)-N,4-dimethyl-1-phenyl-1H-pyrazole-3-carboxamide;
5-(3-(4,5-dichloro-2-(2,2-difluoro-3-methoxypropyl)phenyl)ureido)-N,4-dimethyl-1-phenyl-1H-pyrazole-3-carboxamide;
1-(4,5-dichloro-2-(3-methoxypropyl)phenyl)-3-(4-methyl-3-(2-(4-methylpiperazin-1-yl)ethoxy)-1-phenyl-1H-pyrazol-5-yl)urea;
1-(4,5-dichloro-2-(3-methoxypropyl)phenyl)-3-(4-methyl-3-(2-(1-methylpiperidin-4-yl)ethoxy)-1-phenyl-1H-pyrazol-5-yl)urea;
(S)-1-(4,5-dichloro-2-(3-methoxypropyl)phenyl)-3-(4-methyl-3-((4-methylmorpholin-2-yl)methoxy)-1-phenyl-1H-pyrazol-5-yl)urea;
(R)-1-(4,5-dichloro-2-(3-methoxypropyl)phenyl)-3-(4-methyl-3-((4-methylmorpholin-2-yl)methoxy)-1-phenyl-1H-pyrazol-5-yl)urea;
(S)-1-(4,5-dichloro-2-(3-methoxypropyl)phenyl)-3-(4-methyl-3-((1-methylpiperidin-3-yl)methoxy)-1-phenyl-1H-pyrazol-5-yl)urea;
(R)-1-(4,5-dichloro-2-(3-methoxypropyl)phenyl)-3-(4-methyl-3-((1-methylpiperidin-3-yl)methoxy)-1-phenyl-1H-pyrazol-5-yl)urea;
1-(4,5-dichloro-2-(3-methoxypropyl)phenyl)-3-(4-methyl-3-((1-methylazetidin-3-yl)methoxy)-1-phenyl-1H-pyrazol-5-yl)urea;
(S)-1-(4,5-dichloro-2-(3-methoxypropyl)phenyl)-3-(4-methyl-3-(morpholin-2-ylmethoxy)-1-phenyl-1H-pyrazol-5-yl)urea;
1-(4,5-dichloro-2-(3-methoxypropyl)phenyl)-3-(4-methyl-1-phenyl-3-(2-(piperazin-1-yl)ethoxy)-1H-pyrazol-5-yl)urea;
1-(4,5-dichloro-2-(3-methoxypropyl)phenyl)-3-(4-methyl-1-phenyl-3-(2-(piperidin-4-yl)ethoxy)-1H-pyrazol-5-yl)urea;
1-(4,5-dichloro-2-(3-methoxypropyl)phenyl)-3-(4-methyl-1-phenyl-3-(piperidin-4-ylmethoxy)-1H-pyrazol-5-yl)urea;
1-(4,5-dichloro-2-(3-methoxypropyl)phenyl)-3-(4-methyl-1-phenyl-3-(pyrrolidin-2-ylmethoxy)-1H-pyrazol-5-yl)urea;
(R)-1-(4,5-dichloro-2-(3-methoxypropyl)phenyl)-3-(4-methyl-3-(morpholin-2-ylmethoxy)-1-phenyl-1H-pyrazol-5-yl)urea;
1-(4,5-dichloro-2-(3-methoxypropyl)phenyl)-3-(3-((4-fluoropiperidin-4-yl)methoxy)-4-methyl-1-phenyl-1H-pyrazol-5-yl)urea;
(S)-1-(4,5-dichloro-2-(3-methoxypropyl)phenyl)-3-(4-methyl-1-phenyl-3-(piperidin-3-ylmethoxy)-1H-pyrazol-5-yl)urea;
(R)-1-(4,5-dichloro-2-(3-methoxypropyl)phenyl)-3-(4-methyl-1-phenyl-3-(piperidin-3-ylmethoxy)-1H-pyrazol-5-yl)urea;
1-(4-fluoro-2-(3-methoxypropyl)-5-(trifluoromethyl)phenyl)-3-(3-methoxy-4-methyl-1-phenyl-1H-pyrazol-5-yl)urea;
tert-butyl 4-(2-((5-(3-(4,5-dichloro-2-(3-methoxypropyl)phenyl)ureido)-4-methyl-1-phenyl-1H-pyrazol-3-yl)oxy)ethyl)piperazine-1-carboxylate;
or a pharmaceutically acceptable salt thereof.

9. A pharmaceutical composition, which comprises a compound of Formula I-2 as defined in claim 1 or a pharmaceutically acceptable salt thereof, and a pharmaceutically acceptable diluent or carrier.

10. A process for the preparation of a compound of claim 1, which comprises:
(a) for a compound of Formula I-2 where X is O, coupling a corresponding compound having the formula II

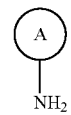

II with a corresponding compound having the formula III

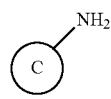

III in the presence carbonyldiimidazole or triphosgene and a base; or
(b) for a compound of Formula I-2 where X is S, coupling a corresponding compound having the formula II

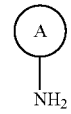

II with a corresponding compound of formula III

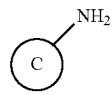
III in the presence di(1H-imidazol-2-yl)methanethione and a base; or (c) for a compound of Formula I-2 where X is O, coupling a corresponding compound having the formula II

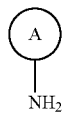
II with a corresponding compound having the formula IV

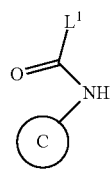
IV where $L^1$ is a leaving group, in the presence of a base; or (d) for a compound of Formula I-2 where X is O, coupling a corresponding compound having the formula V

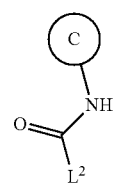
V where $L^2$ is a leaving group, with a corresponding compound having the formula III

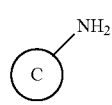
III in the presence of a base; or (e) for a compound of Formula I-2 where X is O, activating a corresponding compound having the formula VI

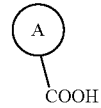
VI with diphenylphosphoryl azide followed by coupling the activated intermediate with a corresponding compound having the formula III

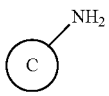
III in the presence a base; or (f) for a compound of Formula I-2 where X is O, coupling a corresponding compound having the formula II

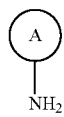
II with a corresponding compound having the formula VII

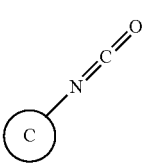
VII in the presence of a base;

(g) for a compound of Formula I-2 where X is O, coupling a corresponding compound having the formula VIII

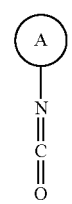
VIII with a corresponding compound having the formula III

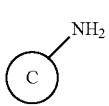
III in the presence of a base; and
optionally removing protecting groups and optionally preparing a pharmaceutically acceptable salt thereof.

* * * * *

UNITED STATES PATENT AND TRADEMARK OFFICE
CERTIFICATE OF CORRECTION

PATENT NO. : 9,790,210 B2
APPLICATION NO. : 14/442604
DATED : October 17, 2017
INVENTOR(S) : Steven Wade Andrews et al.

It is certified that error appears in the above-identified patent and that said Letters Patent is hereby corrected as shown below:

In the Claims

Column 211, Lines 40-48, Claim 1, please delete the following structure:

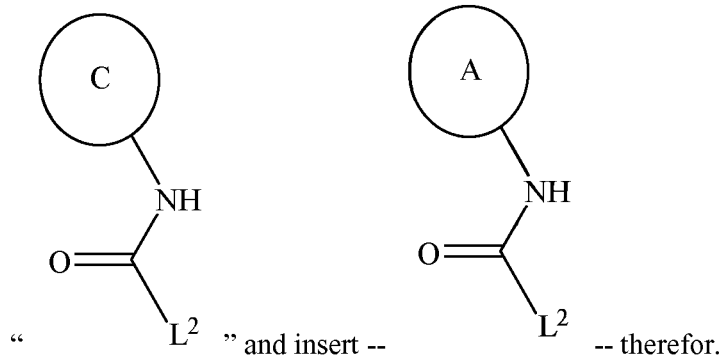

Signed and Sealed this
Fifteenth Day of May, 2018

Andrei Iancu
*Director of the United States Patent and Trademark Office*